US011254947B2

(12) United States Patent
Danon et al.

(10) Patent No.: US 11,254,947 B2
(45) Date of Patent: Feb. 22, 2022

(54) TRUNCATED FORMS OF ATYPICAL CYS HIS RICH THIOREDOXIN 4 (ACHT4) CAPABLE OF INHIBITING ACHT4-MEDIATED OXIDATION OF THE SMALL SUBUNIT OF ADP-GLUCOSE PYROPHOSPHORYLASE (APS1)

(71) Applicant: YEDA RESEARCH AND DEVELOPMENT CO. LTD., Rehovot (IL)

(72) Inventors: Avihai Danon, Moshav Kfar Uria (IL); Erez Eliyahu, Rehovot (IL); Vivekanand Tiwari, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

(21) Appl. No.: 15/753,024

(22) PCT Filed: Aug. 16, 2016

(86) PCT No.: PCT/IL2016/050891
§ 371 (c)(1),
(2) Date: Feb. 15, 2018

(87) PCT Pub. No.: WO2017/029662
PCT Pub. Date: Feb. 23, 2017

(65) Prior Publication Data
US 2019/0119696 A1 Apr. 25, 2019

Related U.S. Application Data

(60) Provisional application No. 62/205,768, filed on Aug. 17, 2015.

(51) Int. Cl.
*C12N 15/82* (2006.01)
*C07K 14/415* (2006.01)
*C12N 9/02* (2006.01)

(52) U.S. Cl.
CPC ........ *C12N 15/8261* (2013.01); *C07K 14/415* (2013.01); *C12N 9/0051* (2013.01); *C12N 15/8245* (2013.01); *Y02A 40/146* (2018.01)

(58) Field of Classification Search
None
See application file for complete search history.

(56) References Cited

U.S. PATENT DOCUMENTS

| 7,135,616 | B2 | 11/2006 | Heard et al. |
| 2015/0067923 | A1 | 3/2015 | Coruzzi et al. |
| 2015/0176021 | A1 | 6/2015 | Vinocur et al. |

OTHER PUBLICATIONS

TAIR: Polymorphism GT21821.Ds5.09.01.2006.jz13.727 (2007) published online on the world wide web atarabidopsis.org/servlets/TairObject?id=500949074&type=polyallele; pp. 1-2 (Year: 2007).*
Dangoor et al. A small family of chloroplast atypical thioredoxins. (2009) Plant Physiology; vol. 149; pp. 1240-1250 (Year: 2009).*
Eliyahu et al. ACHT4-driven oxidation of APS1 attentuates starch synthesis under low light intensity in Arabidopsis plants. (2015) PNAS; vol. 112, pp. 12876-12881 (Year: 2015).*
Theologis et al. *Arabidopsis thaliana* atypical CYS HIS rich thioredoxin 4 mRNA, complete cds. (2014) GenBank Accession NM_100730; pp. 1-3 (Year: 2014).*
Akerman, Susan E., and Sylke Müller. "Peroxiredoxin-linked detoxification of hydroperoxides in Toxoplasma gondii." *Journal of Biological Chemistry* 280.1 (2005): 564-570.
Andersson, B., and J. M. Anderson. "The chloroplast thylakoid membrane—isolation, subfractionation and purification of its supramolecular complexes." *Cell* Components. Springer, Berlin, Heidelberg, 1985. 231-258.
Asada, Kozi. "The water-water cycle in chloroplasts: scavenging of active oxygens and dissipation of excess photons." Annual review of plant biology 50.1 (1999): 601-639.
Ballicora, Miguel A., et al. "Activation of the potato tuber ADP-glucose pyrophosphorylase by thioredoxin." *Journal of Biological Chemistry* 275.2 (2000): 1315-1320.
Bates, George W. "Plant transformation via protoplast electroporation." Plant Cell Culture Protocols. Humana Press, 1999. 359-366.
Belin, C., et al. "A comprehensive study of thiol reduction gene expression under stress conditions in A rabidopsis thaliana." Plant, cell & environment 38.2 (2015): 299-314.
Dangoor, Inbal, et al. "A small family of chloroplast atypical thioredoxins." Plant physiology 149.3 (2009): 1240-1250.
Dangoor, Inbal, et al. "A chloroplast light-regulated oxidative sensor for moderate light intensity in *Arabidopsis*." The Plant Cell 24.5 (2012): 1894-1906.
Danon, Avihai. "Redox reactions of regulatory proteins: do kinetics promote specificity?." *Trends in biochemical sciences*27.4 (2002): 197-203.
European Search Report dated Feb. 12, 2019.
Finer, J. J., K. R. Finer, and T. Ponappa. "Particle bombardment mediated transformation." Plant Biotechnology. Springer, Berlin, Heidelberg, 2000. 59-80.
Fu, Yingbin, et al. "Mechanism of reductive activation of potato tuber ADP-glucose pyrophosphorylase." *Journal of Biological Chemistry* 273.39 (1998): 25045-25052.
Hendriks, Janneke HM, et al. "ADP-glucose pyrophosphorylase is activated by posttranslational redox-modification in response to light and to sugars in leaves of *Arabidopsis* and other plant species." *Plant Physiology* 133.2 (2003): 838-849.
International Search Report for PCT/IL2016/050891 dated Nov. 7, 2016.
Karpinski, Stanislaw, et al. "Systemic signaling and acclimation in response to excess excitation energy in *Arabidopsis*." Science 284.5414 (1999): 654-657.

(Continued)

*Primary Examiner* — Cathy Kingdon Worley
(74) *Attorney, Agent, or Firm* — Mark S. Cohen; Pearl Cohen Zedek Latzer Baratz LLP

(57) ABSTRACT

The present invention provides compositions for attenuating the function of atypical CYS HIS rich thioredoxin 4 (ACHT4), a light-regulated protein expressed in plants and algae that controls starch storage in chloroplast, and methods for increasing plant and algae growth and yield.

30 Claims, 14 Drawing Sheets

Specification includes a Sequence Listing.

(56) References Cited

OTHER PUBLICATIONS

Komari, Toshihiko, et al. "Advances in cereal gene transfer." Current opinion in plant biology 1.2 (1998): 161-165.

Lennartz, Katja, et al. "HCF164 encodes a thioredoxin-like protein involved in the biogenesis of the cytochrome b6f complex in *Arabidopsis*." The Plant Cell 13.11 (2001): 2539-2551.

Lunn, John E., et al. "Sugar-induced increases in trehalose 6-phosphate are correlated with redox activation of ADPglucose pyrophosphorylase and higher rates of starch synthesis in *Arabidopsis thaliana*." Biochemical Journal 397.1 (2006): 139-148.

Mettler, Tabea, et al. "Systems analysis of the response of photosynthesis, metabolism, and growth to an increase in irradiance in the photosynthetic model organism Chlamydomonas reinhardtii." The Plant Cell 26.6 (2014): 2310-2350.

Michalska, Justyna, et al. "NTRC links built-in thioredoxin to light and sucrose in regulating starch synthesis in chloroplasts and amyloplasts." Proceedings of the National Academy of Sciences 106.24 (2009): 9908-9913.

Mugford, Sam T., et al. "Regulatory properties of ADP glucose pyrophosphorylase are required for adjustment of leaf starch synthesis in different photoperiods." Plant Physiology 166.4 (2014): 1733-1747.

Nikkanen, Lauri, and Eevi Rintamäki. "Thioredoxin-dependent regulatory networks in chloroplasts under fluctuating light conditions." Philosophical Transactions of the Royal Society B: Biological Sciences 369.1640 (2014): 20130224.

Parsonage, Derek, P. Andrew Karplus, and Leslie B. Poole. "Substrate specificity and redox potential of AhpC, a bacterial peroxiredoxin." Proceedings of the National Academy of Sciences 105.24 (2008): 8209-8214.

Peskin, Alexander V., et al. "The high reactivity of peroxiredoxin 2 with H2O2 is not reflected in its reaction with other oxidants and thiol reagents." Journal of Biological Chemistry 282.16 (2007): 11885-11892.

Pfannschmidt, Thomas. "Chloroplast redox signals: how photosynthesis controls its own genes." Trends in plant science 8.1 (2003): 33-41.

Pilkington, Sarah M., et al. "Relationship between starch degradation and carbon demand for maintenance and growth in A rabidopsis thaliana in different irradiance and temperature regimes." Plant, cell & environment 38.1 (2015): 157-171.

Polls, Andrea. "Dissecting the superoxide dismutase-ascorbate-glutathione-pathway in chloroplasts by metabolic modeling. Computer simulations as a step towards flux analysis." Plant physiology 126.1 (2001): 445-462.

Porta, Claudine, and George P. Lomonossoff. "Use of viral replicons for the expression of genes in plants." Molecular biotechnology 5.3 (1996): 209.

Rochaix, Jean-David. "Redox regulation of thylakoid protein kinases and photosynthetic gene expression." Antioxidants & redox signaling 18.16 (2013): 2184-2201.

Schuermann, Peter, and Bob B. Buchanan. "The ferredoxin/thioredoxin system of oxygenic photosynthesis." Antioxidants & redox signaling 10.7 (2008): 1235-1274.

Stitt, Mark, and Samuel C. Zeeman. "Starch turnover: pathways, regulation and role in growth." Current opinion in plant biology 15.3 (2012): 282-292.

TAIR: Polymorphism GT21821. Ds5.09.01.2006.JZ13.727 (2007) published online on the world wide web at: Arabidopsis.org/servlets/TairObject?id=50094907&type=pollyallele; pp. 1-2 (Year:2007).

Thormaehlen, Ina, et al. "Inactivation of thioredoxin f1 leads to decreased light activation of ADP-glucose pyrophosphorylase and altered diurnal starch turnover in leaves of *Arabidopsis* plants." Plant, cell & environment 36.1 (2013): 16-29.

Trebitsh, Tova, and Avihai Danon. "Translation of chloroplast psbA mRNA is regulated by signals initiated by both photosystems II and I." Proceedings of the National Academy of Sciences 98.21 (2001): 12289-12294.

\* cited by examiner

TRUNCATED FORMS OF ATYPICAL CYS HIS RICH THIOREDOXIN 4 (ACHT4) CAPABLE OF INHIBITING ACHT4-MEDIATED OXIDATION OF THE SMALL SUBUNIT OF ADP-GLUCOSE PYROPHOSPHORYLASE (APS1)

CROSS-REFERENCE TO RELATED APPLICATIONS

This application is a National Phase Application of PCT International Application No. PCT/IL2016/050891, filed on Aug. 16, 2016, claiming priority from U.S. Provisional Patent Application Ser. No. 62/205,768 filed on Aug. 17, 2015, which are all hereby incorporated by reference.

FIELD OF THE INVENTION

The present invention provides compositions for attenuating the function of atypical CYS HIS rich thioredoxin 4 (ACHT4), a light-regulated protein expressed in plants and algae that controls starch storage in chloroplast, and methods for increasing plant and algae growth and yield.

BACKGROUND OF THE INVENTION

Genetically modified plants with improved agronomic traits such as yield, pest resistance, herbicide tolerance, improved seed compositions, and the like are desired by both farmers and consumers. Although considerable efforts in plant breeding have provided significant gains in desired phenotypes, the ability to introduce specific DNA into plant genomes provides further opportunities for generation of plants with improved and/or unique phenotypes. The ability to develop genetically modified plants with improved traits depends in part on the identification of genes that are useful in recombinant DNA constructs for production of transformed plants with improved properties.

One genetic modification that would be economically desirable would be to increase the growth and yield production of the plant. There is a need to develop a method for increasing growth in plants, regardless of the locale or the environmental conditions.

The *Arabidopsis thaliana* atypical cysteine histidine-rich Trxs (ACHTs) constitute a small family of plant-specific and chloroplast-localized Trxs. They are light-regulated and are good catalysts of 2-Cys Prx reduction.

The expression profile of the ACHT family members suggests that they have distinct roles. The role of ACHT4, a recently identified paralog of ACHT1 in *Arabidopsis*, was previously unknown.

SUMMARY OF THE INVENTION

In one embodiment, the present invention provides compositions for attenuating the function of atypical CYS HIS rich thioredoxin 4 (ACHT4), a light-regulated protein expressed in plants and algae that controls starch storage in chloroplast, and methods for increasing plant and algae growth and yield.

In one embodiment, the present invention provides a recombinant polynucleotide encoding an atypical CYS HIS rich thioredoxin 4 (ACHT4) protein, wherein the C-terminal portion of said ACHT4 protein comprises an inactivating mutation.

In another embodiment, the present invention provides a composition comprising a recombinant polynucleotide encoding an atypical CYS HIS rich thioredoxin 4 (ACHT4) protein, wherein the C-terminal portion of said ACHT4 protein comprises an inactivating mutation.

In another embodiment, the present invention provides an expression vector comprising a recombinant polynucleotide encoding an atypical CYS HIS rich thioredoxin 4 (ACHT4) protein, wherein the C-terminal portion of said ACHT4 protein comprises an inactivating mutation.

In another embodiment, the present invention provides a composition comprising an expression vector comprising a recombinant polynucleotide encoding an atypical CYS HIS rich thioredoxin 4 (ACHT4) protein, wherein the C-terminal portion of said ACHT4 protein comprises an inactivating mutation.

In another embodiment, the present invention provides a cell comprising an expression vector comprising a recombinant polynucleotide encoding an atypical CYS HIS rich thioredoxin 4 (ACHT4) protein, wherein the C-terminal portion of said ACHT4 protein comprises an inactivating mutation.

In another embodiment, the present invention provides a composition comprising a cell comprising an expression vector comprising a recombinant polynucleotide encoding an atypical CYS HIS rich thioredoxin 4 (ACHT4) protein, wherein the C-terminal portion of said ACHT4 protein comprises an inactivating mutation.

In another embodiment, the present invention provides a seed comprising a C-terminal deleted form of an atypical CYS HIS rich thioredoxin 4 (ACHT4) gene.

In another embodiment, the present invention provides a plant, or plant part, comprising a C-terminal deleted form of an atypical CYS HIS rich thioredoxin 4 (ACHT4) gene.

In another embodiment, the present invention provides an algae comprising a C-terminal deleted form of an atypical CYS HIS rich thioredoxin 4 (ACHT4) gene.

In another embodiment, the present invention provides a polypeptide comprising an atypical CYS HIS rich thioredoxin 4 (ACHT4) protein, wherein the C-terminal portion of said ACHT4 protein comprises an inactivating mutation.

In another embodiment, the present invention provides a composition comprising a polypeptide comprising a C-terminal deleted form of atypical CYS HIS rich thioredoxin 4 (ACHT4).

In another embodiment, the present invention provides a method of increasing the yield of a plant or algae comprising contacting a cell from said plant or algae with a polynucleotide encoding a C-terminal deleted form of atypical CYS HIS rich thioredoxin 4 (ACHT4), thereby increasing the yield of said plant or algae.

In another embodiment, the present invention provides a method of increasing the productivity of a plant or algae comprising contacting a cell from said plant or algae with a polynucleotide encoding a C-terminal deleted form of atypical CYS HIS rich thioredoxin 4 (ACHT4), thereby increasing the productivity of said plant or algae.

In another embodiment, the present invention provides a method of increasing the size of a plant or algae comprising contacting a cell from said plant or algae with a polynucleotide encoding a C-terminal deleted form of atypical CYS HIS rich thioredoxin 4 (ACHT4), thereby increasing the size of said plant or algae.

In another embodiment, the present invention provides a method of increasing the biomass of a plant or algae comprising contacting a cell from said plant or algae with a polynucleotide encoding a C-terminal deleted form of atypical CYS HIS rich thioredoxin 4 (ACHT4), thereby increasing the biomass of said plant or algae.

In another embodiment, the present invention provides a method of stimulating the growth of a plant or algae comprising contacting a cell from said plant or algae with a polynucleotide encoding a C-terminal deleted form of atypical CYS HIS rich thioredoxin 4 (ACHT4), thereby stimulating the growth of said plant or algae.

In another embodiment, the present invention provides a method of producing a plant or algae having an enhanced phenotype, wherein said method comprises delivering a recombinant polynucleotide encoding an atypical CYS HIS rich thioredoxin 4 (ACHT4) protein to plant or algae cells, wherein the C-terminal portion of said ACHT4 protein comprises an inactivating mutation, regenerating plants or algae from said cells, and screening said plants or algae to identify a plant having an enhanced phenotype.

Figure 8:
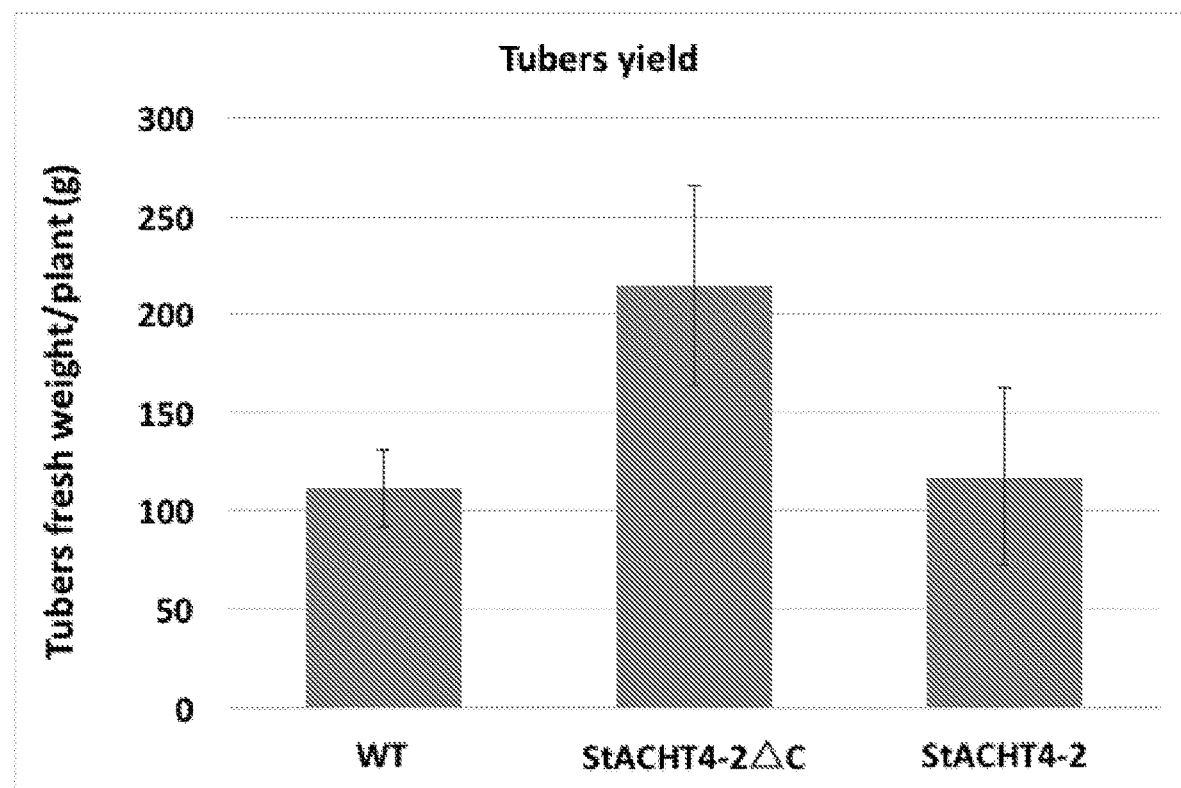

FIG. 8: Effect of OE of StACHT4-2ΔC in potato plants on tubers yield. OE StACHT4-2ΔC in potato plants nearly doubled tubers yield (g per plant) in comparison to WT plants (cultivated Desiree), indicating that StACHT4-2ΔC stimulates the export of photosynthates from the chloroplast which are then directed toward growth. OE of StACHT4-2 did not change growth, confirming that the deletion of StACHT4-2 C-terminus relieves growth attenuation and tubers yield in a similar fashion to *Arabidopsis* AtACHT4ΔC.

Figure 9:
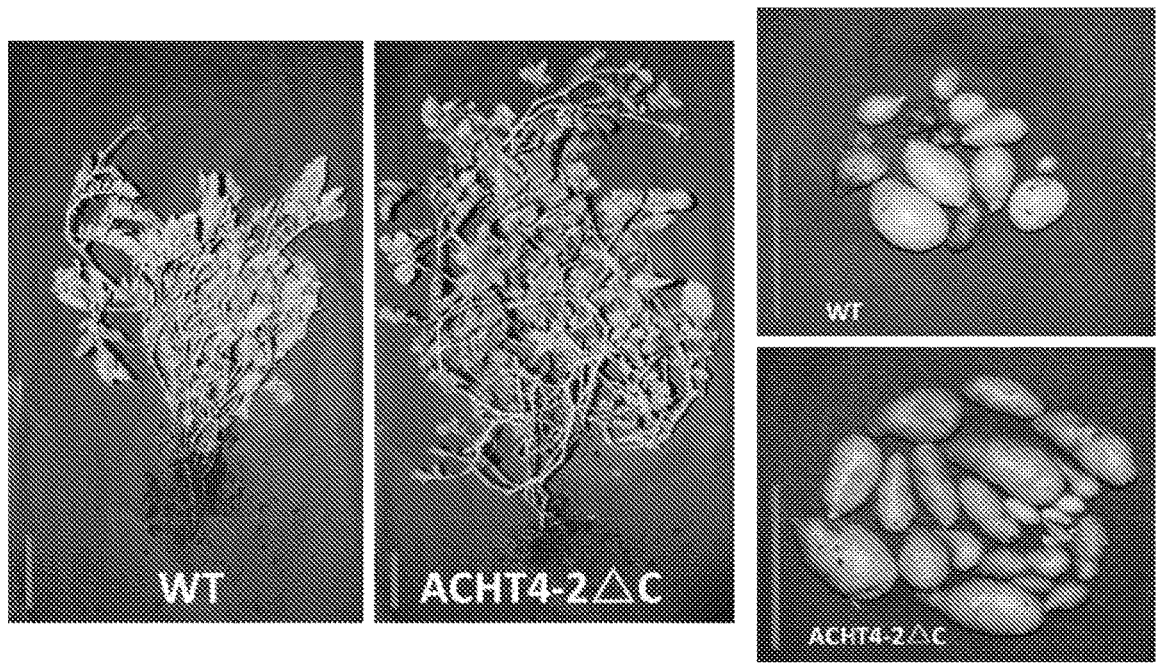

FIG. 9: Photographs of potato plants after 60-days growth in the greenhouse showing higher shoots growth and higher tuber yield in StACHT4-2ΔC-OE plants over WT (cultivated Desiree) plants. Scale bar in each panel represents 10 cm.

Figure 10:
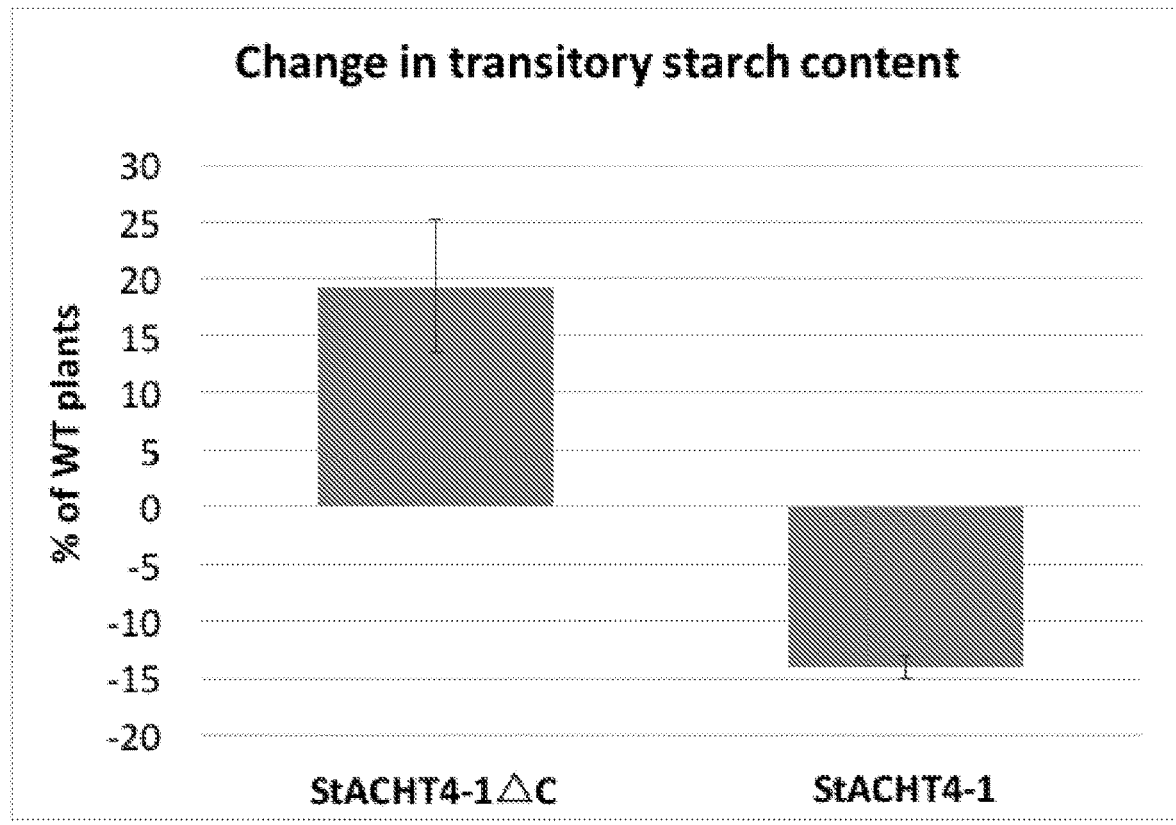

FIG. 10: Percent change of transitory starch level of leaves of 6-weeks old StACHT4-1ΔC OE and StACHT4-1 OE potato plants. Overexpressing (OE) StACHT4-1ΔC in potato plants stimulated transitory starch accumulation in leaves relative to wild type plants. OE of StACHT4-1 decreased transitory starch accumulation, confirming that the C-terminus of StACHT4-1 attenuates starch synthesis in potato leaves.

Figure 11:
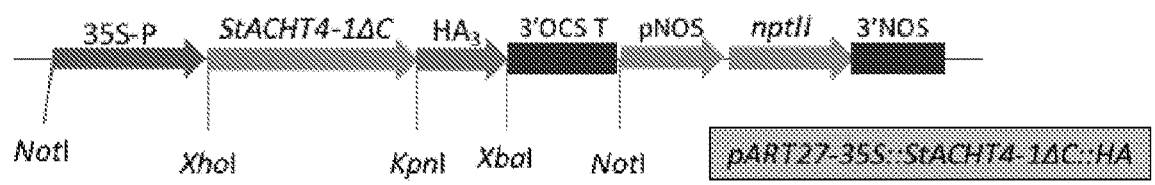

FIG. 11: Schematic representation of plant expression vector construct for the over expression of the four StACHT4 construct. Only the construct of StACHT4-1ΔC is shown.

DETAILED DESCRIPTION OF THE INVENTION

In one embodiment, the present invention provides compositions for attenuating the function and/or expression of atypical CYS HIS rich thioredoxin 4 (ACHT4), a light-regulated protein expressed in plants and algae that controls starch storage in chloroplast, and methods for increasing plant and algae growth and yield.

ACHT4

The *Arabidopsis thaliana* atypical cysteine histidine-rich Trxs (ACHTs) constitute a small family of plant-specific and chloroplast-localized Trxs. They are light-regulated and are good catalysts of 2-Cys Prx reduction.

A recently discovered paralog, AtACHT4, was found by the inventors to attenuate starch synthesis in *Arabidopsis thaliana* by oxidizing a regulatory disulfide on the small subunit (APS1) of the AGPase (ADP-glucose pyrophosphorylase, which catalyzes the first committed step in the starch synthesis pathway; Examples 1-2). The oxidizing reaction of AtACHT4 with AGPase requires the C-terminus of AtACHT4 (Example 2).

Thus, in one embodiment, the present invention provides compositions comprising ACHT4 proteins and nucleic acids and uses thereof. ACHT4 sequences may be from any species comprising such sequences. Table 1 hereinbelow discloses the amino acid sequences of some ACHT4 paralogs in various species, while Table 2 hereinbelow discloses the nucleic acid sequences of some ACHT4 paralogs in various species.

TABLE 1

AGHT4 amino acid sequences

| Organism | Paralogs | Database Accession No. (Genbank unless otherwise specified) | Amino Acid Sequence | SEQ ID NO: |
|---|---|---|---|---|
| *Arabidopsis thaliana* | AtACHT4 | NP_172333.1 | MTEVISKTSLFLGACGNHHRVDDFSFS PVSFGGFGLKKSFSCLKLKSQKPLRSV FYGKQIVFGDSQDESFRRSSAITAQTTL RIGTAQKWWEKGLKDNMREISSAQEL VDSLTNAGDKLVVVDFFSPGCGGCKA LHPKICQFAEMNPDVQFLQVNYEEHK SMCYSLGVHVLPFFRFYRGSQGRVCSF | 1 |

TABLE 1-continued

AGHT4 amino acid sequences

| Organism | Paralogs | Database Accession No. (Genbank unless otherwise specified) | Amino Acid Sequence | SEQ ID NO: |
|---|---|---|---|---|
| | | | SCTNATIKKFRDALAKHGPDRCSLGPT KGLEEKELVALAANKELNFTYTPKPVP VEKEAATPDSNPSLPVPLPSMSSNDEK TLVSAGR | |
| Solanum tuberosum (Potato) | StACHT4-1 | XP_006348023.1; PGSC0003DMP400032814 | MMKLMSKGFMFPSSSDCGEIYHHRPL NLPGICSFPNKSVNLSCLPSLNLSSSCLP RTDFYGRRLVINEGVSKFNRRNSQVV DITAQMSIGIRKAQKWWEKGVQPNMK EVNSAQELVDSLLSAGDKLVVVDFFSP GCGGCKALHPKLCQLAEMNPDVHFLQ VNYEEHKSMCYSLNVHVLPFFRFYRG AEGRVCSFSCTNATIKKFKDALAKYGT DRCTLGPPKGLEEKELLALAANKDLSF NYTPKTEEAPVLVTSQKEVQDTTPPNI ESPLPLPLPLPIASTSSQTAKRDTEKEA YATSGR | 2 |
| Solanum tuberosum (Potato) | StACHT4-2 | XP_006351368.1; PGSC0003DMP400040925 | MKFNRRNHKSAAATAQMSIGIRKAPK WWEKGLQPNMKEVMGAQDLADTLL NAGDKLVVVDFLSPGCGGCKALHPKI CQLAEMNPDVQFLHVNYEEHKSMCYS LNVHVLPFFRFYRGAEGRLCSFSCTNA TIKKFKDALTKYGADCCSLEPVKGLEE KELLALAANKDLSFAYTPKTEEPMPV ALQDAKVIKTSRTSSSCPNTFSLLPLPL PLPLASTSHKAKQDSKSEVF | 3 |
| Zea mays (Maize) | ZmACHT4-1 | NP_001266702.1 | MAAAQAISKGSVVSPCGNRAAPGLLA RRRGAVAARVAPSAARIGGFWRKNAF PGGRLTLRTRRSRAASPAQMNMNLAL GKSMRWWEKGLQPNMREIESAQDLV DALTNAGDRLVVVDFFSPGCGGCRAF HPKICQFAEQNPDVLFLQVNYEEHKS MCHSLHVHVLPLFRFYRGAQGRLCSFS CTNTTIKKFRDALAKHKPDRCSLGPTR GLEESELLALAANKDLQFTYAKEEPEL IPRGDAPGEVVAPEPAKLPAAPKPLVR LGSEERSLVSSGR | 4 |
| Zea mays (Maize) | ZmACHT4-2 | ACR34655.1 | MADALCNGVVASPCGRDVAGRARGA ARAALAESLQVAGHASKTSFSACGRMS VKDSKPRPLSRSLEAAAPGQMNLSFPK AMRWWKKGLHPNMREVESAQDLADS LLSAGDKLVVVDFFSPGCGGCRALHP KIAQFAEKNPGVQFLQVNYETHKSMC YSLRVEVLPFFRFYRGAEGRVSSFSCT NATINKFKDALAKHGAERCSLGPARG LDESELMALAENRDLHFTYDKPGGLV PLAEAIAKEAAAPGGPWLPLPASLLGQ GSDNSLLPSGR | 5 |
| Zea mays (Maize) | ZmACHT4-3 | ACN36361.1 | MAAAQVVAKGSVVSPCGNRAVPGLL GRRRDAVAAQMTPSAVRIGGSWRKN AFPGVRLALGTRRSRPASRSFSASPVQ MNMNLAIGKSMRWWEKGLQPNMREI ESAQDLVDSLINAGERLVVVDFFSPGC GGCRALHPKICQFAERNPDVLFLQVNY EEHKSMCYSLRVHVLPFFRFYRGAQG RLCSFSCTNATVRSCPCFFCSYDYWYV LNNMQHIQNDLY | 6 |
| Oryza sativa (Rice) | OsACHT4-1 | XP_015632287.1 | MAATAAQAVAVKGSVAVPPCGSRGR RRGAVASVRMAAAAATSALRIGRRSP FLGRRLAVGPRRSRPVPRNLVAPVQM NLAFAKATKWWEKGLQPNMREVESA QDLVDSLTNAGDNLVIVDFFSPGCGGC RALHPKICQIAEQNPDVLFLQVNYEEH KSMCYSLHVHVLPFFRFYRGAQGRLC | 7 |

TABLE 1-continued

AGHT4 amino acid sequences

| Organism | Paralogs | Database Accession No. (Genbank unless otherwise specified) | Amino Acid Sequence | SEQ ID NO: |
|---|---|---|---|---|
| | | | SESCTNATIKKFRDALAKHKPDRCSLG PTRGLEESELLALAANKDLQFNYTKKP ELVPSGDAAAAQELDRGSTKLSPPAKP LVKQGSEERSLVSSGR | |
| Orysa sativa (Rice) | OSACHT4-2 | XP_015646723.1 | MAEALCSGSVASPCGEVGVGFAAGLV RGAAAAAALAESVPIGGYSSKSTFPSG RVALTERKARPLPRNLEAAHGQMNLT IGKAMRWWEKCLQPNMREIESAQDLA DSLLNAGDKLVVVDFFSPGCGGCRAL HPKIAQLAEKNPEVLFLQVNYEKHKS MCYSLHVHVLPFFRFYRGAQGRVSSFS CTNATIKKFKDALAKHGPDRCGLGPA KGLEESELMALAINRDLNFTYTPNQDL VPIADALLKEAAAPGGPWLPLPATATQ LFIGSENSLLSSGR | 8 |
| Hordeum vulgare (Barley) | HvACHT4-1 | BAK03063.1 | MATAQAVAKGTVVSPCGTRAAGFGA RRRGAVAARMSPCAPAAVRIGRKSPFL GARLTVGPRRSKLVPRNLVSSPVQMN LAFAKSTKWWEKGLKPNMREIESAQD LVDSLANAGDRLVVVDFFSPGCGGCR ALHPKICQFGEQNPDVLFLQVNYEEHK SMCYSLHVHVLPFFRFYRGAQGRLCSF SCTNATIKKFRDALAKHNPDRCSIGPT RGLEESELLALAANKDLQFTYTKQPEP VPSGDSEFIAPGSPRLPPPAKPLVRQGS GERTLVSSGR | 9 |
| Hardeum vulgare (Barley) | HvACHT4-2 | BAK07858.1 | MANALYGGGVAAPCGDLGAAAALAE SLMGGGYRARSSFPAGRVALAERPLP RSLQVAAAAGQMNGNLTIGKAMRW WEKGTQPNMREVESAQDLADSLLNA GDKLVVVDFFSPGCGGCRALHPKIAQF AERNPDVLFLQVNYEKHKSMCYSLHV HVLPFFRFYRGAQGRVSSFSCTNATIK KFKDALAKHSPDRCSLGPARGLEKAE LLALAENRDLEFTYSEKPTLVPIAEAIR MEAASIGGPWLPLPPAATQPFPLGSEN GSLIPSGR | 10 |
| Triticum aestivum (Wheat) | TaACHT4 | Traslated ORF in 1st frame from mRNA AK335384.1 | MASALCGGGSGSVAAPCGDLGAAAA LAESLPMGAGYRAKSSFPAGRVALAD RPLRRGLQVAAAAGQMNGNLTIGKA MRWWEKVTHPNMREVESAQDLADSL LNAGDKLVVVDFFSPGCGGCRALHPKI AQFAERNPDVLFLQVNYEKHKSMCYS LHVHVLPFFRFYRGAQGRVSSFSCTNA TIKKFKDALAKHSPDRCSLGPARGLEE AELLALAANRDLEFTYNEKPTLVPIAE AIQMEAASIGGPWMPLPAAATQPLTLG SENGSLIPSGR | 11 |
| Manihot esculenta (Cassava) | MeACHT4-1 | OAY44415.1 | MADVLSNTNLVSSSFSSSFTGHRNEQK NSSCRLKGFPRKVNRQTLRLKATSLGS DFHGKRVVLQDNQGKPKRGIYLQMSI KAQHTGLRLKSAPKWWEKGLQPNMR EVTSAQDFVDSLLNAGDKLVIVDFFSP GCGGCKALHPKICQFAEMNPDVLFLH VNYEEHKSMCYSLNIHVLPFFRFYRGA QGRLCSFSCTNATIKKFRDALAKHSPD RCSLGPTKGLEEKELIALASNKDLNFK YAQKPDLPTPIPAKEERVPVVSPSHPNP ALPLPLPLPTASPKSGQGSEEKTLVGSGR | 12 |
| Manihot esculenta (Cassava) | MeACHT4-2 | OAY41970.1 | MAAVSSNTNLVSSSCSSSFSSSQNRPEY RSSRLRVFPQELNHQALRLQTTSLGSD FHGKRVVLQEKPKCKQGISVQSSIKAQ TGLRLKNAKNWWEEELQPNMREVISA QDLVDSLLNAGDKLVIVYFFSPGCGGC RALHPKICQLAKNNADVQFLKVNYEE HKSMCYSLNVHVLPFFRFYRGAQGRV | 13 |

TABLE 1-continued

AGHT4 amino acid sequences

| Organism | Paralogs | Database Accession No. (Genbank unless otherwise specified) | Amino Acid Sequence | SEQ ID NO: |
|---|---|---|---|---|
| | | | CSFSCTNATIKKFKNALAKHTPDRSSL EPTKGLEEKELIALAANKDLNLTYAPK SDKPIPAPTKEEIVPEIPQSLSLALRRSM ELAQGSAEKTLVASGR | |
| Sorghum bicolor | SbACHT4-1 | KXG39469.1 | MAAAQAVAKGSVVAPCGNRAAPGLL GRRRGAVAARMAPSAVRIGASWRKT AFTGGRLALGLGTRRSRPASRSSFASP AQMNMNLAIGKSMRWWEKGLQPNM REIESAQDLVDSLTNAGDKLVIVDFFSP GCGGCRALHPKICQFAEQNPDVLFLQV NYEEHKSMCYSLHVHVLPFFRFYRGA QGRLCSFSCTNATIKKFKDALAKHKPD RCSLGPTRGLEESEFLALAANKDLQFT YTKEPELIPRGDAPGEVIAPEPAKLPAA TKPLVRLGSEERSLVSSGR | 14 |
| Sorghum bicolor | SbACHT4-2 | XP_002465837.1 | MAAAQAMAKGSVGQGSLGRRRGAEA ARVGGSWRKSAFLGGRLAVGPRRPRP VSRILVTSPAVQQTNLSFAKAMKWWQ KGLQPNMRAIQTAQDLADSLTNAGDG LVVVDFFSPGCAGCHALHPKICQFAER NPDVQFLQVNYEEHKSMCHSLHVHVF PFFRFYRGAQGRLCSFSCTNATIKKFR DALAKHRADRCSLGPTRGLEESELLAL AANKDLQFTYTKEAELAPSMEDVAEV MTADRPGLPTSTMPLARQGSEDRALV SSGR | 15 |
| Sorghum bicolor | SbACHT4-3 | KXG36972.1 | MAEALCNGVVASPYGGGDVGVAGRA RGAAKAALAESLPVGGYATKSSFSAG RMSVSDRKPRPLSRNLEAAAAPGQMN LSFPKAMRWWEKGLHPNMREIESAQD LADSLLNAGDKLVVVDFFSPGCGGCR ALHPKIAQFAEKNPDVLFLQVNYETHK SMCYSLHVHVLPFFRFYRGAEGRVSSF SCTNATVRIDHLSNFKNQQMNE | 16 |
| Brassica napus (Rapeseed) | BnACHT4-1 | CDY06319.1 | MAEAAISRTNLIFRGACVNQHKHVDD YSVSSPVSFGLRKSFPSLKVKPFNQFQS SRSSSSITAQTTLRIGTPQKWWEKGLK ENMREISSAQELVDSLTNAGDKLVVV DFFSPGCGGCKALHPKICQLAEQNPDV QFLQVNYEEHKSMCYSLGVHVLPFFR FYRGAHGRVCSFSCTNATIKKFRDALA KHSPDRCSLGPTKGLEEKELVALAAN KELNFSYTPRAVPVEEEEAPVPASNPG LPVAHPSMKANDGKTLVSSGR | 17 |
| Brassica napus (Rapeseed) | BnACHT4-2 | XP_013711973.1 | MAEVISKTSLFFRGACVNHHHHADDF SVSPVSFGLKKSFSSLKQKPLRSDFSGK QILQTFNRSFRSSSVTAQSTLRIGTAQK WWEKGLQENMREISSAQELVDSLADA GDKLVVVDFFSPGCGGCKALHPKMCQ LAEQSADVQFLQVNYEEHKSMCYSLG VHVLPFFRFYRGAQGRVCSFSCTNATI KKFRDALAKHSPDRCSLGPTKGLEEKE LVALAANKELNFSYTPKVVPVEKEAAI PTSNPALPVPHPSMSGSEEKTLVSAGR | 18 |
| Brassica napus (Rapeseed) | BnACHT4-3 | XP_013672630.1 | MAEAAISRTNLIFRGACVTHHHHADD YSVSSSPVSFGLRKSFSSLKLKPPRQID TQFQTFTRSSRASSITAQTTLRIGTPQK WWEKGLKENMREISSAQELVDSLTNA GDKLVVVDFFSPGCGGCKALHPKICQL AEQNPDVQFLQVNYEEHKSMCYSLGV HVLPFFRFYRGAHGRVCSFSCTNATIK KFRDALAKHSPDRCSLGPTKGLEEKEL VALAANKELNFSYTPRAVPVEEEEAPV PASKPGLAVPHPSMSANDEKTLVSAGR | 19 |

TABLE 1-continued

AGHT4 amino acid sequences

| Organism | Paralogs | Database Accession No. (Genbank unless otherwise specified) | Amino Acid Sequence | SEQ ID NO: |
|---|---|---|---|---|
| Brassica napus (Rapeseed) | BnACHT4-4 | XP_013716476.1 | MAEAAISRTNLIFRGACVNQHKHVDD YSVSSPVSFGLRKSFPSLKVKPFNQFQS SRSSSSITAQTALRIGTPQRWWEKGLK ENMREISSAQELVDSLTNAGDKLVVV DFFSPGCGGCKALHPKICQLAEQNPDV QFLQVNYEEHKSMCYSLGVHVLPFFR FYRGAHGRVCSFSCTNATIKKFRDALA KHTPDRCSLGPTKGLEEKELVALAAN KELNFSYTPKDVPVEEEAAPVPVSNPG LPVAHPSMKANDGKTLVSSGR | 20 |
| Brassica napus (Rapeseed) | BnACHT4-5 | XP_013641071.1 | MAEVISKTSLFFGGGACVNHHHHHVD DLSVSPVSFGFKKSFSSSLKQKPLRSDF SGKQILETFNRSFRSSSVTAQSTLRIGT AHKWWEKGSQENMREISSAQDLVDSL ADAGDKLVVVDFFSPGCGGCKALHPK MCQLAEQSPDVQFLQVNYEEHKSMCY SLGVHVLPFFRFYRGAQGRVCSFSCTN ATIKKFRDALAKHSPDRCSLGPTKGLE EKELVALAANKELKFSYTPKVVPVEK EVAIPTSNPGLPVPHPSTMSGSEEKTLV SAGR | 21 |
| Ricinus communis (Castor) | RcACHT4 | XP_002525461.1 | MADVLSKTNLVPSSCCNGYKNQKKD GAFVLKRSCSLKVSSRKFNPQAFGSQK ISLISDFYGKRVIVQEKQLKRGNFHQFS IKAQTGLRLKNAPKWWEKGLQPNMK EITSAQDLVDSLMNAGDKLVIVDFFSP GCGGCKALHPKICQFAEMNPDVQFLQ VNYEEHKSMCYSLNVHVLPFFRFYRG AQGRVCSFSCTNATIKKFKDALAKHTP DRCSLGPTKGLEEKELIALASNKDLNF TCTPKPVQPTAPAQEEIIPAALTPAHVN QTLPLPIPLSTTSLMSAQDLGEKTLVTS GR | 22 |
| Phaseolus vulgaris (Bean) | PvACHT4-1 | XP_007161960.1 | MAEVFTKASFVSSLLGSSQRHHRRVST VPDTCTFVSGVGGSPSLKLKSPILRSWS PSSEFQGKQLLFRVNRGKPNRVSSRLR ASTAAQMTLRTGKVQKWWEKGLQPN MKEVTSAQDLVESLLNAGDKLVVVDF FSPGCGGCKALHPKICQLAEMNPDVQF LQVNYEEHKSMCYSLNVHVLPFFRFY RGAHGRLCSFSCTNATIKKFRDALAKH SPDRCSLGPTKGLEEKELLALAANKDL SFTLPKPLQPEHANEGLATAPAPVPSSE SLPLPSLTLNSEVSQERTLTTAGR | 23 |
| Phaseolus vulgaris (Bean) | PvACHT4-2 | XP_007161924.1 | MAEVLTEASLVSSWHGTTQRHHRRVS TVPNSSSFVSGVGRFPSLKLKSQILRSL SSSSEFQGKKLLFHVNRGLANRISSRLG ASTAAQMTLRIGKGQKWWEKGLQPN MNEVTSAQDLVESLLNAGDKLVVVDF FSPGCGGCKALHPKICQLAEMNPDVQF LQVNYEEHKSMCYSLNVHVLPFFRFY RGAHGRLCSFSCTNATIKKFKDALAKH SPDRCSLGPTKGLEEKELLALAANKDL SFIYAPNPLQPEHENEELATAPAPVPSS ESLPLCHLISEVSKEKTLITAGR | 24 |
| Gossypium histrum (Cotton) | GhACHT4-1 | NP_001313760.1 | MAEVLGKGNLFTTCNYSQTKNLEGGT CLVPKKISGFSLERNGFSSLKVKSQALR SDFNGQRMVFLEKKSMNRRRFCQVPI KAQMQSGLIGRIQKWWEKGLQPNMK EVASAQDLVDSLLNAGDKLVVVDFFS PGCGGCKALHPKICQFAEMNPDVQFL QVNYEEHKSMCYSLNVHVLPFFRFYR GAQGRVCSFSCTNATDCKFRDALAKHT PDRCSLSTTKGLEEKELLALSANKDLS FNYTPIPTHGEILIWKQVPSDSTRKLPL SVPTTSAKQRDSEEKTLVGVGR | 25 |

TABLE 1-continued

AGHT4 amino acid sequences

| Organism | Paralogs | Database Accession No. (Genbank unless otherwise specified) | Amino Acid Sequence | SEQ ID NO: |
|---|---|---|---|---|
| Gossypium histrum (Cotton) | GhACHT4-2 | XP_016753539.1 | MAEVLGKSNLFTACNYSQKKHQEGG VPLFSRRISVFCLRKNSFPSLRLEPQAL RSGFNGQRVVFLEKRSLNERRFCRVPI KAQMQTGLIGKTQKWWEKGNQPNM KEVTSAQDLVDSLLNAGDKLVIVDFFS PGCGGCKALHPKICQLAEMNPDVQFL KVNYEEHKSMCYSLNVHVLPFFRFYR GAQGRLCSFSCTNATIKKFKDALAKHS PDRCSLGPTKGLEEKELLALAANKDLS FNYTPKPVHPAPEEIPVLKEVPSGSSFK LKESEEKTLIGVGR | 26 |
| Gossypium histrum (Cotton) | GhACHT4-3 | XP_016672835.1 | MAEVLGKSNLFTACNCSQKKNQEGGV PLFSRRISAFCLRKNSFPSLKLEPQALRS GFNGQRVVVLEKRSLNERRFCRVPIKA QMQTGLIGKTQKWWEKGNQPNMKEV TSAQDLVDSLLNAGDKLVIVDFFSPGC GGCKALHPKICQLAEMNPDVQFLKLN YEEHKSMCYSLNVHVLPFFRFYRGAQ GRLCSFSCTNATIKKFKDALAKHSPDR CSLGPTKGLEEKELLALAANKDLSFNY TPKPVHPAPEEMPVLEEVPSGSSFRPKE SEEKTLVGVGR | 27 |
| Glycine max (Soybean) | GmACHT4-1 | XP_003548763.1 | MAEVLTKASLVSSSWHGVSQRHHHRR VSTVLSNNTCSFRSGVGKFSSLKMNSQ VLRSWSSSSEFQGKKLVFHVNRGLPNR VNSRLRASTGTQMNLRLGKVQKWWE KGLQPNMKEVTSAQDFVDSLLNAGDK LVVVDFFSPGCGGCKALHPKICQFAEM NPDVQFLQVNYEEHKSMCYSLNVHVL PFFRFYRGAHGRLCSFSCTNATIKKFK DALAKHTPDRCSLGPTIGLEEKELEAL AANKDLSFTYSPKPLQPSHENEELATE TASAPALGSGSLPSPSMTLNAVASNER TLTTSGR | 28 |
| Glycine max (Soybean) | GmACHT4-2 | NP_01276128.1 | MKSQVLRSWSSSSEFQGIKLVFHVNRG LPNRVNSRLRASTGAQMSFKLGKVQK WWEKGLQPNMKEVTSAQDFVDSLLS AGDKLWVDFFSPGCGGCKALHPKIC QFAEMNPDVQFLQVNYEEHKSMCYSL NVHVLPFFRFYRGAHGRLCSFSCTNAT IKKFKDALAKHTPDRCSLGPTKGLEEK ELLALAANKDLSFTNSPEPLQPAHADE ELGTEPAPAPGSKSLPSPSMILNSEVSK KRTLTTSGR | 29 |
| Beta vulgaris (Beet) | BvACHT4 | XP_010672407.1 | MADVLTKSSVFSPTISHHHSGSKNFPIK CSVAVSNRGRLVGISSLRSSFGGVRIAI DKNTSFGSKRRNYQSIDAKMGLSIGKA QKWWEKGLQPNMREITSAEDLVDSLL TAGDTLVVVDFFSPGCGGCRALHPKL CQLAEMNPDVQFLQINYEEHKSMCYS LNVHVLPFFRFYRGAEGRVSSFSCTNA TIKKFKDALAKHNPARCSLGPTKGLEE KELLALAANKDLSFTYTPKPVEAEPVP APALEEVSVKADEQVLAQESLPSFNRK PLSSQPSTVSEEKTLATAAR | 30 |
| Musa acuminate (Banana) | MaACHT4-1 | XP_009416338.1 | MAETLAQRTLLLPGGHLSLPPFCGMRS RPSLAAFTLFSRTKVEPLRSSSCDSKFHGRRL GRRLVVGARRGRPSRARLGSGSEQMV LSFKKAIKWWQKGLQPNMVEIESAEH LVDSLLNAGDKLVIVDFFSPGCGGCRA LHPKICQFAESNQNVLFLQINYEQHKS MCYSLGVHVLPFFRFYRGAHGRLCSFS CTNATKKFKDALAKHITDRCSLGPAR GLEESELLALAANKDLSFNYTSKPVPV PEEIPERIPTSPKLPLHAVRRPAQESEDK ALAAAGR | 31 |

TABLE 1-continued

AGHT4 amino acid sequences

| Organism | Paralogs | Database Accession No. (Genbank unless otherwise specified) | Amino Acid Sequence | SEQ ID NO: |
|---|---|---|---|---|
| Musa acuminate (Banana) | MaACHT4-2 | XP_009406843.1 | MADALAQMTLLSPHGHRSLSRSSDRR NRLVCASKDDLLRSSSSCNSQFHGRRL VIGAQRERPLRGNRGSSSVQMTLSFKK ASKWWEKGLHPNMKDIKSAEDLVDSL SNAGDKLVIVDFFSPGCAGCRALHPKI CQFAELNPDVQFLQLNHEEHKSMCYS LNVHVLPFFRFYRGAHGRLCSFSCTNA TIKKFKDALAKHITERCSLGPAKGLEE TELLALAANKDLSFTYTRTPVPVPDEL AEKAPFNPNLPVHAAARLTLESEDKAF AAAGR | 32 |
| Capsicum annuum (Sweet and Chili Peppers) | CaACHT4 | XP_016552829.1 | MAKLMNKGFVFPSSSDCGHHRPHGISS FPNKSVNLSCLPSTCLLRSYFYGRRLVI NEALPKRNAHVAITVQMSMGIRKVQK WWEKGVQPNMKEVNSAQGLVDSLLS AGDKLVVVDFFSPGCGGCKALHPKLC QLAEMNPDVQFLQNYEEHKSMCYSL NVHLLPFFRFYRGAEGRVCSFSCTNAT IKKFKDALAKYGTDRCTFGPPKGLEEK ELLALAANKELSFNYIPKTEEEPVLVAS QEEVEDRTPNKESPLPLPLPLPISSTSSL KPKQDTEKEAYATSGR | 33 |
| Cicer arietinum (Chick pea) | CaACHT4 | XP_004493141.1 | MAEILTKTSLVSSWHGNRKQQHRRLS MVPNKTCSFNTCVGSFPSLKLKSQFLR SSSFSSEFYGKNTIFRVNRSIPNRINSQF SVSAAPKMTLRIGKIQKWWEKGLQPN MREVTSAQDLVDSLLNAGDKLVIVDF FSPGCQGCRALHPKICQMAEMNPDVE FLQVNYEEHKSMCYSLNVHVLPFFRF YRGAHGRLCSFSCTNATIKKFKDALAK HTPDRCSLEPTKGLEEKELIALSENKDL NFTYTPKPLQPVHTPANEELATTKASP VCSEPLPLPSLTSNSDEVLKERTLTRAGR | 34 |
| Solanum lycopersicum (Tomato) | SlACHT4-1 | XP_004252003.1; Solyc12g019740.1 | MTKLMSKGFIFPSSSDCGEIYDRLRLN LHGICSFPNKSVNLSCLPSLKLKSSSCLP RTDFYGRRLVINEGLSNFNRRVADITA QMSVGIKKAQKWWEKGVQPNMKEV NSAQELVDSLLSAGDKLVVVDFFSPGC GGCKALHPKLCQLAEMNPDVQFLQVN YEEHKSMCYSLNVHVLPFFRFYRGAE GRVCSFSCTNAT1KKFRDALAKYGTDR CTIGSPKGLEEKELLALAANKDLSFNY TPKTEEEP1LVTSQKEVRDRTTPNIESPL PLPLPLPITSTSSQTAKRDTEKEAYATS GR | 35 |
| Solanum lycopersicum (Tomato) | SlACHT4-2 | XP_004249307.1; Solyc10g080730.1 | MEKLLNKAWLPSILNSSGIYHSNQHAI CVFPVKFNRRYHKSAVATAQMSIGIKR APKWWEKGLQPNMKEVTGAQDLVDT LLNGGDKLVVVDFLSPGCGGCKALHP KICQLAEMNPDVQFLHVNYEEHKSMC YSLNVHVLPFFRFYRGAEGRLCSFSCT NATIKKFKDALTKYGADCCSLGPVKG LEEKELLALAANKDLSFAYTPKTEEPV PLALEEVKVIKTSRQSSSHPNTFSPLPLP LPLASTLHTAKQDSKS | 36 |
| Elaeis guineensis (African oilpalm) | EgACHT4-1 | XP_010938119.1 | MMEVLSQSGVMSPCGHRWVVRSCKE RSPSFVGFPRSSSRTIESLMSSSRNSGFH GRRLSIGAWRVNAVKGNFSSTPVQMS LCVGKALKWWEKELQPNMKEIESAQ DLVDSLLNAGDKLVIVDFFSPGCGGCK ALHPKICQFAKLNPDVLFLQVNYEKH KSMCYSLNVHVLPFFRFYRGAHGRLC SFSCTNATDCKFKDALAKHTTDRCSLG PTKGLEESELMALAANKDLSFSYTRKP VPVPSPDEAAEEVVLSPKLPVSSTPRVI QDSEEKALVAAGR | 37 |

TABLE 1-continued

AGHT4 amino acid sequences

| Organism | Paralogs | Database Accession No. (Genbank unless otherwise specified) | Amino Acid Sequence | SEQ ID NO: |
|---|---|---|---|---|
| Elaeis guineensis (African oilpalm) | EgACHT4-2 | XP_010921294.1 | MAEVLGRSGVFSLRGHRSVAPSCQKR SPSFLGFPLSSSRPIGPPRSSSRRFVIGTR RGRSKGNSSSSRVQMSLGVGKSLKW WEKGVQPNMKEIGSAQDLVDSLLNEG DKLVIVDFFSPGCGGCKALHPKICRIAE MNPHVLFLQINYEKHKSMCYSLHVHV LPFFRFYRGAHGRLCSFSCTNATIKKFK DALAKHTTDRCSLGPTKGLEESELVAL AANKDLSFNYTRKPVPVLTPDEAAEK VPLSPKLPVSSAPRVIKDSEDKALVAA GT | 38 |
| Setaria italic (Foxtail millet) | SiACHT4-1 | XP_004984516.2 | MAAAQAVAKGSVVSPCGSRAAPGLLS RRRGAVATRMAPSAVRIGGSWRKTAF LGGRLAVGPRRSRSASRTLVASPVQM NMNLA1GKSMRWWEKGLQPNMREIES AQDLVDSLTNAGDRLVIVDFFSPGCGG CRALHPKICQFAEQNPDVLFLQVNHEE HKSMCYSLHVHVLPFFRFYRGAQGRL CSFSCTNATIKKFKDALAKHKPDRCSI GPTRGLEESELLALAANKDLQFTYTKK PELIPSGDAAAEVIAPEPTKLPAATKPS VKIGSEERSXWSHQEDEMNDL | 39 |
| Setaria italic (Foxtail millet) | SiACHT4-2 | XP_004985651.1 | MAAAQAMAKMSVGSPACNRAAGSLC RWRGAVAVRLGGSWSWRKSPFLGGR MAVGPRRSRPVSRNPVASPVQMNLSF GKTMKWWEKGLQPNMRAIHTAQELV DSLINAGDGLVIVDFFSPGCAGCHALH PKICQFAERNPDVQFLQVNFEEHKSMC HSLHVHVFPFFRFYRGAQGRLCSFSCT NATIKKFKDALAKHKPDRCSLGPIKGL EESELLALAANRDLQFTYTKEQDLAPS MEDGAEVITHDHPRLPAAAKPLVRQG SEDRAVVSSGR | 40 |
| Setaria italic (Foxtail millet) | SiACHT4-3 | XP_004958724.1 | MAEALCNGVVPSPCGGDVGVAGRVS GAAAALAESVPIGGYRTKSSFSAGRM AMTDRKMRPLPRSIEAAPGQMNLSFP KAMRWWEKGLQPNMREIESAQDLAD SLLNAGDKLVVVDFFSPGCGGCRALH AKIAQFAEKNPDVMFLQVNYETHKSM CYSLHVHVLPFFRFYRGAEGRVSSFSC TNATIKKFKDALAKHGPDRCSLGPAR GLEESELMALAANKDLQFTYEKPGLV PLAEAIAKEAAAPGGPWFPLPASATQF LTQGSENSLLSSGR | 41 |
| Chlamydomonas reinhardiii (Single-cell green alga) | CrACHT4 | XP_001697443.1 | MASILNRAGSRSLVFETKQSLRSIPGSL LSLRSVALKPFRTTICAAGALLTARRST SGLGRANGWCQAGRSTGEWWKKDN PPNMRDINSIQELVDALSDAGDRLVIV EFYAQWCNACRALFPKICKIMAENPD VLFLKVNFDDNRDACRTLSVKVLPYF HFYRGAEGRVAAFSATISKLQLFKDAV ETYSAAFCSLEPAPGLAEFPDLIAHPEL HPEEAAEAARRARLASTESEEELHPLA DTPTVVG | 42 |
| Chlorella (Single-cell green alga) | CvACHT4 | XP_005851922.1, partial | WWTKSAPPNWHIKSVQHLVDEMVR AERLAGAGERLVIMDVFAPWCAACKA LYPKLMKLMEERPDVLLLTVNFDENK TVVKAMGVKVLPYFMFYRGKEGKLQ EFSASNKRFHLIQEAIERHSTDRCFLDS TDEEPVLAEFPTVVPAKGISGSLDEPAG RAAGKAVGQPQPVA | 43 |

In another embodiment, the amino acid sequence of ACHT4 is a homolog of any one of the sequences listed in Table 1. In another embodiment, the amino acid sequence of ACHT4 is a paralog of any one of the sequences listed in Table 1. In another embodiment, the amino acid sequence of ACHT4 is a fragment of any one of the sequences listed in Table 1. In another embodiment, the amino acid sequence of ACHT4 is a variant of any one of the sequences listed in Table 1. In another embodiment, the amino acid sequence of ACHT4 comprises any one of the sequences listed in Table 1. In another embodiment, the amino acid sequence of ACHT4 consists essentially of any one of the sequences listed in Table 1. In another embodiment, the amino acid sequence of ACHT4 consists of any one of the sequences listed in Table 1. In another embodiment, the amino acid sequence of ACHT4 corresponds to any one of the sequences listed in Table 1.

In another embodiment, the amino acid sequence of ACHT4 is a homolog of any one of SEQ ID NOs: 1-43. In another embodiment, the amino acid sequence of ACHT4 is a paralog of any one of SEQ ID NOs: 1-43. In another embodiment, the amino acid sequence of ACHT4 is a fragment of any one of SEQ ID NOs: 1-43. In another embodiment, the amino acid sequence of ACHT4 is a variant of any one of SEQ ID NOs: 1-43. In another embodiment, the amino acid sequence of ACHT4 comprises any one of SEQ ID NOs: 1-43. In another embodiment, the amino acid sequence of ACHT4 consists essentially of any one of SEQ ID NOs: 1-43. In another embodiment, the amino acid sequence of ACHT4 consists of any one of SEQ ID NOs: 1-43. In another embodiment, the amino acid sequence of ACHT4 corresponds to any one of SEQ ID NOs: 1-43.

In one embodiment, there is one paralog of ACHT4 in a species. In another embodiment, there are two paralogs of ACHT4 in a species. In another embodiment, there are three paralogs of ACHT4 in a species. In another embodiment, there are four paralogs of ACHT4 in a species. In another embodiment, there are five paralogs of ACHT4 in a species. In another embodiment, there are six paralogs of ACHT4 in a species. In another embodiment, there are seven or more paralogs of ACHT4 in a species.

In one embodiment, a "corresponding sequence" is an amino acid (or nucleic acid) sequence from a first species for which there is a similar or equivalent sequence in a second species, which may be inferred by sequence alignment, as is well known in the art.

TABLE 2

ACHT4 nucleic acid sequences

| Organism | Paralogs | Database Accession No. | Nucleic Acid Sequence | SEQ ID NO: |
|---|---|---|---|---|
| Arabiaiopsis thaliana | AtACHT4 | NM_100730 | ATGACGGAAGTGATTAGCAAAACGAGTTTGTT CTTAGGAGCTTGTGGTAATCATCACCGTGTTGA TGATFTCTCTTTCTCTCCGGTGAGTTTTGGTGG GTTTGGTTTGAAAAAGAGTTTCTCTTGTCTGAA GCTTAAGAGTCAGAAGCCTCTTAGAAGTGTAT TTTACGGAAAACAGATCGTTTTCGGAGATTCTC AAGACGAGAGCTTTCAGAAGATCATCAGCTATC ACAGCTCAGACAACTTTGAGGATTGGGACAGC TCAGAAGTGGTGGGAGAAAGTCTGAAAGAT AACATGAGAGAGATCTCTTCAGCTCAAGAGCT CGTIGATTCTCYFACTAACGCTGGTGATAAGCT TGTTGTTGTTGATTTCTTCTCACCTGGCTGTGG TGGCTGCAAGGCTCTCCATCCTAAGATAGTC AGTTTGCAGAGATGAACCCGGATGTGCAGTTT CTTCAGGTGAATTACGAGGAGCATAAGTCCAT GTGTFATAGTCTTGGTGTCCATGTFCTCCCTTTT TTCCGATTCTACCGTGGCTCTCAGGGTCGTGTT TGCAGCTTTAGCTGTACCAATGCCACGATCAA GAAATTCAGAGATGCCTTGGCAAAGCATGGTC CAGATAGGTGCAGCCTCGGACCGACCAAAGGC CTTGAAGAGAAAGAGCTTGTGGCACTTGCAGC CAACAAAGAACTCAACTTTACTTACACACCAA AGCCTGTACCAGTTGAGAAAGAAGCAGCCACT CCTGATTCAAACCCAAGTCTCCCTGTTCCTCTT CCTTCGATGAGCTCCAATGACGAAAAAACATT GGTCTCCGCAGGGAGATGA | 44 |
| Solarium tuberosum (Potato) | StACHT4-1 | XM_006347961.2; PGSC0003DMT400048452 | ATGATGAAATITGATGAGCAAAGGTTTTATGTT TCCTTCGTCTTCTGATTGTGGTGAAATTTATCA TCATCGTCCTCTITAATCTACCTGGGATCTGTTC TTTTCCCAATAAATCGGTCAATCTTTCTTGTCT TCCTTCGTTGAACCTTTCATCTTCTTGTTTGCCA AGAACCGATTTTTATGGTCTAGATTTGGTTATA AATGAAGGCGTATCCAAGTTCAACCGAAGAAA TTCCCAAGTTGTTGATATCACTGCTCAGATGAG TATTGGAATCAGGAAAGCACAGAAATGGTGGG AGAAAGGGGTTCAACCTAACATGAAAGAGGT GAACAGTGCACAAGAACTTGTTGACTCTCTTTT GAGTGCAGGGGACAAATTAGTTGTTGTTGATT TCTTTTCCCCTGGCTGTGGAGGTTGTAAAGCTC TTCACCCCAAGTTGTGTCAGCTGGCAGAGATG AATCCAGATGTGCATTTTTTACAGGTGAACTAT GAGGAACACAAGTCGATGTGTTACTCTCTTAA TGTACATUTICTCCCATTTTFCCGTTTCTATAG | 45 |

TABLE 2-continued

ACHT4 nucleic acid sequences

| Organism | Paralogs | Database Accession No. | Nucleic Acid Sequence | SEQ ID NO: |
|---|---|---|---|---|
| | | | AGGAGCTGAAGGCCGTGTTTGCAGCTTTAGCT GTACCAATGCCACGATCAAAAAATTCAAAGAT GCACTGGCGAAGTATGGTACAGATCGTTGCAC CCTTGGGCCGCCAAAAGGGCTGGAGGAGAAA GAGCTACTTGCACTGGCAGCTAACAAGGATCT CTCCTTTAATTACACTCCAAAAACAGAAGAAG CACCCGTCCTTGTTACCTCACAAAAGGAAGTT CAGGATACAACTCCTCCAAATATAGAGTCCCC TCTACCACTTCCTCTTCCTCTCCCATTGCGTC AACTAGCTCACAGACGGCCAAACGGGATACAG AGAAAGAAGCATATGCTACTTCTGGTAGATGA | |
| Solanum tuberosum (Potato) | StACHT4-2 | XM_006351306.2; PGSC0003DMT400060823 | ATGATTCAATAGAAGAAATCACAAATCA GCAGCTGCAACTGCTCAGATGAGCATAGGT ATCAGGAAAGCTCCTAAATGGTGGGAGAAA GGACTTCAACCGAATATGAAAGAGGTGATG GGTGCTAAGACCTCGCTGACACCCTTCTA AACGCTGGGGATAAACTAGTCGTTGTCGAT TTCCTTTCCCCTGGCTGTGGAGGCTGCAAA GCCCTTCATCCAAAGATATGTCAGTTAGCA GAGATGAATCCGGATGTGCAGTTTTTACAT GTGAACTATGAGGAACACAAGTCAATGTGT TACTCGCTGAACGTACATGTTCTCCCATTT TTTCGTTTCTATAGAGGTGCTGAAGGTCGT CTTTGTAGCTTTAGTTGCACCAATGCCACG ATAAAAAAATTCAAAGATGCATTGACAAAG TATGGTGCAGATTGTTGCAGCCTCGAACCA GTTAAAGGGCTCGAGGAGAAAGAGCTACTT GCCCTAGCAGCTAATAAGGACCTCTCTTTT GCTTACACACCAAAAACAGAAGAACCAATG CCTGTTGCCTTACAAGATGCTAAGGTGATA AAAACAAGCAGAACATCTTCATCTTGTCCA AATACATTCTCCCTGTTACCACTTCCCCTT CCTCTTCCTCTAGCATCAACTTCACATAAG GCCAAACAGGACTCGAAGAGTGAAGTTTTT TAA | 46 |
| Zea mays (Maize) | ZmACHT4-1 | NM_001279773.1 | ATGGCGGCAGCGCAGGCGATCTCGAAGGGGA GCGTGGTGTCYCCGTGCGGCAATCGAGCGGCG CCGGGCCTCCTTGCCAGGCGGAGGGGTGCCGT GGCGGCGCGGGTGGCGCCGTCAGCGGCGCGG ATCGGGGGCTTCTGGAGGAAGAACGCGTTTCC TGGCGGGAGGCTAACCCTGAGGACGAGGAGA TCCAGGGCCGCGTCACCGGCGCAGATGAACAT GAACCTTGCGCTTGGGAAATCGATGAGGTGGT GGGAGAAGGGGTTGCAGCCCAACATGCGTGA GATCGAGTCCGCCCAAGACCTTGTCGATGCTTT GACCAACGCCGGCGACAGGCTCGTCGTCGTCG ACTTCTTCTCTCCTGGCTGCGGCGGCTGCCGTG CTTTTCACCCCAAGATTTGTCAATTTGCGGAGC AGAATCCAGATGTGCTGTTCTTGCAAGTGAAC TACGAGGAGCACAAGTCTATGTGCCACAGCCT TCATGTCCATGTCCTACCCTTGTTCAGATTCTA CAGGGGAGCACAGGGACGACTCTGTAGCTTCA GTTGTACAAACACAACTATTAAGAAGTTCAGG GATGCACTCGCGAAGCACAAGCCAGATAGATG TAGCCTTGGCCCAACCAGGGGGCTAGAGGAAT CTGAGTTATTAGCCTTGGCGGCAAACAAGGAC CTGCAGTTCACCTACGCGAAGGAGGAACCAGA ACTGATCCCCAGGGGAGATGCFCCMGGGAGG TCGTTGCTCCTGAGCCFGCAAAGCTTCCTGCGG CFCCAAAGCCTTTGGTCAGGCTGGGGTCCGAG GAGAGGTCACTGGTCTCGTCAGGAAGATGA | 47 |
| Zea mays (Maize) | ZmACHT4-2 | BT084302.1 | ATGGCTGACGCGTTGTGCAACGGCGTCGTGGC GTCCCCGTGCGGCCGGGACGTCGCCGGCCGGG CCAGGGGCGCCGCCAGGGCCGCGCTCGCGGAG TCCCTGCAGGTCGCCGGGCACGCCAGCAAGAC CTCCTTCTCCGCCGGGAGGATGTCGGTCAAGG ACAGCAAGCCGAGGCCCCTGTCGCGTAGCCTC GAGGCCGCCGCGCCAGGACAGATGAACCTGTC GTTCCCCAAAGCCATGCGGTGGTGGAAGAAGG GGCTGCACCCCAACATGCGCGAGGTCGAGTCC GCGCAGGACCTGGCCGACTCGCTGCTCAGCGC | 48 |

TABLE 2-continued

ACHT4 nucleic acid sequences

| Organism | Paralogs | Database Accession No. | Nucleic Acid Sequence | SEQ ID NO: |
|---|---|---|---|---|
| | | | CGGCGACAAGCTCGTGGTCGTCGACTTCTTCTC CCCAGGCTGCGGCGGCTGCCGCGCCCFCCACC CCAAGATCGCCCAGTTCGCCGAGAA.GAACCCG GGCCTTGCACTTTCTTGCAGGTGAACTACGAGAC GCACAAGTCCATGTGCTACAGCCFCCGCGTCC ACGTCCTCCCITTCTTCAGGTTCTACCEIGGGAG CCGAGGGCCGGGTCAGCAGCTFCAGCTGCACC AACGCAACGATCAACAAGTFCAAGGACGCGCT CGCCAAGCACGGGGCTGAGAGGTGTAGCCTCG GGCCTGCGCGGGGGCTGGACGAGTCGGAGCTC ATGGCCTTGGCFGAGAACAGGGACCTGCACTF CACCTACGACAAGCCGGGCGGCCTCGTCCCCC TCGCCGAAGCTATTGCCAAGGAGGCTGCCGCA CCGGGAGGCCCGTGGCTTCCTCTGCCTGCGTCC CTGCTCGGCCAGGGATCCGACAACTCATTGCT GCCCTCTGGAAGATAG | |
| Zea mays (Maize) | ZmACHT4-3 | BT069464.1 | ATGGCGGCGGCGCAGGTGGTCGCGAAGGGGAGCGTGG TGTCGCCCTGCGGCAATCGAGCGGTGCCGGGCCTCTT GGGCAGGCGGAGGGATGCCGTGGCGGCGCAGATGACG CCGTCGGCGGTGCGGATCGGGGGCTCCTGGAGGAAGA ACGCGTTTCCTGGCGTGAGGCTAGCCTTGGGGACGAG GAGATCCAGGCCCGCGTCCCGGAGTTTCTCCGCCTCG CCGGTGCAGATGAACATGAACCTTGCGATTGGGAAAT CAATGAGGTGGTGGGAGAAGGGGTTGCAGCCCAACAT GCGTGAGATCGAGTCCGCCCAAGACCTTGTAGATTCC TTAACCAACGCCGGCGAGAGGCTCGTCGTCGTCGACT TCTTCTCCCCTGGCTGCGGCGGCTGCCGTGCTCTTCA CCCGAAGATTTGCCAATTTGCGGAGCGGAACCCTGAT GTGCTGTTCTTGCAAGTGAACTACGAGGAGCACAAGT CTATGTGCTACAGCCTTCGTGTCCATGTGCTACCCTT CTTCAGATTCTACAGAGGAGCACAGGGACGACTCTGC AGCTTCAGCTGTACAAACGCAACTGTAAGATCATGTC CATGTTTCTTCGTTCGTATGATTATTGGTATGTCCT CAATAACATGCAACATATCCAAAATGACCTTTATTGA | 49 |
| Oryza saliva (Rice) | OsACHT4-1 | XM_015776801.1 | ATGGCGGCGACGGCGGCGCAGGCGGTGGCGG TGAAGGGGAGCCITGGCGGTGCCGCCGTGCGGG AGCCGCGGCCGGCGGAGGGGCGCCGTGGCGTC GGTGCGCATGGCGGCGGCGGCGGCGACGTCGG CGTTGCGGATCGGCAGGAGGAGCCCCTTCCTC GGCCCGGAGGCTGGCGGTTGGGCCGAGGAGATC CAGGCCCGTGCCCCGGAATCTCGTCGCGCCGG TGCAGATGAATCTCGCGTTTGCGAAAGCCACG AAGTGGTGGGAGAAGGGATTGCAGCCCAACAT GCGGGAGGTCGAGTCCGCGCAAGACCTCGTCG ACTCCTTGACCAACGCCGGCGACAATCTCGTC ATCGTCGACTTCTTCTCCCCTGGCTGCGGCGGC TGCCGTGCCCTCCACCCCAAGATTTGCCAGATT GCAGAGCAGAATCCGGACGTGCTGTTCTTGCA GGTGAACTATGAGGAGCACAAGTCTATGTGCT ACAGCCTCCATGTTCATGTTCTTCCTTTCTTCA GGTTCTACAGGGGAGCTCAGGGCCGGCTCTGC AGCTTCAGCTGTACTAACGCAACTATTAAGAA GTTCAGGGATGCGCTTGCTAAGCATAAACCAG ATAGATGCAGCCTTGGCCCAACTAGGGGGCTC GAGGAGTCGGAGCTATTGGCGCTGGCTGCGAA CAAGGATCTGCAGTTCAACTACACCAAGAAAC CAGAACTGGTTCCTAGCGGAGATGCCGCAGCT GCCCAGGAATTGGATCGTGGAAGCACAAAGCT TTCTCCACCCGCAAAACCATTGGTCAAGCAGG GCTCTGAAGAGAGGTCCTTGGTCTCATCAGGC AGATGA | 50 |
| Oryza saliva (Rice) | OsACHT4-2 | XM_015791237.1 | ATGGCTGAGGCACTGTGCAGCGGCAGCGTCGC GTCCCCGTGCGGGGAGGTGGGTGTGGGGTTCG CCGCCGGCCTTGTGAGGGGCGCCGCGGCGGCG GCGGCGCTCGCGGAGTCTGTGCCGATTGGTGG GTACAGCAGCAAGAGCACGTTCCCGAGTGGGA GGGTGGCGCTCACGGAGAGGAAGGCGAGGCC CCTGCCACGGAATCTCGAA.GCGGCGCATGGGC AGATGAACCTGACGATTGGGAAGGCCATGAGG TGGTGGGAGAAGTGCCTGCAGCCCAACATGAG GGAGATCGAGTCGGCGCAAGACCTCGCCGACT | 51 |

TABLE 2-continued

ACHT4 nucleic acid sequences

| Organism | Paralogs | Database Accession No. | Nucleic Acid Sequence | SEQ ID NO: |
|---|---|---|---|---|
| | | | CCCTCCTCAACGCCGGCGACAAGCTCGTCGTC GTCGACTTCTTCTCCCCGGGCTGCGGTGGCTGC CGCGCCCTACACCCCAAGATTGCTCAACTAGC CGAGAAGAACCCGGAGGTGCTGITCTTGCAAG TGAACTACGAGAAGCACAAGTCAATGTGCTAC AGCCTCCATGTTCATGTTCTGCCATTCTTCAGG TTCTACAGGGGAGCTCAGGGCCGTGTCAGCAG CTTCAGCTGCACANACGCAACTATCAAGAAGT TCAAGGATGCACTTGCCAAGCATGGTCCGGAC AGGTGTGGCCTCGGCCCGGCGAAGGGGCTCGA GGAGTCGGAGCTCATGGCGTTGGCC.ATAAACA GGGACCTGAACTTCACCTACACACCAAACCAA GACCTTGTCCCAATTGCAGACGCCCTCCTGAA GGAAGCTGCTGCACCTGGAGGTCCATGGCTGC CATTGCCCGCAACGGCGACGCAGCTGTTCATT CAGGGATCTGAGAATTCGCTGTTGTCATCTGG AAGATAG | |
| Horareum vulgare (Barley) | HvACHT4-1 | AK171865.1 | ATGGCGACGGCGCAGGCGGTGGCCAAGGGGA CCGTGGTCTCTCCGTGCGGCACCCGGGCCGCA GGATTTGGAGCCCGGCGGCGGGGCGCCGTGGC GGCCCGCATGTCGCCCTGCGCGCCGGCGGCGG TGCGGATCGGCAGGAAAAGCCCGTTTCTTGGC GCTAGGCTCACGGTCGGTCCCAGGAGATCCAA GCTCGTTCCCCGGAATCTTGTCTCCTCACCGGT GCAGATGAACCTTGCGTTTGCGAAATCCACCA AGTGGTGGGAAAAGGGTCTGAAGCCCAACATG AGGGAGATCGAGTCCGCCCAGGACCTCGTCGA CTCGTTGGCTAACGCCGGCGACAGGCTCGTCG TTGTTGACTTCTTCTCCCCTGGCTGCGGCGGCT GCCGTGCCCTCCACCCAAAGATTTGCCAGTTTG GGGAGCAGAACCCAGATGTGCTGTTCTTGCAA GTGAACTACGAGGAACACAAGTCCATGTGCTA CAGCCTCCATGTCCATGTGCTGCCCTTCTTCAG GTTCTACAGGGGAGCCCAGGGCCGCCTCTGCA GCTTCAGCTGTACTAACGCAACCATAAAGAAG TTCAGGGATGCGCTTGCCAAGCATAATCCTGA TAGGTGTAGCATTGGTCCAACCAGGGGCCTCG AGGAGTCTGAGCTGCTGGCTTTGGCTGCGAAC AAGGACCTGCAGTTCACATACACCiAAGCAGCC AGAACCAGTTCCGAGTGGTGATTCCGAGTTCA TTGCTCCTGGGAGCCCAAGGCTTCCTCCACCTG CAAAACCATTGGTTCGGCAGGGTTCCGGAGAG AGGACCTTGGTCTCATCAGGAAGATGA | 52 |
| Horareum vulgare (Barley) | HvACHT4-2 | AK376663.1 | ATGGCCAACGCGCTTTACGGCGGCGGCGTGGC GGCGCCGTGCGGTGACTTGGGCGCCGCGGCCG CGCTCGCGGAGTCTTTGCCGATGGGCGGCGGG TACCGCGCGAGGAGCTCCTTCCCCGCCGGGAG GGTGGCGCTGGCGGAGAGGCCCCTGCCCCGGA GCCTCCAGGTGGCGGCCGCTGCTGGACAGATG AACGGGAACCTGACGATTGGCAAGGCCATGAG GTGGTGGGAGAAGGGGACGCAGCCCAACATG AGGGAGGTCGAGTCCGCGCAAGACCTCGCCGA CTCCCTGCTCAACGCCGGCGACAAGCTCGTCG TCGTCGACTTCTTCTCCCCCGGCTGCGGTGGCT GCCGCGCGCTCCACCCCAAGATTGCGCAGTTC GCCGAGCGTAATCCGGACGTGCTGTTCCTGCA AGTCAACTACGAGAAGCACAAGTCCATGTGCT ACAGCCTCCATGTCCATGTCCTCCCTTTCTTCA GGTTCTACAGGGGAGCTCAGGGCAGGGTCAGC AGCTTCAGCTGCACCAACGCAACCATAAAGAA GTTCAAGGACGCCCTCGCAAAGCACTCGCCGG ACAGGTGCAGCCTCGGCCGGCGCGGGGGCTT GAGAAGGCGGAGCTCTTGGCTCTGGCTGAGAA CAGGGACCMGAATTCACCTACAGCGAGAAGC CGACACTTGTGCCGATCGCAGAGGCCATCAGG ATGGAAGCMCCTCAATCGGAGGCCCATGGCT GCCATTGCCTCCGGCCGCGACGCAGCCGTITC CTCTGGGATCCGAGAATGGCTCGCTCATCCCCT CTGGAAGATAG | 53 |

TABLE 2-continued

ACHT4 nucleic acid sequences

| Organism | Paralogs | Database Accession No. | Nucleic Acid Sequence | SEQ ID NO: |
|---|---|---|---|---|
| Triticum aestivum (Wheat) | TaACHT4 | AK335384.1 | ATGGCCAGCGCGCTATGCGGCGGCGGCAGCGG CAGCGTGGCGGCGCCGTGCGGGGACTTGGGCG CCGCGGCGGCGCTCGCGGAGTCTTTGCCGATG GGCGCCGGGTACCGCGCCAAGAGCTCCTTCCC CGCCGGGAGGGTGGCGCTGGCGGACAGGCCCC TGCGCCGGGGCCTCCAAGTGGCGGCGGCTGCT GGACAGATGAACGGGAACCTGACGATTGGCA AGGCCATGAGGTGGTGGGAGAAGGTGACGCA CCCCAATATGAGGGAGGTCGAGTCCGCGCAAG ACCTCGCCGACTCCCTGCTCAACGCCGGCGAC AAGCTCGTCGTCGTCGACTTCTTCTCCCCCGGC TGCGGTGGCTGCCGCGCTCTCCACCCCAAGAT TGCGCAGTTCGCTGAGCGGAATCCGGACGTGC TGTTCCTGCAAGTCAACTACGAGAAGCACAAG TCCATGTGCTACAGCCTCCATGTCCATGTCCTC CCTFFCTTCAGGTTCTACAGGGGAGCCCAGGG CAGGGTCAGCAGCTTCAGCTGCACAAATGCAA CCATCAAGAAGTTCAAGGACGCCCTCGCAAAG CACTCGCCGGACAGGTGCAGCCTCGGCCCGGC GCGGGGGCTCGAGGAGGCGGAGCTCTTGGCTC TGGCGGCAAAGAGGGACCTGGAATTCACCTAC AACGAGAAGCCGACGCTGGTGCCGATCGCCGA GGCTATCCAGATGGAAGCTGCCTCCATTGGCG GCCCATGGATGCCATTGCCCGCGGCCGCGACG CAGCCGCTCACTCTGGGATCTGAGAATGGCTC GCTGATCCCCTCCGGAAGATAG | 54 |
| Manihot esculenta (Cassava) | MeACHT4-1 | Manes. 08 G148200.1 Downloaded From Phytozome | AIGGCTGATGTTTTGAGCAATACCAATCTGGTT TCTTCTTCTCTTCATCTTTTACTGGTCACC GAAACGAGCAGAAAAATAGCTCTTGCAGGCTA AAAGGGTTCCCCCGAAAAGTGAATCGTCAGAC TTTGAGATTGAAAGCGACATCGCTTGGCAGTG ATTTTCATGGAAAGAGGGTTGTTCTTCAAGAC AATCAAGGCAAACCCAAGAGAGGGATTTATCT TCAAATGTCAATAAGGCTCAGCATACTGGCC TTAGACTCAAGAGTGCTCCAAAATGGTGGGAA AAAGGATTGCAACCCAACATGAGGGAGGTGA CCTCTGCTCAAGACTTTGTGGACTCCCTCTTGA ACGCTGGAGATAAACTTGTCATTGTTGATTTCT TCTCCCCTGGTTGTGGTGGCTGCAAGGCTCTCC ATCCCAAGATATGTCAGTTTGCAGAGATGAAC CCAGATGTGCTGTTCCTTCATGTGAATTATGAG GAACATAAATCCATGTGTTTATAGCCTCAATAT CCATGTGCTTCCCTTCTTCAGGTTTTATCGAGG GGCGCAAGGCCGGTTATGCAGCTTTAGCTGCA CTAATGCTACGATAAAAAAATTCAGAGATGCA CTGGCCAAGCACTCTCCAGACCGGTGCAGTCT CGGGCCAACAAAAGGGCTGGAGGAGAAAGAG CTTATTGCATTGGCTTCCAACAAAGATCTCAAC TTCAAATATGCACAGAAACCAGATCTGCCAAC GCCAATTCCTGCCAAGGAAGAGAGAGTGCCAG TAGTATCCCATCTCATCCAAATCCAGCTCTAC CTCTACCTCTTCCTCTTCCCACAGCAAGTCCAA AATCTGGACAAGGCTCAGAGGAGAAAACGTTG GTCGGATCAGGGAGATGA | 55 |
| Manihot esculenta (Cassava) | MeACHT4-2 | Manes.09G143500.1 Downloaded from Phytozome | ATGGCCGCTGTTTCTAGCAACACCAATCTTGTT TCTTCTTCTTGTTCTTCATCCTTTAGTTCTTCGC AAAACCGCCCCGAATACCGCTCTTCCAGGCTC AGAGTGTTCCCTCAGGAATTGAATCATCAGGC TTTGAGATTACAAACTACGTCGCTTGGCAGTG ATTTTCATGGAAAGAGGGTTGTTCTTCAAGAA AAACCAAAATGCAAACAAGGGATTTCCGTTCA AAGCTCAATTAAGGCTCAGCAGACTGGCCTTA GACTCAAGAATGCTAAAAATTGGTGGGAGGAG GAGTTGCAACCCAACATGAGGGAGGTGATCTC TGCTCAAGATCTTGTGGACTCCCTCCTTAATGC TGGCGATAAGCTTTCTTCATTGTTTATTTCTTCTC CCCTGGCTGTGGTGGCTGTAGGGCTCTCCATCC CAAGATATGTCAATTGGCAAAGAACAATGCAG ATGTGCAGTTTCTTAAAGTGAACTATGAGGAG CACAAATCCATGTGTTATAGCCTCAATGTTCAT GTCCTTCCATTCTTCAGGTTTTACAGAGGGGCT CAAGGCCGAGTCTGCAGCTTTAGCTGCACCAA | 56 |

TABLE 2-continued

ACHT4 nucleic acid sequences

| Organism | Paralogs | Database Accession No. | Nucleic Acid Sequence | SEQ ID NO: |
|---|---|---|---|---|
| | | | CGCCACGATCAAGAAATTTAAAAATGCATTGG CCAAGCACACCCCAGACAGATCCAGCCTCGAG CCAACAAAAGGGCTGGAGGAGAAAGAGCTCA TTGCATTGGCTGCCAATAAAGATCTCAACTTA ACATATGCACCAAAATCAGATAAGCCAATCCC AGCTCCAACTAAGGAAGAGATAGTACCCGAAA TTCCCCAATCTCTTTCTCTTGCTCTTCGTAGGA GTATGGAGCTTGCTCAAGGCTCAGCCGAAAAG ACCTTGGTCGCTTCAGGGAGATGA | |
| Sorghum bicolor | SbACHT4-1 | gnl\|SbGDB\| Sb01g036620.1 Downloaded from Phytozome | ATGGCGGCAGCGCAGGCGGTCGCGAAGGGGA GCGTGGTTGCGCCGTGCGGCAATCGAGCGGCG CCGGGCCTCCTTGGCAGGCGGAGGGGTGCCGT GGCGGCGCGGATGGCGCCGTCGGCGGTGCGGA TCGGGGCCTCATGGAGGAAGACCGCGTTTACA GGCGGGAGGCTAGCCTTGGGGTTGGGGACGAG GAGATCCAGGCCCGCGTCCCGGAGTTCTTTCG CGTCGCCGGCGCAGATGAACATGAACCTTGCG ATTGGGAAATCGATGAGGTGGTGGGAGAAGG GGTTGCAGCCCAACATGCGTGAGATCGAGTCC GCCCAAGACCTTGTCGATTCCTTGACCAACGC CGGCGACAAGCTCGTCATCGTCGACTTCTTCTC CCCTGGCTGCGGCGGCTGCCGTGCTCTTCACCC GAAGATTTGTCAATTTGCGGAGCAGAACCCAG ATGTGCTGTTCTTGCAAGTGAACTACGAGGAG CACAAGTCTATGTGCTACAGTCTTCATGTCCAT GTCCTACCCTTCTTCAGATTCTACAGGGGAGCA CAGGGACGGCTCTGCAGCTTCAGTTGTACAAA CGCAACCATTAAGAAGTTCAAGGATGCACTTG CGAAGCACAAGCCAGATAGATGTAGCCTTGGC CCAACCAGGGGGCTAGAGGAATCGGAGTTTTT AGCCTTCGCAGCAAACAAGGACCTGCAGTTCA CCTACACCAAGGAGCCAGAACTGATTCCCAGG GGAGATGCTCCTGGGGAGGTCATTGCTCCCGA GCCTGCAAAGCTTCCTGCGGCCACAAAGCCTT TGGTCAGGCTGGGGTCCGAAGAAAGGTCCTTG GTCTCATCAGGAAGATGA | 57 |
| Sorghum bicolor | SbACHT4-2 | XM_002465792.1 | ATGGCGGCGGCGCAGGCGATGGCGAAAGGGA GCGTGGGGCAGGGGTCTCTTGGTCGGCGGAGG GGCGCCGAGGCGGCGCGGGTCGGAGGATCAT GGAGGAAGAGCGCGTTCCTCGGCGGGAGGCTG GCGGTTGGGCCCAGGAGACCGAGACCCGTGTC CCGGATTCTAGTTACGTCGCCGGCGGTGCAGC AGACGAACCTTTCATTTGCGAAAGCCATGAAG TGGTGGCAGAAGGGATTGCAGCCCAACATGCG GGCGATCCAGACCGCCCAAGACCTCGCCGATT CCTTGACCAACGCCGGCGACGGGCTCGTCGTC GTCGACTTCTTCTCACCCGGCTGCGCTGGCTGC CATGCTCTCCACCCCAAGATTTGTCAGTTCGCG GAGAGGAACCCGGATGTGCAGTTCCTGCAGGT GAACTATGAGGAGCACAAGTCTATGTGCCACA GCCTTCACGTTCATGTGTTCCCTTTCTTCAGGT TCTACAGGGGAGCTCAGGGTCGGCTCTGCAGC TTCAGCTGTACCAATGCAACTATTAAGAAGTT CAGGGATGCACTTGCAAAGCACAGAGCTGATA GATGCAGCCTTGGCCCTACTCGGGGACTAGAA GAATCAGAATTGTTGGCCCTGGCTGCAAACAA GGACCTGCAGTTCACCTACACCAAGGAGGCAG AACTGGCTCCAAGCATGGAAGATGTCGCAGAG GTTATGACTGCTGACCGTCCAGGGCTTCCGAC ATCAACAATGCCATTGGCAAGGCAGGGATCTG AGGACAGGGCCTTGGTCTCGTCAGGAAGATGA | 58 |
| Sorghum bicolor | SbACHT4-3 | gnl\|SbGDB\| Sb02g043280.2 Downloaded from Phytozome | ATGGCTGAGGCGTTGTGCAACGGCGTCGTGGC GTCGCCGTACGGCGGCGGGGACGTGGGCGTCG CCGGCCGGGCCAGGGGCGCCGCCAAGGCCGC GCTCGCGGAGTCCCTGCCGGTCGGCGGGTACG CCACCAAGAGCTCCTTCTCCGCCGGGAGGATG TCGGTGTCGGACAGGAAGCCGAGGCCCCTGTC TCGGAACCTCGAGGCCGCCGCCGCGCCTGGAC AGATGAACCTGTCGTTTCCCAAGGCCATGCGG TGGTGGGAGAAGGGGCTGCACCCCAACATGCG GGAGATCGAGTCCGCGCAGGACCTCGCCGACT | 59 |

TABLE 2-continued

ACHT4 nucleic acid sequences

| Organism | Paralogs | Database Accession No. | Nucleic Acid Sequence | SEQ ID NO: |
|---|---|---|---|---|
| | | | CCCTCCTCAACGCCGGCGACAAGCTCGTCGTC GTCGATTTTTTCTCCCCAGGCTGCGGCGGCTGC CGCGCTCTCCACCCCAAGATTGCCCAGTTCGCC GAGAAGAACCCGGACGTGCTGTTCCTGCAAGT GAACTACGAGACGCACAAGTCCATGTGCTACA GCCTCCACGTCCATGTCCTCCCGTTCTTCAGGT TCTACAGGGGAGCCGAGGGACGGGTCAGCAG CTTCAGCTGCACCAATGCAACGGTAAGAATCG ACCACCTCTCCAACTTCAAGAACCAGCAGATG AATGAATGA | |
| Brassica napus (Rapeseed) | BnACHT4-1 | BnaA09g48840D | ATGGCGGAAGCAGCAATCAGCAGAACGAAT CTGATCTTCCGAGGAGCTTGCGTGAATCAAC ACAAGCATGTAGATGATTACTCTGTCTCATC ACCTGTGAGTTTCGGTTTGAGAAAGAGCTTC CCTTCTCTGAAGGTGAAGCCTTTAATCAATT CCAGAGCTCCCGATCATCATCATCCATCACA GCTCAGACAACGTTGAGGATTGGGACGCCTC AGAAATGGTGGGAGAAGGGTCTGAAAGAGA ACATGAGAGAGATCTCTTCAGCTCAGGAGCT TGTTGACTCTTTAACCAACGCTGGTGATAAG CTCGTTGTGGTTGACTTCTTCTCTCCTGGCTG TGGTGGATGCAAGGCTCTTCATCCTAAGATA TGTCAGTTGGCAGAGCAGAACCCTGATGTGC AGTTTCTTCAGGTGAACTACGAGGAGCACAA GTCCATGTGTTACAGTCTCGGTGTCCACGTCC TCCCGTTTTTCAGATTCTACCGTGGCGCTCAT GGTCGTGTCTGCAGCTTCAGCTGCACCAATG CTACGATCAAGAAGTTCAGAGATGCATTGGC GAAGCATAGTCCGGATAGGTGCAGCCTTGGA CCGACCAAAGGGCTTGAAGAGAAGGAGCTT GTGGCACTTGCAGCCAACAAAGAACTCAACT TTAGTTACACACCGAGGGCTGTACCAGTTGA GGAAGAAGAAGCTCCCGTCCCCGCTTCAAAC CCTGGTCTCCCTGTTGCTCATCCATCGATGAA GGCCAATGATGGAAAGACATTGGTCTCCTCA GGGAGATGA | 60 |
| Brassica napus (Rapeseed) | BnACHT4-2 | XM_013856519.1; LOC106415750 | ATGGCGGAGGTAATCAGCAAAACGAGTTTGTT CTTCCGAGGAGCTTGCGTGAATCACCACCACC ACGCAGATGACTTCTCCGTCTCGCCGGTGAGTT TCGGTCTCAAAAAGAGTTTCTCTTCTCTCAAGC AGAAGCCTCTTAGAAGCGACTTCTCTGGAAAA CAGATCCTACAGACCTTCAACAGGAGCTTCCG ATCATCATCCGTTACCGCTCAGTCAACGCTGA GGATTGGGACAGCTCAGAAGTGGTGGGAGAA AGGTCTGCAAGAGAACATGAGAGAGATCTCTT CGGCGCAAGAGCTCGTCGACTCTCTCGCCGAC GCTGGCGATAAGCTCGTCGTGGTTGACTTCTTC TCTCCTGGCTGCGGCGGATGCAAGGCTCTGCA TCCTAAGATGTGCCAGCTGGCGGAGCAGAGCG CTGATGTGCAGTTTCTTCAGGTGAACTACGAG GAGCACAAGTCCATGTGTTATAGCCTCGGTGT CCACGTCCTCCCGTTTTTTCGGTTCTACCGTGG CGCTCAGGGTCGCGTCTGTAGCTTTAGCTGTAC TAATGCTACGATAAAGAAATTTAGAGACGCGT TGGCGAAGCATAGTCCGGATAGGTGCAGCCTT GGACCAACCAAGGGGCTTGAAGAGAAAGAGC TTGTGGCACTTGCAGCCAATAAAGAACTCAAC TTTAGTTACACGCCGAAGGTTGTACCTGTTGAG AAAGAAGCAGCTATTCCCACTTCCAACCCGGC ACTCCCTGTTCCTCATCCATCGATGAGTGGCAG TGAGGAGAAGACATTGGTCTCTGCAGGGAGGT GA | 61 |
| Brassica napus (Rapeseed) | BnACHT4-3 | XM_013817176.1; LOC106377028 | ATGGCGGAAGCAGCAATTAGCAGAACGAATCT GATCTTCAGAGGAGCTTGCGTGACTCACCACC ACCATGCAGATGATTACTCTGTCTCATCATCAC CTGTGAGTTTCGGTCTGAGAAAGAGCTTCTCTT CTCTCAAGCTGAAGCCTCCAGAGACAGATCGAT ACTCAATTCCAGACCTTCACAAGGAGCTCCCG AGCATCATCCATCACAGCTCAGACGACGCTGA GGATCGGGACGCCTCAGAAATGGTGGGAGAA GGGTCTGAAAGAGAACATGAGAGAGATCTCTT | 62 |

TABLE 2-continued

ACHT4 nucleic acid sequences

| Organism | Paralogs | Database Accession No. | Nucleic Acid Sequence | SEQ ID NO: |
|---|---|---|---|---|
| | | | CAGCTCAGGAGCTTGTTGACTCTCTAACCAAC GCTGGTGATAAGCTCGTTGTGGTTGACTTCTTC TCTCTTGGCTGCGGTTGGATGCAAGGCTCTTCAT CCTAAGATATGTCAGTTGGCAGAGCAGAACCC TGATGTGCAGTTTCTTCAGGTGAACTACGAGG AGCACAAGTCCATGTGTTACAGTCTCGGTGTC CACGTCCTCCCTTTCTTTCGATTCTACCGTGGC GCTCACGGTCGTGTCTGCAGCTTCAGCTGCAC AAATGCTACGATCAAGAAGTTCAGAGATGCAT TGGCGAAGCATAGTCCAGATAGGTGCAGCCTC GGACCGACCAAAGGGCTTGAAGAGAAGGAGC TTGTGGCGCTTGCGGCCAACAAAGAACTCAAC TTTAGTTACACACCGAGGGCTGTACCAGTTGA GGAAGAAGAAGCTCCCGTCCCCGCTTCAAAAC CAGGTCTTGCTGTTCCTCATCCATCGATGAGCG CCAATGATGAGAAGACATTGGTCTCCGCAGGG AGATGA | |
| Brassica napus (Rapeseed) | BnACHT4-4 | XM_013861022.1; LOC106420177 | ATGGCGGAAGCAGCAATCAGCAGAACGAATCT GATCTTCCGAGGAGCTTGCGTGAATCAACACA AGCATGTAGATGATTACTCTGTCTCATCACCTG TGAGTTTCGGTCTGAGAAAGAGCTTCCCTTCTC TGAAGGTGAAGCCTTTTAATCAATTCCAGAGC TCCCGATCATCATCATCCATCACAGCTCAGAC AGCGTTGAGGATTGGGACGCCTCAGAGATGGT GGGAGAAGGGTTTGAAAGAGAACATGAGAGA GATCTCTTCAGCTCAGGAGCTCGTTGACTCTCT AACCAACGCTGGTGATAAGCTCGTTGTGGTTG ACTTCTTTTCTCCTGGCTGTGGTGGATGCAAGG CTCTTCATCCTAAGATATGTCAGTTGGCAGAGC AGAACCCTGATGTGCAGTTTCTTCAGGTGAAC TACGAGGAGCACAAGTCCATGTGTTACAGTCT CGGTGTCCACGTCCTTCCGTTTTTCAGATTCTA CCGTGGCGCTCATGGTCGTGTCTGCAGCTTCAG CTGCACCAATGCTACGATAAAGAAGTTCAGAG ATGCATTGGCGAAGCATACTCCGGATAGGTGC AGCCTTGGACCGACCAAAGGGTTGAAGAGAA GGAGCTTGTGGCACTTGCAGCCAACAAAGAAC TCAACTTTAGTTACACACCGAAGGATGTACCA GTTGAGGAAGAGGCAGCTCCCGTCCCCGTTTC AAACCCTGGTCTCCCTGTTGCTCATCCATCGAT GAAGGCCAATGATGGAAAGACATTGGTCTCCT CAGGGAGATGA | 63 |
| Brassica napus (Rapeseed) | BnACHT4-5 | XM_013785617.1; LOC106346322 | ATGGCGGAGGTAATCAGCAAAACGAGTTTGTT CTTCGGAGGAGGAGCTTGCGTGAATCACCACC ACCACCACGTAGATGACTTGTCTGTCTCACCG GTGAGTTTCGGTTTCAAAAAGAGTTTCTCTTCT TCTCTCAAGCAGAAGCCTCTTAGAAGCGACTT CTCTGGAAAACAGATCCTAGAGACCTTCAACA GGAGCTTCCGATCATCATCCGTCACCGCTCAGT CGACGCTGAGGATTTGGGACAGCTCACAAGTGG TGGGAGAAAGGCTCTCAAGAGAACATGAGAG AGATCTCTTCGGCGCAAGACCTCGTCGACTCTC TCGCCGACGCTGCGATAAGCTCGTCGTGGTT GACTTCTTCTCCCCTGGCTGCGGGGGATGCAA GGCTCTGCATCCTAAGATGTGCCAGCTGGCGG AGCAGAGCCCTGATGTGCAGTTTCTTCAGGTG AATTACGAGGAGCACAAGTCCATGTGTTACAG TCTCGGTGTCCATGTCCTTCCCTTTTTCGATTT TATCGAGGCGCTCAGGGTCGTGTCTGTAGCTTT AGCTGTACCAATGCTACGATAAAGAAATTTAG AGACGCGTTGGCGAAGCATAGTCCGGATAGGT GCAGCCTTGGACCAACCAAGGGGCTTGAAGAG AAAGAGCTTGTGGCGCTTGCAGCTAATAAAGA ACTAAAGTTTTAGTTACACGCCGAAGGTTGTAC CTGTTGAGAAAGAGGTTGCCATCCCCACTTCA AACCCTGGTCTCCCTGTTCCTCATCCATCGACG ATGAGCGGCAGTGAGGAGAAGACGTTGGTCTC TGCAGGGAGGTGA | 64 |
| Ricinus communis (Castor) | RcACHT4 | XM_002525415.2; LOC8276541 | ATGGCTGATGTTTTGAGCAAGACCAATCTTGTT CCTTCGTCTTGTTGTAATGGTTACAAGAACCAG AAGAAAGATGGTGCCTTCGTTCTAAAAAGAAG | 65 |

TABLE 2-continued

ACHT4 nucleic acid sequences

| Organism | Paralogs | Database Accession No. | Nucleic Acid Sequence | SEQ ID NO: |
|---|---|---|---|---|
| | | | TTGCAGTCTTAAGGTGTCATCTAGGAAATTCA ATCCTCAGGCTTTCGGATCACAGAAGATATCA CTTATTTCTGATTTTTATGGCAAGAGGGTTATT GTTCAAGAAAAACAACTCAAGAGAGGGAATTT TCATCAATTTTCAATTAAGGCTCAGACTGGACT GAGACTCAAGAATGCTCCAAATGGTGGGAAA AGGGGTTGCAACCAAACATGAAGGAGATCACC TCTGCACAAGACCTTGTGGACTCCCTTATGAAT GCTGGGGACAAACTTGTAATTGTTGATTTCTTC TCCCCTGGCTGTGGTGGCTGCAAAGCTCTCCAT CCAAAGATATGTCAATTTGCGGAGATGAACCC TGATGTCCAGTTTCTTCAGGTGAATTATGAGGA ACATAAATCCATGTGTTATAGCCTCAATGTAC ACGTACTGCCATTCTTTAGATTTTACCGAGGGG CTCAAGGCCGAGTATGCAGCTTTAGCTGTACT AATGCCACGATTAAGAAATTTAAAGATGCATT AGCCAAGCACACCCCAGACCGATGCAGCCTCG GGCCAACCAAAGGGCTGGAGGAGAAAGAGCT TATTGCGTTGGCTTCTAACAAAGATCTCAACTT TACATGCACACCAAAACCAGTTCAACCAACTG CTCCTGCTCAGGAAGAGATAATACCAGCAGCA CTCACCCCAGCTCATGTGAATCAAACCCTACCT CTTCCTATTCCTCTCTACAACAAGCCTGATG TCTGCCCAAGACTTGGGGGAGAAAACCTTGGT TACTTCTGGGAGATAG | |
| Phaseolus vulgaris (Bean) | PvACHT4-1 | XM_007161898.1; PHAVU_001G112200g | ATGGCTGAAGTTTTTACCAAGGCGAGTTTCGTT TCTTCTTTGCTTGGTAGTAGTAGTCAACGCCACCAT CGAAGGGTGTCGACGGTTCCTGATACTTGTAC CTTTGTTTCTGGCGTCGGACTGGTCTCCTTCTCT CAAGTTAAAGTCTCCGATTCTCAGATCTTGGTC CCCTTCTTCTGAGTTTCAGGGTAAACAGCTTCT CTTTCGTGTAAATAGAGGAAAGCCCAACAGGG TCAGTTCGCGGTTGAGAGCGTCAACTGCTGCT CAGATGACCCTTAGAATAGGGAAAGTTCAAAA ATGGTGGGAAAAGGGGCTTCAACCCAACATGA AGAGGTGACTTCGGCCCAAGACCTTGTGGAA TCACTGTTAAACGCAGGGGACAAGTTGGTGGT GGTTGATTTCTTCTCTCCTGGTTGTGGTGGCTG CAAAGCCCTTCACCCTAAGATATGTCAACTGG CAGAGATGAATCCTGATGTTCAATTCCTTCAG GTGAACTATGAGGAGCATAAGTCCATGTGTTA TAGCCTCAATGTCCATGTTCTACCCTTCTTCCG CTTCTATAGAGGTGCTCATGGTCGATTATGTAG CTTTTAGCTGCACCAATGCCACGATCAAGAAGT TTAGAGACGCATTGGCCAAACACTCCCCAGAT AGATGCAGCTTGGCTCCCAACCAAAGGGTTAGA GGAGAAAGAGCTCCTAGCTCTTGCTGCCAACA AAGATCTTTCCTTTACCTTGCCAAAACCTTTAC AACCTGAACACGCAAATGAAGGGTTGGCAACT GCTCCTGCTCCTGTTCCTAGTTCAGAATCTCTT CCTTTACCTTCACTGACCCTCAATTCTGAGGTC TCCCAAGAGAGAACCTTGACCACTGCTGGGAG ATGA | 66 |
| Phaseolus vulgaris (Bean) | PvACHT4-2 | XM_007161862.1; PHAVU_001G109200g | ATGGCTGAGGTTTTGACCGAGGCAAGTTTGGT TCTTCTTCGTGGCATGGTACTACTCAACGCCACCA TCGAAGAGTATCGACAGTTCCCAATTCTTCTAG CTTCGTTTCTGGCGTTGGAAGGTTCCCTTCTCT CAAGTTAAAGTCTCAGATTCTCAGATCCCTCTC CTCTTCTTCTGAGTTTCAGGGTAAAAAGCTTCT CTTTCATGTAAATAGAGGACTAGCCAACAGAA TCACTTTCGCGGTTGGGAGCTTCAACTGCAGCG CAGATGACCCTTAGAATAGGGAAAGGTCAGAA ATGGTGGGAAAAGGGGCTTCAACCCAACATGA ATGAGGTGACTTCCGCCCAAGATCTTGTAGAA TCACTGTTAAACGCAGGGGACAAGTTAGTGGT GGTTGATTTCTTCTCTCCTGGTTGTGGTGGCTG CAAAGCCCTTCACCCTAAGATATGTCAACTGG CAGAGATGAATCCTGATGTTCAATTCCTTCAG GTGAACTATGAGGAACATAAGTCCATGTGTTA TAGCCTCAATGTCCATGTTCTTCCCTTCTTCCG CTTCTATAGAGGTGCTCATGGTCGATTATGTAG CTTTTAGCTGCACCAATGCCACGATCAAGAAGT | 67 |

TABLE 2-continued

ACHT4 nucleic acid sequences

| Organism | Paralogs | Database Accession No. | Nucleic Acid Sequence | SEQ ID NO: |
|---|---|---|---|---|
| | | | TTAAAGATGCATTGGCCAAACACTCCCCAGAT<br>AGATGCAGCTTGGGCCCAACCAAAGGGTTAGA<br>GGAAAAAGAGCTCCTAGCTCTTGCTGCCAACA<br>AAGATCTTTCGTTCATCTACGCACCAAATCCCT<br>TACAACCTGAACATGAAAATGAAGAGTTGGCT<br>ACTGCTCCCGCTCCTGTTCCTAGTTCAGAGTCT<br>CTTCCTTTGTGTCACCTCATTTCTGAGGTCTCC<br>AAAGAGAAAACCTTGATCACTGCTGGGAGATGA | |
| Gossypium histrum (Cotton) | GhACHT4-1 | NM_001326831.1; LOC107894997 | ATGGCTGAAGTTTTGGGGAAGGGAAATCTGTT<br>TACGACTTGTAACTATAGTCAGACGAAGAATC<br>TAGAAGGTGGAACTTGTTTGGTTCCTAAGAAA<br>ATTTCTGGGTTTTCTTTAGAAAGGAACGGTTTT<br>TCTTCTTTAAAGGTTAAATCTCAGGCTTTAAGA<br>AGTGATTTTAATGGGCAAAGAATGGTTTTTTTG<br>GAGAAGAAAAGTATGAACAGGCGAAGGTTTT<br>GTCAAGTTCCCATCAAAGCACAGATGCAAAGT<br>GGTCTTATTGGTCGAATTCAGAAATGGTGGGA<br>GAAAGGGCTTCAACCAAATATGAAAGAAGTTG<br>CATCTGCACAAGACCTAGTAGACTCTCTTCTGA<br>ATGCTGGTGATAAGCTTGTTGTGGTAGATTTCT<br>TCTCCCCTGGTTGTGGTGGTTGCAAGGCTCTTC<br>ATCCCAAGATTTGCCAATTTGCAGAGATGAAT<br>CCAGATGTGCAGTTTCTTCAGGTTAATTACGAG<br>GAGCACAAGTCAATGTGCTATAGCCTTAATGT<br>CCATGTGCTGCCTTTCTTCCGGTTCTATCGAGG<br>TGCGCAGGGGCGTGTATGCAGCTTTAGTTGTA<br>CCAATGCCACCTATCAAAAAATTCAGAGATGCA<br>TTAGCCAAACACACACCTGATCGGTGTAGCCT<br>CAGCACGACAAAAGGGCTCGAGGAGAAGGAG<br>CTTTTGGCATTATCTGCGAACAAAGACCTTTCC<br>TTCAACTACACACCAATTCCCACACATGGAGA<br>GATTCTTATATGGAAACAAGTTCCATCTGATTC<br>AACGAGAAAGCTCCCGCTTTCAGTCCCGACAA<br>CATCCGCAAACAAAGGGACAGTGAGGAGAA<br>AACCTTGGTTGGTGTCGGAAGATGA | 68 |
| Gossypium histrum (Cotton) | GhACHT4-2 | XM_01688050.1; LOC107961887 | ATGGCTGAAGTTTTGGGGAAGTCAAATCTGTT<br>TACAGCTTGTAACTATAGTCAGAAGAAGCATC<br>AAGAAGGTGGCGTTCCTTTGTTTTCCAGGAGA<br>ATCTCTGTGTTTTGTTTGAGAAAGAATAGTTTT<br>CCTTCTTTGAGGTTGGAACCTCAAGCTTTGAGG<br>AGTGGTTTTAATGGTCAAAGAGTGGTTTTTTTA<br>GAGAAAAGAAGTCTAAATGAGAGAAGGTTCT<br>GTCGAGTTCCCATTAAAGCACAGATGCAAACT<br>GGGCTTATTGGTAAAACTCAAAAGTGGTGGGA<br>GAAGGGGAATCAACCAAATATGAAAGAAGTG<br>ACATCTGCACAAGACCTGGTGGACTCACTTTT<br>GAATGCTGGGGATAAACTTGTTATAGTGGATT<br>TCTTCTCTCCTGGTTGTGGTGGCTGCAAGGCTC<br>TTCATCCCAAGATTTGCCAATTGGCAGAGATG<br>AATCCGGATGTGCACTTTCCTTAAGGTGAACTA<br>TGAGGAGCATAAATCCATGTGTTATAGCCTTA<br>ATGTACATGTGTTGCCTTTCTTTAGGTTCTATA<br>GAGGAGCTCAGGGTTCGTCTATGCACTCTTTAGC<br>TGCACCAATGCCACGATCAAAAAATTCAAAGA<br>TGCATTGGCCAAGCACTCACCAGACCGATGCA<br>GCCTTGGGCCGACAAAAGGTCTCGAGGAGAAG<br>GAGCTTTTGGCATTAGCTGCCAACAAAGACCT<br>TTCCTTCAACTACACACCGAAACCAGTTCATCC<br>TGCACCGGAAGAAATTCCGGTGCTGAAAGAAG<br>TTCCATCCGGTTCATCCTTCAAGCTAAAAGAA<br>AGCGAGGAGAAGACCTTGATTGGTGTGGGAG<br>ATGA | 69 |
| Gossypium histrum (Cotton) | GhACHT4-3 | XM_016817346.1; LOC107892305 | ATGGCTGAAGTTTTGGGGAAGTCAAATCTGTT<br>TACAGCTTGTAACTGTAGTCAGAAGAAGAATC<br>AAGAAGGTGGCGTTCCTTTGTTTTCTAGGAGA<br>ATCTCTGCGTTTTGTTTGAGAAAGAATAGTTTT<br>CCTTCTTTGAAGTTGGAACCTCAAGCTTTGAGG<br>AGTGGTTTTAATGGTCAAAGAGTGGTTGTTTTA<br>GAGAAAAGAAGTCTAAATGAGAGAAGGTTCT<br>GTCGAGTTCCCATTAAAGCACAGATGCAAACA<br>GGGCTTATTGGTAAAACCCAAAAGTGGTGGGA | 70 |

TABLE 2-continued

ACHT4 nucleic acid sequences

| Organism | Paralogs | Database Accession No. | Nucleic Acid Sequence | SEQ ID NO: |
|---|---|---|---|---|
| | | | GAAGGGGAATCAACCAAATATGAAAGAAGTG ACATCTGCACAAGACCTGGTGGACTCACTTTT GAATGCTGGGGATAAACTTGTTATAGTGGATT TTTTCTCTCCTGGTTGTGGTGGCTGCAAGGCTC TTCATCCCAAGATTTGCCAATTGGCAGAGATG AATCCGGATGTGCACTTTCCTTAAGCTGAACTA TGAGGAGCATAAATCCATGTGTTATAGCCTTA ATGTACATGTGTTGCCTTTCTTTAGGTTCTATA GAGGAGCTCAGGGTCGTTTATGCAGCTTTAGC TGCACCAATGCCACGATCAAAAAATTCAAAGA TGCATTGGCCAAGCACTCACCAGACCGATGCA GCCTTGGGCCGACAAAAGGTCTCGAGGAGAAG GAGCTTTTGGCATTAGCTGCCAACAAAGACCT TTCCTTCAACTACACACCGAAACCAGTTCATCC TGCACCAGAAGAAATGCCGGTGCTGGAAGAA GTTCCATCCGGTTCATCCTTCAGGCCAAAAGA AAGCGAGGAGAAGACCTTGGTTGGTGTGGGGA GATGA | |
| Glycine max (Soybean) | GmACHT4-1 | XM_003548715.3; LOC100816892 | ATGGCGGAGGTTTTAACCAAGGCGAGTTTGGT TTCATCTTCTTGGCATGGGGTTAGTCAACGGCA TCATCATCGAAGGGTTTCAACGGTTCTTTCAAA TAATACATGTAGCTTCCGTTCCGGCGTGGGAA AGTTCTCTTCTTTGAAGATGAATTCTCAGGTTC TCAGATCTTGGTCCTCTTCTTCTGAGTTTCAGG GTAAAAAGCTTGTCTTTCATGTAAATAGAGGA TTACCCAATAGGGTCAATTCGCGGTTGAGAGC TTCTACTGGGACTCAGATGAACCTTAGACTAG GGAAAGTTCAGAAATGGTGGGAAAAGGGGCT TCAACCCAACATGAAAGAGGTGACTTCAGCAC AAGACTTTGTGGATTTCACTGTTAAACGCAGGG GACAAGTTGGTGGTGGTTGATTTCTTCTCTCCT GGTTGTGGTGGCTGCAAAGCCCTTCATCCTAA GATATGCCAATTTGCAGAGATGAATCCTGATG TTCAGTTCCTTCAGGTGAACTATGAGGAGCAT AAGTCCATGTGTTATAGCCTTAATGTCCATGTT CTTCCCTTCTTCCGATTCTATAGAGGCGCTCAC GGTCGATTATGTAGCTTTAGCTGCACCAATGCC ACGATCAAGAAGTTCAAAGATGCATTAGCCAA ACACACCCCAGACAGATGCAGCTTAGGCCCAA CCATAGGGTTAGAGGAGAAAGAACTCGAAGCT CTTGCTGCCAACAAAGATCTTTCCTTCACCTAC TCACCAAAACCATTACAACCTTCACATGAAAA CGAAGAGTTGGCAACCGAAACTGCTTCTGCTC CGGCTCTTGGTTCAGGATCTCTTCCTTCACCTT CAATGACCCTCAATGCTGTGGCCTCTAATGAG AGAACCTTGACCACTTCTGGGAGATGA | 71 |
| Glycine max (Soybean) | GmACHT4-2 | NM_001289199.1; LOC100784901 | ATGAAGTCTCAGGTTCTCAGATCTTGGTCCTCT TCTTCTGAGTTTCAGGGTATAAAGCTTGTCTTT CATGTAAATAGAGGATTACCCAATAGGGTCAA TTCGCGCTTGAGAGCTTCAACTGGGGCTCAGA TGAGCTTTAGACTAGGGAAAGTTCAGAAATGG TGGGAAAAGGGGCTTCAACCCAACATGAAGG AGGTGACTTCGGCACAAGACTTTGTGGATTCA CTGTTAAGCGCAGGGGACAAGTTGGTGGTGGT TGATTTCTTCTCTCCCGGTTGTGGTGGCTGCAA AGCCCTTCATCCTAAGATATGTCAATTTGCAGA GATGAATCCTGATGTTCAGTTCCTTCAGGTGAA CTATGAGGAGCATAAGTCCATGTGTTATAGCC TTAATGTCCATGTTCTTCCCTTCTTCCGATTCTA TAGAGGTGCTCATGGTCGATTATGTAGCTTTAG CTGCACCAATGCCACGATCAAGAAGTTTAAAG ATGCATTGGCCAAACACACCCCAGATAGATGC AGCTTGGGCCCAACCAAAGGGTTAGAAGAGA AAGAGCTTCTAGCTCTTGCTGCCAACAAAGAT CTTTCCTTCACCAACTCACCAGAACCTTTACAA CCTGCACATGCAGATGAAGAGTTGGGAACCGA ACCTGCTCCTGCTCCTGGTTCAAAATCTCTTCC TTCACCTTCAATGATTCTCAATTCTGAGGTCTC TAAAAAGAGAACCTTAACCACTTCAGGGAGAT GA | 72 |

TABLE 2-continued

ACHT4 nucleic acid sequences

| Organism | Paralogs | Database Accession No. | Nucleic Acid Sequence | SEQ ID NO: |
|---|---|---|---|---|
| Beta vulgaris (Beet) | BvACHT4 | XM_010674105.1; LOC104888985 | ATGGCGGATGTTCTTACCAAATCCAGTGTTTTT TCTCCAACAATTTCTCATCATCATAGTGGAAGT AAAAATTTTCCAATTAAATGTTCAGTTGCAGTG AGTAATCGAGGGAGATTAGTTGGAATTTCTTC GTTGAGGAGTAGTTTTGGTGGTGTAAGAATTG CGATCGATAAAAATACCAGTTTTGGGTCAAAA AGGAGGAATTACCAATCAATTGATGCTAAGAT GGGTCTGAGCATCGGCAAAGCACAGAAATGGT GGGAGAAAGGACTCCAGCCAAATATGAGAGA GATAACTTCTGCGGAAGACCTAGTCGATTCTTT ACTAACAGCAGGAGATACATTAGTTGTCGTTG ATTTTTTCTCTCCTGGATGTGGAGGCTGCAGAG CTCTTCATCCTAAGTTGTGTCAATTGGCAGAGA TGAACCCTGATGTCCAGTTTCTTCAGATTAACT ACGAAGAACATAAATCAATGTGTTACAGTCTT AATGTTCATGTTCTTCCCTTCTTTCGGTTTTACA GAGGGGCTGAAGGCCGGGTTTCCAGCTTCAGC TGTACAAATGCAACGATTAAGAAATTCAAGGA TGCTTTGGCGAAGCATAACCCAGCAAGGTGTA GCCTTGGGCCAACAAAGGGCCTAGAAGAGAA GGAGCTTCTTGCTCTTGCTGCCAACAAAGACCT TTCATTTACCTATACACCAAAGCCTGTGGAAG CGGAACCCGTACCCGCACCTGCACTTGAAGAA GTCTCTGTTAAGGCTGACGAACAAGTCTTAGC ACAAGAATCTCTCCCTTCTTTCAACAGGAAGC CTCTTAGCTCACAACCATCAACCGTGAGTGAA GAGAAAACTCTAGCTACTGCTGCGAGATGA | 73 |
| Musa acuminate (Banana) | MaACHT4-1 | XM_009418063.1; LOC103996979 | ATGGCGGAAACTTTGGCTCAGAGGACCCTCCT TTTGCCTGGCGGGCATCTTTCTTTGCCGCCGTT TTGCGGGATGCGGAGCCGCCCTTCTCTTTGCGG CGTTCACTCTCTTTTCACGTACCAAGGTTGAGC CCTTGAGGTCTTCTTCTTGTGATAGCAAGTTCC ATGGGAGGAGACTGGTCGTTGGGGCGCGGAG AGGGAGGCCCTCGAGGGCACGCCTCGGTTCTG GCTCTGAACAGATGGTTCTGTCGTTCAAGAAG GCTATAAAATGGTGGCAGAAGGGGCTTCAACC CAATATGGTGGAGATCGAGTCGGCTGAGCATC TCGTCGACTCCTTATTGAACGCCGGCGACAAG CTTGTTATTGTGGATTTCTTCTCTCCCCAGGGTGT GGAGGCTGCAGAGCGCTTCATCCAAAGATTTG CCAGTTCGCCGAATCGAATCAAAATGTTTTGTT TCTCCAAATAAATTATGAGCAACATAAGTCGA TGTGCTACAGCTTGGGTGTCCATGTTCTCCCCT TCTTTAGGTTCTATCGCGGAGCACACGGGCGC CTGTGCAGCTTCAGCTGCACCAATGCAACTATT AAGAAATTTAAAGATGCTTTGGCCAAGCACAT CACTGACAGATGCAGCCTTGGGCCAGCTAGGG GGCTGGAGGAGTCAGAGCTCTTGGCTTTGGCC GCAAACAAAGATCTCTCATTTAACTACACAAG CAAGCCAGTTCCTGTGCCTGAAGAGATTCCAG AGAGAATTCCAACAAGCCCGAAACTCCCTCTT CATGCTGTCCGTAGACCTGCCCAGGAATCCGA GGACAAGGCCCTCGCCGCAGCTGGGAGATGA | 74 |
| Musa acuminate (Banana) | MaACHT4-2 | XM_009408568.1; LOC103989652 | ATGGCGGATGCTTTGGCTCAAATGACGCTCCTT TCGCCCCATGGCCACCGTTCTTTGTCGCGCTCT TCCGACCGGAGAAACCGCCTTGTTTGTGCGTC AAAGGATGATCTCTTGAGGTCTTCGTCTTCTTG TAATAGCCAGTTCCATGGGAGAAGGCTGGTTA TTGGCGCACAGAGAGAGAGGCCGTTGAGAGG CAACCGAGGTTCTAGCTCTGTGCAGATGACTC TGTCCTTTAAGAAGGCTTCGAAATGGTGGGAG AAGGGGCTTCATCCCAATATGAAGGACATCAA GTCGGCTGAGGATCTCGTCGACTCCTTGTCGA ACGCGGGCGACAAGCTCGTCATCGTGGATTTC TTCTCCCCAGGATGTGCAGGCTGCAGAGCCCT CCACCCAAAGATCTGCCAATTCGCAGAGTTGA ATCCAGACGTTCAATTTCTCCAACTAAACCAC GAGGAACACAAGTCCATGTGCTACAGCTTGAA TGTCCATGTTCTCCCCTTCTTTAGGTTCTATCGC GGAGCGCACGGTCGCCTGTGCAGCTTCAGCTG CACCAATGCAACCATCAAGAAATTTAAGGATG CTTTGGCGAAGCACATCACCGAAAGATGCAGT | 75 |

TABLE 2-continued

ACHT4 nucleic acid sequences

| Organism | Paralogs | Database Accession No. | Nucleic Acid Sequence | SEQ ID NO: |
|---|---|---|---|---|
| | | | CTTGGGCCAGCCAAGGGGCTGGAGGAGACGG AGCTCCTTGCCTTGGCTGCAAACAAGGATCTCT CCTTCACCTACACAAGAACGCCTGTTCCCGTAC CTGATGAGCTTGCAGAGAAAGCTCCATTTAAC CCAAACCTACCTGTGCATGCTGCTGCTAGACTC ACCCTGGAATCTGAGGACAAGGCTTTTGCCGC AGCCGGTAGATGA | |
| Capsicum annuum (Sweet and Chili Peppers) | CaACHT4 | XM_016697343.1; LOC107852277 | ATGGCAAAATTGATGAACAAAGGTTTTGTGTT TCCTTCATCTTCTGATTGTGGTCATCATCGCCC TCATGGGATTTCTTCTTTCCCCAATAAATCGGT CAATCTTTCTTGTCTTCCATCTACTTGTCTGCTA AGAAGCTATTTTTATGGTCGTAGATTGGTCATA AATGAAGCCCTACCCAAAAGAAATGCCCACGT TGCAATCACTGTCCAGATGAGTATGGGAATCA GGAAAGTACAGAAATGGTGGGAGAAAGGGGT TCAACCTAACATGAAAGAAGTGAACAGTGCTC AAGGCCTTGTTGACTCTCTTTTGAGTGCAGGAG ATAAATTAGTAGTTGTTGATTTCTTTTCCCCTG GCTGCGGTGGCTGCAAAGCCCTTCACCCTAAG TTGTGTCAGCTGGCAGAGATGAATCCAGATGT GCAGTTTTTACAGGTGAACTATGAGGAACACA AGTCCATGTGTTACTCTCTTAACGTGCACCTTC TCCCATTTTTCCGTTTCTATAGAGGAGCTGAAG GTCGTGTTTGCAGCTTTAGCTGTACCAATGCCA CGATAAAAAAATTTAAAGATGCATTGGCAAAG TATGGTACAGATCGTTGCACCTTTGGACCACC GAAAGGGCTTGAGGAGAAAGAGCTACTTGCAT TGGCAGCTAACAAGGAACTCTCGTTTAATTAC ATTCCAAAAACAGAAGAAGAACCTGTCCTTGT TGCCTCACAAGAGGAAGTTGAGGACAGAACTC CAAATAAAGAGTCCCCTCTACCACTTCCTCTTC CTCTACCCATTAGCTCAACTAGCTCACTGAAGC CCAAACAGGATACAGAGAAAGAAGCGTATGC TACTTCTGGTAGATAG | 76 |
| Cicer arietinum (Chick pea) | CaACHT4 | XM_004493084.2; LOC101501672 | ATGGCTGAAATTTTGACCAAGACAAGTTTGGT TTCATCTTGGCATGGGAACAGAAAACAGCAAC ATCGAAGGTTGTCCATGGTTCCCAATAAGACT TGTAGCTTCAACACTTGCGTGGGAAGTTTCCCA TCTTTGAAGCTAAAATCTCAGTTTCTTAGATCT TCCTCTTTTTCATCTGAGTTTTATGGGAAAAAT ACTATCTTTCGTGTAAATAGATCAATACCCAAC AGGATTAATTCACAATTTTCAGTTTCAGCTGCG CCTAAGATGACACTTAGAATAGGAAAAATTCA GAAATGGTGGGAAAAGGGGCTTCAACCTAACA TGAGAGAAGTGACTTCAGCTCAAGATCTTGTA GATTCACTTTTAAACGCAGGGGACAAACTTGT CATTGTTGACTTTTTCTCTCCTGGTTGTGGTGG CTGCAGAGCCCTTCACCCTAAGATATGTCAAA TGGCAGAGATGAATCCTGATGTTGAGTTCCTTC AAGTGAACTATGAAGAGCATAAATCCATGTGT TATAGCCTTAATGTTCATGTCCTTCCTTTCTTCC GCTTCTATAGAGGCGCTCATGGTCGCTTATGCA GCTTTAGCTGCACCAATGCCACGATCAAGAAG TTTAAAGATGCATTGGCCAAACACACTCCAGA TAGATGCAGCTTGGAACCAACCAAAGGGTTAG AGGAGAAAGAGCTCATAGCTTTATCTGAAAAC AAAGATCTTAACTTCACATACACACCCAAACC TCTTCAACCTGTGCATACACCTGCAAATGAAG AGTTGGCGACAACCAAAGCCTCTCCTGTTTGTT CGGAGCCTCTTCCTTTACCTTCATTGACCTCGA ATTCTGATGAAGTCTTGAAGGAGAGAACCCTG ACAAGGGCTGGAAGATGA | 77 |
| Solanum lycopersicum (Tomato) | SlACHT4-1 | XM_004251955.2; LOC101244843 | ATGACGAAATTGATGAGCAAAGGTTTTATCTT TCCTTCTTCTTCTTCTGATTGTGGTGAAATTTAT GATCGTCTTCGTCTTAATCTACATGGGATCTGT TCTTTTCCCAATAAATCGGTCAATCTTTCTTGT CTTCCTTCGTTGAAGCTTTCTTCTTCTTGTTTGC CAAGAACCGATTTTTATGGTCGTAGATTGGTTA TAAATGAAGGCTTATCCAATTTCAACCGAAGA GTTGCTGATATCACTGCTCAGATGAGTGTTGG AATCAAGAAAGCACAGAAATGGTGGGAGAAA | 78 |

TABLE 2-continued

ACHT4 nucleic acid sequences

| Organism | Paralogs | Database Accession No. | Nucleic Acid Sequence | SEQ ID NO: |
|---|---|---|---|---|
| | | | GGGGTTCAACCTAACATGAAAGAAGTGAACAG TGCACAAGAACTTGTTGACTCTCTATTGAGTGC AGGGGATAAATTAGTTGTTGTTGATTTCTTTTC TCCTGGCTGTGGAGGTTGTAAAGCTCTTCACCC CAAGTTGTGTCAGCTGGCAGAGATGAATCCAG ATGTGCAGTTTTTACAGGTGAACTATGAGGAA CACAAGTCGATGTGTTACTCTCTTAATGTACAT GTTCTCCCGTTTTTCCGTTTCTATAGAGGAGCT GAAGGCCGTGTTTGCAGCTTTAGCTGTACCAA TGCCACGATCAAAAAATTCAGAGATGCATTGG CGAAGTATGGTACAGATCGTTGCACCATTGGG TCACCCAAAGGGCTTGAGGAGAAAGAGCTACT TGCATTGGCAGCTAACAAGGATCTTTCCTTTAA TTACACTCCAAAAACAGAAGAAGAACCCATCC TCGTTACCTCACAAAAGGAAGTTCGGGATAGA ACTACTCCAAATATAGAGTCCCCTCTACCACTT CCTCTTCCTCTCCCATTACGTCAACTAGCTCA CAGACGGCCAAACGGGATACAGAGAAAGAAG CATATGCTACTTCTGGTAGATGA | |
| Solanum lycopersicum (Tomato) | SlACHT4-2 | XM_004249259.2; LOC101244047 | ATGGAGAAATTGTTGAATAAGGCAGTATTTCT TCCATCAATTTTGAATTCTAGTGGTATTTATCA TTCTAATCAACATGCGATTTGTGTTTTCCAGT GAAATTCAATAGAAGATATCACAAATCAGCAG TTGCTACTGCTCAGATGAGCATAGGTATCAAG AGAGCTCCTAAATGGTGGGAGAAAGGACTTCA ACCGAATATGAAAGAGGTGACGGGTGCTCAAG ACCTCGTTGACACCCTTCTAAACGGTGGGGAT AAACTAGTCGTTGTTGATTTCCTTTCCCCTGGC TGTGGAGGCTGCAAAGCCCTTCATCCAAAGAT ATGTCAGTTAGCAGAGATGAATCCGGATGTGC AGTTTTTGCATGTGAACTATGAGGAACACAAG TCAATGTGTTACTCGCTGAACGTACATGTTCTC CCATTTTTCCGTTTCTATAGAGGTGCTGAAGGT CGTCTTTGTAGCTTTAGTTGCACCAATGCCACG ATAAAAAAATTCAAAGATGCATTGACAAAGTA TGGTGCAGATTGTTGCAGCCTCGGACCAGTTA AAGGGCTCGAGGAGAAAGAGCTACTTGCCCTA GCGGCTAATAAGGACCTATCTTTTGCTTACACA CCAAAAACAGAAGAACCAGTGCCTCTTGCCTT AGAAGAAGTTAAGGTGATAAAAACAAGTAGA CAATCTTCATCTCATCCCAATACATTCTCCCCA TTACCACTTCCTCTTCCTCTAGCATCAACTTTG CATACGGCCAAACAGGACTCAAAGAGTTAA | 79 |
| Elaeis guineemis (African oilpalm) | EgACHT4-1 | XM_010939817.1; LOC105057263 | ATGATGGAGGTTTTGAGTCAGAGCGGTGTTAT GTCGCCGTGCGGGCATCGTTGGGTGGTCCGTT CTTGCAAGGAGAGGAGCCCTTCTTTTGTTGGGT TTCCTCGCTCTTCCTCTCGGACGATCGAGTCTC TGATGTCTTCTTCTCGGAATAGCGGTTTCCATG GGAGGAGATTGAGCATTGGGGCTTGGAGAGTG AATGCCGTGAAGGGGAATTTTAGTTCTACCCC CGTACAGATGAGCCTCTGCGTTGGAAAGGCTT TGAAATGGTGGGAGAAGGAGCTCCAGCCCAAC ATGAAGGAGATCGAGTCGGCCCAGGATCTCGT CGACTCTTTATTGAACGCAGGAGACAAGCTTG TCATAGTAGATTTCTTCTCCCCTGGTTGTGGAG GCTGCAAAGCCCTCCATCCAAAGATTTGCCAG TTTGCAAAGCTGAACCCAGATGTTCTCTTCCTC CAAGTAAACTATGAAAGCACAAATCCATGTG TTATAGCTTAAATGTCCATGTTCTTCCCTTTTTT AGGTTtTACAGGGGAGCACACGGTCGTCTTTG TAGCTTCAGCTGCACCAATGCAACTATTAAGA AATTTAAAGATGCTTTGGCCAAGCACACCACA GACAGATGCAGCCTGGGCCCAACAAAGGGGCT GGAGGAATCAGAGCTCATGGCTCTGGCTGCAA ACAAGGATCTCTCTTTCAGTTACAAGAAAG CCAGTCCCTGTTCCCTCGCCAGATGAGGCTGC AGAGGAAGTTGTGCTCAGCCCAAAACTTCCGG TTTCTTCAACTCCAAGAGTCATCCAAGATTCGG AGGAGAAGGCTCTGGTGGCAGCTGGGAGATGA | 80 |
| Elaeis guineemis | EgACHT4-2 | XM_010922992.1; LOC105044909 | ATGGCGGAGGTTTGGGCAGGAGCGGCGTGTT CTCGCTGCGCGGGCACCGTTCCGTGGCCCCTTC | 81 |

TABLE 2-continued

ACHT4 nucleic acid sequences

| Organism | Paralogs | Database Accession No. | Nucleic Acid Sequence | SEQ ID NO: |
|---|---|---|---|---|
| (African oilpalm) | | | TTGCCAGAAGAGGAGCCCTTCTTTTCTTGGGTT TCCTCTCTCATCCTCTCGGCCGATCGGGCCTCC TAGGTCGTCTTCTCGGAGATTTGTTATCGGGAC TCGGAGAGGGAGGTCCATCAAGGGAAATTCTA GCTCTTCCCGTGTACAGATGAGCCTCGGCGTTG GAAAGTCATTGAAGTGGTGGGAGAAGGGTGTG CAGCCCAACATGAAGGAGATTGGATCGGCCCA GGATCTTGTTGACTCCTTATTGAATGAAGGAG ACAAGCTTGTTATCGTAGATTTCTTCTCCCCTG GTTGTGGAGGCTGCAAAGCCCTCCATCCAAAG ATTTGCCGGATTGCGGAGATGAACCCACATGT TCTCTTCCTCCAAATAAACTATGAGAAGCACA AGTCCATGTGTTATAGCTTGCATGTTCACGTTC TCCCCTTTTTTAGGTTTTACCGGGGAGCTCACG GTCGCCTTTGTAGCTTCAGCTGCACCAATGCAA CTATTAAGAAATTTAAAGATGCATTGGCCAAA CACACCACAGACAGATGCAGCCTTGGGCCAAC AAAGGGGCTGGAAGAATCAGAGCTTGTGGCTC TGGCTGCAAACAAGGATCTCTCCTTCAATTAC ACAAGAAAACCGGTTCCTGTTCTCACACCAGA CGAGGCTGCAGAGAAAGTTCCTCTTAGCCCAA AACTTCCAGTGTCTTCAGCCCAAGAGTCATC AAAGATTCTGAGGACAAGGCCCTCGTTGCAGC TGGGACATGA | |
| Setaria italic (Foxtail millet) | SiACHT4-1 | XM_004984459.3; LOC101779469 | ATGGCGGCGGCGCAGGCGGTCGCGAAGGGCA GCGTGGTGTCGCCGTGCGGCAGCAGGGCCGCG CCGGGGCTCCTGAGTCGGCGGAGGGGCCGCGT GGCGACGCGGATGGCGCCGTCGGCGGTGCGGA TCGGGGGCTCCTGGAGGAAGACCGCGTTCCTC GGCGGTAGGCTGGCGGTCGGGCCGAGGAGATC CAGGTCCGCGTCCCGGACCCTCGTCGCGTCGC CGGTGCAGATGAACATGAACCTTGCGATTGGG AAATCCATGAGGTGGTGGGAGAAGGGGCTGC AGCCCAACATGCGGGAGATCGAGTCCGCCCAG GATCTCGTCGATTCCTTGACCAACGCCGGCGA CAGACTCGTCATCGTGGACTTCTTCTCCCCCGG CTGCGGCGGTTGCCGTGCTCTTCACCCCAAGAT TTGCCAGTTTGCGGAGCAGAACCCGGATGTGC TGTTCTTGCAAGTGAACCATGAGGAGCACAAG TCTATGTGCTACAGCCTCCATGTCCACGTCCTC CCATTCTTCAGGTTCTACAGGGGAGCTCAGGG ACGGCTCTGCAGCTTCAGTTGTACCAACGCAA CTATCAAGAAGTTCAAGGATGCACTTGCAAAG CACAAACCGGATAGATGTAGCATTGGCCCAAC TAGAGGGCTGGAGGAATCAGAGTTATTAGCAT TGGCTGCAAACAAGGACTTGCAGTTCACCTAC ACCAAGAAGCCAGAACTGATCCCCAGCGGAG ATGCTGCTGCTGAGGTCATTGCTCCCGAGCCTA CAAAGCTTCCTGCGGCAACAAAGCCGTCGGTC AAGATAGGGTCCGAGGAGAGGTCCNNTTGGTC TCATCAGGAAGATGAGATGAATGACCTCTAG | 82 |
| Setaria italic (Foxtail millet) | SiACHT4-2 | XM_004985594.1; LOC101775678 | ATGGCGGCAGCGCAGGCGATGGCGAAGATGA GCGTGGGGTCGCCGGCCTGCAATCGGGCTGCG GGATCCCTCTGCCGGTGGAGGGGAGCCGTGGC GGTGCGGCTCGGAGGATCCTGGTCCTGGAGGA AGAGCCCGTTCCTCGGCGGGAGGATGGCGGTT GGGCCCAGGAGATCGAGGCCCGTGTCCCGGAA TCCTGTTGCGTCGCCGGTGCAGATGAACCTTTC ATTTGGGAAAACCATGAAGTGGTGGGAGAAG GGATTGCAGCCCAACATGCGGGCGATCCACAC CGCCCAAGAACTCGTCGATTCCTTGATCAACG CCGGCGACGGGTCGTCATAGTCGACTTCTTCT CACCTGGCTGCGCCGGCTGCCATGCCCTCCATC CCAAGATTTGCCAGTTTGCGGAGCGGAACCCA GATGTGCAGTTCCTGCAAGTGAACTTTGAGGA GCACAAGTCTATGTGCCACAGCCTTCATGTTCA TGTGTTCCCTTTCTTCAGATTCTACAGGGGAGC TCAGGGCCGGCTCTGCAGCTTCAGCTGTACCA ATGCAACTATCAAGAAGTTCAAGGATGCGCTT GCAAAGCACAAACCAGATAGATGTAGCCTTGG CCCAATTAAGGGGCTAGAGGAATCAGAGCTAC TGGCTTTGGCTGCAAACAGGGACCTGCAGTTC | 83 |

TABLE 2-continued

ACHT4 nucleic acid sequences

| Organism | Paralogs | Database Accession No. | Nucleic Acid Sequence | SEQ ID NO: |
|---|---|---|---|---|
| | | | ACCTACACCAAGGAGCAAGATCTGGCTCCGAG CATGGAAGATGGCGCAGAGGTCATCACTCATG ACCATCCAAGGCTTCCTGCAGCAGCAAAGCCG CTGGTCAGGCAGGGGTCTGAGGACAGGGCTGT GGTCTCATCGGGAAGATAA | |
| Setaria italic (Foxtail millet) | SiACHT4-3 | XM_004958667.1; LOC101759010 | ATGGCTGAGGCTTTGTGCAACGGCGTCGTGCC GTCGCCGTGCGGCGGGGACGTGGGCGTGGCCG GCCGGGTCAGTGGCGCCGCGGCGGCGCTAGCG GAGTCCGTGCCGATCGGCGGCTACCGCACCAA GAGCTCCTTCTCCGCAGGGAGGATGGCCATGA CCGACAGGAAGATGAGGCCCCTGCCTCGGAGC ATCGAGGCCGCGCCTGGACAGATGAACCTGTC GTTTCCTAAGGCCATGCGGTGGTGGGAGAAGG GGCTGCAGCCCAACATGCGGGAGATCGAGTCC GCGCAAGACCTCGCCGACTCCCTGCTCAACGC CGGCGACAAGCTCGTCGTCGTCGACTTCTTCTC CCCTGGCTGCGGCGGCTGCCGCGCCCTGCATG CCAAGATTGCCCAGTTTGCCGAGAAGAACCCA GATGTGATGTTCCTGCAAGTGAACTATGAGAC GCACAAGTCCATGTGCTACAGCCTCCATGTCC ATGTCCTCCCTTTCTTCAGGTTCTACAGGGGAG CCGAGGGACGGGTCAGCAGCTTCAGCTGCACA AATGCAACTATCAAGAAGTTCAAGGACGCGCT CGCAAAGCACGGACCTGACAGGTGCAGCCTCG GCCCTGCACGGGGGCTGGAGGAGTCGGAGCTC ATGGCCTTGGCTGCAAACAAGGACCTGCAATT CACCTACGAGAAGCCGGGCCTTGTCCCACTTG CAGAAGCCATTGCCAAGGAGGCTGCTGCACCA GGAGGCCCGTGGTTCCCTTTGCCTGCGTCCGCG ACGCAGTTCCTCACTCAGGGATCAGAGAATTC ATTGCTGTCATCCGGAAGATAG | 84 |
| Chlamydomonas reinhardtii (Single-cell green alga) | CrACHT4 | XM_001697391.1 | ATGGCCAGCATACTAAATCGTGCCGGTTCAAG GTCGTTAGTTTTTGAGACTAAGCAGTCATTGCG TTCTATTCCTGGCAGCCTTTTATCGCTGCGGTC AGTGGCGCTGAAGCCATTCCGGACAACCATCT GCGCGGCGGGAGCGCTGCTGACTGCACGGCGC TCGACATCAGGCCTCGGGCGCGCCAACGGGGT CGTTTGCCAAGCAGGGCGTAGCACTGGGGAAT GGTGGAAGAAGGACAACCCCCCAAACATGCG GGACATCAACTCAATTCAGGAGCTGGTTGACG CTCTGTCGGATGCCGGAGACCGCCTCGTCATT GTGGAGTTCTACGCCCAGTGGTGCAACGCCTG CCGCGCGCTATTCCCCAAGATCTGCAAAATCA TGGCTGAGAACCCGGACGTGCTCTTCCTCAAA GTGAACTTTGACGACAACCGTGACGCGTGCCG CACCCTGAGCGTCAAGGTGCTGCCGTACTTCC ACTTCTACCGCGGTGCGGAGGGCCGTGTGGCG GCCTTCAGCGCCACCATCAGCAAGTTGCAGCT GTTCAAGGATGCCGTGGAGACCTACAGCGCCG CCTTCTGCAGCCTGGAGCCCGCGCCGGGGCTG GCGGAGTTCCCCGACCTCATCGCGCACCCGGA GCTGCACCCGGAGGAGGCCGCAGAGGCGGCG CGGCGCGCGCGGCTGGCGTCCACCGAGTCGGA GGAGGAGTTGCATCCGCTGGCCGACACGCCGA CTGTGGTGGGATAG | 85 |
| Chlorella (Single-cell green alga) | CvACHT4 | XM_005851860.1 partial cds | TGGTGGACCAAGTCTGCGCCGCCCAATGTAGT GCACATCAAGTCTGTGCAGCACTTGGTGGACG AAATGGTGAGGGCTGAGAGGCTGGCGGGCGCT GGCGAGCGGCTGGTGATCATGGATGTGTTTGC GCCCTGGTGCGCCGCCTGCAAGGCGCTGTACC CCAAGCTGATGAAGCTGATGGAGGAGCGCCCC GATGTGCTGCTGCTGACGGTAAACTTTGATGA GAACAAGACGGTGGTGAAGGCCATGGGGGTC AACGGTCCTGCCGTACTTCATGTTCTATCGCGGC | 86 |

TABLE 2-continued

ACHT4 nucleic acid sequences

| Organism | Paralogs | Database Accession No. | Nucleic Acid Sequence | SEQ ID NO: |
|---|---|---|---|---|
| | | | AAGGAGGGCAAGCTGCAGGAGTTCTCGGCCAG CAACAAGCGATTCCACCTCATCCAGGAAGCCA TTGAGCGGCACAGCACCGATCGCTGCTTCCTG GATAGCACCGACGAGGAGCCTGTGCTTGCAGA GTTCCCCACTGTCGTCCCCGCCAAGGGCATCA GCGGCAGCTTGGATGAGCCGGCCGGCCGTGCG GCCGGCAAGGCGGTGGGCCAGCCGCAGCCCGT GGCCTGA | |

In another embodiment, the nucleic acid sequence of ACHT4 is a homolog of any one of the sequences listed in Table 2. In another embodiment, the nucleic acid sequence of ACHT4 is a paralog of any one of the sequences listed in Table 2. In another embodiment, the nucleic acid sequence of ACHT4 is a fragment of any one of the sequences listed in Table 2. In another embodiment, the nucleic acid sequence of ACHT4 is a variant of any one of the sequences listed in Table 2. In another embodiment, the nucleic acid sequence of ACHT4 comprises any one of the sequences listed in Table 2. In another embodiment, the nucleic acid sequence of ACHT4 consists essentially of any one of the sequences listed in Table 2. In another embodiment, the nucleic acid sequence of ACHT4 consists of any one of the sequences listed in Table 2. In another embodiment, the nucleic acid sequence of ACHT4 corresponds to any one of the sequences listed in Table 2.

In another embodiment, the nucleic acid sequence of ACHT4 is a homolog of any one of SEQ ID NOs: 44-86. In another embodiment, the nucleic acid sequence of ACHT4 is a paralog of any one of SEQ ID NOs: 44-86. In another embodiment, the nucleic acid sequence of ACHT4 is a fragment of any one of SEQ ID NOs: 44-86. In another embodiment, the nucleic acid sequence of ACHT4 is a variant of any one of SEQ ID NOs: 44-86. In another embodiment, the nucleic acid sequence of ACHT4 comprises any one of SEQ ID NOs: 44-86. In another embodiment, the nucleic acid sequence of ACHT4 consists essentially of any one of SEQ ID NOs: 44-86. In another embodiment, the nucleic acid sequence of ACHT4 consists of any one of SEQ ID NOs: 44-86. In another embodiment, the nucleic acid sequence of ACHT4 corresponds to any one of SEQ ID NOs: 44-86.

ACHT4ΔC

In one embodiment, the present invention provides a recombinant polynucleotide encoding an atypical CYS HIS rich thioredoxin 4 (ACHT4) protein, wherein the C-terminal portion of said ACHT4 protein comprises an inactivating mutation.

The inventors have demonstrated herein that over-expression (OE) of a C-terminal truncated form of AtACHT4 (AtACHT4ΔC, in which there is a 47 amino acid deletion of the C-terminus) has a dominant negative effect in Arabidopsis plants. AtACHT4ΔC overexpression relieves the oxidation of AGPase and boosts starch synthesis. In contrast, the OE of the full length ACHT4 does not, confirming that the C-terminus of AtACHT4 is indeed required for the attenuation of starch synthesis and the authenticity of the stimulating effect of AtACHT4-C-Del.

In addition, as demonstrated in Example 2, the stimulation of starch synthesis by AtACHT4-C-Del results in a significant increase in transitory starch content in Arabidopsis leaves and stimulates growth, indicating that AtACHT4ΔC stimulates the export of photosynthates from the chloroplast which are then directed toward plant metabolism and growth.

There are homologs of the ACHT4 found in Arabidopsis (AtACHT4), and in other species including potato, cassava, maize, rice, barley, wheat, sorghum, rapeseed, castor, bean, cotton, soybean, beet, banana, peppers, chickpea, tomato, oil palm, millet, several species of algae, and other plants and algae (Tables 1-2). As described in Example 3, ACHT4 in potato (paralogs StACHT4-2 and StACHT4-1) is similarly involved in attenuating starch synthesis and growth, and overexpression of the C-terminally deleted forms of StACHT4-1 and StACHT4-2, respectively, disinhibits (i.e. promotes) starch synthesis and nearly doubles tuber yield and plant shoot growth, respectively.

Since ACHT4 is expressed in all major crop and biofuel species, including rice and corn, attenuation of ACHT4 through dominant negative C-terminal deletions or other means, represents a promising new target for increasing plant growth and yield in all major crop and biofuel species.

In one embodiment, the inactivating mutation in the ACHT4 gene as described in the methods and compositions of the present invention is a deletion mutation. In another embodiment, the inactivating mutation is an insertion mutation. In another embodiment, the inactivating mutation is a substitution mutation. In another embodiment, the inactivating mutation is a null mutation. In another embodiment, the inactivating mutation is another type of mutation known in the art. In one embodiment, the insertion, deletion or substitution mutation comprises an insertion, deletion or substitution of a single nucleic acid, while in another embodiment, it comprises an insertion, deletion or substitution of 1-5 nucleic acids, 1-10 nucleic acids, 5-20 nucleic acids, 10-50 nucleic acids, 25-100 nucleic acids, 100-500 nucleic acids, 300-400 nucleic acids, 200-500 nucleic acids, or 500 or more nucleic acids.

In one embodiment, the mutation is a dominant negative mutation. In one embodiment, a dominant negative mutation (also called an antimorphic mutation) comprises an altered gene product that acts antagonistically to, attenuates, or inhibits the function(s) of the wild-type allele.

In one embodiment, the inactivating mutation in the C-terminal portion of ACHT4 is a deletion of the entire C-terminal portion of ACHT4. In another embodiment, the inactivating mutation in the C-terminal is a deletion of a portion of the C-terminal portion of ACHT4.

In one embodiment, a "corresponding sequence" is a nucleic acid (or amino acid) sequence from a first species for which there is a similar or equivalent sequence in a second species, which may be inferred by sequence alignment, as is well known in the art.

In another embodiment, the inactivating mutation in the C-terminal is a deletion of the final 141-207 nucleic acids of the ACHT4 gene. In another embodiment, the inactivating mutation in the C-terminal is a deletion of the final 150-225 nucleic acids of the ACHT4 gene. In another embodiment, the inactivating mutation in the C-terminal is a deletion of the final 150-300 nucleic acids of the ACHT4 gene. In another embodiment, the inactivating mutation in the C-terminal is a deletion of the final 75-150 nucleic acids of the ACHT4 gene. In another embodiment, the inactivating mutation in the C-terminal is a deletion of the final 3-75 nucleic acids of the ACHT4 gene. In another embodiment, the inactivating mutation in the C-terminal is a deletion of the final 3-30 nucleic acids of the ACHT4 gene. In another embodiment, the inactivating mutation in the C-terminal is a deletion of the final 75-225 nucleic acids of the ACHT4 gene. In another embodiment, the inactivating mutation in the C-terminal is a deletion of the final 3-60 nucleic acids of the ACHT4 gene. In another embodiment, the inactivating mutation in the C-terminal is a deletion of the final 60-120 nucleic acids of the ACHT4 gene. In another embodiment, the inactivating mutation in the C-terminal is a deletion of the final 120-180 nucleic acids of the ACHT4 gene. In another embodiment, the inactivating mutation in the C-terminal is a deletion of the final 150-225 nucleic acids of the ACHT4 gene.

In one embodiment, an inactivating mutation in the C-terminal of ACHT4 comprises a deletion of nucleic acids 687-825 of any one of the sequences listed in Table 2 or a corresponding nucleic acid sequence from another species. In another embodiment, an inactivating mutation in the C-terminal of ACHT4 comprises a deletion of nucleic acids 651-825 of any one of the sequences listed in Table 2 or a corresponding nucleic acid sequence from another species. In another embodiment, an inactivating mutation in the C-terminal of ACHT4 comprises a deletion of nucleic acids 600-825 of any one of the sequences listed in Table 2 or a corresponding nucleic acid sequence from another species. In another embodiment, an inactivating mutation in the C-terminal of ACHT4 comprises a deletion of nucleic acids 801-825 of any one of the sequences listed in Table 2 or a corresponding nucleic acid sequence from another species. In another embodiment, an inactivating mutation in the C-terminal of ACHT4 comprises a deletion of nucleic acids 699-825 of any one of the sequences listed in Table 2 or a corresponding nucleic acid sequence from another species. In another embodiment, an inactivating mutation in the C-terminal of ACHT4 comprises a deletion of nucleic acids 750-825 of any one of the sequences listed in Table 2 or a corresponding nucleic acid sequence from another species. In another embodiment, an inactivating mutation in the C-terminal of ACHT4 comprises a deletion of nucleic acids 774-825 of any one of the sequences listed in Table 2 or a corresponding nucleic acid sequence from another species. In another embodiment, an inactivating mutation in the C-terminal of ACHT4 comprises a deletion of nucleic acids 687-750 of any one of the sequences listed in Table 2 or a corresponding nucleic acid sequence from another species.

In another embodiment, an inactivating mutation in the C-terminal of ACHT4 comprises a deletion of nucleic acids 699-903 of any one of the sequences listed in Table 2 or a corresponding nucleic acid sequence from another species. In another embodiment, an inactivating mutation in the C-terminal of ACHT4 comprises a deletion of nucleic acids 600-903 of any one of the sequences listed in Table 2 or a corresponding nucleic acid sequence from another species. In another embodiment, an inactivating mutation in the C-terminal of ACHT4 comprises a deletion of nucleic acids 651-903 of any one of the sequences listed in Table 2 or a corresponding nucleic acid sequence from another species. In another embodiment, an inactivating mutation in the C-terminal of ACHT4 comprises a deletion of nucleic acids 750-903 of any one of the sequences listed in Table 2 or a corresponding nucleic acid sequence from another species. In another embodiment, an inactivating mutation in the C-terminal of ACHT4 comprises a deletion of nucleic acids 801-903 of any one of the sequences listed in Table 2 or a corresponding nucleic acid sequence from another species. In another embodiment, an inactivating mutation in the C-terminal of ACHT4 comprises a deletion of nucleic acids 849-903 of any one of the sequences listed in Table 2 or a corresponding nucleic acid sequence from another species. In another embodiment, an inactivating mutation in the C-terminal of ACHT4 comprises a deletion of nucleic acids 876-903 of any one of the sequences listed in Table 2 or a corresponding nucleic acid sequence from another species. In another embodiment, an inactivating mutation in the C-terminal of ACHT4 comprises a deletion of nucleic acids 825-903 of any one of the sequences listed in Table 2 or a corresponding nucleic acid sequence from another species. In another embodiment, an inactivating mutation in the C-terminal of ACHT4 comprises a deletion of nucleic acids 699-801 of any one of the sequences listed in Table 2 or a corresponding nucleic acid sequence from another species. In another embodiment, an inactivating mutation in the C-terminal of ACHT4 comprises a deletion of nucleic acids 699-849 of any one of the sequences listed in Table 2 or a corresponding nucleic acid sequence from another species.

In another embodiment, an inactivating mutation in the C-terminal of ACHT4 comprises a deletion of nucleic acids 486-690 of any one of the sequences listed in Table 2 or a corresponding nucleic acid sequence from another species. In another embodiment, an inactivating mutation in the C-terminal of ACHT4 comprises a deletion of nucleic acids 501-690 of any one of the sequences listed in Table 2 or a corresponding nucleic acid sequence from another species. In another embodiment, an inactivating mutation in the C-terminal of ACHT4 comprises a deletion of nucleic acids 549-690 of any one of the sequences listed in Table 2 or a corresponding nucleic acid sequence from another species. In another embodiment, an inactivating mutation in the C-terminal of ACHT4 comprises a deletion of nucleic acids 600-690 of any one of the sequences listed in Table 2 or a corresponding nucleic acid sequence from another species. In another embodiment, an inactivating mutation in the C-terminal of ACHT4 comprises a deletion of nucleic acids 651-690 of any one of the sequences listed in Table 2 or a corresponding nucleic acid sequence from another species. In another embodiment, an inactivating mutation in the C-terminal of ACHT4 comprises a deletion of nucleic acids 486-651 of any one of the sequences listed in Table 2 or a corresponding nucleic acid sequence from another species. In another embodiment, an inactivating mutation in the C-terminal of ACHT4 comprises a deletion of nucleic acids 486-600 of any one of the sequences listed in Table 2 or a corresponding nucleic acid sequence from another species. In another embodiment, an inactivating mutation in the C-terminal of ACHT4 comprises a deletion of nucleic acids 486-549 of any one of the sequences listed in Table 2 or a corresponding nucleic acid sequence from another species. In another embodiment, an inactivating mutation in the C-terminal of ACHT4 comprises a deletion of nucleic acids 486-501 of any one of the sequences listed in Table 2 or a corresponding nucleic acid sequence from another species.

In another embodiment, an inactivating mutation in the C-terminal of ACHT4 comprises insertion of a non-native sequence into a portion of the C-terminal of ACHT4 encoding the C-terminal of ACHT4, wherein said the C-terminal of ACHT4 is inactivated as a result.

In another embodiment, an inactivating mutation in the C-terminal of ACHT4 comprises substitution of nucleic acid residues, as is known to one of skill in the art. In another embodiment, an inactivating mutation in the C-terminal of ACHT4 consists essentially of any of the mutations listed hereinabove. In another embodiment, an inactivating mutation in the C-terminal of ACHT4 consists of any of the mutations listed hereinabove.

In another embodiment, the present invention provides a composition comprising a recombinant polynucleotide encoding an atypical CYS HIS rich thioredoxin 4 (ACHT4) protein, wherein the C-terminal portion of said ACHT4 protein comprises an inactivating mutation.

In another embodiment, the present invention provides an expression vector comprising a recombinant polynucleotide encoding an atypical CYS HIS rich thioredoxin 4 (ACHT4) protein, wherein the C-terminal portion of said ACHT4 protein comprises an inactivating mutation.

In one embodiment, "expression" as used herein refers to transcription of DNA to produce RNA. The resulting RNA may be without limitation mRNA encoding a protein, antisense RNA that is complementary to an mRNA encoding a protein, or an RNA transcript comprising a combination of sense and antisense gene regions, such as for use in RNAi technology. Expression as used herein may also refer to production of encoded protein from mRNA.

In another embodiment, the present invention provides a composition comprising an expression vector comprising a recombinant polynucleotide encoding an atypical CYS HIS rich thioredoxin 4 (ACHT4) protein, wherein the C-terminal portion of said ACHT4 protein comprises an inactivating mutation.

Recombinant Polynucleotides

In one embodiment, "recombinant polynucleotide" refers to a polynucleotide having a genetically engineered modification introduced through manipulation via mutagenesis, restriction enzymes, and the like. Recombinant polynucleotides may comprise DNA segments obtained from different sources, or DNA segments obtained from the same source, but which have been manipulated to join DNA segments which do not naturally exist in the joined form. A recombinant polynucleotide may exist outside of the cell, for example as a PCR fragment, or integrated into a genome, such as a plant genome.

The present invention contemplates the use of polynucleotides effective for imparting an enhanced phenotype to genetically modified plants or algae expressing said polynucleotides. Exemplary polynucleotides for use in the present invention are provided herein in Table 2 (SEQ ID NO: 44 through SEQ ID NO: 86). A subset of the nucleic molecules of this invention includes fragments of the disclosed polynucleotides consisting of oligonucleotides of at least 15, preferably at least 16 or 17, more preferably at least 18 or 19, and even more preferably at least 20 or more, consecutive nucleotides. Such oligonucleotides are fragments of the larger molecules having a sequence provided herein in Table 2 (SEQ ID NO: 44 through SEQ ID NO: 86), and find use, for example as probes and primers for detection of the polynucleotides of the present invention.

Also of interest in the present invention are variants of the polynucleotides provided herein. Such variants may be naturally occurring, including homologous polynucleotides from the same or a different species, or may be non-natural variants, for example polynucleotides synthesized using chemical synthesis methods, or generated using recombinant DNA techniques. Degeneracy of the genetic code provides the possibility to substitute at least one base of the protein encoding sequence of a gene with a different base without causing the amino acid sequence of the polypeptide produced from the gene to be changed. Hence, a polynucleotide useful in the present invention may have any base sequence that has been changed from the sequences in Table 2 (SEQ ID NO: 44 to SEQ ID NO: 86) by substitution in accordance with degeneracy of the genetic code.

Homologs of the polynucleotides provided herein will generally demonstrate significant identity with the polynucleotides provided herein. A polynucleotide of the present invention is substantially identical to a reference polynucleotide if, when the sequences of the polynucleotides are optimally aligned there is about 60% nucleotide equivalence; more preferably 70%; more preferably 80% equivalence; more preferably 85% equivalence; more preferably 90%; more preferably 95%; and/or more preferably 98% or 99% equivalence over a comparison window. A comparison window is preferably at least 50-100 nucleotides, and more preferably is the entire length of the polynucleotide provided herein. Optimal alignment of sequences for aligning a comparison window may be conducted by algorithms; preferably by computerized implementations of these algorithms (such as the Wisconsin Genetics Software Package). The reference polynucleotide may be a full-length molecule or a portion of a longer molecule. Preferentially, the window of comparison for determining polynucleotide identity of protein encoding sequences is the entire coding region.

Promoters

In one embodiment, a polynucleotide of the present invention is operatively linked in a recombinant polynucleotide to a promoter functional in a plant or alga to provide for expression of the polynucleotide in the sense orientation such that a desired polypeptide is produced. Also considered are embodiments wherein a polynucleotide is operatively linked to a promoter functional in a plant to provide for expression of the polynucleotide in the antisense orientation such that a complementary copy of at least a portion of an mRNA native to the target plant host is produced. Such a transcript may contain both sense and antisense regions of a polynucleotide, for example where RNAi methods are used for gene suppression.

In one embodiment, the promoter of the expression vector of the present invention is operably linked to the polynucleotide. In one embodiment, the promoter is a constitutive promoter. In another embodiment, the promoter is an inducible promoter. In another embodiment, the promoter is a tissue-specific promoter.

In one embodiment, a promoter used in the compositions and methods of the present invention is cisgenic, i.e. is a promoter that is native to the plant.

Recombinant polynucleotides of the present invention are assembled in recombinant DNA constructs using methods known to those of ordinary skill in the art. Thus, DNA constructs used for transforming plant cells will comprise a polynucleotide one desires to introduce into a target plant. Such constructs will also typically comprise a promoter operatively linked to said polynucleotide to provide for expression in the target plant. Other construct components may include additional regulatory elements, such as 5' or 3' untranslated regions (such as polyadenylation sites), intron regions, and transit or signal peptides.

Numerous promoters that are active in plant cells have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens*, caulimovirus promoters such as the cauliflower mosaic virus or figwort mosaic virus promoters.

These and numerous other promoters that function in plant cells are known to those skilled in the art and available for use in recombinant polynucleotides of the present invention to provide for expression of desired genes in genetically modified plant cells.

Furthermore, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted in the forward or reverse orientation 5' or 3' to the coding sequence. In some instances, these 5' enhancing elements are introns. Deemed to be particularly useful as enhancers are the 5' introns of the rice actin 1 and rice actin 2 genes. Examples of other enhancers that can be used in accordance with the invention include elements from the CaMV 35S promoter, octopine synthase genes, the maize alcohol dehydrogenase gene, the maize shrunken 1 gene and promoters from non-plant eukaryotes.

Organ-Specific Promoters

In other aspects of the invention, expression in plant seed tissues is desired to effect improvements in seed composition. In one embodiment, promoters for use for seed composition modification include promoters from seed genes such as napin, globulin 1, glutelin 1, and peroxiredoxin antioxidant.

In still other aspects of the invention, preferential expression in plant green tissues is desired. In one embodiment, promoters for expression in plant green tissues include those from genes such as SSU, aldolase and pyruvate orthophosphate dikinase (PPDK).

Recombinant constructs prepared in accordance with the invention will also in one embodiment, include a 3' untranslated DNA region that typically contains a polyadenylation sequence following the polynucleotide coding region. Examples of useful 3' UTRs include those from the nopaline synthase gene of *Agrobacterium tumefaciens* (nos), a gene encoding the small subunit of a ribulose-1,5-bisphosphate carboxylase-oxygenase (rbcS), and the T7 transcript of *Agrobacterium tumefaciens*.

Constructs and vectors may also include a transit peptide for targeting of a gene target to a plant organelle, particularly to a chloroplast, leucoplast or other plastid organelle.

Host Cells

In another embodiment, the present invention provides a cell comprising an expression vector comprising a recombinant polynucleotide encoding an atypical CYS HIS rich thioredoxin 4 (ACHT4) protein, wherein the C-terminal portion of said ACHT4 protein comprises an inactivating mutation.

In one embodiment, the cell is from an *Arabidopsis*. In one embodiment, the cell is from *Arabidopsis thaliana*. In one embodiment, the cell is from a crop plant. In one embodiment, the crop plant is *Solanum tuberosum* (Potato). In another embodiment, the crop plant is *Zea mays* (Maize). In another embodiment, the crop plant is *Oryza sativa* (Rice). In another embodiment, the crop plant is *Manihot esculenta* (Cassava). In another embodiment, the crop plant is *Hordeum vulgare* (Barley). In another embodiment, the crop plant is *Triticum aestivum* (Wheat). In another embodiment, the crop plant is *Sorghum bicolor*. In another embodiment, the crop plant is *Brassica napus* (Rapeseed). In another embodiment, the crop plant is *Ricinus communis* (Castor). In another embodiment, the crop plant is *Phaseolus vulgaris* (Bean). In another embodiment, the crop plant is *Gossypium histrum* (Cotton). In another embodiment, the crop plant is *Glycine max* (Soybean). In another embodiment, the crop plant is *Beta vulgaris* (Beet). In another embodiment, the crop plant is *Musa acuminate* (Banana). In another embodiment, the crop plant is *Capsicum annuum* (Sweet and Chili Peppers). In another embodiment, the crop plant is *Cicer arietinum* (Chick pea). In another embodiment, the crop plant is *Solanum lycopersicum* (Tomato). In another embodiment, the crop plant is *Elaeis guineensis* (African oilpalm). In another embodiment, the crop plant is *Setaria italic* (Foxtail millet).

In another embodiment, the crop plant is a food crop. In another embodiment, the crop plant is a nutritionally enhanced food crop.

In another embodiment, the cell is a moss cell. In one embodiment, the moss is *Physcomitrella patens*. In another embodiment, the cell is an algae cell. In one embodiment, the algae cell is *Chlamydomonas reinhardtii*. In another embodiment, the algae cell is *Ostreococcus tauri*. In another embodiment, the algae cell is a *Chlorella*.

Provided herein are host cells that contain a vector, e.g., a DNA plasmid and support the replication and/or expression of the vector. Host cells may be prokaryotic cells such as *E. coli*, or eukaryotic cells such as yeast, plant, insect, amphibian, or mammalian cells. In some embodiments, host cells are monocotyledonous or dicotyledonous plant cells. In other embodiments monocotyledonous host cell is a maize host cell. In certain embodiments, the host cell utilized in the methods of the present invention is transiently transfected with the nucleic acid molecules of the invention.

In some embodiments, the host cell utilized in the methods of the present invention is a plant protoplast. Plant protoplasts are plant cells that had their entire plant cell wall enzymatically removed prior to the introduction of the molecule of interest. The complete removal of the cell wall disrupts the connection between cells producing a homogenous suspension of individualized cells which allows more uniform and large scale transfection experiments. This comprises, but is not restricted to protoplast fusion, electroporation, liposome-mediated transfection, and polyethylene glycol-mediated transfection. Protoplast preparation is therefore a very reliable and inexpensive method to produce millions of cells.

In particular embodiments, the plant protoplast is derived from one of the following genuses: *Acorus, Aegilops, Allium, Amborella, Antirrhinum, Apium, Arabidopsis, Arachis, Beta. Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Limm, Liriodendron, Lotus, Lupinus. Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea,* or *Zinnia*. In some embodiments, the host cell is derived from a genus that is different from the genus from which the ACHT4 gene is derived.

Also provided herein are plant cells having the nucleotide sequence constructs of the invention. A further aspect of the present invention provides a method of making such a plant cell involving introduction of a vector including the construct into a plant cell. For integration of the construct into the plant genome, such introduction will be followed by recombination between the vector and the plant cell genome to introduce the sequence of nucleotides into the genome. RNA encoded by the introduced nucleic acid construct may then be transcribed in the cell and descendants thereof, including cells in plants regenerated from transformed material. A gene stably incorporated into the genome of a plant is passed from generation to generation to descendants of the plant, so such descendants should show the desired phenotype.

Optionally, germ line cells may be used in the methods described herein rather than, or in addition to, somatic cells. The term "germ line cells" refers to cells in the plant organism which can trace their eventual cell lineage to either the male or female reproductive cell of the plant. Other cells, referred to as "somatic cells" are cells which give rise to leaves, roots and vascular elements which, although important to the plant, do not directly give rise to gamete cells. Somatic cells, however, also may be used. With regard to callus and suspension cells which have somatic embryogenesis, many or most of the cells in the culture have the potential capacity to give rise to an adult plant. If the plant originates from single cells or a small number of cells from the embryogenic callus or suspension culture, the cells in the callus and suspension can therefore be referred to as germ cells. In the case of immature embryos which are prepared for treatment by the methods described herein, certain cells in the apical meristem region of the plant have been shown to produce a cell lineage which eventually gives rise to the female and male reproductive organs. With many or most species, the apical meristem is generally regarded as giving rise to the lineage that eventually will give rise to the gamete cells. An example of a non-gamete cell in an embryo would be the first leaf primordia in corn which is destined to give rise only to the first leaf and none of the reproductive structures.

In another embodiment, the present invention provides a composition comprising a cell comprising an expression vector comprising a recombinant polynucleotide encoding an atypical CYS HIS rich thioredoxin 4 (ACHT4) protein, wherein the C-terminal portion of said ACHT4 protein comprises an inactivating mutation.

Seeds

In another embodiment, the present invention provides a seed comprising a C-terminal deleted form of an atypical CYS HIS rich thioredoxin 4 (ACHT4) gene.

The present invention is directed to seed from a genetically modified plant, wherein the genome of said seed comprises an exogenous polynucleotide comprising a functional portion of an encoding region for a polypeptide provided herein, and wherein plants grown from said seed exhibit an enhanced phenotype as compared to the phenotype of a control plant. In one embodiment, the enhanced phenotype is increased yield. Exogenous polynucleotides of the present invention include recombinant polynucleotides providing for expression of mRNA encoding a polypeptide.

Plants and Plant Parts

In another embodiment, the present invention provides a plant, or plant part, comprising a C-terminal deleted form of an atypical CYS HIS rich thioredoxin 4 (ACHT4) gene.

The present invention provides a plant comprising a C-terminal deleted form of an ACHT4 gene. Transformed seeds and plant parts are also encompassed. In one embodiment, the plant part is a seed. In another embodiment, the plant part is a leaf. In another embodiment, the plant part is a stem. In another embodiment, the plant part is a root. In another embodiment, the plant part is a flower. In another embodiment, the plant part is a tuber. In another embodiment, the plant part is a fruit.

In one embodiment, a plant of the present invention is any plant that comprises an ACHT4 gene or homolog.

In one embodiment, a plant of the present invention is a crop plant. In one embodiment, the crop plant is *Solanum tuberosum* (Potato). In another embodiment, the crop plant is *Zea mays* (Maize). In another embodiment, the crop plant is *Oryza sativa* (Rice). In another embodiment, the crop plant is *Manihot esculenta* (Cassava). In another embodiment, the crop plant is *Hordeum vulgare* (Barley). In another embodiment, the crop plant is *Triticum aestivum* (Wheat). In another embodiment, the crop plant is *Sorghum bicolor*. In another embodiment, the crop plant is *Brassica napus* (Rapeseed). In another embodiment, the crop plant is *Ricimus communis* (Castor). In another embodiment, the crop plant is *Phaseolus vulgaris* (Bean). In another embodiment, the crop plant is *Gossypium histrum* (Cotton). In another embodiment, the crop plant is *Glycine max* (Soybean). In another embodiment, the crop plant is *Beta vulgaris* (Beet). In another embodiment, the crop plant is *Musa acuminate* (Banana). In another embodiment, the crop plant is *Capsicum annuum* (Sweet and Chili Peppers). In another embodiment, the crop plant is *Cicer arietinum* (Chick pea). In another embodiment, the crop plant is *Solanum lycopersicum* (Tomato). In another embodiment, the crop plant is *Elaeis guineensis* (African oilpalm). In another embodiment, the crop plant is *Setaria italic* (Foxtail millet).

In another embodiment, the crop plant is a food crop. In another embodiment, the crop plant is a nutritionally enhanced food crop.

In another embodiment, a plant of the present invention is an *Arabidopsis*. In one embodiment, the *Arabidopsis* plant is *Arabidopsis thaliana*. In another embodiment, the *Arabidopsis* plant is *Arabidopsis arenicola, Arabidopsis arenosa, Arabidopsis cebennensis, Arabidopsis croatica, Arabidopsis halleri, Arabidopsis lyrata, Arabidopsis neglecta, Arabidopsis pedemontana*, or *Arabidopsis suecica*.

In another embodiment, a plant of the present invention is a moss. In one embodiment, the moss is a Sphagnum. In one embodiment, the Sphagnum species is *cristatum* or *subnitens*. In one embodiment, the moss is used for peat. In one embodiment, peat is used for fuel, as a horticultural soil additive, and in smoking malt in the production of Scotch whisky. In another embodiment, the moss is used for decorative purposes, such as in gardens and in the florist trade. In another embodiment, the moss is used as insulation. In another embodiment, the moss is used as an absorber of liquids. In another embodiment, moss is used for first-aid dressings, for diapers or napkins. In another embodiment, the moss is a *Physcomitrella patens*. In another embodiment, the moss is a *Fontinalis antipyretica* which, in one embodiment, is used to subdue fires.

In one embodiment, the plant is an ornamental plant.

Plants included in the invention are any plants amenable to transformation techniques, including gymnosperms and angiosperms, both monocotyledons and dicotyledons.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, offspring, clone or descendant. Plant extracts and derivatives are also provided.

Algae

In another embodiment, the present invention provides an alga comprising a C-terminal deleted form of an atypical CYS HIS rich thioredoxin 4 (ACHT4) gene.

In one embodiment, the alga is a microalga. In one embodiment, the species of the alga is selected from the following species: *Ankistrodesmus, Botryococcus braunii, Chlorella, Chlorella protothecoides* (autotrophic/heterothrophic), *Crypthecodinium cohnii, Cyclotella, Dunaliella tertiolecta, Gracilaria, Hantzschia, Nannochloris, Nannochloropsis, Neochloris oleoabundans, Nitzschia, Phaeodactylum tricornutum, Pleurochrysis carterae* (also called CCMP647), *Sargassum, Scenedesmus, Schizochytrium, Stichococcus, Tetraselmis suecica,* and *Thalassiosira pseudonana*. In another embodiment, the alga is a *Chlamydomonas reinhardtii*. In another embodiment, the alga is a *Ostreococcus tauri*.

In another embodiment, the present invention provides a polypeptide comprising a C-terminal deleted form of atypical CYS HIS rich thioredoxin 4 (ACHT4).

Proteins and Polypeptides

Polypeptides considered in the present invention are entire proteins or at least a sufficient portion of the entire protein to impart the relevant biological activity of the protein, e.g. enhanced plant phenotype. The term "protein" also includes molecules consisting of one or more polypeptide chains. Thus, a polypeptide useful in the present invention may constitute an entire protein having the desired biological activity, or may constitute a portion of an oligomeric protein having multiple polypeptide chains. Polypeptides useful for generation of genetically modified plants having enhanced properties include the polypeptide provided herein as SEQ ID NOs: 1-43, as well as homologs of such polypeptides.

Figure 4A:
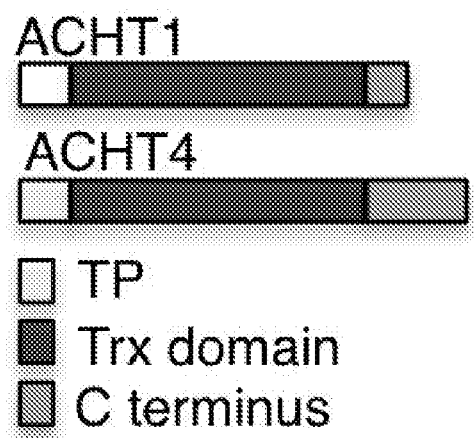
FIG. 4A: Schematic representation comparing ACHT1 and ACHT4 protein sequences. ACHT4 is comprised of a chloroplast targeting transit peptide (TP) followed by a conserved thioredoxin (Trx) domain and long C-terminus domain.
Figure 4B:
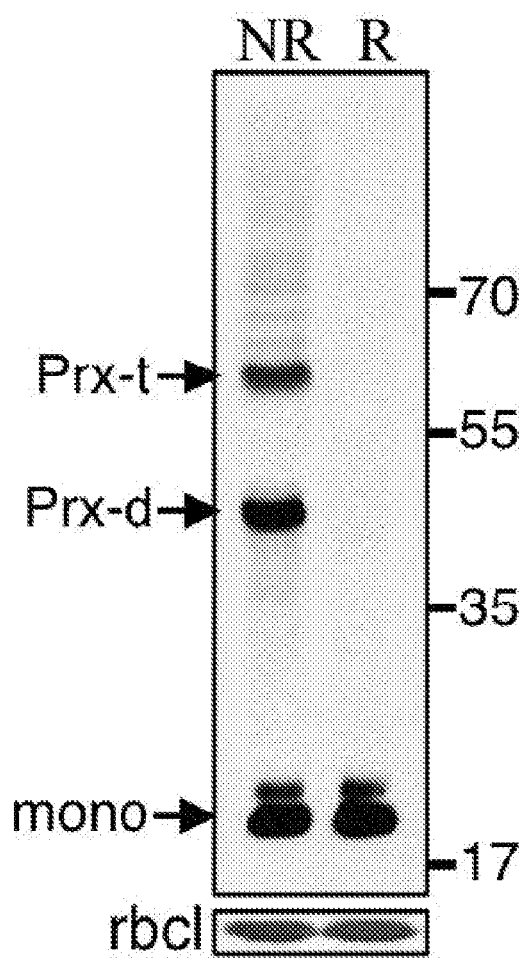
FIG. 4B: Immunoblot assay of intermolecular disulfide complexes of ACHT4ΔC as in FIG. 1B.

In one embodiment, the inactivating mutation in the C-terminal portion of ACHT4 is a deletion of the entire C-terminal domain of ACHT4. In one embodiment, the C-terminal domain of ACHT4 is the sequence that is downstream of the conserved thioredoxin (Trx) domain (as depicted in FIG. 4A). In another embodiment, the inactivating mutation in the C-terminal is a deletion of a portion of the C-terminal domain of ACHT4. In another embodiment, the inactivating mutation in the C-terminal is a deletion of the 47 amino acid C-terminal portion of ACHT4.

In one embodiment, the amino acid sequence of the C-terminal of ACHT4 comprises:

```
                                        (SEQ ID NO: 87)
KELNFTYTPKPVPVEKEAATPDSNPSLPVPLPSMSSNDEKTLVSAGR.
```

In another embodiment, the amino acid sequence of the C-terminal of ACHT4 is a homolog of SEQ ID NO: 87. In another embodiment, the amino acid sequence of the C-terminal of ACHT4 is a paralog of SEQ ID NO: 87. In another embodiment, the amino acid sequence of the C-terminal of ACHT4 is a fragment of SEQ ID NO: 87. In another embodiment, the amino acid sequence of the C-terminal of ACHT4 is a variant of SEQ ID NO: 87. In another embodiment, the amino acid sequence of the C-terminal of ACHT4 comprises SEQ ID NO: 87. In another embodiment, the amino acid sequence of the C-terminal of ACHT4 corresponds to SEQ ID NO: 87.

In another embodiment, the inactivating mutation in the C-terminal is a deletion of the 68-69 amino acid C-terminal portion of ACHT4.

In one embodiment, the amino acid sequence of the C-terminal of ACHT4 comprises:

```
                                        (SEQ ID NO: 88)
AANKDLSFNYTPKTEEAPVLVTSQKEVQDTTPPNIESPLPLPLPLPIAST

SSQTAKRDTEKEAYATSGR.
```

In another embodiment, the amino acid sequence of the C-terminal of ACHT4 comprises:

```
                                        (SEQ ID NO: 89)
AANKDLSFAYTPKTEEPMPVALQDAKVIKTSRTSSSCPNTFSLLPLPLPL

PLASTSHKAKQDSKSEVF.
```

In another embodiment, the amino acid sequence of the C-terminal of ACHT4 is a homolog any one of SEQ ID NOs: 88-89. In another embodiment, the amino acid sequence of the C-terminal of ACHT4 is a paralog any one of SEQ ID NOs: 88-89. In another embodiment, the amino acid sequence of the C-terminal of ACHT4 is a fragment any one of SEQ ID NOs: 88-89. In another embodiment, the amino acid sequence of the C-terminal of ACHT4 is a variant any one of SEQ ID NOs: 88-89. In another embodiment, the amino acid sequence of the C-terminal of ACHT4 comprises any one of SEQ ID NOs: 88-89. In another embodiment, the amino acid sequence of the C-terminal of ACHT4 corresponds to any one of SEQ ID NOs: 88-89.

In another embodiment, the inactivating mutation in the C-terminal is a deletion of the final 47-69 amino acids of the C-terminal portion of ACHT4. In another embodiment, the inactivating mutation in the C-terminal is a deletion of the final 50-75 amino acids of the C-terminal portion of ACHT4. In another embodiment, the inactivating mutation in the C-terminal is a deletion of the final 50-100 amino acids of the C-terminal portion of ACHT4. In another embodiment, the inactivating mutation in the C-terminal is a deletion of the final 25-50 amino acids of the C-terminal portion of ACHT4. In another embodiment, the inactivating mutation in the C-terminal is a deletion of the final 1-25 amino acids of the C-terminal portion of ACHT4. In another embodiment, the inactivating mutation in the C-terminal is a deletion of the final 1-10 amino acids of the C-terminal portion of ACHT4. In another embodiment, the inactivating mutation in the C-terminal is a deletion of the final 25-75 amino acids of the C-terminal portion of ACHT4. In another embodiment, the inactivating mutation in the C-terminal is a deletion of the final 1-20 amino acids of the C-terminal portion of ACHT4. In another embodiment, the inactivating mutation in the C-terminal is a deletion of the final 20-40 amino acids of the C-terminal portion of ACHT4. In another embodiment, the inactivating mutation in the C-terminal is a deletion of the final 40-60 amino acids of the C-terminal portion of ACHT4. In another embodiment, the inactivating mutation in the C-terminal is a deletion of the final 50-70 amino acids of the C-terminal portion of ACHT4.

In one embodiment, an inactivating mutation in the C-terminal of ACHT4 comprises a deletion of amino acids 229-275 of any one of the sequences listed in Table 1 or a corresponding amino acid sequence from another species. In another embodiment, an inactivating mutation in the C-terminal of ACHT4 comprises a deletion of amino acids 250-275 of any one of the sequences listed in Table 1 or a corresponding amino acid sequence from another species. In another embodiment, an inactivating mutation in the C-terminal of ACHT4 comprises a deletion of amino acids 260-275 of any one of the sequences listed in Table 1 or a corresponding amino acid sequence from another species. In another embodiment, an inactivating mutation in the C-terminal of ACHT4 comprises a deletion of amino acids 240-275 of any one of the sequences listed in Table 1 or a corresponding amino acid sequence from another species. In another embodiment, an inactivating mutation in the C-terminal of ACHT4 comprises a deletion of amino acids 229-240 of any one of the sequences listed in Table 1 or a corresponding amino acid sequence from another species. In another embodiment, an inactivating mutation in the C-terminal of ACHT4 comprises a deletion of amino acids 229-250 of any one of the sequences listed in Table 1 or a corresponding amino acid sequence from another species. In another embodiment, an inactivating mutation in the C-terminal of ACHT4 comprises a deletion of amino acids 229-260 of any one of the sequences listed in Table 1 or a corresponding amino acid sequence from another species. In another embodiment, an inactivating mutation in the C-terminal of ACHT4 comprises a deletion of amino acids 229-270 of any one of the sequences listed in Table 1 or a corresponding amino acid sequence from another species.

In another embodiment, an inactivating mutation in the C-terminal of ACHT4 comprises a deletion of amino acids 233-301 of any one of the sequences listed in Table 1 or a corresponding amino acid sequence from another species. In another embodiment, an inactivating mutation in the C-terminal of ACHT4 comprises a deletion of amino acids 240-301 of any one of the sequences listed in Table 1 or a corresponding amino acid sequence from another species. In another embodiment, an inactivating mutation in the C-terminal of ACHT4 comprises a deletion of amino acids 250-301 of any one of the sequences listed in Table 1 or a corresponding amino acid sequence from another species. In another embodiment, an inactivating mutation in the C-terminal of ACHT4 comprises a deletion of amino acids 260-301 of any one of the sequences listed in Table 1 or a corresponding amino acid sequence from another species. In another embodiment, an inactivating mutation in the C-terminal of ACHT4 comprises a deletion of amino acids 275-301 of any one of the sequences listed in Table 1 or a corresponding amino acid sequence from another species. In another embodiment, an inactivating mutation in the C-terminal of ACHT4 comprises a deletion of amino acids 290-301 of any one of the sequences listed in Table 1 or a corresponding amino acid sequence from another species. In another embodiment, an inactivating mutation in the C-terminal of ACHT4 comprises a deletion of amino acids 233-250 of any one of the sequences listed in Table 1 or a corresponding amino acid sequence from another species. In another embodiment, an inactivating mutation in the C-terminal of ACHT4 comprises a deletion of amino acids 233-275 of any one of the sequences listed in Table 1 or a corresponding amino acid sequence from another species. In another embodiment, an inactivating mutation in the C-terminal of ACHT4 comprises a deletion of amino acids 233-290 of any one of the sequences listed in Table 1 or a corresponding amino acid sequence from another species.

In another embodiment, an inactivating mutation in the C-terminal of ACHT4 comprises a deletion of amino acids 162-230 of any one of the sequences listed in Table 1 or a corresponding amino acid sequence from another species. In another embodiment, an inactivating mutation in the C-terminal of ACHT4 comprises a deletion of amino acids 175-230 of any one of the sequences listed in Table 1 or a corresponding amino acid sequence from another species. In another embodiment, an inactivating mutation in the C-terminal of ACHT4 comprises a deletion of amino acids 200-230 of any one of the sequences listed in Table 1 or a corresponding amino acid sequence from another species. In another embodiment, an inactivating mutation in the C-terminal of ACHT4 comprises a deletion of amino acids 220-230 of any one of the sequences listed in Table 1 or a corresponding amino acid sequence from another species. In another embodiment, an inactivating mutation in the C-terminal of ACHT4 comprises a deletion of amino acids 162-175 of any one of the sequences listed in Table 1 or a corresponding amino acid sequence from another species. In another embodiment, an inactivating mutation in the C-terminal of ACHT4 comprises a deletion of amino acids 162-200 of any one of the sequences listed in Table 1 or a corresponding amino acid sequence from another species. In another embodiment, an inactivating mutation in the C-terminal of ACHT4 comprises a deletion of amino acids 162-220 of any one of the sequences listed in Table 1 or a corresponding amino acid sequence from another species.

In another embodiment, an inactivating mutation in the C-terminal of ACHT4 comprises insertion of a non-native sequence into a portion of the C-terminal of ACHT4 encoding the C-terminal of ACHT4, wherein said the C-terminal of ACHT4 is inactivated as a result.

In another embodiment, an inactivating mutation in the C-terminal of ACHT4 comprises substitution of amino acid residues, such as a substitution of polar for non-polar residues, non-polar for polar residues, charged for uncharged residues, positively charged for negatively charged residues, or vice versa, or a combination thereof, as is known to one of skill in the art. In another embodiment, an inactivating mutation in the C-terminal of ACHT4 consists essentially of any of the mutations listed hereinabove. In another embodiment, an inactivating mutation in the C-terminal of ACHT4 consists of any of the mutations listed hereinabove.

In one embodiment, an ACHT4 protein having an inactivating mutation in the C-terminal portion is a truncated ACHT4. In another embodiment, an ACHT4 protein having an inactivating mutation in the C-terminal portion is represented as ACHT4ΔC. In one embodiment, the truncated form of ACHT4 comprises:

(SEQ ID NO: 90)
MTEVISKTSLFLGACGNHHRVDDFSFSPVSFGGFGLKKSFSCLKLKSQKP

LRSVFYGKQIVFGDSQDESFRRSSAITAQTTLRIGTAQKWWEKGLKDNMR

EISSAQELVDSLTNAGDKLVVVDFFSPGCGGCKALHPKICQFAEMNPDVQ

FLQVNYEEHKSMCYSLGVHVLPFFRFYRGSQGRVCSFSCTNATIKKFRDA

LAKHGPDRCSLGPTKGLEEKELVALAAN.

In another embodiment, the truncated form of ACHT4 comprises:

```
                                                (SEQ ID NO: 91)
MMKLMSKGFMFPSSSDCGEIYHHRPLNLPGICSFPNKSVNLSCLPSLNLS

SSCLPRTDFYGRRLVINEGVSKFNRRNSQVVDITAQMSIGIRKAQKWWEK

GVQPNMKEVNSAQELVDSLLSAGDKLVVVDFFSPGCGGCKALHPKLCQLA

EMNPDVHFLQVNYEEHKSMCYSLNVHVLPFFRFYRGAEGRVCSFSCTNAT

IKKFKDALAKYGTDRCTLGPPKGLEEKELLAL.
```

In another embodiment, the truncated form of ACHT4 comprises:

```
                                                (SEQ ID NO: 92)
MKFNRRNHKSAAATAQMSIGIRKAPKWWEKGLQPNMKEVMGAQDLADTLL

NAGDKLVVVDFLSPGCGGCKALHPKICQLAEMNPDVQFLHVNYEEHKSMC

YSLNVHVLPFFRFYRGAEGRLCSFSCTNATIKKFKDALTKYGADCCSLEP

VKGLEEKELLAL.
```

In another embodiment, the amino acid sequence of the C-terminal of ACHT4 is a homolog any one of SEQ ID NOs: 90-92. In another embodiment, the amino acid sequence of the C-terminal of ACHT4 is a paralog any one of SEQ ID NOs: 90-92. In another embodiment, the amino acid sequence of the C-terminal of ACHT4 is a fragment any one of SEQ ID NOs: 90-92. In another embodiment, the amino acid sequence of the C-terminal of ACHT4 is a variant any one of SEQ ID NOs: 90-92. In another embodiment, the amino acid sequence of the C-terminal of ACHT4 comprises any one of SEQ ID NOs: 90-92. In another embodiment, the amino acid sequence of the C-terminal of ACHT4 corresponds to any one of SEQ ID NOs: 90-92.

Homologs of the polypeptides of the present invention may be identified by comparison of the amino acid sequence of the polypeptide to amino acid sequences of polypeptides from the same or different plant sources, e.g. manually or by using known homology-based search algorithms such as those commonly known and referred to as BLAST, FASTA, and Smith-Waterman. As used herein, a homolog is a peptide from the same or a different organism that performs the same biological function as the polypeptide to which it is compared. An orthologous relation between two organisms is not necessarily manifest as a one-to-one correspondence between two genes, because a gene can be duplicated or deleted after organism phylogenetic separation, such as speciation. For a given polypeptide, there may be no ortholog or more than one ortholog. Other complicating factors include alternatively spliced transcripts from the same gene, limited gene identification, redundant copies of the same gene with different sequence lengths or corrected sequence. A local sequence alignment program, e.g. BLAST, can be used to search a database of sequences to find similar sequences, and the summary Expectation value (E-value) used to measure the sequence base similarity.

A further aspect of the invention comprises functional homolog proteins which differ in one or more amino acids from those of a polypeptide provided herein as the result of one or more of the well-known conservative amino acid substitutions, e.g. valine is a conservative substitute for alanine and threonine is a conservative substitute for serine. Conservative substitutions for an amino acid within the native polypeptide sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine. A further aspect of the invention comprises polypeptides that differ in one or more amino acids from those of a described protein sequence as the result of deletion or insertion of one or more amino acids in a native sequence.

Homologs of the polypeptides provided herein will generally demonstrate significant identity with the polypeptides provided herein. In one embodiment, the present invention provides polypeptides with at least about 50% sequence identity. In one embodiment, the present invention provides polypeptides with at least about 70% sequence identity. In one embodiment, the present invention provides polypeptides with at least about 80% sequence identity with an amino acid sequence of any of the amino acid sequences listed in Table 1. In one embodiment, the present invention provides polypeptides with higher identity to such a polypeptide sequence, e.g. 90% to 990, identity. Identity of protein homologs is determined by optimally aligning the amino acid sequence of a putative protein homolog with a defined amino acid sequence and by calculating the percentage of identical and conservatively substituted amino acids over the window of comparison. Preferentially, the window of comparison for determining identity is the entire polypeptide sequence disclosed herein, e.g. the full sequence of any one of the sequences listed in Table 1.

In another embodiment, the present invention provides a composition comprising a polypeptide comprising a C-terminal deleted form of atypical CYS HIS rich thioredoxin 4 (ACHT4).

Methods of Use for Plants Expressing ACHT4ΔC

In another embodiment, the present invention provides a method of increasing the yield of a plant or algae comprising contacting a cell from said plant or algae with a polynucleotide encoding a C-terminal deleted form of atypical CYS HIS rich thioredoxin 4 (ACHT4), thereby increasing the yield of said plant or algae.

In another embodiment, the present invention provides a method of increasing the productivity of a plant or algae comprising contacting a cell from said plant or algae with a polynucleotide encoding a C-terminal deleted form of atypical CYS HIS rich thioredoxin 4 (ACHT4), thereby increasing the productivity of said plant or algae.

In another embodiment, the present invention provides a method of increasing the size of a plant or algae comprising contacting a cell from said plant or algae with a polynucleotide encoding a C-terminal deleted form of atypical CYS HIS rich thioredoxin 4 (ACHT4), thereby increasing the size of said plant or algae.

In another embodiment, the present invention provides a method of increasing the biomass of a plant or algae comprising contacting a cell from said plant or algae with a polynucleotide encoding a C-terminal deleted form of atypical CYS HIS rich thioredoxin 4 (ACHT4), thereby increasing the biomass of said plant or algae.

In another embodiment, the present invention provides a method of stimulating the growth of a plant or algae comprising contacting a cell from said plant or algae with a polynucleotide encoding a C-terminal deleted form of atypical CYS HIS rich thioredoxin 4 (ACHT4), thereby stimulating the growth of said plant or algae.

In another embodiment, the present invention provides a method of enhancing the starch content of a plant or algae comprising contacting a cell from said plant or algae with a polynucleotide encoding a C-terminal deleted form of atypical CYS HIS rich thioredoxin 4 (ACHT4), thereby enhancing the starch content of said plant or algae.

In one embodiment, the plant or algae has enhanced starch in transitory starch stores. In another embodiment, the plant or algae has enhanced starch in non-transitory starch stores. In one embodiment, the plant has enhanced starch content in one or more leaves. In another embodiment, the plant has enhanced starch content in the roots. In another embodiment, the plant has enhanced starch content in the stem. In another embodiment, the plant has enhanced starch content in one or more seeds. In another embodiment, the plant has enhanced starch content in its tubers. In another embodiment, the plant has enhanced starch content in its fruit. In another embodiment, the plant has enhanced starch content in one or more of its flowers.

In one embodiment, the present invention provides methods comprising the step of "contacting" a cell with a polynucleotide or expression vector as described herein. In one embodiment, plants are genetically modified using a microbial vector comprising ACHT4ΔC. In one embodiment, the microbial vector is *Agrobacterium tumefaciens*. In another embodiment, plants are genetically modified using microprojectile bombardment. In one embodiment, corn, rice, and other cereal grains are genetically modified using microprojectile bombardment. In another embodiment, plants are genetically modified using electroporation. In another embodiment, plants are genetically modified using microinjection, which in one embodiment, is direct microinjection of genetically modified DNA into anchored cells. In another embodiment, plants are genetically modified using transposons or transposable elements.

In one embodiment, the step of contacting is performed in vitro. In another embodiment, the step of contacting is performed in vivo.

In one embodiment, the ACHT4ΔC is integrated into the plant or algae chromosome. In another embodiment, the ACHT4ΔCis expressed from a vector.

Methods of Producing Genetically Modified Plants

In another embodiment, the present invention provides a method of producing a plant having an enhanced phenotype, wherein said method comprises transforming plant cells with a recombinant polynucleotide encoding an atypical CYS HIS rich thioredoxin 4 (ACHT4) protein, wherein the C-terminal portion of said ACHT4 protein comprises an inactivating mutation, regenerating plants from said cells, and screening said plants to identify a plant having an enhanced phenotype.

In another embodiment, the present invention provides a method of producing an algae having an enhanced phenotype, wherein said method comprises delivering a recombinant polynucleotide encoding an atypical CYS HIS rich thioredoxin 4 (ACHT4) protein to algae cells, wherein the C-terminal portion of said ACHT4 protein comprises an inactivating mutation, growing algae from said cells, and screening said algae to identify a plant having an enhanced phenotype.

Genetically modified plant seed provided by this invention may be grown to generate genetically modified plants having an enhanced phenotype as compared to an appropriate control line. Such seed is obtained by screening transformed plants for enhanced phenotypes resulting from the introduction of a recombinant polynucleotide into the genomic DNA of tissue from a parental line. The recombinant polynucleotide is introduced into the genome to produce genetically modified cells that can be cultured into genetically modified plants having an enhanced phenotype as compared to the parental line or other appropriate control. Such genetically modified cells are cultured into genetically modified plants that produce progeny genetically modified seed. Preferably, multiple genetically modified plants (events) comprising the recombinant polynucleotides are evaluated, e.g. from 2 to 20 or more genetically modified events, to identify a desired enhanced phenotype. Although the design of a recombinant polynucleotide is based on a rational expectation of a phenotypic modification, the present invention also contemplates that unexpected, yet desired enhanced phenotypes may be obtained.

Genetically modified plants grown from genetically modified seed as described herein will have improved phenotypes that contribute to increased yield or other increased plant value, including, for example, improved seed quality. Of particular interest are plants having altered cell division, enhanced plant growth and development, stress tolerance, including tolerance to abiotic and biotic stress, altered seed or flower development, improved light response, and enhanced carbon and/or nitrogen metabolism, transport or utilization properties.

Genetic Modification

In one embodiment, the present invention provides a cisgenic plant. In one embodiment, a cisgenic plant of the present invention is genetically modified, in one embodiment, comprises a second copy of a gene in which a portion of said gene is deleted, but contains no foreign or heterologous genes. In one embodiment, the promoters used in the expression of ACHT4ΔC are cisgenic. In one embodiment, food crops of the present invention are cisgenic.

In another embodiment, the present invention provides a transgenic plant. In one embodiment, a transgenic plant of the present invention is genetically modified with foreign or heterologous genes. In one embodiment, transgenic plants of the present invention are used for biofuel. In another embodiment, transgenic plants of the present invention are food crop plants.

Any method or delivery system may be used for the delivery and/or transformation (plant cells)/transfection (algae cells) of the nucleic acid vectors encoding ACHT4 and homologs, paralogs, etc. in the host cell, e.g., plant protoplast. The vectors may be delivered to the host cell either alone, or in combination with other agents. Transient expression systems may also be used. Homologous recombination may also be used.

Transformation may be accomplished by a wide variety of means, as is known to those of ordinary skill in the art. Such methods include, but are not limited to, *Agrobacterium-* mediated transformation (e.g., Komari et al., 1998, Curr. Opin. Plant Biol., 1:161), including floral dip transformation, particle bombardment mediated transformation (e.g., Finer et al., 1999, Curr. Top. Microbiol. Immunol., 240:59), protoplast electroporation (e.g., Bates, 1999, Methods Mol. Biol., 111:359), viral infection (e.g., Porta and Lomonossoff, 1996, Mol. Biotechnol. 5:209), microinjection, and liposome injection. Other exemplary delivery systems that can be used to facilitate uptake by a cell of the nucleic acid include calcium phosphate and other chemical mediators of intracellular transport, microinjection compositions, and homologous recombination compositions (e.g., for integrating a gene into a preselected location within the chromosome of the cell). Alternative methods may involve, for example, the use of liposomes, electroporation, or chemicals that increase free (or "naked") DNA uptake, transformation using viruses or pollen and the use of microprojection. Standard molecular biology techniques are common in the art (e.g., Sambrook et al., 1989, Molecular Cloning: A Laboratory Manual, 2nd ed., Cold Spring Harbor Laboratory Press, New York).

For the *Agrobacterium tumefaciens*-based plant transformation system, additional elements present on transformation constructs will, in one embodiment, include T-DNA left and right border sequences to facilitate incorporation of the recombinant polynucleotide into the plant genome.

In one embodiment, DNA is inserted randomly, i.e. at a non-specific location, in the genome of a target plant line. In another embodiment, DNA insertion is targeted in order to achieve site-specific integration, e.g. to replace an existing gene in the genome, to use an existing promoter in the plant genome, or to insert a recombinant polynucleotide at a predetermined site known to be active for gene expression. Several site specific recombination systems exist which are known to function in plants including cre-lox and FLP-FRT.

Transformation methods of this invention are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making genetically modified plants of this invention, e.g. various media and recipient target cells, transformation of immature embryos and subsequent regeneration of fertile genetically modified plants are known in the art.

In one embodiment, the method of transformation of algae comprises any of the methods as described hereinabove. In one embodiment, transformation of algae is accomplished using glass bead-assisted transformation, particle gun-mediated (biolistic) transformation, treatment with cellulolytic enzymes to weaken their cell walls, or homologous recombination.

Markers of Genetic Transformation

In one embodiment, DNA is introduced into only a small percentage of target cells in any one experiment. Marker genes are used to provide an efficient system for identification of those cells that are stably transformed by receiving and integrating a genetically modified DNA construct into their genomes. Preferred marker genes provide selective markers that confer resistance to a selective agent, such as an antibiotic or herbicide. Potentially transformed cells are exposed to the selective agent. In the population of surviving cells will be those cells where, generally, the resistance-conferring gene has been integrated and expressed at sufficient levels to permit cell survival. Cells may be tested further to confirm stable integration of the exogenous DNA. Useful selective marker genes include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS).

Screenable markers which provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known. It is also contemplated that combinations of screenable and selectable markers will be useful for identification of transformed cells.

Cells that survive exposure to the selective agent, or cells that have been scored positive in a screening assay, may be cultured in regeneration media and allowed to mature into plants. Developing plantlets can be transferred to soil less plant growth mix, and hardened off, e.g., in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are preferably matured either in a growth chamber or greenhouse. Plants are regenerated from about 6 weeks to 10 months after a transformant is identified, depending on the initial tissue. During regeneration, cells are grown to plants on solid media at about 19 to 28° C. After regenerating plants have reached the stage of shoot and root development, they may be transferred to a greenhouse for further growth and testing. Plants may be pollinated using conventional plant breeding methods known to those of skill in the art and seed produced.

Progeny may be recovered from transformed plants and tested for expression of the exogenous recombinant polynucleotide. Useful assays include, for example, "molecular biological" assays, such as Southern and Northern blotting and PCR; "biochemical" assays, such as detecting the presence of RNA, e.g. double stranded RNA, or a protein product, e.g., by immunological means (ELISAs and Western blots) or by enzymatic function; plant part assays, such as leaf or root assays; and also, by analyzing the phenotype of the whole regenerated plant.

One of skill in the art will be able to select an appropriate vector for introducing the encoding nucleic acid sequence in a relatively intact state. Thus, any vector which will produce a host cell, e.g., plant protoplast, carrying the introduced encoding nucleic acid should be sufficient. The selection of the vector, or whether to use a vector, is typically guided by the method of transformation selected.

Plant Regeneration

Following transformation, plant cells transformed with a plant expression vector may be regenerated, e.g., from single cells, callus tissue or leaf discs according to standard plant tissue culture techniques. Almost any plant can be entirely regenerated from cells, tissues, and organs of the plant using methods that are known in the art.

The transformed plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

Normally, a plant cell is regenerated to obtain a whole plant from the transformation process. The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension. The culture media will generally contain various amino acids and hormones, necessary for growth and regeneration. Examples of hormones utilized include auxins and cytokinins. Efficient regeneration will depend on the medium, on the genotype, and on the history of the culture. If these variables are controlled, regeneration is reproducible. Regeneration also occurs from plant callus, explants, organs or parts.

In vegetatively propagated crops, the mature genetically modified plants are propagated by utilizing cuttings or tissue culture techniques to produce multiple identical plants. Selection of desirable genetically modified plants is made and new varieties are obtained and propagated vegetatively for commercial use.

In seed propagated crops, mature genetically modified plants can be self-crossed to produce a homozygous inbred plant. The resulting inbred plant produces seed containing the genetic mutation. These seeds can be grown to produce plants that would produce the selected phenotype, e.g., increased lateral root growth, uptake of nutrients, overall plant growth and/or vegetative or reproductive yields.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences. Genetically modified plants expressing a selectable marker can be screened for transmission of the nucleic acid of the present invention by, for example, standard immunoblot and DNA detection techniques. Genetically modified plant cells are also typically evaluated on levels of expression of the genetically modified nucleic acid. Expression at the RNA level can be determined initially to identify and quantitate expression-positive plants. Standard techniques for RNA analysis can be employed and include PCR amplification assays using oligonucleotide primers designed to amplify only the genetically modified RNA templates and solution hybridization assays using genetically modified nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using genetically modified nucleic acid specific polynucleotide probes and antibodies, respectively, to localize sites of expression within genetically modified tissue. Generally, a number of genetically modified lines are usually screened for the incorporated nucleic acid to identify and select plants with the most appropriate expression profiles.

In one embodiment, the present invention provides a genetically modified plant that is homozygous for the introduced genetically modified nucleic acid; i.e., a genetically modified plant that contains two added nucleic acid sequences, one gene at the same locus on each chromosome of a chromosome pair. A homozygous genetically modified plant can be obtained by sexually mating (selfing) a heterozygous genetically modified plant that contains a single added genetically modified nucleic acid, germinating some of the seed produced and analyzing the resulting plants produced for altered expression of a polynucleotide of the present invention relative to a control plant (i.e., native, non-genetically modified). Back-crossing to a parental plant and out-crossing with a non-genetically modified plant are also contemplated.

Transformed plant cells which are derived by any of the above transformation techniques can be cultured to regenerate a whole plant which possesses the transformed genotype. Such regeneration techniques often rely on manipulation of certain phytohormones in a tissue culture growth medium.

Products of Genetically Modified Plants and Algae

Engineered plants exhibiting the desired physiological and/or agronomic changes can be used directly in agricultural production.

Thus, provided herein are products derived from the genetically modified plants or methods of producing genetically modified plants provided herein. In certain embodiments, the products are commercial products. Some non-limiting example include genetically engineered trees for e.g., the production of pulp, paper, paper products or lumber; tobacco, e.g., for the production of cigarettes, cigars, or chewing tobacco: crops, e.g., for the production of fruits, vegetables and other food, including grains, e.g., for the production of wheat, bread, flour, rice, corn; and canola, sunflower, e.g., for the production of oils or biofuels.

Biofuels

In one embodiment, biofuels are derived from a genetically engineered plant or algae of the present invention.

In one embodiment, a biofuel is a fuel that is produced through contemporary biological processes, such as agriculture and anaerobic digestion, as opposed to a fuel produced by geological processes such as those involved in the formation of fossil fuels, such as coal and petroleum, from prehistoric biological matter. Biofuels can be derived directly from plants, or indirectly from agricultural wastes.

In one embodiment, plants or plant parts as described herein are used as biofuel.

In one embodiment, algae are used as a biofuel. In one embodiment, the biofuel is selected from the group consisting of: biodiesel, ethanol, biojet fuel, and green gasoline.

In one embodiment, the biofuel is an alcohol fuel, such as bioethanol. In one embodiment, the bioethanol is produced by fermentation of sugars derived from wheat, corn, sugar beets, sugar cane, molasses, or a combination thereof. In another embodiment, the bioethanol is produced by fermentation of any sugar or starch from which alcoholic beverages such as whiskey, can be made (such as barley, potato and fruit waste, etc).

Thus, in one embodiment, the present invention provides a biofuel comprising genetically modified plants or plant parts of the present invention. In one embodiment, the present invention provides a process of producing a biofuel comprising: delivering a recombinant polynucleotide encoding a C-terminal-inactivated ACHT4 to plant or algae cells, regenerating plants or algae from said cells, screening said plants or algae to identify a plant having enhanced yield, extracting sugar or starch from some or all portions of said plant or algae or progeny thereof, fermenting said sugars to produce an alcoholic mixture, and distilling said alcohol from said mixture. Methods for producing biofuels from plants and plant parts are known in the art.

In one embodiment, algae are a sustainable source for essential omega-3 fatty acids.

In another embodiment, algae of the present invention are used as commodity animal feeds. In another embodiment, algae of the present invention are used as a source for foods. In one embodiment, essential omega-3 fatty acids from algae are used in infant formula and other food products and vitamins. In another embodiment, carbohydrates and emulsifiers produced from seaweeds are used in food products. In another embodiment, *Spirulina* is used in food products.

In another embodiment, algae of the present invention are used as a source for specialty feeds.

In one embodiment, algae contain carbohydrates, proteins, vegetable oils, micronutrients, vitamins, as well as valuable pigments used in animal feeds, such as beta carotene, lutein and astaxanthin. In another embodiment, algae is used as a source of feed in aquaculture operations, including as feed for fish and shellfish like clams, oysters, mussels and scallops.

In another embodiment, algae of the present invention are used as a source for chemicals. In one embodiment, the chemical is a plastic. In one embodiment, the chemical is a fertilizer. In one embodiment, the alga is seaweed. In one embodiment, some microalgae fix atmospheric nitrogen and could be a source of organic fertilizers ("green manure").

In another embodiment, algae of the present invention are used as a source for cosmetics. In one embodiment, the cosmetic is a skin-care product. In one embodiment, the cosmetic provide UV protection. In another embodiment, algae of the present invention are used as a source for pharmaceuticals.

In one embodiment, multiple products from the same algal biomass are possible.

In certain embodiments, commercial products are derived from a genetically engineered species of woody, ornamental or decorative, crop or cereal, fruit or vegetable plant, and algae (e.g., *Chlamydomonas reinhardii*), which may be used in the compositions and methods provided herein. Non-limiting examples of plants include plants from the genus *Arabidopsis* or the genus *Oryza*. Other examples include plants from the genuses *Acorus, Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea*, or *Zinnia*.

In some embodiments, commercial products are derived from a genetically engineered gymnosperms and angiosperms, both monocotyledons and dicotyledons. Examples of monocotyledonous angiosperms include, but are not limited to, asparagus, field and sweet corn, barley, wheat, rice, sorghum, onion, pearl millet, rye and oats and other cereal grains. Examples of dicotyledonous angiosperms include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals.

In certain embodiments, commercial products are derived from a genetically engineered woody species, such as poplar, pine, *sequoia*, cedar, oak, etc.

In other embodiments, commercial products are derived from a genetically engineered plant including, but are not limited to, wheat, cauliflower, tomato, tobacco, corn, petunia, trees, etc.

In certain embodiments, commercial products are derived from genetically engineered crop plants, for example, cereals and pulses, maize, wheat, potatoes, tapioca, rice, *sorghum*, millet, cassava, barley, pea, and other root, tuber, or seed crops. In one embodiment, commercial products are derived from a genetically engineered cereal crops, including, but are not limited to, any species of grass, or grain plant (e.g., barley, corn, oats, rice, wild rice, rye, wheat, millet, *sorghum*, triticale, etc.), non-grass plants (e.g., buckwheat flax, legumes or soybeans, etc.). In another embodiment, commercial products are derived from a genetically engineered grain plants that provide seeds of interest, oil-seed plants and leguminous plants. In other embodiments, commercial products are derived from a genetically engineered grain seed, such as corn, wheat, barley, rice, *sorghum*, rye, etc. In yet other embodiments, commercial products are derived from a genetically engineered oil seed plants, such as cotton, soybean, safflower, sunflower, *Brassica*, maize, alfalfa, palm, coconut, etc. In certain embodiments, commercial products are derived from a genetically engineered oil-seed rape, sugar beet, maize, sunflower, soybean, or *sorghum*. In some embodiments, commercial products are derived from genetically engineered leguminous plants, such as beans and peas (e.g., guar, locust bean, fenugreek, soybean, garden beans, cowpea, mungbean, lima bean, fava bean, lentils, chickpea, etc.)

In certain embodiments, commercial products are derived from a genetically engineered horticultural plant of the present invention, such as lettuce, endive, and vegetable brassicas including cabbage, broccoli, and cauliflower, and carnations and geraniums; tomato, tobacco, cucurbits, carrot, strawberry, sunflower, tomato, pepper, chrysanthemum, poplar, eucalyptus, and pine.

In still other embodiments, commercial products are derived from a genetically engineered corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum, Nicotiana benthamiana*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Peryea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prinus amygdalus*), sugar beets (*Beta vulgaris*), oats, barley, *Arabidopsis* spp., vegetables, ornamentals, and conifers.

Enhanced Phenotype

In one embodiment, "enhanced phenotype" as used herein refers to a measurable improvement in a crop trait including, but not limited to, yield increase, including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. Many agronomic traits can affect "yield", including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Other traits that can affect yield include, efficiency of germination (including germination in stressed conditions), growth rate (including growth rate in stressed conditions), seed size, composition of seed (starch, oil, protein) and characteristics of seed fill.

In another embodiment, the present invention also provides genetically modified plants that demonstrate enhanced phenotypic properties that may or may not confer an increase in overall plant yield. Such properties include enhanced plant morphology, plant physiology or enhanced components of the mature seed harvested from the genetically modified plant. In another embodiment, the present invention also provides genetically modified plants with enhancements in seed oil, tocopherol, protein and starch components, including increases in the quantity of any of these components, alterations in the ratios of any of these components, or production of new types of these components that do not exist in the seed from control plants. By way of example, increases in total tocopherol content are desirable, as are increases in the relative percentage of alpha-tocopherol produced by plants.

In one embodiment, "increased yield" of a genetically modified plant of the present invention may be evidenced and measured in a number of ways, including test weight, seed number per plant, seed weight, seed number per unit area (i.e. seeds, or weight of seeds, per acre), bushels per acre, tonnes per acre, tons per acre, kilo per hectare. Increased yield may result from improved utilization of key biochemical compounds, such as nitrogen, phosphorous and carbohydrate, or from improved responses to environmental stresses, such as cold, heat, drought, salt, and attack by pests or pathogens. Polynucleotides of the present invention may also be used to provide plants having improved growth and development, and ultimately increased yield, as the result of modified expression of plant growth regulators or modification of cell cycle or photosynthesis pathways.

Use for Gene Suppression

In one embodiment, polynucleotides of the present invention include recombinant polynucleotides providing for expression of mRNA encoding a polypeptide. In another embodiment, polynucleotides of the present invention include recombinant polynucleotides providing for expression of mRNA complementary to at least a portion of an mRNA native to the target plant for use in suppression of the ACHT4 gene.

In one embodiment, "gene suppression" is used herein to refer to reduction or suppression of expression of a target protein in a host cell as the result of transcription of a recombinant polynucleotide provided herein, wherein the polynucleotide is oriented with respect to a promoter to provide for production of RNA having a gene silencing effect, such as antisense RNA or interfering RNA (RNAi).

Other Methods of Down-Regulating ACHT4 Protein Expression in Plants and Algae

In another embodiment, the present invention provides an antibody against a polypeptide comprising a C-terminal deleted form of atypical CYS HIS rich thioredoxin 4 (ACHT4).

In one embodiment, down-regulation of ACHT4 protein is partial. In another embodiment, the down-regulation completely eliminates protein activity by decreasing overall steady state levels of the protein associated therewith.

In one embodiment, down-regulation of ACHT4 protein comprises decreasing the levels of ACHT4 protein. In another embodiment, down-regulation of ACHT4 protein comprises decreasing the activity of ACHT4 protein.

In one embodiment, the down-regulation is achieved by antisense RNA. In another embodiment, the down-regulation is achieved by ribozyme technology, which, in one embodiment, works at the RNA translational level and involves making catalytic RNA molecules which bind to and cleave the mRNA of interest. Both of these were found effective in regulating protein levels in plants. In another embodiment, the down-regulation is achieved by co-suppression.

In another embodiment, the down-regulation is achieved using antibodies. In one embodiment, the antibody is a monoclonal antibody. In another embodiment, the down-regulation is achieved using functional fragments of antibodies, which in one embodiment, is a single chain antibody (SCAb).

In one embodiment, the antibody binds to ACHT4ΔC. In another embodiment, the antibody binds to ACHT4.

In another embodiment, the present invention provides methods for using antibodies to ACHT4 and/or ACHT4ΔC as described herein and functional fragments thereof (e.g., Fv or Fab fragments), for increasing plant or algae yield and/or growth comprising administering said antibody to a plant or alga. Methods for producing antibodies and functional fragments of antibodies are known in the art.

In another embodiment, the present invention provides methods for using antisense RNA, ribozymes, etc for increasing plant or algae yield and/or growth comprising transforming said plant or alga with said RNA or ribozyme.

Combinations of Modified Genetic Traits

The present invention also encompasses genetically modified plants with stacked engineered traits, e.g. a crop having an enhanced phenotype resulting from expression of a recombinant polynucleotide provided herein, in combination with herbicide and/or pest resistance traits. For example, genes of the current invention can be stacked with other traits of agronomic interest, such as a trait providing herbicide resistance, for example a RoundUp Ready trait, or insect resistance, such as using a gene from *Bacillus thuringensis* to provide resistance against lepidopteran, coliopteran, homopteran, hemiopteran, and other insects. Herbicides for which resistance is useful in a plant include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides and gluphosinate herbicides.

All patents, patent applications, and scientific publications cited herein are hereby incorporated by reference in their entirety.

The following examples are presented in order to more fully illustrate the preferred embodiments of the invention. They should in no way be construed, however, as limiting the broad scope of the invention.

EXAMPLES

Example 1

ACHT4-Driven Oxidation of APS1 Attenuates Starch Synthesis Under Low Light Intensity in *Arabidopsis* Plants Materials and Methods Plant Material and Growth Conditions

*Arabidopsis thaliana* var Columbia were grown under a 8/16 h light/dark cycle at 20° C./18° C., respectively, at 80 µE*m−2*s−1 (unless otherwise stated) for 3-4 weeks. Thylakoid membranes were isolated as previously described.

Generation of Genetically Modified Plants

ACHT4, ACHT4MT (in which the non-nucleophilic cysteine of the active site was replaced with a serine), ACHT4ΔC and ACHT1 open reading frames were ligated upstream and in frame of the HA3 affinity tag and under the control of the 35S promotor into pART7 vector. All four constructs were used to transform *Arabidopsis* leaves using a standard floral dip transformation protocol (Clough and Bent Plant J. 1998 December; 16(6):735-43, incorporated herein by reference in its entirety). In short, the floral dip transformation method involves simple dipping of developing floral tissues into a solution containing *Agrobacterium tumefaciens*, 5% sucrose and 500 microliters per litre of surfactant Silwet L-77.

Protein Redox Assays, Immunoblot and Affinity Purification Analyses

The disulfide state of plant-extracted proteins, the identification of intermolecular disulfide complexes, and their isolation by immunoprecipitation were assayed in planta as previously described. The mass-spectrometry (MS) analysis is detailed in Table 3.

TABLE 3

Identification of 2-Cys Prx and APS1 as ACHT4 targets by mass-spectrometry

| Protein name | Queries matched | Score | Protein sequence coverage (%) | Protein length (aa) |
|---|---|---|---|---|
| 2-CYS-PRX | APDFEAEAVFDQEFIK (3) (SEQ ID NO: 93) LNTEVLGVSVDSVFSHLAWVQTDR (2) (SEQ ID NO: 94) SGGLGDLNYPLISDVTK (2) (SEQ ID NO: 95) SFGVLIHDQGIALR (2) (SEQ ID NO: 96) GLFIIDK (1) (SEQ ID NO: 97) EGVIQHSTINNLGIGR (1) (SEQ ID NO: 98) TLQALQYIQENPDEVCPAGWKPGEK (2) (SEQ ID NO: 99) | 478 | 44 | 266 |
| APS1 | LIDIPVSNCLNSNISK (1) (SEQ ID NO: 100) IYVLTQFNSASLNR (2) (SEQ ID NO: 101) NEGFVENTLAAQQSPENPNWFQGTADAVR (4) (SEQ ID NO: 102) ETDADITVAALPMDEQR (1) (SEQ ID NO: 103) VDTTILGLDDQR (1) (SEQ ID NO: 104) EMPFIASMGIYVVSR (1) (SEQ ID NO: 105) NQFPGANDFGSEVIPGATSLGLR (3) (SEQ ID NO: 106) VQAYLYDGYWEDIGTIEAFYNANLGITK (1) (SEQ ID NO: 107) KPVPDFSFYDR (1) (SEQ ID NO: 108) MLDADVTDSVIGEGCVIK (1) (SEQ ID NO: 109) IINSDNVQEAAR (1) (SEQ ID NO: 110) | 572 | 37 | 520 |

The Mass-spectrometry analysis was performed by the Biological Mass Spectrometry Unit at Weizmann Institute of Science by online reversed-phase nano-liquid chromatography, electrospray ionization tandem mass spectrometric analyses. Survey scans were recorded in the FT-mode followed by data-dependent collision-induced dissociation of the 7 most intense ions in the linear ion trap. Raw spectra were processed using open-source software DTA Super-Charge. The data were searched with MASCOT (Matrix Science, London, UK) against a Swissprot or NCBI database. Control samples treated with DTT or derived from wild-type plants, allowed for the subtraction of nonspecific background proteins.

Trapped intermolecular disulfide protein complexes were incubated overnight at 4° C. in RIPA buffer (1% sodium deoxycholate, 0.1% SDS, 1% Triton X-100, 10 mM Tris-HCl, pH 8, and 140 mM NaCl) with either anti-HA (Sigma A2095) resin or anti-2-Cys Prx- or anti-APS1-coated protein G beads (Amersham). The proteins were eluted with either reducing or nonreducing 2× sample buffer and separated on SDS-PAGE gels for immunoblots or for MS analysis. Anti-APS1 polyclonal antibodies were raised in rabbits at GenScript HK Ltd., using a purified peptide (CILGLDDQRAKEMPF (SEQ ID NO: 111)). 2-Cys Prx-specific polyclonal antibodies were as in Dangoor, 2009 Plant Physiol. 149:1240-1250, which is incorporated herein by reference in its entirety. Mouse monoclonal anti-HA antibodies (SIGMA H9658) were used in protein blot assays.

Starch Analysis

Starch content of 0.8 g samples of two month-old rosettes was analyzed using the SIGMA starch assay kit (SA20-1KT). Every replicate included ten rosettes.

Accession Numbers

Sequence data can be found in the *Arabidopsis* Genome Initiative or GenBank/EMBL databases under the following accession numbers: ACHT4 (AT1G08570), 2-Cys PrxA (At3g11630), and APS1 (AT5G48300).

Results

Reoxidation of ACHT4 by 2-Cys Prx Shortly after Illumination

Figure 1A:
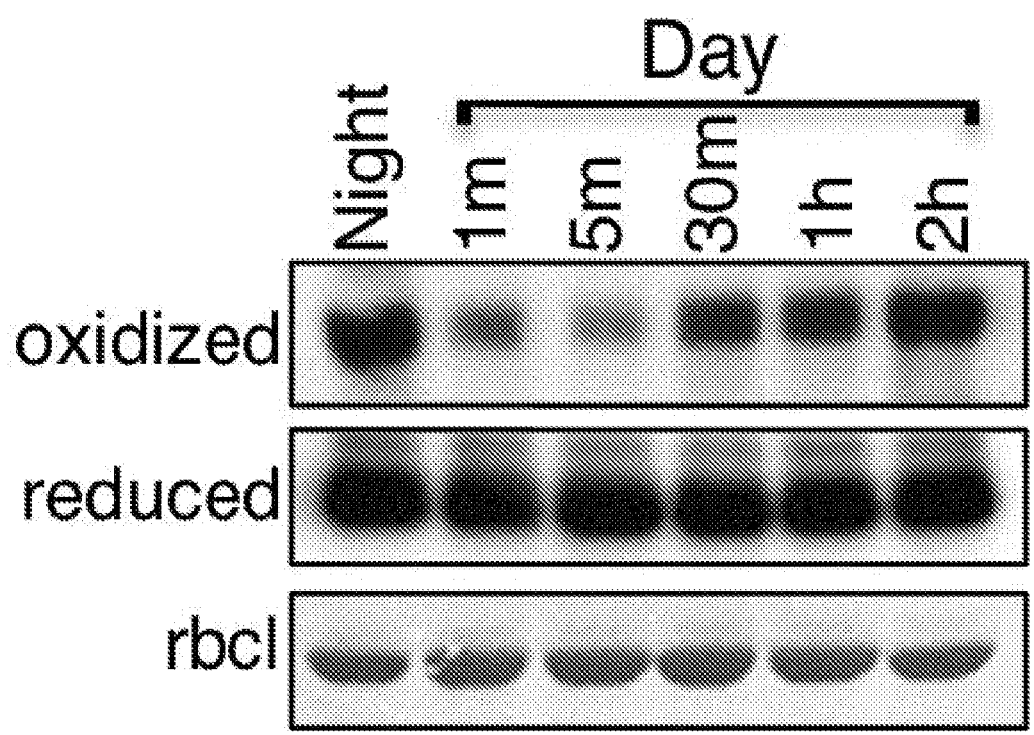
FIG. 1A: Immunoblot assay showing the oxidized state of ACHT4 active-site Cys residues captured in plants expressing ACHT4 fused with HA-tag at the end of the night (oxidized) and at 1 min (m), 5 min, 30 min, 1 h, and 2 h after beginning of illumination. Analysis of the purified proteins under reducing conditions (reduced), indicated that the changes in the oxidized level of ACHT4 were not the result of altered protein content. Equal loading was verified by ribulose-1,5-bis-phosphate carboxylase/oxygenase (RBCL) levels.

In order to examine whether other thylakoid-associated members of the ACHT family have similar or unique roles to that of ACHT1, we analyzed the redox state changes of the ACHT4 catalytic site following the onset of growth light (80 to 100 µE*m−2*s−1) after a typical 16 h night period in plants expressing ACHT4 (Dangoor, 2009). The catalytic site of ACHT4 was found to be mostly disulfide-bonded at the end of the night and to undergo rapid reduction within 1 min of exposure to the light (FIG. 1A). As reported for ACHT1, significant oxidation of the ACHT4 catalytic site was observed within 30 min of illumination and counteracted its reductive state. Thereafter, ACHT4 redox state appeared to be in a dynamic quasi-oxidized state. A control experiment demonstrated that the total amount of ACHT4 did not change significantly (FIG. 1A, reduced panel) under the experimental conditions.

Figure 1B:
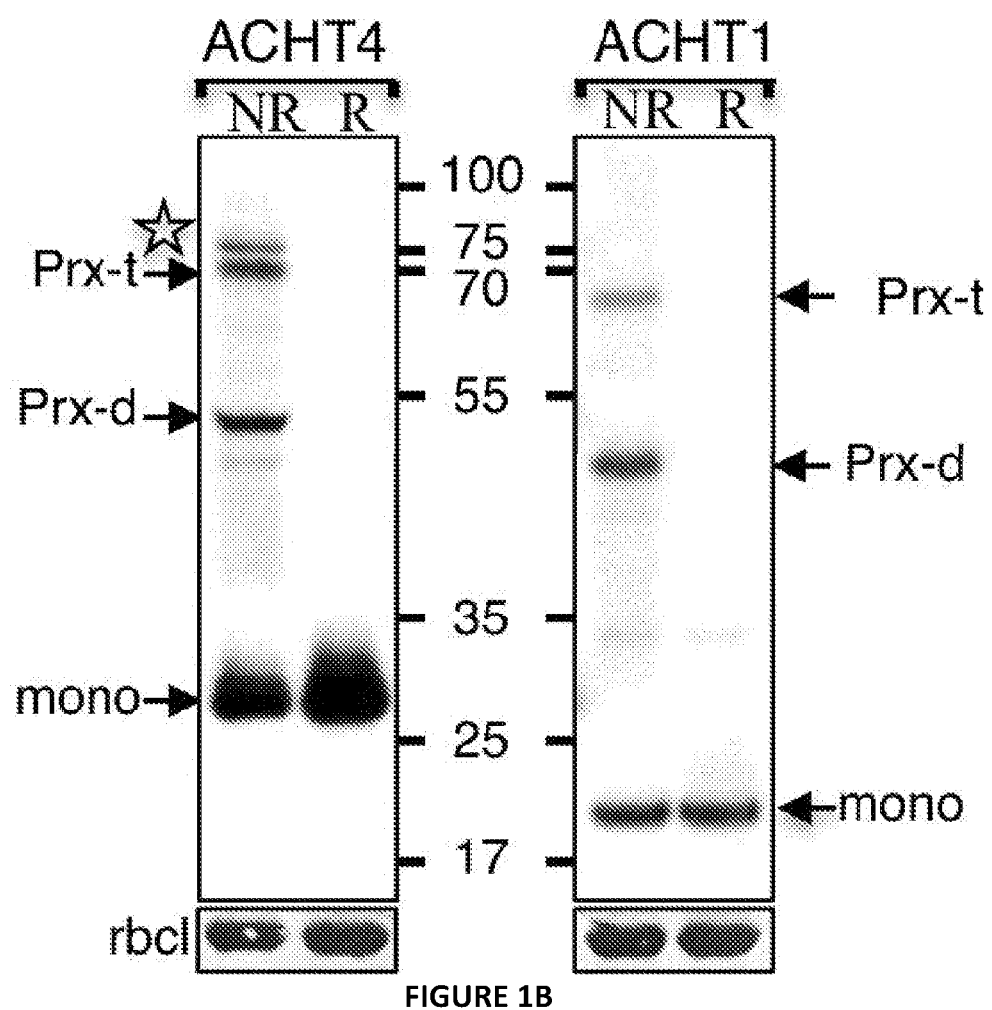
FIG. 1B: Immunoblot assay showing the ACHT4 intermolecular disulfide complexes, 2-Cys Prx heterotrimeric (Prx-t) and heterodimeric (Prx-d), and a unique additional complex (marked with an asterisk) extracted under nonreducing conditions (NR) from plants expressing either ACHT4MT or ACHT1MT. The conversion of the complexes to the monomer (mono) by chemical reduction (R) indicated the disulfide nature of the complexes.

To investigate the identity of the proteins that ACHT4 exchanges disulfides with in planta, we captured as in (Dangoor, 2012, The Plant Cell 24(5):1894-1906, which is incorporated herein by reference in its entirety) its intermolecular disulfide reaction intermediates. Protein blot analysis of denatured, but not reduced, plant extracts identified three intermolecular disulfide-linked ACHT4-containing protein complexes, verified by their susceptibility to chemical reduction by dithiothreitol (DTT) (FIG. 1B, ACHT4 panel). A comparison to the ACHT1 intermolecular disulfide-linked protein complexes (FIG. 1B, ACHT1 panel) showed that two of the main ACHT4 complexes, with estimated sizes of ~55 kDa and ~70 kDa, corresponded to the combined molecular weight of the previously characterized heterodimeric and the heterotrimeric ACHT1 and 2-Cys Prx complexes, respectively (Dangoor, 2012). Interestingly, an additional third intermolecular disulfide ACHT4 complex (marked with asterisk), with a higher molecular weight than that of the ACHT4 2-Cys Prx heterotrimer, and which did not form in ACHT1 extracts, was identified as well.

Figure 1C:
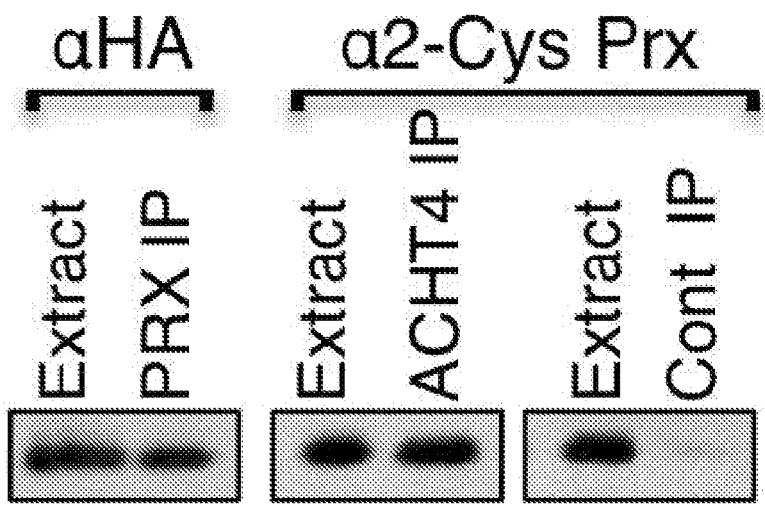
FIGS. 1C and 1D: Reciprocal immunoprecipitation identified 2-Cys Prx (C) and APS1 (D) as the intermolecular disulfide partners of ACHT4. Immunoblot assay of proteins immunoprecipitated with anti-HA (ACHT4 IP), anti-2-Cys Prx (Prx IP), and anti-APS1 (APS IP) affinity matrixes or with a nonspecific matrix (Control IP) from plants expressing ACHT4MT. Purified proteins were run under reducing conditions and blotted with antibodies specific to the HA-tagged ACHT4 (aHA), 2-Cys Prx (αPrx) or APS1 (αAPS1).

To verify the authenticity of ACHT4-2-Cys Prx intermolecular disulfide complexes, they were pulled down in a reciprocal analysis performed under non-reducing denaturing conditions, with either anti-HA (for ACHT4) or anti-2-Cys Prx sera. Protein blot analysis of denatured and reduced samples identified the 2-Cys Prx in the anti-HA pulled down complexes and ACHT4 in the anti-2-Cys Prx pulled down complexes (FIG. 1C). As expected, mass-spectrometry analysis identified both ACHT4 and 2-Cys Prx in the gel slice containing the heterotrimer complex but not in a corresponding gel slice containing extracts that were separated under reducing conditions (Table 3). We concluded that ACHT4 exchanged disulfides with the 2-Cys Prx in plants, in a similar manner as that reported for ACHT1.

APS1 is a Unique Target of ACHT4

Figure 1D:
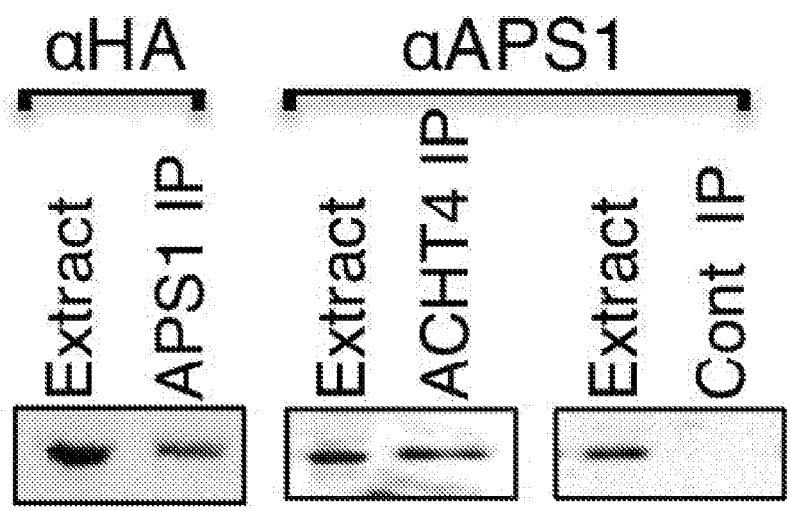

The comparison of the intermolecular disulfide complexes formed in planta by ACHT4 and ACHT1 uncovered a major disulfide linked complex unique to ACHT4 (FIG. 1B). A mass spectrometry analysis identified APS1 in the gel slice containing the unique complex of ACHT4 but not in a corresponding reduced gel slice (Table 3). To verify these findings, the protein intermolecular disulfide complexes were reciprocally pulled-down under non-reducing denaturing conditions with either anti-HA, for ACHT4, or anti-APS1. Protein blot analyses identified the APS1 in the anti-HA pulled down complexes and ACHT4 in the anti-APS1 pulled down complexes (FIG. 1D), suggesting that APS1 is a target protein of ACHT4. These findings also implied that although ACHT1 and ACHT4 share a similar mode of oxidation by 2-Cys Prx, they differ in at least one major target, suggesting that they may serve to regulate distinctive processes.

ACHT4 Participates in the Diurnal Redox Regulation of AGPase

Figure 2A:
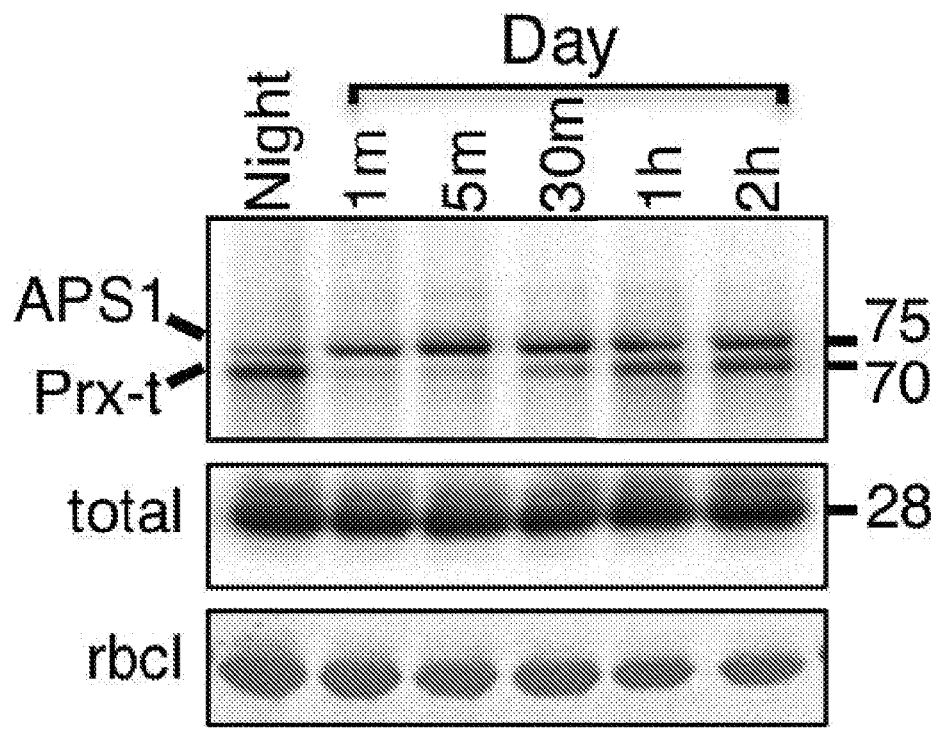
FIG. 2A: Immunoblot assay with HA Ab showing the ACHT4 intermolecular disulfide complexes during the transition from night to day.

The trapping in vivo of APS1-ACHT4 and 2-Cys Prx-ACHT4 disulfide exchange reaction intermediates (RIs) opened the possibility of studying the environmental stimuli that influence ACHT4-driven AGPase redox control. First, we analyzed the changes in the 2-Cys Prx-ACHT4 and APS1-ACHT4 RIs, and the corresponding changes in the APS1 redox state upon light onset of plants grown under a 8/16 h light/dark regime. Intriguingly, the low APS1-ACHT4 RI level and the high 2-Cys Prx-ACHT4 level in the dark contrasted each other (FIG. 2A). Since the 2-Cys Prx RIs were high in the dark also with ACHT1 (Dangoor, 2012), it suggested that the ACHT4 disulfide transfer reaction with APS1 differs from the reducing reaction of either ACHT1 or ACHT4 with 2-Cys Prx (Dangoor, 2009). As the dark is a relatively stable condition, i.e. changes in redox state of reacting proteins are not expected, these finding could conceivably reflect an opposite directionality of the disulfide transfer reaction, ACHT4 to APS1 versus 2-Cys Prx to ACHT4, which could possibly be derived from dissimilar redox midpoint potentials of the proteins. Consequently, the contrasting levels of ACHT4 RIs in the dark would be a result of the levels of its two substrates, high level of oxidized 2-Cys Prx and low level of reduced APS1.

Notably, the increase in the level of APS1-ACHT4 RIs upon illumination (FIG. 2A) matched the increase in reduction of APS1 at this time period, further supporting this notion. The APS1-ACHT4 RI level approached steady state level after a 30 min transition period in the light. The 2-Cys Prx-ACHT4 RI levels (FIG. 2A) showed a similar pattern to those of 2-Cys Prx-ACHT1 (Dangoor, 2012) also during illumination, a transient decrease, then an increased level, which reached a steady state after the 30 min transition period in the light.

Figure 2B:
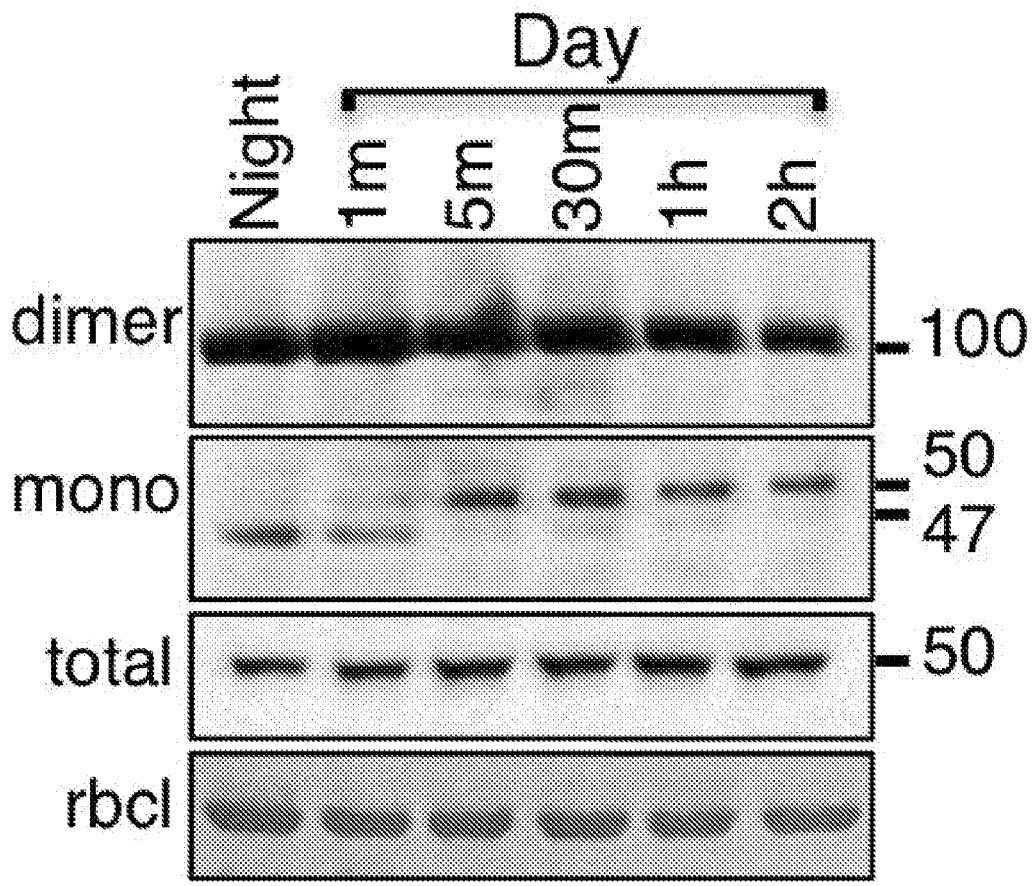
FIG. 2B: Immunoblot assay showing APS1 redox state during the transition from night to day. The panels of APS1 dimer and the monomer were taken from the same immunoblot exposure.
Figure 2C:
FIG. 2C: Immunoblot assay with APS1 Ab of gel slice of 50 kDa monomer extracted from plants in the dark (D) or in the light (L) before (−DTT) and after (+DTT) chemical reduction with DTT.
Figure 2D:
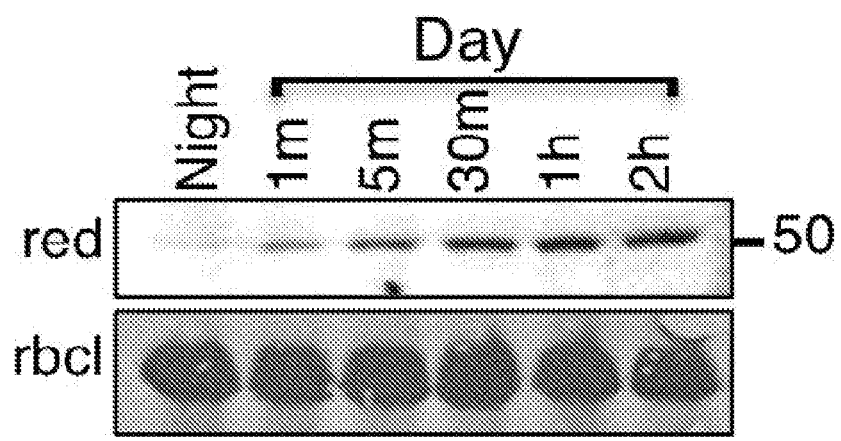
FIG. 2D: Immunoblot assay with APS1 Ab showing the reduced 50 kDa APS1 monomer (red). Equal loading was verified as in FIG. 1. The results shown are representative of three independent experiments.

The analysis of the concomitant changes in the redox state of APS1 showed that APS1 was resting in the inactive intermolecular disulfide form in the dark (FIG. 2B). In addition, in dark conditions, a monomeric form of APS1 with slightly lower molecular weight (MW) that was converted to the monomeric form with the expected MW during the first 5 min of illumination was observed. The conversion of the faster migrating form to the slower form upon illumination, suggested that the lower MW monomer could be a compacted APS1 form bearing an intramolecular disulfide, the reduction of which creates a stretched molecule in the light. To verify that, we compared the migration of the APS1 monomer purified from dark protein extracts and chemically reduced, with DTT, in vitro, to the monomer purified from light extracts (FIG. 2C). The DTT-reduced monomer derived from dark extracts migrated parallel to the monomer from light extract, whereas the DTT-reduced monomer isolated from light extracts did not alter its migration, indicating that an APS1 intramolecular disulfide indeed participated in the redox control of APS1. Thus, we analyzed the monomeric APS1 via a methodology that exclusively measures the levels of reduced monomer. In this method, the reduced cysteines are first blocked with N-ethyl maleimide (NEM), and the disulfides are then chemically reduced and reacted with methoxypolyethylene glycol-maleimide (mPEG). We found that the level of reduced monomer was barely detectable in the dark, gradually increased during the 30 min transition period and reached a steady state level thereafter (FIG. 2D). In parallel, 2-Cys Prx-ACHT4 RI levels, indicative of ACHT4 oxidative signal, were low during the transition period and also reached relatively stable values only thereafter (FIG. 2A), suggesting that the oxidative signal of ACHT4 dynamically counteracted APS1 reduction by Trx-f1, and approached a dynamic equilibrium after 30 min in the light.

Figure 2E:
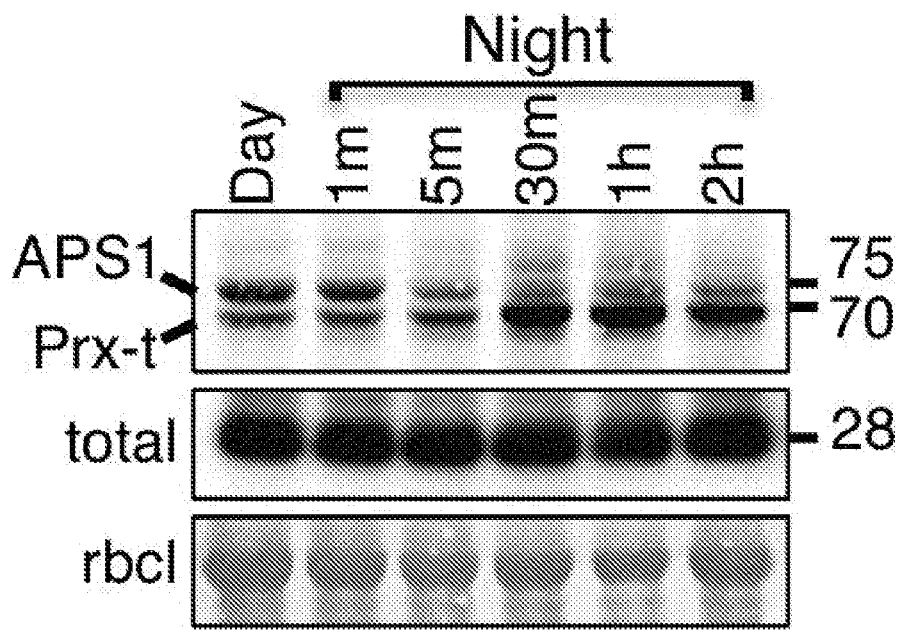
FIG. 2E: Immunoblot assay with HA Ab showing the ACHT4 intermolecular disulfide complexes during the transition from day to night.
Figure 2F:
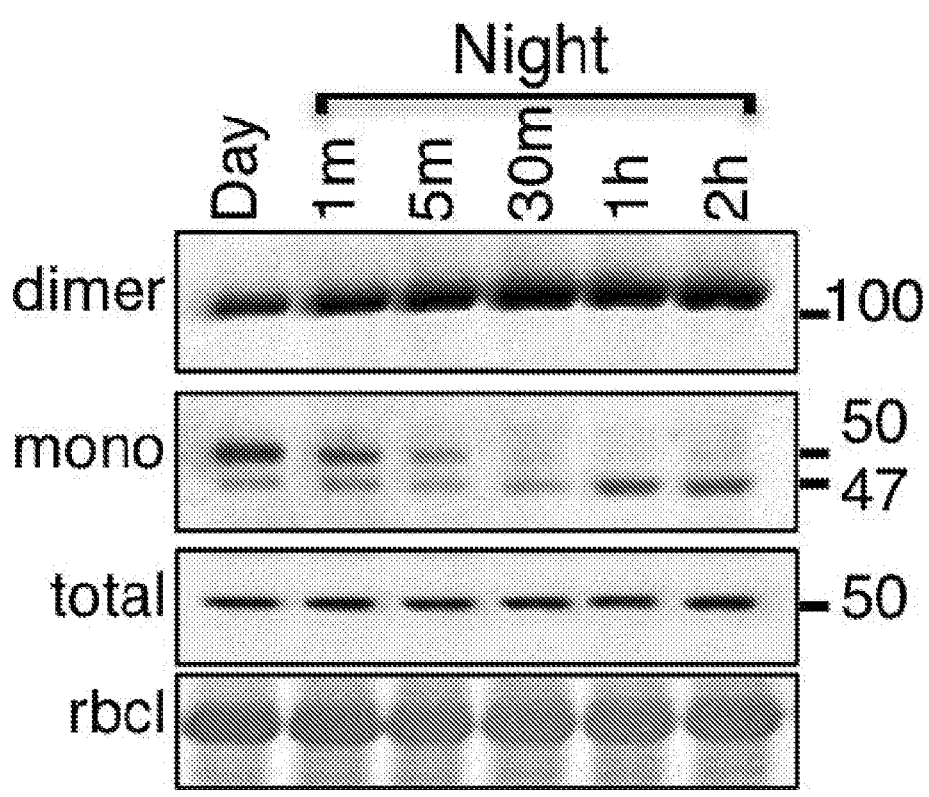
FIG. 2F: Immunoblot assay showing APS1 redox state during the transition from day to night. The panels of APS1 dimer and the monomer were taken from the same immunoblot exposure.

Both 2-Cys Prx ACHT4 and APS1 RI levels and APS1 redox state after the light was switched off, i.e. the period in which oxidation is expected to turn off AGPase, were inverse to those observed after the onset of light. The 2-Cys Prx-ACHT4 RI remained stable during the first 5 min and then increased, suggesting increased oxidation by 2-Cys Prx during that time period (FIG. 2E). Levels of the reduced monomeric APS1 form gradually decreased alongside a concomitant increase in the oxidized, intramolecular disulfide-bearing monomer and intermolecular disulfide-linked dimer (FIG. 2F). At the same time, the level of the APS1 reaction intermediate, which was high at the end of the day, gradually decreased and reached levels similar to those observed before the beginning of the day (FIG. 2E). These results are consistent with an increased oxidation rate of APS1 by ACHT4 during the transition from day to night, resulting in diminishing APS1 activity.

Figure 3A:
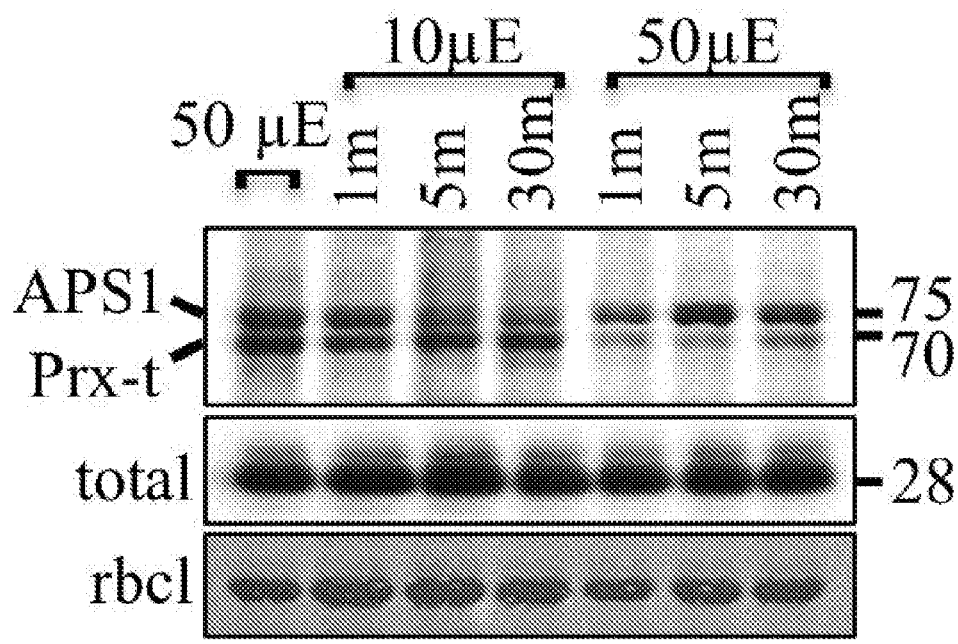
FIG. 3A: Immunoblot assay showing the ACHT4 intermolecular disulfide complexes in plants treated for 2-hrs with 50 μE*m−2*s−1 light intensity (50 μE) and after abrupt decreased (10 μE) followed by abrupt increased light intensity (50 μE). Equal protein loading was verified as in FIG. 1. The results shown are representative of three independent experiments.
Figure 3B:
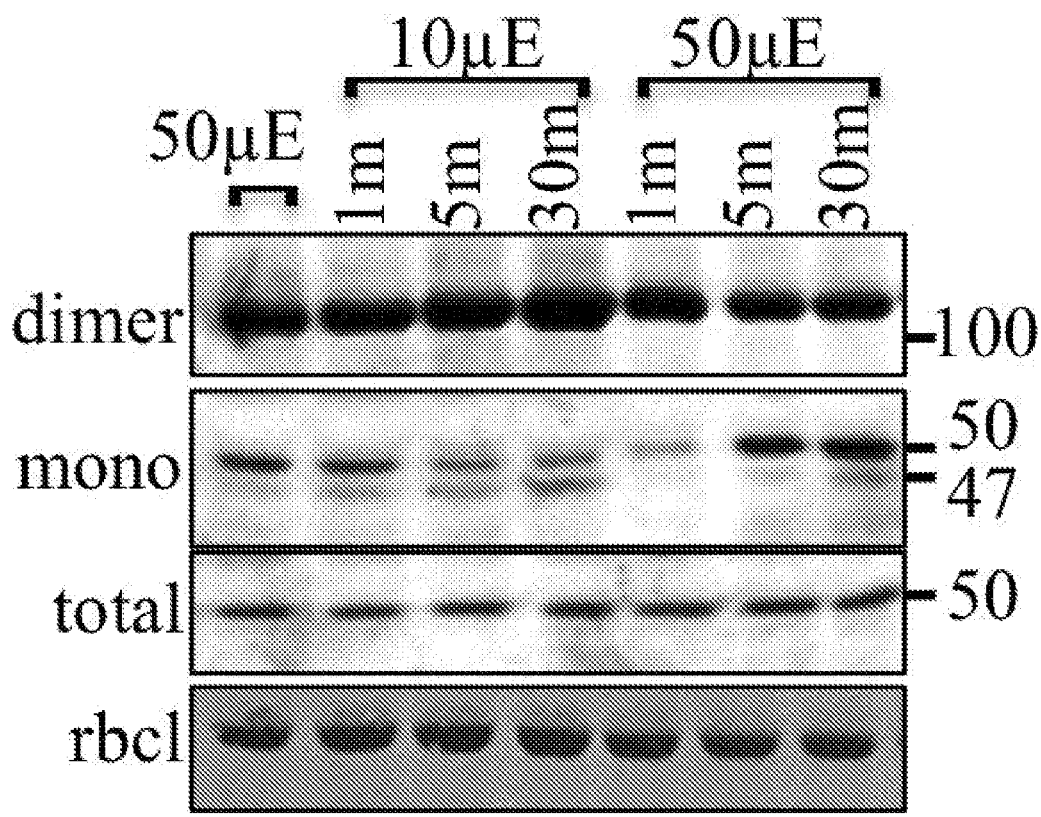
FIG. 3B: Immunoblot assay showing the APS1 redox state in plants treated for 2-hrs with 50 μE*m−2*s−1 light intensity (50 μE) and after abrupt decreased (10 μE) followed by abrupt increased light intensity (50 μE). Equal protein loading was verified as in FIG. 1. The results shown are representative of three independent experiments.

ACHT4 Participates in the Regulation of APS1 During Fluctuations in Light Intensity We found that ACHT4 participated in the diurnal regulation of APS1, that has been proposed to influence the day and night cycles of starch synthesis and degradation. The reactions of ACHT4 with APS1 and 2-Cys Prx, as judged by the levels of their disulfide exchange reaction intermediates, seemed to reach balanced levels after a transition period in the light (FIG. 2A), as manifested by APS1 activation levels (FIG. 2B), suggesting that ACHT4 oxidation of APS1 is active and dynamically counteracting its reduction by Trx-f1 during the day. Such activity might be important for the rationing of photosynthates to starch and sugars exported from the chloroplast during the day. Alternatively, as shown in the unicellular green alga *Chlamydomonas reinhardtii*, such activity may regulate the levels of starch to be used as a transient pool for reduced carbon in a fluctuating light environment. We tested this hypothesis by subjecting the plants to small fluctuations of light intensity during the day. Interestingly, when light intensity was reduced to $10\ \mu E^*m-2^*s-1$ after a 2-hour $50\ \mu E^*m-2^*s-1$ light regime, APS1-ACHT4 RI levels declined within 5 min, and rose again when the light intensity was switched back to $50\ \mu E^*m-2^*s-1$ (FIG. 3A). While 2-Cys Prx-ACHT4 RI levels remained steady upon decreased light intensity, they rapidly declined following the transfer back to the higher light intensity (FIG. 3A). In parallel, a lower ratio of reduced to oxidized APS1 was obtained following the transfer to the lower light and a higher ratio was observed upon increased light intensity (FIG. 3B). These results suggest that, in addition to its diurnal role of ACHT4-driven oxidation of APS1 in the beginning of the night, it may also participate in the dynamic regulation of AGPase activity in response to natural fluctuations in light intensity. Furthermore, the reduction of APS1 upon increased light intensity occurred rapidly in comparison to its oxidation upon decreased light intensity (FIG. 3B), suggesting that AGPase redox regulation might also play a role in stimulating a transient burst of starch synthesis to accommodate an abruptly increased light intensity. The concomitant gradual decrease of both APS1-ACHT4 RIs levels and reduced APS1 upon lowering the light intensity and the abrupt increase in both upon increased intensity further supported the notion that ACHT4 reacted with the reduced APS1.

Example 2

Expression of C-Terminal Truncated Form of AtACHT4 Increases Transitory Starch Content in *Arabidopsis* Leaves and Increases Plant Biomass The C-Terminus of ACHT4 is Important for its Reaction with APS1

Figure 4C:
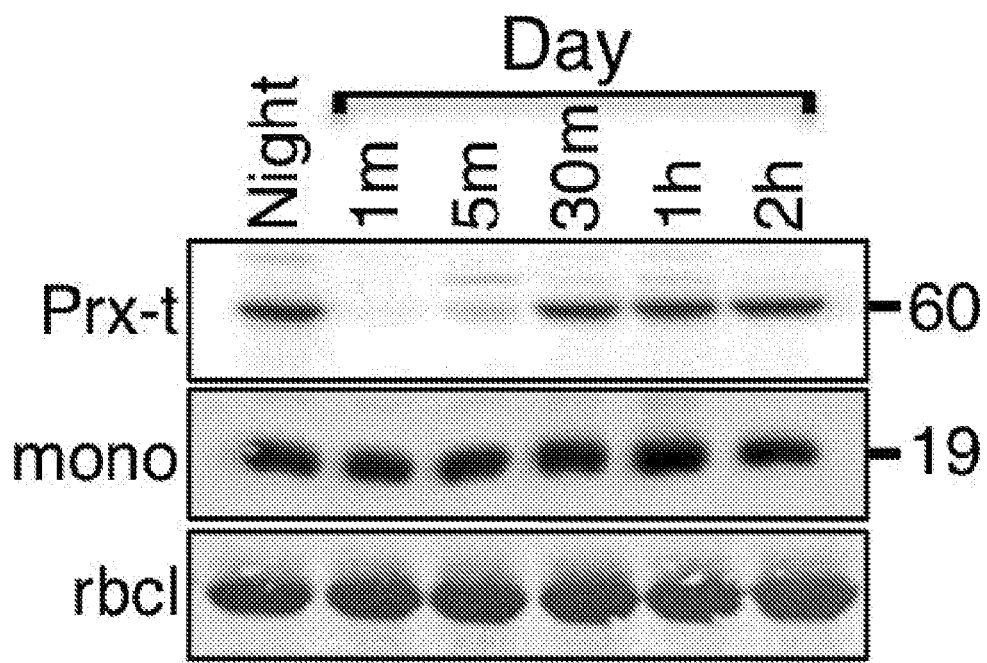
FIG. 4C: Immunoblot assay with HA Ab showing the ACHT4ΔC intermolecular disulfide complexes during the transition from night to day.

We then assessed whether the distinct 47-amino acid-long ACHT4 C-terminus (FIG. 4A) is responsible for its in planta differences from ACHT1, by analyzing the 2-Cys Prx and APS1 RIs in plants expressing ACHT4 lacking the C-terminus (ACHT4ΔC). Notably, the ACHT4ΔC form reacted with 2-Cys Prx, and formed the two intermolecular disulfide-linked 2-Cys Prx ACHT4 RIs, but failed altogether to interact with APS1 (FIG. 2B). The preferential reaction of ACHT4ΔC with the 2-Cys Prx and not with APS1 was maintained throughout the transition from night to day (FIG. 4C). Moreover, the profile of the reaction of ACHT4ΔC with 2-Cys Prx during the first 2 hr of illumination was similar to that of ACHT4, indicating that the oxidation of ACHT4ΔC by 2-Cys Prx does not involve the protein's C-terminus and that the C-terminus deletion only affected ACHT4-driven redox control of APS1.

Figure 4D:
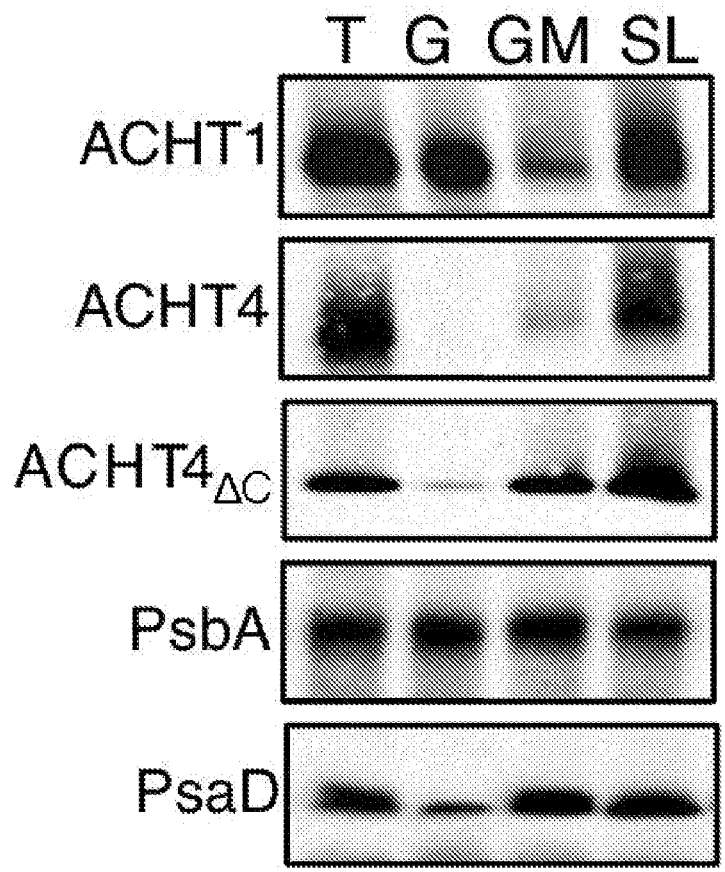
FIG. 4D: Immunoblot assay of thylakoid membranes (T), enriched grana (G), grana margin (GM) and stroma lamellae (SL) and decorated with anti-HA Ab (ACHT1, ACHT4, ACHT4ΔC), or with Ab against the PS II protein PsbA (PsbA) or the PS I protein PsaD Ab (PsaD).

Both ACHT4 and ACHT1 are thylakoid-associated proteins. The distinct reaction of ACHT4, and not of ACHT1, with APS1, prompted us to investigate whether the disparity might be due to different thylakoid localization, either the grana, the grana margins, or the stroma lamella. Protein blot analysis showed that ACHT1 was primarily found in both the grana and the stroma lamella domains, whereas ACHT4 was mainly present in the stroma lamella domain and was undetectable in the grana (FIG. 4D), further promoting distinct roles of ACHT4 and ACHT1. The membrane association of ACHT4ΔC was then analyzed to determine whether ACHT4 localization is influenced by its unique C-terminus. Only a small increase in the partitioning of ACHT4ΔC to the grana margins was observed, suggesting that the ACHT4 C-terminus deletion effect on its disulfide exchange reaction with APS1 was direct and not mediated via its thylakoid domain localization.

Figure 5A:
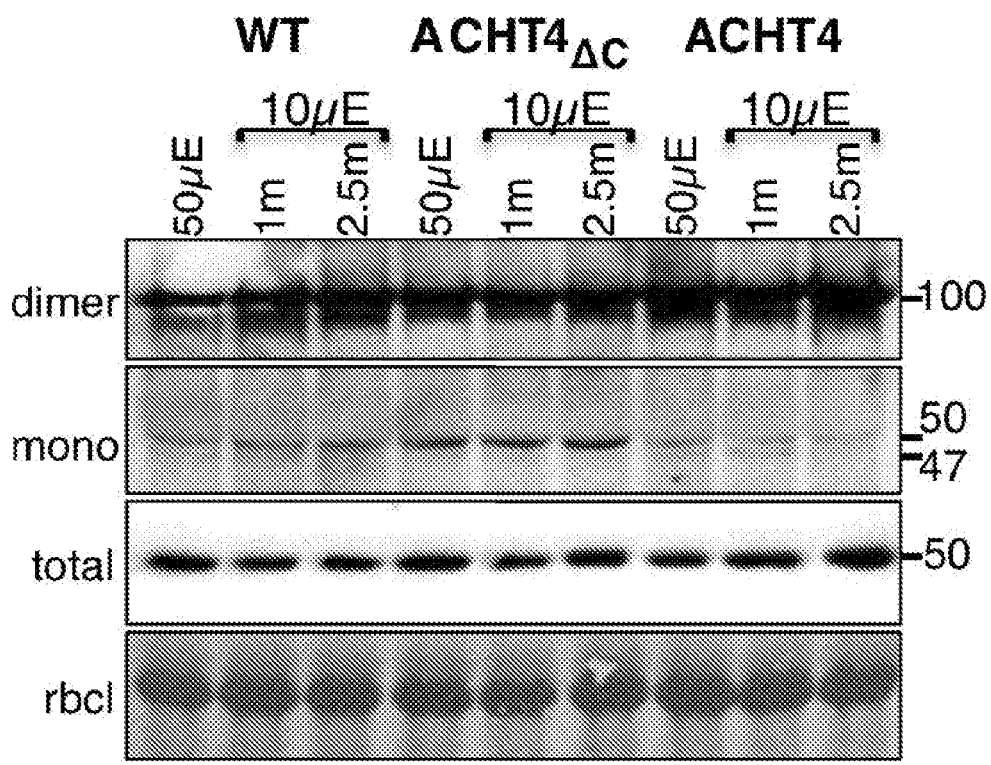
FIG. 5A: Immunoblot assay with APS1 Ab showing APS1 redox state in WT plants (WT), plants expressing increased level of ACHT4ΔC (ACHT4ΔC), or plants expressing increased level of ACHT4 (ACHT4). Equal protein loading was verified as in FIG. 1.
Figure 5B:
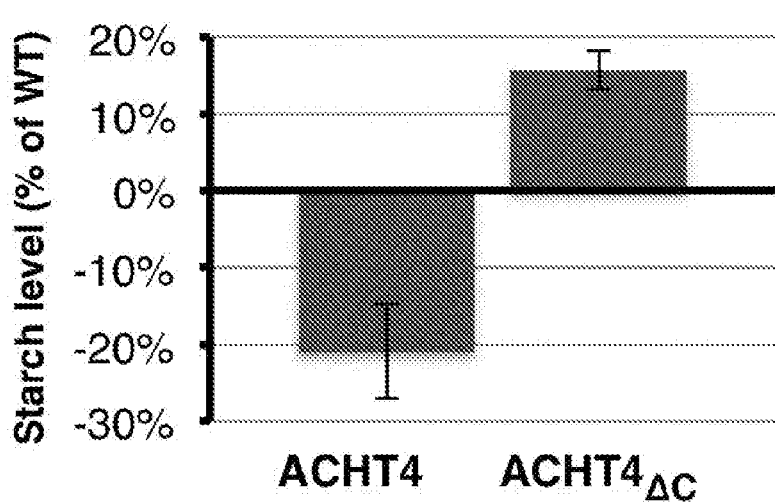
FIG. 5B: Leaves starch content of plants expressing increased level of ACHT4ΔC, or plants expressing increased level of ACHT4 relative to that of WT plants. The results shown are representative of three independent experiments.

The finding that the deletion of the ACHT4 C-terminus diminished its disulfide exchange reaction with APS1 (FIG. 2B) facilitated studying the effect of ACHT4 on APS1 redox state and on transitory starch content. We first compared the APS1 redox state after two hours in the light, representing steady state conditions in which transitory starch is synthesized, and when light intensity was reduced, conditions in which APS1 is being oxidized (FIG. 3). Consistently with the expected oxidative role of ACHT4 and the dominant negative effect of the C-terminus deletion, plants expressing increased levels of ACHT4 exhibited lower levels of reduced APS1 monomer, and plants expressing ACHT4ΔC contained higher levels of the reduced APS1 monomer, than WT plants (FIG. 5A). Next, in order to determine whether the influence of ACHT4 on the redox state of APS1 impacts starch accumulation, we assayed the starch content of WT ACHT4 and ACHT4ΔC plants at the end of the day (FIG. 5B). In agreement with the changes in the APS1 redox state, plants expressing ACHT4 showed reduced starch levels, whereas plants expressing ACHT4ΔC contained increased starch levels. These results corroborate the notion that disulfides transferred by ACHT4 to APS1 are used in planta to fine-tune APS1 activity by counterbalancing the reduction of APS1 by the reductive type Trxs.

Expression of AtACHT4ΔC Also Increases *Arabidopsis* Biomass by 10%

Stimulation of starch synthesis results not only in increased accumulation of transitory starch in *Arabidopsis* leaves, it also stimulates growth, indicating that OE of AtACHT4ΔC stimulates the export of photosynthates from the chloroplast which are then directed toward growth and biomass accumulation.

Figure 6A:
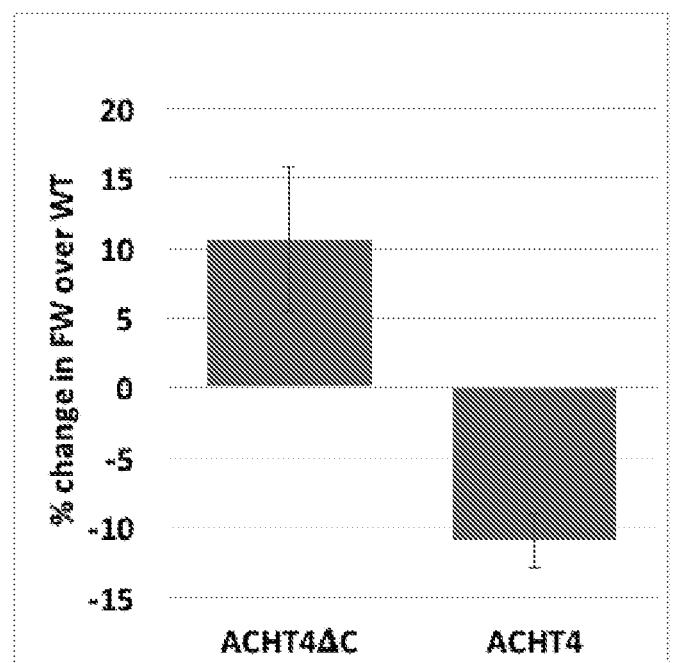
FIGS. 6A and 6B: Effect of overexpression of AtACHT4ΔC on biomass accumulation in *Arabidopsis* plants. Overexpressing (OE) AtACHT4ΔC in *Arabidopsis* plants stimulated growth (fresh weight, FW, FIG. 6A; dry weight, DW, FIG. 6B) in comparison to wild type plants, indicating that OE of AtACHT4ΔC stimulates the export of photosynthates from the chloroplast which are then directed toward growth. The OE of AtACHT4 decreased growth, confirming that the C-terminus of ACHT4 attenuates growth.
Figure 6B:
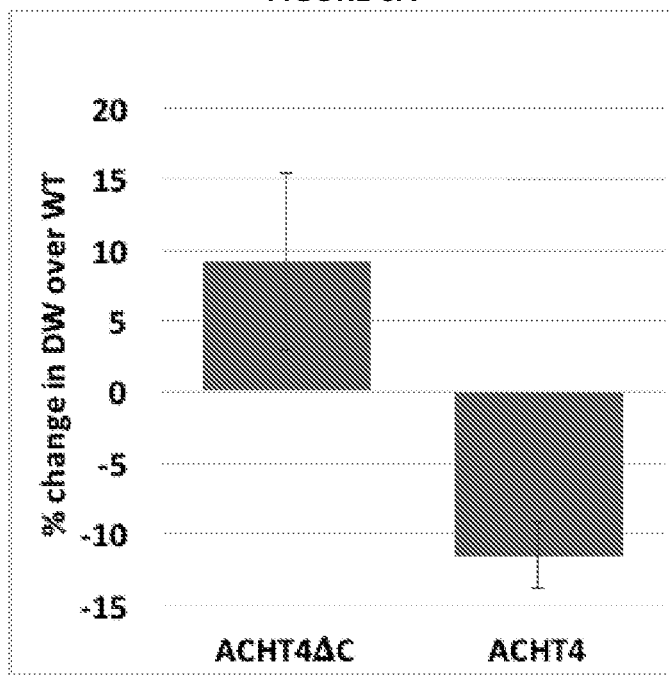

AtACHT4ΔC-OE, AtACHT4-OE and WT lines were grown under long day (18 h/6 h of light/dark cycle at 21° C./18° C.) for 4 weeks. The plants shoot was excised and fresh weight (FW) were recorded. The tissues were dried at 60° C. for 4 days and dry weight (DW) were recorded. The FW of AtACHT4ΔC-OE plants was increased by 10.6% (FIG. 6A) and the DW was increased by 9.1% over those of WT (FIG. 6B), indicating that AtACHT4ΔC stimulates the export of photosynthates from the chloroplast which are then directed toward growth. The FW of AtACHT4 OE plants was decreased by 10.9% (FIG. 6A) and the DW was increased by 11.5% over those of WT (FIG. 6B), confirming that the C-terminus of ACHT4 attenuates growth.

Example 3

Expression of C-Terminal Truncated Form of Potato StACHT4-2 and StACHT4-1 Paralogs Increases Correspondingly Potato Tuber Yield and Transitory Starch Content in Leaves Potato Plants

Figure 7:
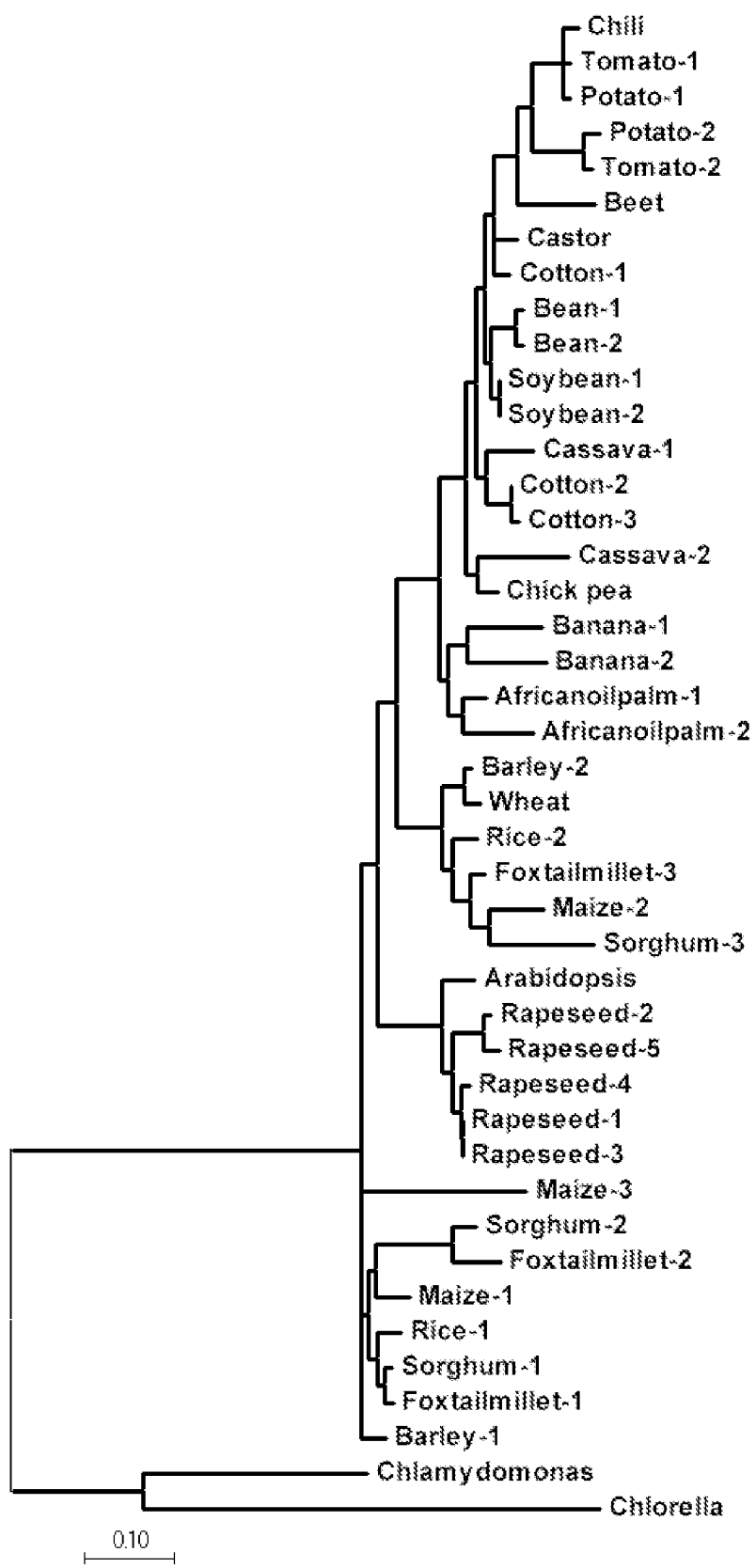
FIG. 7: A phylogenetic tree showing that *Arabidopsis* has one paralog of ACHT4 where other crop plants, including potato, maize, rice, barley, wheat, *sorghum*, castor, bean, rapeseed, cotton, soybean, beat, banana, chili, chickpea, tomato, African oilpalm, Foxtail millet, cassava and the algae *Chlamydomonas* and *Chlorella* have one to five paralogs. The blastP analysis for *Arabidopsis* ACHT4 (AtACHT4) was performed against several crop plants, biofuel plants and algae genomes database. Pairwise distance analysis of proteins was performed using MEGA 7 program and the proteins closely related to AtACHT4 were aligned and then phylogenetic tree was constructed. The amino acid sequences of proteins were downloaded from respective databases and have accession numbers or protein ID as follow: *Arabidopsis* (*Arabidopsis thaliana*: NP_172333.1; SEQ ID NO: 1); Potato-1 (*Solanum tuberosum*: XP_006348023.1; SEQ ID NO: 2); Potato-2 (*Solanum tuberosum*: XP_006351368.1; SEQ ID NO: 3); Maize-1 (*Zea mays*: NP_001266702.1; SEQ ID NO: 4); Maize-2 (*Zea mays*: ACR34655.1; SEQ ID NO: 5); Maize-3 (*Zea* mays: ACN36361.1; SEQ ID NO: 6); Rice-1 (*Oryza sativa*: XP_015632287.1; SEQ ID NO: 7); Rice-2 (*Oryza sativa*: XP_015646723.1; SEQ ID NO: 8); Barley-1 (*Hordeum vulgare*: BAK03063.1; SEQ ID NO: 9); Barley-2 (*Hordeum vulgare*: BAK07858.1; SEQ ID NO: 10); Wheat (*Triticum aestivum*: Traslated ORF in 1$^{st}$ frame from mRNA AK335384.1; SEQ ID NO: 11); Cassava-1 (*Manihot esculenta*: OAY44415.1; SEQ ID NO: 12); Cassava-2 (*Manihot esculenta*: OAY41970.1; SEQ ID NO: 13); Sorghum-1 (*Sorghum bicolor*: KXG39469.1; SEQ ID NO: 14); Sorghum-2 (*Sorghum bicolor*: XP_002465837.1; SEQ ID NO: 15); Sorghum-3 (*Sorghum bicolor*: KXG36972.1; SEQ ID NO: 16); Rapeseed-1 (*Brassica napus*: CDY06319.1; SEQ ID NO: 17); Rapeseed-2 (*Brassica napus*: XP_013711973.1; SEQ ID NO: 18); Rapeseed-3 (*Brassica napus*: XP_013672630.1; SEQ ID NO: 19); Rapeseed-4 (*Brassica napus*: XP_013716476.1; SEQ ID NO: 20); Rapeseed-5 (*Brassica napus*: XP_013641071.1; SEQ ID NO: 21); Castor (*Ricinus communis*: XP_002525461.1; SEQ ID NO: 22); Bean-1 (*Phaseolus vulgaris*: XP_007161960.1; SEQ ID NO: 23); Bean-2 (*Phaseolus vulgaris*: XP_007161924.1; SEQ ID NO: 24); Cotton-1 (*Gossypium histrum*: NP_001313760.1; SEQ ID NO: 25); Cotton-2 (*Gossypium histrum*: XP_016753539.1; SEQ ID NO: 26); Cotton-3 (*Gossypium histrum*: XP_016672835.1; SEQ ID NO: 27); Soybean-1 (*Glycine max*: XP_003548763.1; SEQ ID NO: 28); Soybean-2 (*Glycine max*: NP_001276128.1; SEQ ID NO: 29); Beet (*Beta vulgaris*: XP_010672407.1; SEQ ID NO: 30); Banana-1 (*Musa acuminata*: XP_009416338.1; SEQ ID NO: 31); Banana-2 (*Musa acuminata*: XP_009406843.1; SEQ ID NO: 32); Chili (*Capsicum annuum*: XP_016552829.1; SEQ ID NO: 33); Chick pea (*Cicer arietinum*: XP_004493141.1; SEQ ID NO: 34); Tomato-1 (*Solanum lycopersicum*: XP_004252003.1; SEQ ID NO: 35); Tomato-2 (*Solanum lycopersicum*: XP_004249307.1; SEQ ID NO: 36); African oilpalm-1 (*Elaeis guineensis*: XP_010938119.1; SEQ ID NO: 37); African oilpalm-2 (*Elaeis guineensis*: XP_010921294.1; SEQ ID NO: 38); Foxtail millet-1 (*Setaria italica*: XP_004984516.2; SEQ ID NO: 39); Foxtail millet-2 (*Setaria italica*: XP_004985651.1; SEQ ID NO: 40); Foxtail millet-3 (*Setaria italica*: XP_004958724.1; SEQ ID NO: 41); Chlamydomonas (*Chlamydomonas reinhardtii*: XP_001697443.1; SEQ ID NO: 42); Chlorella (*Chlorella variabilis*: XP_005851922.1; SEQ ID NO: 43).

*Arabidopsis* has one paralog of ACHT4 where other crop plants, including potato, maize, rice, barley, wheat, *sorghum*, castor, bean, rapeseed, cotton, soybean, beat, banana, chili, chickpea, tomato, African oilpalm, Foxtail millet, cassava and the algae *Chlamydomonas* and *Chlorella* have one to five paralogs (FIG. 7).

Materials and Methods

Identification and Over Expression of AtACHT Homologs in Potato

We analyzed the potato genome for AtACHT4 homologs. Protein blast (blastP) analysis of AtACHT against the genome database of potato (solgenomics.net) identified two paralogs, StACHT4-1 (XP_006348023.1) and StACHT4-2 (XP_006351368.1). A 69 and 68 amino acid long tail region at the C-terminus of StACHT4-1 and StACHT4-2, correspondingly, were identified. Four constructs of StACHT4-1ΔC and StACHT4-2ΔC, StACHT4-1, and StACHT4-2 were custom synthesized by Hy-Laboratories Ltd., Israel, were subcloned into pART7 vector under control of CaMV35S promoter and OCS terminator. HA (Human influenza hemagglutinin) tag was fused in frame at the C-terminus of each of the protein coding sequences. All four StACHT4::pART7 and StACHT4-2ΔC:: pART7 constructs were digested with NotI and subcloned into pART27 plant expression vector (FIG. 11) and used to transform potato leaf discs (*Solanum tuberosum* cv. Desiree) using a standard *agrobacterium*-based transformation protocol. Positive transformants were identified by PCR analysis and protein expression was verified by immunoblot analysis using anti-HA antibody.

Results

The Over Expression of StACHT4-2ΔC in Potato Plants Nearly Doubles the Tubers Yield in Comparison to WT Plants The StACHT4-2ΔC-OE and WT plants (*Solanum tuberosum* cv. Desiree) were planted on May 22nd 2016 and were grown for 60 days in the green-house. Plants were harvested, tubers were collected, counted and their fresh weight was recorded (FIG. 8). The yield analysis of the StACHT4-2ΔC-OE lines showed 91% increase in the total tuber yield per plant as compared to WT plants. Photographs of representative plants show the increase in biomass accumulation of both shoots and tubers (FIG. 9).

StACHT4-1ΔC OE Lines Accumulated Increased Level of Transitory Starch in Leaves

To test whether StACHT4-1ΔC OE proteins regulate transitory starch content, young green leaves from 6-weeks old green-house grown plant were collected and analyzed for the starch content by Sigma starch assay kit (Catalog Number SA20) with some modifications. Approximately, 0.25-0.5 g fresh leaves were ground to fine powder using liquid nitrogen and then suspended into 20 ml DMSO and 5 ml of 8M HCl solution. The suspensions were incubated for 30 min at 60° C. and then 50 ml water was added to it. The pH was adjusted between 4 and 5, allowed to cool and volume adjusted till 100 ml. From these samples 400 μl were mixed with same volume of starch assay reagent, incubated for 15 min at 60° C. and then allowed to cool at room temperature. Then 200 μl of starch assay mixture were mixed with same volume of glucose assay reagent, incubated at room temperature for 15 min and then absorbance was recorded at 340 nm. Simultaneously, standard starch powder (provided in kit) at concentration of 0, 2, 4, 6, 8 and 10 mg were also used for starch assay and a standard curve was plotted using the absorbance data. The absorbance recorded from the leaves sample of potato transgenic lines were then used to calculate the starch level in leaves using formula obtained from the standard curve. Notably, the StACHT4-1ΔC OE lines accumulated 19% higher starch content relative to WT plants (FIG. 10).

OE of the potato paralogs StACHT4-2ΔC and StACHT4-1ΔC relieves growth and starch synthesis attenuation, as was found for OE of *Arabidopsis* AtACHT4ΔC. However, in potato, each of the two potato paralogs has a unique function. OE expression of StACHT4-2ΔC stimulated the allocation of photosynthates towards growth and near doubles tuber yield and plants shoot growth (FIGS. 8-9), whereas OE expression of StACHT4-1ΔC stimulated transitory starch (FIG. 10). Importantly, OE of the full length protein of either StACHT4-2 (FIG. 8) or StACHT4-1 (FIG. 10) did not result in the stimulating effect, again demonstrating that the expressed C-terminus truncated form of ACHT4 has a negative dominant effect, in StACHT4-2ΔC or StACHT4-1-ΔC, as well as in AtACHT4ΔC.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A recombinant polynucleotide encoding a C-terminally truncated form of an atypical CYS HIS rich thioredoxin 4 (ACHT4) protein, wherein said ACHT4 protein is selected from the group consisting of any one of the sequences set forth in SEQ ID NOs: 1-5, 7-15, 17-41, and wherein said truncated form of ACHT4 protein has:
   i. a thioredoxin (Trx) domain; and
   ii. a deletion of the final 47-69 amino acids of the C-terminal portion of ACHT4; and
   wherein said truncated form of ACHT4 protein has a diminished ability to interact with the small subunit of ADP-glucose pyrophosphorylase (APS1) as compared with the corresponding wild-type endogenous ACHT4 protein.

2. The polynucleotide of claim 1, wherein said truncated form of ACHT4 protein has an amino acid sequence of any one of SEQ ID NOs: 90-92.

3. A composition comprising the polynucleotide of claim 1.

4. An expression vector comprising the polynucleotide of claim 1.

5. The expression vector of claim 4 comprising a constitutive, inducible, or tissue-specific promoter operably linked to the polynucleotide and optionally wherein-said promoter further comprises one or more enhancer sequences.

6. A composition comprising the expression vector of claim 4.

7. A cell comprising the expression vector of claim 4.

8. The cell of claim 7, wherein said cell is an *Arabidopsis* cell, a crop plant cell, or a potato (*Solarium tuberosum*) cell.

9. A composition comprising the cell of claim 7.

10. A seed comprising a gene encoding a C-terminally truncated form of ACHT4 protein, wherein said ACHT4 protein is selected from the group consisting of any one of the sequences set forth in SEQ ID NOs: 1-5, 7-15, 17-41, and wherein said truncated form of ACHT4 protein has:
    i. a thioredoxin (Trx) domain; and
    ii. a deletion of the final 47-69 amino acids of the C-terminal portion of ACHT4; and
    wherein said truncated form of ACHT4 protein has a diminished ability to interact with the small subunit of ADP-glucose pyrophosphorylase (APS1) as compared with the corresponding wild-type endogenous ACHT4 protein of a wild type plant.

11. A plant or plant part having an enhanced phenotype, comprising a gene encoding a C-terminally truncated form of ACHT4 protein, wherein said ACHT4 protein is selected from the group consisting of any one of the sequences set forth in SEQ ID NOs: 1-5, 7-15, 17-41, and wherein said truncated form of ACHT4 protein has:
    i. a thioredoxin (Trx) domain; and
    ii. a deletion of the final 47-69 amino acids of the C-terminal portion of ACHT4; and
    wherein said truncated form of ACHT4 protein has a diminished ability to interact with the small subunit of ADP-glucose pyrophosphorylase (APS1) as compared with the corresponding wild-type endogenous ACHT4 protein, and wherein said enhanced phenotype is an increased yield, productivity, size, biomass or starch content, compared to a wild-type plant.

12. The plant part of claim 11, wherein said plant part is a seed, a leaf, a stem, a root, a flower, a tuber, or a fruit.

13. The plant or plant part of claim 11, wherein said plant is an *Arabidopsis thaliana* or *Solamum tuberosum* (potato) plant.

14. A bio el comprising the plant or plant part of claim 11.

15. A method of increasing the yield, productivity, size, or biomass of a plant, or stimulating the growth or enhancing the starch content of a plant, comprising contacting a cell from said plant with a polynucleotide encoding a C-terminally truncated form of ACHT4 protein, wherein said ACHT4 protein is selected from the group consisting of any one of the sequences set forth in SEQ ID NOs: 1-5, 7-15, 17-41, and wherein said truncated form of ACHT4 protein has:
    i. a thioredoxin (Trx) domain; and
    ii. a deletion of the final 47-69 amino acids of the C-terminal portion of ACHT4; and
    wherein said truncated form of ACHT4 protein has a diminished ability to interact with the small subunit of ADP-glucose pyrophosphorylase (APS1) as compared with the corresponding wild-type endogenous ACHT4 protein.

16. The method of claim 15, wherein said plant is an *Arabidopsis* plant, a crop plant, a *Solanum tuberosum* (potato) plant, or a moss plant.

17. The method of claim 15, wherein said polynucleotide is part of an expression vector.

18. The method of claim 17, wherein said truncated form of ACHT4 protein is overexpressed.

19. The method of claim 15, wherein said contacting is via transformation into cells.

20. The method of claim 19, wherein said transformation is via agroinfiltration.

21. A method of producing a plant having an enhanced phenotype, wherein said method comprises delivering a recombinant polynucleotide encoding a C-terminally truncated form of ACHT4 protein to plant or algae cells, regenerating plants from said cells, and screening said plants or algae to identify a plant having an enhanced phenotype, wherein said ACHT4 protein is selected from the group consisting of any one of the sequences set forth in SEQ ID NOs: 1-5, 7-15, 17-41, and wherein said truncated form of ACHT4 protein has:

i. a thioredoxin (Trx) domain; and ii. a deletion of the final 47-69 amino acids of the C-terminal portion of ACHT4; and wherein said truncated form of ACHT4 protein has a diminished ability to interact with the small subunit of ADP-glucose pyrophosphorylase (APS1) as compared with the corresponding wild-type, endogenous ACHT4 protein.

22. The method of claim 21, wherein said plant is an *Arabidopsis* plant, a crop plant, a *Solanum tuberosum* (potato) plant, or a moss plant.

23. The method of claim 21, wherein said polynucleotide is part of an expression vector.

24. The method of claim 23, wherein said truncated form of ACHT4 protein is overexpressed.

25. The method of claim 21, wherein said delivering of the recombinant polynucleotide is via transformation into cells.

26. The method of claim 25, wherein said transformation is via agroinfiltration.

27. The method of claim 21, wherein said phenotype is increased yield.

28. The method of claim 21, wherein said phenotype is increased biomass.

29. The method of claim 21, wherein said plant or algae has enhanced starch content in transitory starch stores.

30. The method of claim 21, wherein said plant has enhanced starch content in one or more leaves.

\* \* \* \* \*

SEQUENCE LISTING

<160> NUMBER OF SEQ ID NOS: 111

<210> SEQ ID NO 1
<211> LENGTH: 275
<212> TYPE: PRT
<213> ORGANISM: Arabidopsis thaliana

<400> SEQUENCE: 1

```
Met Thr Glu Val Ile Ser Lys Thr Ser Leu Phe Leu Gly Ala Cys Gly
1               5                   10                  15

Asn His His Arg Val Asp Asp Phe Ser Phe Ser Pro Val Ser Phe Gly
            20                  25                  30

Gly Phe Gly Leu Lys Lys Ser Phe Ser Cys Leu Lys Leu Lys Ser Gln
        35                  40                  45

Lys Pro Leu Arg Ser Val Phe Tyr Gly Lys Gln Ile Val Phe Gly Asp
    50                  55                  60

Ser Gln Asp Glu Ser Phe Arg Arg Ser Ser Ala Ile Thr Ala Gln Thr
65                  70                  75                  80

Thr Leu Arg Ile Gly Thr Ala Gln Lys Trp Trp Glu Lys Gly Leu Lys
                85                  90                  95

Asp Asn Met Arg Glu Ile Ser Ser Ala Gln Glu Leu Val Asp Ser Leu
            100                 105                 110

Thr Asn Ala Gly Asp Lys Leu Val Val Val Asp Phe Phe Ser Pro Gly
        115                 120                 125

Cys Gly Gly Cys Lys Ala Leu His Pro Lys Ile Cys Gln Phe Ala Glu
    130                 135                 140

Met Asn Pro Asp Val Gln Phe Leu Gln Val Asn Tyr Glu Glu His Lys
145                 150                 155                 160

Ser Met Cys Tyr Ser Leu Gly Val His Val Leu Pro Phe Phe Arg Phe
                165                 170                 175

Tyr Arg Gly Ser Gln Gly Arg Val Cys Ser Phe Ser Cys Thr Asn Ala
            180                 185                 190

Thr Ile Lys Lys Phe Arg Asp Ala Leu Ala Lys His Gly Pro Asp Arg
        195                 200                 205

Cys Ser Leu Gly Pro Thr Lys Gly Leu Glu Glu Lys Glu Leu Val Ala
    210                 215                 220

Leu Ala Ala Asn Lys Glu Leu Asn Phe Thr Tyr Thr Pro Lys Pro Val
225                 230                 235                 240

Pro Val Glu Lys Glu Ala Ala Thr Pro Asp Ser Asn Pro Ser Leu Pro
                245                 250                 255

Val Pro Leu Pro Ser Met Ser Ser Asn Asp Glu Lys Thr Leu Val Ser
            260                 265                 270

Ala Gly Arg
        275
```

<210> SEQ ID NO 2
<211> LENGTH: 301
<212> TYPE: PRT
<213> ORGANISM: Solanum tuberosum

<400> SEQUENCE: 2

```
Met Met Lys Leu Met Ser Lys Gly Phe Met Phe Pro Ser Ser Ser Asp
1               5                   10                  15
Cys Gly Glu Ile Tyr His His Arg Pro Leu Asn Leu Pro Gly Ile Cys
            20                  25                  30
Ser Phe Pro Asn Lys Ser Val Asn Leu Ser Cys Leu Pro Ser Leu Asn
        35                  40                  45
Leu Ser Ser Ser Cys Leu Pro Arg Thr Asp Phe Tyr Gly Arg Arg Leu
    50                  55                  60
Val Ile Asn Glu Gly Val Ser Lys Phe Asn Arg Arg Asn Ser Gln Val
65                  70                  75                  80
Val Asp Ile Thr Ala Gln Met Ser Ile Gly Ile Arg Lys Ala Gln Lys
                85                  90                  95
Trp Trp Glu Lys Gly Val Gln Pro Asn Met Lys Glu Val Asn Ser Ala
            100                 105                 110
Gln Glu Leu Val Asp Ser Leu Leu Ser Ala Gly Asp Lys Leu Val Val
        115                 120                 125
Val Asp Phe Phe Ser Pro Gly Cys Gly Gly Cys Lys Ala Leu His Pro
    130                 135                 140
Lys Leu Cys Gln Leu Ala Glu Met Asn Pro Asp Val His Phe Leu Gln
145                 150                 155                 160
Val Asn Tyr Glu Glu His Lys Ser Met Cys Tyr Ser Leu Asn Val His
                165                 170                 175
Val Leu Pro Phe Phe Arg Phe Tyr Arg Gly Ala Glu Gly Arg Val Cys
            180                 185                 190
Ser Phe Ser Cys Thr Asn Ala Thr Ile Lys Lys Phe Lys Asp Ala Leu
        195                 200                 205
Ala Lys Tyr Gly Thr Asp Arg Cys Thr Leu Gly Pro Pro Lys Gly Leu
    210                 215                 220
Glu Glu Lys Glu Leu Leu Ala Leu Ala Ala Asn Lys Asp Leu Ser Phe
225                 230                 235                 240
Asn Tyr Thr Pro Lys Thr Glu Glu Ala Pro Val Leu Val Thr Ser Gln
                245                 250                 255
Lys Glu Val Gln Asp Thr Thr Pro Pro Asn Ile Glu Ser Pro Leu Pro
            260                 265                 270
Leu Pro Leu Pro Leu Pro Ile Ala Ser Thr Ser Ser Gln Thr Ala Lys
        275                 280                 285
Arg Asp Thr Glu Lys Glu Ala Tyr Ala Thr Ser Gly Arg
    290                 295                 300
```

<210> SEQ ID NO 3
<211> LENGTH: 230
<212> TYPE: PRT
<213> ORGANISM: Solanum tuberosum

<400> SEQUENCE: 3

```
Met Lys Phe Asn Arg Arg Asn His Lys Ser Ala Ala Ala Thr Ala Gln
1               5                   10                  15
Met Ser Ile Gly Ile Arg Lys Ala Pro Lys Trp Glu Lys Gly Leu
            20                  25                  30
```

```
Gln Pro Asn Met Lys Glu Val Met Gly Ala Gln Asp Leu Ala Asp Thr
             35                  40                  45

Leu Leu Asn Ala Gly Asp Lys Leu Val Val Asp Phe Leu Ser Pro
 50                  55                  60

Gly Cys Gly Gly Cys Lys Ala Leu His Pro Lys Ile Cys Gln Leu Ala
 65                  70                  75                  80

Glu Met Asn Pro Asp Val Gln Phe Leu His Val Asn Tyr Glu His
                 85                  90                  95

Lys Ser Met Cys Tyr Ser Leu Asn Val His Val Leu Pro Phe Phe Arg
                100                 105                 110

Phe Tyr Arg Gly Ala Glu Gly Arg Leu Cys Ser Phe Ser Cys Thr Asn
            115                 120                 125

Ala Thr Ile Lys Lys Phe Lys Asp Ala Leu Thr Lys Tyr Gly Ala Asp
        130                 135                 140

Cys Cys Ser Leu Glu Pro Val Lys Gly Leu Glu Lys Glu Leu Leu
145                 150                 155                 160

Ala Leu Ala Ala Asn Lys Asp Leu Ser Phe Ala Tyr Thr Pro Lys Thr
                165                 170                 175

Glu Glu Pro Met Pro Val Ala Leu Gln Asp Ala Lys Val Ile Lys Thr
            180                 185                 190

Ser Arg Thr Ser Ser Ser Cys Pro Asn Thr Phe Ser Leu Leu Pro Leu
        195                 200                 205

Pro Leu Pro Leu Pro Leu Ala Ser Thr Ser His Lys Ala Lys Gln Asp
210                 215                 220

Ser Lys Ser Glu Val Phe
225                 230

<210> SEQ ID NO 4
<211> LENGTH: 276
<212> TYPE: PRT
<213> ORGANISM: Zea mays

<400> SEQUENCE: 4

Met Ala Ala Ala Gln Ala Ile Ser Lys Gly Ser Val Val Ser Pro Cys
 1               5                  10                  15

Gly Asn Arg Ala Ala Pro Gly Leu Leu Ala Arg Arg Gly Ala Val
             20                  25                  30

Ala Ala Arg Val Ala Pro Ser Ala Ala Arg Ile Gly Gly Phe Trp Arg
         35                  40                  45

Lys Asn Ala Phe Pro Gly Gly Arg Leu Thr Leu Arg Thr Arg Arg Ser
 50                  55                  60

Arg Ala Ala Ser Pro Ala Gln Met Asn Met Asn Leu Ala Leu Gly Lys
 65                  70                  75                  80

Ser Met Arg Trp Trp Glu Lys Gly Leu Gln Pro Asn Met Arg Glu Ile
                 85                  90                  95

Glu Ser Ala Gln Asp Leu Val Asp Ala Leu Thr Asn Ala Gly Asp Arg
            100                 105                 110

Leu Val Val Asp Phe Phe Ser Pro Gly Cys Gly Cys Arg Ala
        115                 120                 125

Phe His Pro Lys Ile Cys Gln Phe Ala Glu Gln Asn Pro Asp Val Leu
130                 135                 140

Phe Leu Gln Val Asn Tyr Glu Glu His Lys Ser Met Cys His Ser Leu
145                 150                 155                 160

His Val His Val Leu Pro Leu Phe Arg Phe Tyr Arg Gly Ala Gln Gly
```

```
                165                 170                 175
Arg Leu Cys Ser Phe Ser Cys Thr Asn Thr Thr Ile Lys Lys Phe Arg
            180                 185                 190

Asp Ala Leu Ala Lys His Lys Pro Asp Arg Cys Ser Leu Gly Pro Thr
            195                 200                 205

Arg Gly Leu Glu Glu Ser Glu Leu Leu Ala Leu Ala Ala Asn Lys Asp
            210                 215                 220

Leu Gln Phe Thr Tyr Ala Lys Glu Pro Glu Leu Ile Pro Arg Gly
225                 230                 235                 240

Asp Ala Pro Gly Glu Val Val Ala Pro Glu Pro Ala Lys Leu Pro Ala
            245                 250                 255

Ala Pro Lys Pro Leu Val Arg Leu Gly Ser Glu Arg Ser Leu Val
            260                 265                 270

Ser Ser Gly Arg
            275

<210> SEQ ID NO 5
<211> LENGTH: 272
<212> TYPE: PRT
<213> ORGANISM: Zea mays

<400> SEQUENCE: 5

Met Ala Asp Ala Leu Cys Asn Gly Val Ala Ser Pro Cys Gly Arg
1               5                   10                  15

Asp Val Ala Gly Arg Ala Arg Gly Ala Ala Arg Ala Ala Leu Ala Glu
            20                  25                  30

Ser Leu Gln Val Ala Gly His Ala Ser Lys Thr Ser Phe Ser Ala Gly
            35                  40                  45

Arg Met Ser Val Lys Asp Ser Lys Pro Arg Pro Leu Ser Arg Ser Leu
            50                  55                  60

Glu Ala Ala Ala Pro Gly Gln Met Asn Leu Ser Phe Pro Lys Ala Met
65                  70                  75                  80

Arg Trp Trp Lys Lys Gly Leu His Pro Asn Met Arg Glu Val Glu Ser
                85                  90                  95

Ala Gln Asp Leu Ala Asp Ser Leu Leu Ser Ala Gly Asp Lys Leu Val
            100                 105                 110

Val Val Asp Phe Phe Ser Pro Gly Cys Gly Gly Cys Arg Ala Leu His
            115                 120                 125

Pro Lys Ile Ala Gln Phe Ala Glu Lys Asn Pro Gly Val Gln Phe Leu
            130                 135                 140

Gln Val Asn Tyr Glu Thr His Lys Ser Met Cys Tyr Ser Leu Arg Val
145                 150                 155                 160

His Val Leu Pro Phe Phe Arg Phe Tyr Arg Gly Ala Glu Gly Arg Val
                165                 170                 175

Ser Ser Phe Ser Cys Thr Asn Ala Thr Ile Asn Lys Phe Lys Asp Ala
            180                 185                 190

Leu Ala Lys His Gly Ala Glu Arg Cys Ser Leu Gly Pro Ala Arg Gly
            195                 200                 205

Leu Asp Glu Ser Glu Leu Met Ala Leu Ala Glu Asn Arg Asp Leu His
            210                 215                 220

Phe Thr Tyr Asp Lys Pro Gly Gly Leu Val Pro Leu Ala Glu Ala Ile
225                 230                 235                 240

Ala Lys Glu Ala Ala Pro Gly Gly Pro Trp Leu Pro Leu Pro Ala
            245                 250                 255
```

-continued

```
Ser Leu Leu Gly Gln Gly Ser Asp Asn Ser Leu Leu Pro Ser Gly Arg
            260                 265                 270
```

<210> SEQ ID NO 6
<211> LENGTH: 221
<212> TYPE: PRT
<213> ORGANISM: Zea mays

<400> SEQUENCE: 6

```
Met Ala Ala Ala Gln Val Val Ala Lys Gly Ser Val Val Ser Pro Cys
1               5                   10                  15

Gly Asn Arg Ala Val Pro Gly Leu Leu Gly Arg Arg Arg Asp Ala Val
                20                  25                  30

Ala Ala Gln Met Thr Pro Ser Ala Val Arg Ile Gly Gly Ser Trp Arg
            35                  40                  45

Lys Asn Ala Phe Pro Gly Val Arg Leu Ala Leu Gly Thr Arg Arg Ser
50                  55                  60

Arg Pro Ala Ser Arg Ser Phe Ser Ala Ser Pro Val Gln Met Asn Met
65                  70                  75                  80

Asn Leu Ala Ile Gly Lys Ser Met Arg Trp Trp Glu Lys Gly Leu Gln
                85                  90                  95

Pro Asn Met Arg Glu Ile Glu Ser Ala Gln Asp Leu Val Asp Ser Leu
            100                 105                 110

Thr Asn Ala Gly Glu Arg Leu Val Val Asp Phe Phe Ser Pro Gly
        115                 120                 125

Cys Gly Gly Cys Arg Ala Leu His Pro Lys Ile Cys Gln Phe Ala Glu
    130                 135                 140

Arg Asn Pro Asp Val Leu Phe Leu Gln Val Asn Tyr Glu Glu His Lys
145                 150                 155                 160

Ser Met Cys Tyr Ser Leu Arg Val His Val Leu Pro Phe Phe Arg Phe
                165                 170                 175

Tyr Arg Gly Ala Gln Gly Arg Leu Cys Ser Phe Ser Cys Thr Asn Ala
            180                 185                 190

Thr Val Arg Ser Cys Pro Cys Phe Phe Cys Ser Tyr Asp Tyr Trp Tyr
        195                 200                 205

Val Leu Asn Asn Met Gln His Ile Gln Asn Asp Leu Tyr
    210                 215                 220
```

<210> SEQ ID NO 7
<211> LENGTH: 279
<212> TYPE: PRT
<213> ORGANISM: Oryza sativa

<400> SEQUENCE: 7

```
Met Ala Ala Thr Ala Ala Gln Ala Val Ala Val Lys Gly Ser Val Ala
1               5                   10                  15

Val Pro Pro Cys Gly Ser Arg Gly Arg Arg Gly Ala Val Ala Ser
                20                  25                  30

Val Arg Met Ala Ala Ala Ala Thr Ser Ala Leu Arg Ile Gly Arg
            35                  40                  45

Arg Ser Pro Phe Leu Gly Arg Leu Ala Val Gly Pro Arg Arg Ser
50                  55                  60

Arg Pro Val Pro Arg Asn Leu Val Ala Pro Val Gln Met Asn Leu Ala
65                  70                  75                  80

Phe Ala Lys Ala Thr Lys Trp Trp Glu Lys Gly Leu Gln Pro Asn Met
                85                  90                  95
```

```
Arg Glu Val Glu Ser Ala Gln Asp Leu Val Asp Ser Leu Thr Asn Ala
             100                 105                 110

Gly Asp Asn Leu Val Ile Val Asp Phe Phe Ser Pro Gly Cys Gly Gly
        115                 120                 125

Cys Arg Ala Leu His Pro Lys Ile Cys Gln Ile Ala Glu Gln Asn Pro
    130                 135                 140

Asp Val Leu Phe Leu Gln Val Asn Tyr Glu Glu His Lys Ser Met Cys
145                 150                 155                 160

Tyr Ser Leu His Val His Val Leu Pro Phe Phe Arg Phe Tyr Arg Gly
                165                 170                 175

Ala Gln Gly Arg Leu Cys Ser Phe Ser Cys Thr Asn Ala Thr Ile Lys
            180                 185                 190

Lys Phe Arg Asp Ala Leu Ala Lys His Lys Pro Asp Arg Cys Ser Leu
        195                 200                 205

Gly Pro Thr Arg Gly Leu Glu Glu Ser Glu Leu Leu Ala Leu Ala Ala
    210                 215                 220

Asn Lys Asp Leu Gln Phe Asn Tyr Thr Lys Lys Pro Glu Leu Val Pro
225                 230                 235                 240

Ser Gly Asp Ala Ala Ala Gln Glu Leu Asp Arg Gly Ser Thr Lys
                245                 250                 255

Leu Ser Pro Pro Ala Lys Pro Leu Val Lys Gln Gly Ser Glu Glu Arg
            260                 265                 270

Ser Leu Val Ser Ser Gly Arg
            275

<210> SEQ ID NO 8
<211> LENGTH: 279
<212> TYPE: PRT
<213> ORGANISM: Oryza sativa

<400> SEQUENCE: 8

Met Ala Glu Ala Leu Cys Ser Gly Ser Val Ala Ser Pro Cys Gly Glu
1               5                   10                  15

Val Gly Val Gly Phe Ala Ala Gly Leu Val Arg Gly Ala Ala Ala Ala
            20                  25                  30

Ala Ala Leu Ala Glu Ser Val Pro Ile Gly Gly Tyr Ser Ser Lys Ser
        35                  40                  45

Thr Phe Pro Ser Gly Arg Val Ala Leu Thr Glu Arg Lys Ala Arg Pro
    50                  55                  60

Leu Pro Arg Asn Leu Glu Ala Ala His Gly Gln Met Asn Leu Thr Ile
65                  70                  75                  80

Gly Lys Ala Met Arg Trp Trp Glu Lys Cys Leu Gln Pro Asn Met Arg
                85                  90                  95

Glu Ile Glu Ser Ala Gln Asp Leu Ala Asp Ser Leu Leu Asn Ala Gly
            100                 105                 110

Asp Lys Leu Val Val Val Asp Phe Phe Ser Pro Gly Cys Gly Gly Cys
        115                 120                 125

Arg Ala Leu His Pro Lys Ile Ala Gln Leu Ala Glu Lys Asn Pro Glu
    130                 135                 140

Val Leu Phe Leu Gln Val Asn Tyr Glu Lys His Lys Ser Met Cys Tyr
145                 150                 155                 160

Ser Leu His Val His Val Leu Pro Phe Phe Arg Phe Tyr Arg Gly Ala
                165                 170                 175

Gln Gly Arg Val Ser Ser Phe Ser Cys Thr Asn Ala Thr Ile Lys Lys
            180                 185                 190
```

```
Phe Lys Asp Ala Leu Ala Lys His Gly Pro Asp Arg Cys Gly Leu Gly
            195                 200                 205

Pro Ala Lys Gly Leu Glu Glu Ser Glu Leu Met Ala Leu Ala Ile Asn
        210                 215                 220

Arg Asp Leu Asn Phe Thr Tyr Thr Pro Asn Gln Asp Leu Val Pro Ile
225                 230                 235                 240

Ala Asp Ala Leu Leu Lys Glu Ala Ala Pro Gly Gly Pro Trp Leu
                245                 250                 255

Pro Leu Pro Ala Thr Ala Thr Gln Leu Phe Ile Gln Gly Ser Glu Asn
        260                 265                 270

Ser Leu Leu Ser Ser Gly Arg
        275

<210> SEQ ID NO 9
<211> LENGTH: 276
<212> TYPE: PRT
<213> ORGANISM: Hordeum vulgare

<400> SEQUENCE: 9

Met Ala Thr Ala Gln Ala Val Ala Lys Gly Thr Val Val Ser Pro Cys
1               5                   10                  15

Gly Thr Arg Ala Ala Gly Phe Gly Ala Arg Arg Gly Ala Val Ala
            20                  25                  30

Ala Arg Met Ser Pro Cys Ala Pro Ala Val Arg Ile Gly Arg Lys
        35                  40                  45

Ser Pro Phe Leu Gly Ala Arg Leu Thr Val Gly Pro Arg Arg Ser Lys
    50                  55                  60

Leu Val Pro Arg Asn Leu Val Ser Ser Pro Val Gln Met Asn Leu Ala
65                  70                  75                  80

Phe Ala Lys Ser Thr Lys Trp Trp Glu Lys Gly Leu Lys Pro Asn Met
                85                  90                  95

Arg Glu Ile Glu Ser Ala Gln Asp Leu Val Asp Ser Leu Ala Asn Ala
            100                 105                 110

Gly Asp Arg Leu Val Val Val Asp Phe Phe Ser Pro Gly Cys Gly Gly
        115                 120                 125

Cys Arg Ala Leu His Pro Lys Ile Cys Gln Phe Gly Glu Gln Asn Pro
130                 135                 140

Asp Val Leu Phe Leu Gln Val Asn Tyr Glu Glu His Lys Ser Met Cys
145                 150                 155                 160

Tyr Ser Leu His Val His Val Leu Pro Phe Phe Arg Phe Tyr Arg Gly
                165                 170                 175

Ala Gln Gly Arg Leu Cys Ser Phe Ser Cys Thr Asn Ala Thr Ile Lys
            180                 185                 190

Lys Phe Arg Asp Ala Leu Ala Lys His Asn Pro Asp Arg Cys Ser Ile
        195                 200                 205

Gly Pro Thr Arg Gly Leu Glu Glu Ser Glu Leu Leu Ala Leu Ala Ala
    210                 215                 220

Asn Lys Asp Leu Gln Phe Thr Tyr Thr Lys Gln Pro Glu Pro Val Pro
225                 230                 235                 240

Ser Gly Asp Ser Glu Phe Ile Ala Pro Gly Ser Pro Arg Leu Pro Pro
                245                 250                 255

Pro Ala Lys Pro Leu Val Arg Gln Gly Ser Gly Glu Arg Thr Leu Val
            260                 265                 270

Ser Ser Gly Arg
```

<210> SEQ ID NO 10
<211> LENGTH: 270
<212> TYPE: PRT
<213> ORGANISM: Hordeum vulgare

<400> SEQUENCE: 10

Met Ala Asn Ala Leu Tyr Gly Gly Val Ala Ala Pro Cys Gly Asp
1               5                   10                  15

Leu Gly Ala Ala Ala Ala Leu Ala Glu Ser Leu Pro Met Gly Gly
                20                  25                  30

Tyr Arg Ala Arg Ser Ser Phe Pro Ala Gly Arg Val Ala Leu Ala Glu
                35                  40                  45

Arg Pro Leu Pro Arg Ser Leu Gln Val Ala Ala Ala Gly Gln Met
    50                  55                  60

Asn Gly Asn Leu Thr Ile Gly Lys Ala Met Arg Trp Trp Glu Lys Gly
65                  70                  75                  80

Thr Gln Pro Asn Met Arg Glu Val Glu Ser Ala Gln Asp Leu Ala Asp
                85                  90                  95

Ser Leu Leu Asn Ala Gly Asp Lys Leu Val Val Asp Phe Phe Ser
                100                 105                 110

Pro Gly Cys Gly Gly Cys Arg Ala Leu His Pro Lys Ile Ala Gln Phe
                115                 120                 125

Ala Glu Arg Asn Pro Asp Val Leu Phe Leu Gln Val Asn Tyr Glu Lys
                130                 135                 140

His Lys Ser Met Cys Tyr Ser Leu His Val His Val Leu Pro Phe Phe
145                 150                 155                 160

Arg Phe Tyr Arg Gly Ala Gln Gly Arg Val Ser Ser Phe Ser Cys Thr
                165                 170                 175

Asn Ala Thr Ile Lys Lys Phe Lys Asp Ala Leu Ala Lys His Ser Pro
                180                 185                 190

Asp Arg Cys Ser Leu Gly Pro Ala Arg Gly Leu Glu Lys Ala Glu Leu
                195                 200                 205

Leu Ala Leu Ala Glu Asn Arg Asp Leu Glu Phe Thr Tyr Ser Glu Lys
                210                 215                 220

Pro Thr Leu Val Pro Ile Ala Glu Ala Ile Arg Met Glu Ala Ala Ser
225                 230                 235                 240

Ile Gly Gly Pro Trp Leu Pro Leu Pro Pro Ala Ala Thr Gln Pro Phe
                245                 250                 255

Pro Leu Gly Ser Glu Asn Gly Ser Leu Ile Pro Ser Gly Arg
                260                 265                 270

<210> SEQ ID NO 11
<211> LENGTH: 273
<212> TYPE: PRT
<213> ORGANISM: Triticum aestivum

<400> SEQUENCE: 11

Met Ala Ser Ala Leu Cys Gly Gly Gly Ser Val Ala Ala Pro
1               5                   10                  15

Cys Gly Asp Leu Gly Ala Ala Ala Leu Ala Glu Ser Leu Pro Met
                20                  25                  30

Gly Ala Gly Tyr Arg Ala Lys Ser Ser Phe Pro Ala Gly Arg Val Ala
                35                  40                  45

Leu Ala Asp Arg Pro Leu Arg Arg Gly Leu Gln Val Ala Ala Ala Ala

Gly Gln Met Asn Gly Asn Leu Thr Ile Gly Lys Ala Met Arg Trp Trp
65                  70                  75                  80

Glu Lys Val Thr His Pro Asn Met Arg Glu Val Ser Ala Gln Asp
                85                  90                  95

Leu Ala Asp Ser Leu Leu Asn Ala Gly Asp Lys Leu Val Val Asp
            100                 105                 110

Phe Phe Ser Pro Gly Cys Gly Gly Cys Arg Ala Leu His Pro Lys Ile
        115                 120                 125

Ala Gln Phe Ala Glu Arg Asn Pro Asp Val Leu Phe Leu Gln Val Asn
130                 135                 140

Tyr Glu Lys His Lys Ser Met Cys Tyr Ser Leu His Val His Val Leu
145                 150                 155                 160

Pro Phe Phe Arg Phe Tyr Arg Gly Ala Gln Gly Arg Val Ser Ser Phe
                165                 170                 175

Ser Cys Thr Asn Ala Thr Ile Lys Lys Phe Lys Asp Ala Leu Ala Lys
            180                 185                 190

His Ser Pro Asp Arg Cys Ser Leu Gly Pro Ala Arg Gly Leu Glu Glu
        195                 200                 205

Ala Glu Leu Leu Ala Leu Ala Ala Asn Arg Asp Leu Glu Phe Thr Tyr
210                 215                 220

Asn Glu Lys Pro Thr Leu Val Pro Ile Ala Glu Ala Ile Gln Met Glu
225                 230                 235                 240

Ala Ala Ser Ile Gly Gly Pro Trp Met Pro Leu Pro Ala Ala Ala Thr
                245                 250                 255

Gln Pro Leu Thr Leu Gly Ser Glu Asn Gly Ser Leu Ile Pro Ser Gly
            260                 265                 270

Arg

<210> SEQ ID NO 12
<211> LENGTH: 296
<212> TYPE: PRT
<213> ORGANISM: Manihot esculenta

<400> SEQUENCE: 12

Met Ala Asp Val Leu Ser Asn Thr Asn Leu Val Ser Ser Ser Phe Ser
1               5                   10                  15

Ser Ser Phe Thr Gly His Arg Asn Glu Gln Lys Asn Ser Ser Cys Arg
            20                  25                  30

Leu Lys Gly Phe Pro Arg Lys Val Asn Arg Gln Thr Leu Arg Leu Lys
        35                  40                  45

Ala Thr Ser Leu Gly Ser Asp Phe His Gly Lys Arg Val Val Leu Gln
50                  55                  60

Asp Asn Gln Gly Lys Pro Lys Arg Gly Ile Tyr Leu Gln Met Ser Ile
65                  70                  75                  80

Lys Ala Gln His Thr Gly Leu Arg Leu Lys Ser Ala Pro Lys Trp Trp
                85                  90                  95

Glu Lys Gly Leu Gln Pro Asn Met Arg Glu Val Thr Ser Ala Gln Asp
            100                 105                 110

Phe Val Asp Ser Leu Leu Asn Ala Gly Asp Lys Leu Ile Val Asp
        115                 120                 125

Phe Phe Ser Pro Gly Cys Gly Gly Cys Lys Ala Leu His Pro Lys Ile
130                 135                 140

Cys Gln Phe Ala Glu Met Asn Pro Asp Val Leu Phe Leu His Val Asn

```
            145                 150                 155                 160

Tyr Glu Glu His Lys Ser Met Cys Tyr Ser Leu Asn Ile His Val Leu
                165                 170                 175

Pro Phe Phe Arg Phe Tyr Arg Gly Ala Gln Gly Arg Leu Cys Ser Phe
                180                 185                 190

Ser Cys Thr Asn Ala Thr Ile Lys Lys Phe Arg Asp Ala Leu Ala Lys
                195                 200                 205

His Ser Pro Asp Arg Cys Ser Leu Gly Pro Thr Lys Gly Leu Glu Glu
                210                 215                 220

Lys Glu Leu Ile Ala Leu Ala Ser Asn Lys Asp Leu Asn Phe Lys Tyr
225                 230                 235                 240

Ala Gln Lys Pro Asp Leu Pro Thr Pro Ile Pro Ala Lys Glu Glu Arg
                245                 250                 255

Val Pro Val Val Ser Pro Ser His Pro Asn Pro Ala Leu Pro Leu Pro
                260                 265                 270

Leu Pro Leu Pro Thr Ala Ser Pro Lys Ser Gly Gln Gly Ser Glu Glu
                275                 280                 285

Lys Thr Leu Val Gly Ser Gly Arg
                290                 295

<210> SEQ ID NO 13
<211> LENGTH: 286
<212> TYPE: PRT
<213> ORGANISM: Manihot esculenta

<400> SEQUENCE: 13

Met Ala Ala Val Ser Ser Asn Thr Asn Leu Val Ser Ser Ser Cys Ser
1               5                   10                  15

Ser Ser Phe Ser Ser Ser Gln Asn Arg Pro Glu Tyr Arg Ser Ser Arg
                20                  25                  30

Leu Arg Val Phe Pro Gln Glu Leu Asn His Gln Ala Leu Arg Leu Gln
                35                  40                  45

Thr Thr Ser Leu Gly Ser Asp Phe His Gly Lys Arg Val Val Leu Gln
            50                  55                  60

Glu Lys Pro Lys Cys Lys Gln Gly Ile Ser Val Gln Ser Ser Ile Lys
65                  70                  75                  80

Ala Gln Thr Gly Leu Arg Leu Lys Asn Ala Lys Asn Trp Trp Glu Glu
                85                  90                  95

Glu Leu Gln Pro Asn Met Arg Glu Val Ile Ser Ala Gln Asp Leu Val
                100                 105                 110

Asp Ser Leu Leu Asn Ala Gly Asp Lys Leu Val Ile Val Tyr Phe Phe
                115                 120                 125

Ser Pro Gly Cys Gly Gly Cys Arg Ala Leu His Pro Lys Ile Cys Gln
                130                 135                 140

Leu Ala Lys Asn Asn Ala Asp Val Gln Phe Leu Lys Val Asn Tyr Glu
145                 150                 155                 160

Glu His Lys Ser Met Cys Tyr Ser Leu Asn Val His Val Leu Pro Phe
                165                 170                 175

Phe Arg Phe Tyr Arg Gly Ala Gln Gly Arg Val Cys Ser Phe Ser Cys
                180                 185                 190

Thr Asn Ala Thr Ile Lys Lys Phe Lys Asn Ala Leu Ala Lys His Thr
                195                 200                 205

Pro Asp Arg Ser Ser Leu Glu Pro Thr Lys Gly Leu Glu Glu Lys Glu
                210                 215                 220
```

```
Leu Ile Ala Leu Ala Ala Asn Lys Asp Leu Asn Leu Thr Tyr Ala Pro
225                 230                 235                 240

Lys Ser Asp Lys Pro Ile Pro Ala Pro Thr Lys Glu Glu Ile Val Pro
            245                 250                 255

Glu Ile Pro Gln Ser Leu Ser Leu Ala Leu Arg Arg Ser Met Glu Leu
        260                 265                 270

Ala Gln Gly Ser Ala Glu Lys Thr Leu Val Ala Ser Gly Arg
        275                 280                 285
```

<210> SEQ ID NO 14
<211> LENGTH: 283
<212> TYPE: PRT
<213> ORGANISM: Sorghum bicolor

<400> SEQUENCE: 14

```
Met Ala Ala Ala Gln Ala Val Ala Lys Gly Ser Val Val Ala Pro Cys
1               5                   10                  15

Gly Asn Arg Ala Ala Pro Gly Leu Leu Gly Arg Arg Gly Ala Val
            20                  25                  30

Ala Ala Arg Met Ala Pro Ser Ala Val Arg Ile Gly Ala Ser Trp Arg
        35                  40                  45

Lys Thr Ala Phe Thr Gly Gly Arg Leu Ala Leu Gly Leu Gly Thr Arg
50                  55                  60

Arg Ser Arg Pro Ala Ser Arg Ser Ser Phe Ala Ser Pro Ala Gln Met
65                  70                  75                  80

Asn Met Asn Leu Ala Ile Gly Lys Ser Met Arg Trp Trp Glu Lys Gly
                85                  90                  95

Leu Gln Pro Asn Met Arg Glu Ile Glu Ser Ala Gln Asp Leu Val Asp
            100                 105                 110

Ser Leu Thr Asn Ala Gly Asp Lys Leu Val Ile Val Asp Phe Phe Ser
        115                 120                 125

Pro Gly Cys Gly Gly Cys Arg Ala Leu His Pro Lys Ile Cys Gln Phe
    130                 135                 140

Ala Glu Gln Asn Pro Asp Val Leu Phe Leu Gln Val Asn Tyr Glu Glu
145                 150                 155                 160

His Lys Ser Met Cys Tyr Ser Leu His Val His Val Leu Pro Phe Phe
                165                 170                 175

Arg Phe Tyr Arg Gly Ala Gln Gly Arg Leu Cys Ser Phe Ser Cys Thr
            180                 185                 190

Asn Ala Thr Ile Lys Lys Phe Lys Asp Ala Leu Ala Lys His Lys Pro
        195                 200                 205

Asp Arg Cys Ser Leu Gly Pro Thr Arg Gly Leu Glu Glu Ser Glu Phe
    210                 215                 220

Leu Ala Leu Ala Ala Asn Lys Asp Leu Gln Phe Thr Tyr Thr Lys Glu
225                 230                 235                 240

Pro Glu Leu Ile Pro Arg Gly Asp Ala Pro Gly Glu Val Ile Ala Pro
                245                 250                 255

Glu Pro Ala Lys Leu Pro Ala Ala Thr Lys Pro Leu Val Arg Leu Gly
            260                 265                 270

Ser Glu Glu Arg Ser Leu Val Ser Ser Gly Arg
        275                 280
```

<210> SEQ ID NO 15
<211> LENGTH: 266
<212> TYPE: PRT
<213> ORGANISM: Sorghum bicolor

<400> SEQUENCE: 15

```
Met Ala Ala Ala Gln Ala Met Lys Gly Ser Val Gly Gln Gly Ser
1               5                   10                  15

Leu Gly Arg Arg Arg Gly Ala Glu Ala Ala Arg Val Gly Gly Ser Trp
            20                  25                  30

Arg Lys Ser Ala Phe Leu Gly Gly Arg Leu Ala Val Gly Pro Arg Arg
            35                  40                  45

Pro Arg Pro Val Ser Arg Ile Leu Val Thr Ser Pro Ala Val Gln Gln
50                  55                  60

Thr Asn Leu Ser Phe Ala Lys Ala Met Lys Trp Trp Gln Lys Gly Leu
65                  70                  75                  80

Gln Pro Asn Met Arg Ala Ile Gln Thr Ala Gln Asp Leu Ala Asp Ser
                85                  90                  95

Leu Thr Asn Ala Gly Asp Gly Leu Val Val Asp Phe Phe Ser Pro
            100                 105                 110

Gly Cys Ala Gly Cys His Ala Leu His Pro Lys Ile Cys Gln Phe Ala
            115                 120                 125

Glu Arg Asn Pro Asp Val Gln Phe Leu Gln Val Asn Tyr Glu Glu His
130                 135                 140

Lys Ser Met Cys His Ser Leu His Val His Val Phe Pro Phe Phe Arg
145                 150                 155                 160

Phe Tyr Arg Gly Ala Gln Gly Arg Leu Cys Ser Phe Ser Cys Thr Asn
                165                 170                 175

Ala Thr Ile Lys Lys Phe Arg Asp Ala Leu Ala Lys His Arg Ala Asp
            180                 185                 190

Arg Cys Ser Leu Gly Pro Thr Arg Gly Leu Glu Glu Ser Glu Leu Leu
            195                 200                 205

Ala Leu Ala Ala Asn Lys Asp Leu Gln Phe Thr Tyr Thr Lys Glu Ala
210                 215                 220

Glu Leu Ala Pro Ser Met Glu Asp Val Ala Glu Val Met Thr Ala Asp
225                 230                 235                 240

Arg Pro Gly Leu Pro Thr Ser Thr Met Pro Leu Ala Arg Gln Gly Ser
                245                 250                 255

Glu Asp Arg Ala Leu Val Ser Ser Gly Arg
            260                 265
```

<210> SEQ ID NO 16
<211> LENGTH: 205
<212> TYPE: PRT
<213> ORGANISM: Sorghum bicolor

<400> SEQUENCE: 16

```
Met Ala Glu Ala Leu Cys Asn Gly Val Val Ala Ser Pro Tyr Gly Gly
1               5                   10                  15

Gly Asp Val Gly Val Ala Gly Arg Ala Arg Gly Ala Ala Lys Ala Ala
            20                  25                  30

Leu Ala Glu Ser Leu Pro Val Gly Gly Tyr Ala Thr Lys Ser Ser Phe
            35                  40                  45

Ser Ala Gly Arg Met Ser Val Ser Asp Arg Lys Pro Arg Pro Leu Ser
50                  55                  60

Arg Asn Leu Glu Ala Ala Ala Pro Gly Gln Met Asn Leu Ser Phe
65                  70                  75                  80

Pro Lys Ala Met Arg Trp Trp Glu Lys Gly Leu His Pro Asn Met Arg
                85                  90                  95
```

```
Glu Ile Glu Ser Ala Gln Asp Leu Ala Asp Ser Leu Leu Asn Ala Gly
            100                 105                 110

Asp Lys Leu Val Val Asp Phe Ser Pro Gly Cys Gly Gly Cys
            115                 120                 125

Arg Ala Leu His Pro Lys Ile Ala Gln Phe Ala Glu Lys Asn Pro Asp
    130                 135                 140

Val Leu Phe Leu Gln Val Asn Tyr Glu Thr His Lys Ser Met Cys Tyr
145                 150                 155                 160

Ser Leu His Val His Val Leu Pro Phe Phe Arg Phe Tyr Arg Gly Ala
                165                 170                 175

Glu Gly Arg Val Ser Ser Phe Ser Cys Thr Asn Ala Thr Val Arg Ile
            180                 185                 190

Asp His Leu Ser Asn Phe Lys Asn Gln Gln Met Asn Glu
    195                 200                 205

<210> SEQ ID NO 17
<211> LENGTH: 261
<212> TYPE: PRT
<213> ORGANISM: Brassica napus

<400> SEQUENCE: 17

Met Ala Glu Ala Ala Ile Ser Arg Thr Asn Leu Ile Phe Arg Gly Ala
1               5                   10                  15

Cys Val Asn Gln His Lys His Val Asp Asp Tyr Ser Val Ser Ser Pro
                20                  25                  30

Val Ser Phe Gly Leu Arg Lys Ser Phe Pro Ser Leu Lys Val Lys Pro
            35                  40                  45

Phe Asn Gln Phe Gln Ser Ser Arg Ser Ser Ser Ile Thr Ala Gln
    50                  55                  60

Thr Thr Leu Arg Ile Gly Thr Pro Gln Lys Trp Trp Glu Lys Gly Leu
65              70                  75                  80

Lys Glu Asn Met Arg Glu Ile Ser Ala Gln Glu Leu Val Asp Ser
                85                  90                  95

Leu Thr Asn Ala Gly Asp Lys Leu Val Val Asp Phe Phe Ser Pro
            100                 105                 110

Gly Cys Gly Gly Cys Lys Ala Leu His Pro Lys Ile Cys Gln Leu Ala
        115                 120                 125

Glu Gln Asn Pro Asp Val Gln Phe Leu Gln Val Asn Tyr Glu Glu His
    130                 135                 140

Lys Ser Met Cys Tyr Ser Leu Gly Val His Val Leu Pro Phe Phe Arg
145                 150                 155                 160

Phe Tyr Arg Gly Ala His Gly Arg Val Cys Ser Phe Ser Cys Thr Asn
                165                 170                 175

Ala Thr Ile Lys Lys Phe Arg Asp Ala Leu Ala Lys His Ser Pro Asp
            180                 185                 190

Arg Cys Ser Leu Gly Pro Thr Lys Gly Leu Glu Glu Lys Glu Leu Val
        195                 200                 205

Ala Leu Ala Ala Asn Lys Glu Leu Asn Phe Ser Tyr Thr Pro Arg Ala
    210                 215                 220

Val Pro Val Glu Glu Glu Ala Pro Val Ala Ser Asn Pro Gly
225                 230                 235                 240

Leu Pro Val Ala His Pro Ser Met Lys Ala Asn Asp Gly Lys Thr Leu
            245                 250                 255

Val Ser Ser Gly Arg
```

<210> SEQ ID NO 18
<211> LENGTH: 268
<212> TYPE: PRT
<213> ORGANISM: Brassica napus

<400> SEQUENCE: 18

| | | | | | | | | | | | | | | | |
|---|---|---|---|---|---|---|---|---|---|---|---|---|---|---|---|
| Met | Ala | Glu | Val | Ile | Ser | Lys | Thr | Ser | Leu | Phe | Phe | Arg | Gly | Ala | Cys |
| 1 | | | | 5 | | | | | 10 | | | | | 15 | |
| Val | Asn | His | His | His | His | Ala | Asp | Asp | Phe | Ser | Val | Ser | Pro | Val | Ser |
| | | | 20 | | | | | 25 | | | | | 30 | | |
| Phe | Gly | Leu | Lys | Lys | Ser | Phe | Ser | Leu | Lys | Gln | Lys | Pro | Leu | Arg | |
| | | 35 | | | | | 40 | | | | | 45 | | | |
| Ser | Asp | Phe | Ser | Gly | Lys | Gln | Ile | Leu | Gln | Thr | Phe | Asn | Arg | Ser | Phe |
| | 50 | | | | | 55 | | | | | 60 | | | | |
| Arg | Ser | Ser | Ser | Val | Thr | Ala | Gln | Ser | Thr | Leu | Arg | Ile | Gly | Thr | Ala |
| 65 | | | | | 70 | | | | | 75 | | | | | 80 |
| Gln | Lys | Trp | Trp | Glu | Lys | Gly | Leu | Gln | Glu | Asn | Met | Arg | Glu | Ile | Ser |
| | | | | 85 | | | | | 90 | | | | | 95 | |
| Ser | Ala | Gln | Glu | Leu | Val | Asp | Ser | Leu | Ala | Asp | Ala | Gly | Asp | Lys | Leu |
| | | | 100 | | | | | 105 | | | | | 110 | | |
| Val | Val | Val | Asp | Phe | Phe | Ser | Pro | Gly | Cys | Gly | Gly | Cys | Lys | Ala | Leu |
| | | 115 | | | | | 120 | | | | | 125 | | | |
| His | Pro | Lys | Met | Cys | Gln | Leu | Ala | Glu | Gln | Ser | Ala | Asp | Val | Gln | Phe |
| | 130 | | | | | 135 | | | | | 140 | | | | |
| Leu | Gln | Val | Asn | Tyr | Glu | Glu | His | Lys | Ser | Met | Cys | Tyr | Ser | Leu | Gly |
| 145 | | | | | 150 | | | | | 155 | | | | | 160 |
| Val | His | Val | Leu | Pro | Phe | Phe | Arg | Phe | Tyr | Arg | Gly | Ala | Gln | Gly | Arg |
| | | | | 165 | | | | | 170 | | | | | 175 | |
| Val | Cys | Ser | Phe | Ser | Cys | Thr | Asn | Ala | Thr | Ile | Lys | Lys | Phe | Arg | Asp |
| | | | 180 | | | | | 185 | | | | | 190 | | |
| Ala | Leu | Ala | Lys | His | Ser | Pro | Asp | Arg | Cys | Ser | Leu | Gly | Pro | Thr | Lys |
| | | 195 | | | | | 200 | | | | | 205 | | | |
| Gly | Leu | Glu | Glu | Lys | Glu | Leu | Val | Ala | Leu | Ala | Ala | Asn | Lys | Glu | Leu |
| | 210 | | | | | 215 | | | | | 220 | | | | |
| Asn | Phe | Ser | Tyr | Thr | Pro | Lys | Val | Val | Pro | Val | Glu | Lys | Glu | Ala | Ala |
| 225 | | | | | 230 | | | | | 235 | | | | | 240 |
| Ile | Pro | Thr | Ser | Asn | Pro | Ala | Leu | Pro | Val | Pro | His | Pro | Ser | Met | Ser |
| | | | | 245 | | | | | 250 | | | | | 255 | |
| Gly | Ser | Glu | Glu | Lys | Thr | Leu | Val | Ser | Ala | Gly | Arg | | | | |
| | | | 260 | | | | | 265 | | | | | | | |

<210> SEQ ID NO 19
<211> LENGTH: 269
<212> TYPE: PRT
<213> ORGANISM: Brassica napus

<400> SEQUENCE: 19

| | | | | | | | | | | | | | | | |
|---|---|---|---|---|---|---|---|---|---|---|---|---|---|---|---|
| Met | Ala | Glu | Ala | Ala | Ile | Ser | Arg | Thr | Asn | Leu | Ile | Phe | Arg | Gly | Ala |
| 1 | | | | 5 | | | | | 10 | | | | | 15 | |
| Cys | Val | Thr | His | His | His | Ala | Asp | Asp | Tyr | Ser | Val | Ser | Ser | Ser | |
| | | | 20 | | | | | 25 | | | | | 30 | | |
| Pro | Val | Ser | Phe | Gly | Leu | Arg | Lys | Ser | Phe | Ser | Leu | Lys | Leu | Lys | |
| | | 35 | | | | | 40 | | | | | 45 | | | |
| Pro | Pro | Arg | Gln | Ile | Asp | Thr | Gln | Phe | Gln | Thr | Phe | Thr | Arg | Ser | Ser |

```
                 50                  55                  60
Arg Ala Ser Ser Ile Thr Ala Gln Thr Thr Leu Arg Ile Gly Thr Pro
 65                  70                  75                  80

Gln Lys Trp Trp Glu Lys Gly Leu Lys Glu Asn Met Arg Glu Ile Ser
                 85                  90                  95

Ser Ala Gln Glu Leu Val Asp Ser Leu Thr Asn Ala Gly Asp Lys Leu
            100                 105                 110

Val Val Val Asp Phe Phe Ser Pro Gly Cys Gly Cys Lys Ala Leu
        115                 120                 125

His Pro Lys Ile Cys Gln Leu Ala Glu Gln Asn Pro Asp Val Gln Phe
        130                 135                 140

Leu Gln Val Asn Tyr Glu Glu His Lys Ser Met Cys Tyr Ser Leu Gly
145                 150                 155                 160

Val His Val Leu Pro Phe Phe Arg Phe Tyr Arg Gly Ala His Gly Arg
                165                 170                 175

Val Cys Ser Phe Ser Cys Thr Asn Ala Thr Ile Lys Lys Phe Arg Asp
            180                 185                 190

Ala Leu Ala Lys His Ser Pro Asp Arg Cys Ser Leu Gly Pro Thr Lys
            195                 200                 205

Gly Leu Glu Glu Lys Glu Leu Val Ala Leu Ala Ala Asn Lys Glu Leu
        210                 215                 220

Asn Phe Ser Tyr Thr Pro Arg Ala Val Pro Val Glu Glu Glu Glu Ala
225                 230                 235                 240

Pro Val Pro Ala Ser Lys Pro Gly Leu Ala Val Pro His Pro Ser Met
                245                 250                 255

Ser Ala Asn Asp Glu Lys Thr Leu Val Ser Ala Gly Arg
            260                 265
```

<210> SEQ ID NO 20
<211> LENGTH: 261
<212> TYPE: PRT
<213> ORGANISM: Brassica napus

<400> SEQUENCE: 20

```
Met Ala Glu Ala Ala Ile Ser Arg Thr Asn Leu Ile Phe Arg Gly Ala
 1                   5                  10                  15

Cys Val Asn Gln His Lys His Val Asp Asp Tyr Ser Val Ser Ser Pro
                20                  25                  30

Val Ser Phe Gly Leu Arg Lys Ser Phe Pro Ser Leu Lys Val Lys Pro
            35                  40                  45

Phe Asn Gln Phe Gln Ser Ser Arg Ser Ser Ser Ile Thr Ala Gln
 50                  55                  60

Thr Ala Leu Arg Ile Gly Thr Pro Gln Arg Trp Trp Glu Lys Gly Leu
 65                  70                  75                  80

Lys Glu Asn Met Arg Glu Ile Ser Ser Ala Gln Glu Leu Val Asp Ser
                85                  90                  95

Leu Thr Asn Ala Gly Asp Lys Leu Val Val Asp Phe Phe Ser Pro
            100                 105                 110

Gly Cys Gly Cys Lys Ala Leu His Pro Lys Ile Cys Gln Leu Ala
        115                 120                 125

Glu Gln Asn Pro Asp Val Gln Phe Leu Gln Val Asn Tyr Glu Glu His
        130                 135                 140

Lys Ser Met Cys Tyr Ser Leu Gly Val His Val Leu Pro Phe Phe Arg
145                 150                 155                 160
```

```
Phe Tyr Arg Gly Ala His Gly Arg Val Cys Ser Phe Ser Cys Thr Asn
                165                 170                 175

Ala Thr Ile Lys Lys Phe Arg Asp Ala Leu Ala Lys His Thr Pro Asp
            180                 185                 190

Arg Cys Ser Leu Gly Pro Thr Lys Gly Leu Glu Glu Lys Glu Leu Val
        195                 200                 205

Ala Leu Ala Ala Asn Lys Glu Leu Asn Phe Ser Tyr Thr Pro Lys Asp
    210                 215                 220

Val Pro Val Glu Glu Ala Ala Pro Val Pro Val Ser Asn Pro Gly
225                 230                 235                 240

Leu Pro Val Ala His Pro Ser Met Lys Ala Asn Asp Gly Lys Thr Leu
                245                 250                 255

Val Ser Ser Gly Arg
                260

<210> SEQ ID NO 21
<211> LENGTH: 272
<212> TYPE: PRT
<213> ORGANISM: Brassica napus

<400> SEQUENCE: 21

Met Ala Glu Val Ile Ser Lys Thr Ser Leu Phe Gly Gly Gly Ala
1               5                   10                  15

Cys Val Asn His His His His Val Asp Asp Leu Ser Val Ser Pro
                20                  25                  30

Val Ser Phe Gly Phe Lys Lys Ser Phe Ser Ser Leu Lys Gln Lys
            35                  40                  45

Pro Leu Arg Ser Asp Phe Ser Gly Lys Gln Ile Leu Glu Thr Phe Asn
50                  55                  60

Arg Ser Phe Arg Ser Ser Ser Val Thr Ala Gln Ser Thr Leu Arg Ile
65                  70                  75                  80

Gly Thr Ala His Lys Trp Trp Glu Lys Gly Ser Gln Glu Asn Met Arg
                85                  90                  95

Glu Ile Ser Ser Ala Gln Asp Leu Val Asp Ser Leu Ala Asp Ala Gly
            100                 105                 110

Asp Lys Leu Val Val Val Asp Phe Phe Ser Pro Gly Cys Gly Gly Cys
        115                 120                 125

Lys Ala Leu His Pro Lys Met Cys Gln Leu Ala Glu Gln Ser Pro Asp
    130                 135                 140

Val Gln Phe Leu Gln Val Asn Tyr Glu Glu His Lys Ser Met Cys Tyr
145                 150                 155                 160

Ser Leu Gly Val His Val Leu Pro Phe Phe Arg Phe Tyr Arg Gly Ala
                165                 170                 175

Gln Gly Arg Val Cys Ser Phe Ser Cys Thr Asn Ala Thr Ile Lys Lys
            180                 185                 190

Phe Arg Asp Ala Leu Ala Lys His Ser Pro Asp Arg Cys Ser Leu Gly
        195                 200                 205

Pro Thr Lys Gly Leu Glu Glu Lys Glu Leu Val Ala Leu Ala Ala Asn
    210                 215                 220

Lys Glu Leu Lys Phe Ser Tyr Thr Pro Lys Val Pro Val Glu Lys
225                 230                 235                 240

Glu Val Ala Ile Pro Thr Ser Asn Pro Gly Leu Pro Val Pro His Pro
                245                 250                 255

Ser Thr Met Ser Gly Ser Glu Glu Lys Thr Leu Val Ser Ala Gly Arg
            260                 265                 270
```

<210> SEQ ID NO 22
<211> LENGTH: 296
<212> TYPE: PRT
<213> ORGANISM: Ricinus communis

<400> SEQUENCE: 22

Met Ala Asp Val Le

Thr Phe Val Ser Gly Val Gly Ser Pro Ser Leu Lys Leu Lys Ser
                35                  40                  45

Pro Ile Leu Arg Ser Trp Ser Pro Ser Glu Phe Gln Gly Lys Gln
 50                  55                  60

Leu Leu Phe Arg Val Asn Arg Gly Lys Pro Asn Arg Val Ser Ser Arg
 65                  70                  75                  80

Leu Arg Ala Ser Thr Ala Ala Gln Met Thr Leu Arg Ile Gly Lys Val
                 85                  90                  95

Gln Lys Trp Trp Glu Lys Gly Leu Gln Pro Asn Met Lys Glu Val Thr
                100                 105                 110

Ser Ala Gln Asp Leu Val Glu Ser Leu Leu Asn Ala Gly Asp Lys Leu
                115                 120                 125

Val Val Val Asp Phe Phe Ser Pro Gly Cys Gly Gly Cys Lys Ala Leu
130                 135                 140

His Pro Lys Ile Cys Gln Leu Ala Glu Met Asn Pro Asp Val Gln Phe
145                 150                 155                 160

Leu Gln Val Asn Tyr Glu Glu His Lys Ser Met Cys Tyr Ser Leu Asn
                165                 170                 175

Val His Val Leu Pro Phe Phe Arg Phe Tyr Arg Gly Ala His Gly Arg
180                 185                 190

Leu Cys Ser Phe Ser Cys Thr Asn Ala Thr Ile Lys Lys Phe Arg Asp
                195                 200                 205

Ala Leu Ala Lys His Ser Pro Asp Arg Cys Ser Leu Gly Pro Thr Lys
210                 215                 220

Gly Leu Glu Glu Lys Glu Leu Leu Ala Leu Ala Asn Lys Asp Leu
225                 230                 235                 240

Ser Phe Thr Leu Pro Lys Pro Leu Gln Pro Glu His Ala Asn Glu Gly
                245                 250                 255

Leu Ala Thr Ala Pro Ala Pro Val Pro Ser Ser Glu Ser Leu Pro Leu
                260                 265                 270

Pro Ser Leu Thr Leu Asn Ser Glu Val Ser Gln Glu Arg Thr Leu Thr
                275                 280                 285

Thr Ala Gly Arg
                290

<210> SEQ ID NO 24
<211> LENGTH: 291
<212> TYPE: PRT
<213> ORGANISM: Phaseolus vulgaris

<400> SEQUENCE: 24

Met Ala Glu Val Leu Thr Glu Ala Ser Leu Val Ser Ser Trp His Gly
1               5                   10                  15

Thr Thr Gln Arg His His Arg Arg Val Ser Thr Val Pro Asn Ser Ser
                20                  25                  30

Ser Phe Val Ser Gly Val Gly Arg Phe Pro Ser Leu Lys Leu Lys Ser
                35                  40                  45

Gln Ile Leu Arg Ser Leu Ser Ser Ser Glu Phe Gln Gly Lys Lys
 50                  55                  60

Leu Leu Phe His Val Asn Arg Gly Leu Ala Asn Arg Ile Ser Ser Arg
 65                  70                  75                  80

Leu Gly Ala Ser Thr Ala Ala Gln Met Thr Leu Arg Ile Gly Lys Gly
                 85                  90                  95

Gln Lys Trp Trp Glu Lys Gly Leu Gln Pro Asn Met Asn Glu Val Thr

```
            100                 105                 110
Ser Ala Gln Asp Leu Val Glu Ser Leu Leu Asn Ala Gly Asp Lys Leu
            115                 120                 125

Val Val Val Asp Phe Phe Ser Pro Gly Cys Gly Gly Cys Lys Ala Leu
130                 135                 140

His Pro Lys Ile Cys Gln Leu Ala Glu Met Asn Pro Asp Val Gln Phe
145                 150                 155                 160

Leu Gln Val Asn Tyr Glu Glu His Lys Ser Met Cys Tyr Ser Leu Asn
                165                 170                 175

Val His Val Leu Pro Phe Phe Arg Phe Tyr Arg Gly Ala His Gly Arg
            180                 185                 190

Leu Cys Ser Phe Ser Cys Thr Asn Ala Thr Ile Lys Lys Phe Lys Asp
            195                 200                 205

Ala Leu Ala Lys His Ser Pro Asp Arg Cys Ser Leu Gly Pro Thr Lys
            210                 215                 220

Gly Leu Glu Glu Lys Glu Leu Leu Ala Leu Ala Asn Lys Asp Leu
225                 230                 235                 240

Ser Phe Ile Tyr Ala Pro Asn Pro Leu Gln Pro Glu His Glu Asn Glu
                245                 250                 255

Glu Leu Ala Thr Ala Pro Ala Pro Val Pro Ser Ser Glu Ser Leu Pro
            260                 265                 270

Leu Cys His Leu Ile Ser Glu Val Ser Lys Lys Thr Leu Ile Thr
            275                 280                 285

Ala Gly Arg
    290

<210> SEQ ID NO 25
<211> LENGTH: 287
<212> TYPE: PRT
<213> ORGANISM: Gossypium histrum

<400> SEQUENCE: 25

Met Ala Glu Val Leu Gly Lys Gly Asn Leu Phe Thr Thr Cys Asn Tyr
1               5                   10                  15

Ser Gln Thr Lys Asn Leu Glu Gly Gly Thr Cys Leu Val Pro Lys Lys
            20                  25                  30

Ile Ser Gly Phe Ser Leu Glu Arg Asn Gly Phe Ser Ser Leu Lys Val
            35                  40                  45

Lys Ser Gln Ala Leu Arg Ser Asp Phe Asn Gly Gln Arg Met Val Phe
50                  55                  60

Leu Glu Lys Lys Ser Met Asn Arg Arg Arg Phe Cys Gln Val Pro Ile
65                  70                  75                  80

Lys Ala Gln Met Gln Ser Gly Leu Ile Gly Arg Ile Gln Lys Trp Trp
                85                  90                  95

Glu Lys Gly Leu Gln Pro Asn Met Lys Glu Val Ala Ser Ala Gln Asp
            100                 105                 110

Leu Val Asp Ser Leu Leu Asn Ala Gly Asp Lys Leu Val Val Val Asp
            115                 120                 125

Phe Phe Ser Pro Gly Cys Gly Gly Cys Lys Ala Leu His Pro Lys Ile
            130                 135                 140

Cys Gln Phe Ala Glu Met Asn Pro Asp Val Gln Phe Leu Gln Val Asn
145                 150                 155                 160

Tyr Glu Glu His Lys Ser Met Cys Tyr Ser Leu Asn Val His Val Leu
                165                 170                 175
```

```
Pro Phe Phe Arg Phe Tyr Arg Gly Ala Gln Gly Arg Val Cys Ser Phe
            180                 185                 190

Ser Cys Thr Asn Ala Thr Ile Lys Lys Phe Arg Asp Ala Leu Ala Lys
        195                 200                 205

His Thr Pro Asp Arg Cys Ser Leu Ser Thr Thr Lys Gly Leu Glu Glu
    210                 215                 220

Lys Glu Leu Leu Ala Leu Ser Ala Asn Lys Asp Leu Ser Phe Asn Tyr
225                 230                 235                 240

Thr Pro Ile Pro Thr His Gly Glu Ile Leu Ile Trp Lys Gln Val Pro
                245                 250                 255

Ser Asp Ser Thr Arg Lys Leu Pro Leu Ser Val Pro Thr Thr Ser Ala
            260                 265                 270

Lys Gln Arg Asp Ser Glu Glu Lys Thr Leu Val Gly Val Gly Arg
        275                 280                 285

<210> SEQ ID NO 26
<211> LENGTH: 279
<212> TYPE: PRT
<213> ORGANISM: Gossypium histrum

<400> SEQUENCE: 26

Met Ala Glu Val Leu Gly Lys Ser Asn Leu Phe Thr Ala Cys Asn Tyr
1               5                   10                  15

Ser Gln Lys Lys His Gln Glu Gly Gly Val Pro Leu Phe Ser Arg Arg
            20                  25                  30

Ile Ser Val Phe Cys Leu Arg Lys Asn Ser Phe Pro Ser Leu Arg Leu
        35                  40                  45

Glu Pro Gln Ala Leu Arg Ser Gly Phe Asn Gly Gln Arg Val Val Phe
    50                  55                  60

Leu Glu Lys Arg Ser Leu Asn Glu Arg Arg Phe Cys Arg Val Pro Ile
65                  70                  75                  80

Lys Ala Gln Met Gln Thr Gly Leu Ile Gly Lys Thr Gln Lys Trp Trp
                85                  90                  95

Glu Lys Gly Asn Gln Pro Asn Met Lys Glu Val Thr Ser Ala Gln Asp
            100                 105                 110

Leu Val Asp Ser Leu Leu Asn Ala Gly Asp Lys Leu Val Ile Val Asp
        115                 120                 125

Phe Phe Ser Pro Gly Cys Gly Gly Cys Lys Ala Leu His Pro Lys Ile
    130                 135                 140

Cys Gln Leu Ala Glu Met Asn Pro Asp Val Gln Phe Leu Lys Val Asn
145                 150                 155                 160

Tyr Glu Glu His Lys Ser Met Cys Tyr Ser Leu Asn Val His Val Leu
                165                 170                 175

Pro Phe Phe Arg Phe Tyr Arg Gly Ala Gln Gly Arg Leu Cys Ser Phe
            180                 185                 190

Ser Cys Thr Asn Ala Thr Ile Lys Lys Phe Lys Asp Ala Leu Ala Lys
        195                 200                 205

His Ser Pro Asp Arg Cys Ser Leu Gly Pro Thr Lys Gly Leu Glu Glu
    210                 215                 220

Lys Glu Leu Leu Ala Leu Ala Ala Asn Lys Asp Leu Ser Phe Asn Tyr
225                 230                 235                 240

Thr Pro Lys Pro Val His Pro Ala Pro Glu Glu Ile Pro Val Leu Lys
                245                 250                 255

Glu Val Pro Ser Gly Ser Ser Phe Lys Leu Lys Glu Ser Glu Glu Lys
            260                 265                 270
```

```
Thr Leu Ile Gly Val Gly Arg
        275

<210> SEQ ID NO 27
<211> LENGTH: 279
<212> TYPE: PRT
<213> ORGANISM: Gossypium histrum

<400> SEQUENCE: 27

Met Ala Glu Val Leu Gly Lys Ser Asn Leu Phe Thr Ala Cys Asn Cys
1               5                   10                  15

Ser Gln Lys Lys Asn Gln Glu Gly Gly Val Pro Leu Phe Ser Arg Arg
            20                  25                  30

Ile Ser Ala Phe Cys Leu Arg Lys Asn Ser Phe Pro Ser Leu Lys Leu
        35                  40                  45

Glu Pro Gln Ala Leu Arg Ser Gly Phe Asn Gly Gln Arg Val Val Val
    50                  55                  60

Leu Glu Lys Arg Ser Leu Asn Glu Arg Phe Cys Arg Val Pro Ile
65                  70                  75                  80

Lys Ala Gln Met Gln Thr Gly Leu Ile Gly Lys Thr Gln Lys Trp Trp
                85                  90                  95

Glu Lys Gly Asn Gln Pro Asn Met Lys Glu Val Thr Ser Ala Gln Asp
            100                 105                 110

Leu Val Asp Ser Leu Leu Asn Ala Gly Asp Lys Leu Val Ile Val Asp
        115                 120                 125

Phe Phe Ser Pro Gly Cys Gly Gly Cys Lys Ala Leu His Pro Lys Ile
    130                 135                 140

Cys Gln Leu Ala Glu Met Asn Pro Asp Val Gln Phe Leu Lys Leu Asn
145                 150                 155                 160

Tyr Glu Glu His Lys Ser Met Cys Tyr Ser Leu Asn Val His Val Leu
                165                 170                 175

Pro Phe Phe Arg Phe Tyr Arg Gly Ala Gln Gly Arg Leu Cys Ser Phe
            180                 185                 190

Ser Cys Thr Asn Ala Thr Ile Lys Lys Phe Lys Asp Ala Leu Ala Lys
        195                 200                 205

His Ser Pro Asp Arg Cys Ser Leu Gly Pro Thr Lys Gly Leu Glu Glu
    210                 215                 220

Lys Glu Leu Leu Ala Leu Ala Ala Asn Lys Asp Leu Ser Phe Asn Tyr
225                 230                 235                 240

Thr Pro Lys Pro Val His Pro Ala Pro Glu Glu Met Pro Val Leu Glu
                245                 250                 255

Glu Val Pro Ser Gly Ser Ser Phe Arg Pro Lys Glu Ser Glu Glu Lys
            260                 265                 270

Thr Leu Val Gly Val Gly Arg
        275

<210> SEQ ID NO 28
<211> LENGTH: 299
<212> TYPE: PRT
<213> ORGANISM: Glycine max

<400> SEQUENCE: 28

Met Ala Glu Val Leu Thr Lys Ala Ser Leu Val Ser Ser Ser Trp His
1               5                   10                  15

Gly Val Ser Gln Arg His His Arg Arg Val Ser Thr Val Leu Ser
            20                  25                  30
```

Asn Asn Thr Cys Ser Phe Arg Ser Gly Val Gly Lys Phe Ser Ser Leu
         35                  40                  45

Lys Met Asn Ser Gln Val Leu Arg Ser Trp Ser Ser Ser Glu Phe
 50                  55                  60

Gln Gly Lys Lys Leu Val Phe His Val Asn Arg Gly Leu Pro Asn Arg
 65                  70                  75                  80

Val Asn Ser Arg Leu Arg Ala Ser Thr Gly Thr Gln Met Asn Leu Arg
                 85                  90                  95

Leu Gly Lys Val Gln Lys Trp Trp Glu Lys Gly Leu Gln Pro Asn Met
                 100                 105                 110

Lys Glu Val Thr Ser Ala Gln Asp Phe Val Asp Ser Leu Leu Asn Ala
                 115                 120                 125

Gly Asp Lys Leu Val Val Asp Phe Phe Ser Pro Gly Cys Gly Gly
        130                 135                 140

Cys Lys Ala Leu His Pro Lys Ile Cys Gln Phe Ala Glu Met Asn Pro
145                 150                 155                 160

Asp Val Gln Phe Leu Gln Val Asn Tyr Glu His Lys Ser Met Cys
                 165                 170                 175

Tyr Ser Leu Asn Val His Val Leu Pro Phe Arg Phe Tyr Arg Gly
                 180                 185                 190

Ala His Gly Arg Leu Cys Ser Phe Ser Cys Thr Asn Ala Thr Ile Lys
                 195                 200                 205

Lys Phe Lys Asp Ala Leu Ala Lys His Thr Pro Asp Arg Cys Ser Leu
210                 215                 220

Gly Pro Thr Ile Gly Leu Glu Glu Lys Glu Leu Glu Ala Leu Ala Ala
225                 230                 235                 240

Asn Lys Asp Leu Ser Phe Thr Tyr Ser Pro Lys Pro Leu Gln Pro Ser
                 245                 250                 255

His Glu Asn Glu Glu Leu Ala Thr Glu Thr Ala Ser Ala Pro Ala Leu
                 260                 265                 270

Gly Ser Gly Ser Leu Pro Ser Pro Ser Met Thr Leu Asn Ala Val Ala
                 275                 280                 285

Ser Asn Glu Arg Thr Leu Thr Thr Ser Gly Arg
                 290                 295

<210> SEQ ID NO 29
<211> LENGTH: 248
<212> TYPE: PRT
<213> ORGANISM: Glycine max

<400> SEQUENCE: 29

Met Lys Ser Gln Val Leu Arg Ser Trp Ser Ser Ser Glu Phe Gln
 1               5                   10                  15

Gly Ile Lys Leu Val Phe His Val Asn Arg Gly Leu Pro Asn Arg Val
                 20                  25                  30

Asn Ser Arg Leu Arg Ala Ser Thr Gly Ala Gln Met Ser Phe Arg Leu
         35                  40                  45

Gly Lys Val Gln Lys Trp Trp Glu Lys Gly Leu Gln Pro Asn Met Lys
 50                  55                  60

Glu Val Thr Ser Ala Gln Asp Phe Val Asp Ser Leu Leu Ser Ala Gly
 65                  70                  75                  80

Asp Lys Leu Val Val Val Asp Phe Phe Ser Pro Gly Cys Gly Gly Cys
                 85                  90                  95

Lys Ala Leu His Pro Lys Ile Cys Gln Phe Ala Glu Met Asn Pro Asp

```
            100                 105                 110
Val Gln Phe Leu Gln Val Asn Tyr Glu Glu His Lys Ser Met Cys Tyr
        115                 120                 125

Ser Leu Asn Val His Val Leu Pro Phe Phe Arg Phe Tyr Arg Gly Ala
        130                 135                 140

His Gly Arg Leu Cys Ser Phe Ser Cys Thr Asn Ala Thr Ile Lys Lys
145                 150                 155                 160

Phe Lys Asp Ala Leu Ala Lys His Thr Pro Asp Arg Cys Ser Leu Gly
                165                 170                 175

Pro Thr Lys Gly Leu Glu Glu Lys Glu Leu Leu Ala Leu Ala Ala Asn
                180                 185                 190

Lys Asp Leu Ser Phe Thr Asn Ser Pro Glu Pro Leu Gln Pro Ala His
                195                 200                 205

Ala Asp Glu Glu Leu Gly Thr Glu Pro Ala Pro Ala Pro Gly Ser Lys
                210                 215                 220

Ser Leu Pro Ser Pro Ser Met Ile Leu Asn Ser Glu Val Ser Lys Lys
225                 230                 235                 240

Arg Thr Leu Thr Thr Ser Gly Arg
                245

<210> SEQ ID NO 30
<211> LENGTH: 289
<212> TYPE: PRT
<213> ORGANISM: Beta vulgaris

<400> SEQUENCE: 30

Met Ala Asp Val Leu Thr Lys Ser Ser Val Phe Ser Pro Thr Ile Ser
1               5                   10                  15

His His His Ser Gly Ser Lys Asn Phe Pro Ile Lys Cys Ser Val Ala
                20                  25                  30

Val Ser Asn Arg Gly Arg Leu Val Gly Ile Ser Ser Leu Arg Ser Ser
            35                  40                  45

Phe Gly Gly Val Arg Ile Ala Ile Asp Lys Asn Thr Ser Phe Gly Ser
        50                  55                  60

Lys Arg Arg Asn Tyr Gln Ser Ile Asp Ala Lys Met Gly Leu Ser Ile
65                  70                  75                  80

Gly Lys Ala Gln Lys Trp Trp Glu Lys Gly Leu Gln Pro Asn Met Arg
                85                  90                  95

Glu Ile Thr Ser Ala Glu Asp Leu Val Asp Ser Leu Leu Thr Ala Gly
                100                 105                 110

Asp Thr Leu Val Val Asp Phe Phe Ser Pro Gly Cys Gly Gly Cys
            115                 120                 125

Arg Ala Leu His Pro Lys Leu Cys Gln Leu Ala Glu Met Asn Pro Asp
        130                 135                 140

Val Gln Phe Leu Gln Ile Asn Tyr Glu Glu His Lys Ser Met Cys Tyr
145                 150                 155                 160

Ser Leu Asn Val His Val Leu Pro Phe Phe Arg Phe Tyr Arg Gly Ala
                165                 170                 175

Glu Gly Arg Val Ser Ser Phe Ser Cys Thr Asn Ala Thr Ile Lys Lys
                180                 185                 190

Phe Lys Asp Ala Leu Ala Lys His Asn Pro Ala Arg Cys Ser Leu Gly
                195                 200                 205

Pro Thr Lys Gly Leu Glu Glu Lys Glu Leu Leu Ala Leu Ala Ala Asn
            210                 215                 220
```

```
Lys Asp Leu Ser Phe Thr Tyr Thr Pro Lys Pro Val Glu Ala Glu Pro
225                 230                 235                 240

Val Pro Ala Pro Ala Leu Glu Glu Val Ser Val Lys Ala Asp Glu Gln
            245                 250                 255

Val Leu Ala Gln Glu Ser Leu Pro Ser Phe Asn Arg Lys Pro Leu Ser
            260                 265                 270

Ser Gln Pro Ser Thr Val Ser Glu Glu Lys Thr Leu Ala Thr Ala Ala
            275                 280                 285

Arg

<210> SEQ ID NO 31
<211> LENGTH: 278
<212> TYPE: PRT
<213> ORGANISM: Musa acuminate

<400> SEQUENCE: 31

Met Ala Glu Thr Leu Ala Gln Arg Thr Leu Leu Pro Gly Gly His
1               5                   10                  15

Leu Ser Leu Pro Pro Phe Cys Gly Met Arg Ser Arg Pro Ser Leu Ala
                20                  25                  30

Ala Phe Thr Leu Phe Ser Arg Thr Lys Val Glu Pro Leu Arg Ser Ser
            35                  40                  45

Ser Cys Asp Ser Lys Phe His Gly Arg Arg Leu Val Val Gly Ala Arg
50                  55                  60

Arg Gly Arg Pro Ser Arg Ala Arg Leu Gly Ser Gly Ser Glu Gln Met
65                  70                  75                  80

Val Leu Ser Phe Lys Lys Ala Ile Lys Trp Trp Gln Lys Gly Leu Gln
                85                  90                  95

Pro Asn Met Val Glu Ile Glu Ser Ala Glu His Leu Val Asp Ser Leu
            100                 105                 110

Leu Asn Ala Gly Asp Lys Leu Val Ile Val Asp Phe Phe Ser Pro Gly
            115                 120                 125

Cys Gly Gly Cys Arg Ala Leu His Pro Lys Ile Cys Gln Phe Ala Glu
130                 135                 140

Ser Asn Gln Asn Val Leu Phe Leu Gln Ile Asn Tyr Glu Gln His Lys
145                 150                 155                 160

Ser Met Cys Tyr Ser Leu Gly Val His Val Leu Pro Phe Phe Arg Phe
                165                 170                 175

Tyr Arg Gly Ala His Gly Arg Leu Cys Ser Phe Ser Cys Thr Asn Ala
            180                 185                 190

Thr Ile Lys Lys Phe Lys Asp Ala Leu Ala Lys His Ile Thr Asp Arg
            195                 200                 205

Cys Ser Leu Gly Pro Ala Arg Gly Leu Glu Glu Ser Glu Leu Leu Ala
210                 215                 220

Leu Ala Ala Asn Lys Asp Leu Ser Phe Asn Tyr Thr Ser Lys Pro Val
225                 230                 235                 240

Pro Val Pro Glu Glu Ile Pro Glu Arg Ile Pro Thr Ser Pro Lys Leu
                245                 250                 255

Pro Leu His Ala Val Arg Arg Pro Ala Gln Glu Ser Glu Asp Lys Ala
            260                 265                 270

Leu Ala Ala Ala Gly Arg
            275

<210> SEQ ID NO 32
<211> LENGTH: 272
```

```
<212> TYPE: PRT
<213> ORGANISM: Musa acuminate

<400> SEQUENCE: 32

Met Ala Asp Ala Leu Ala Gln Met Thr Leu Leu Ser Pro His Gly His
1               5                   10                  15

Arg Ser Leu Ser Arg Ser Asp Arg Arg Asn Arg Leu Val Cys Ala
            20                  25                  30

Ser Lys Asp Asp Leu Leu Arg Ser Ser Ser Cys Asn Ser Gln Phe
        35                  40                  45

His Gly Arg Arg Leu Val Ile Gly Ala Gln Arg Glu Arg Pro Leu Arg
    50                  55                  60

Gly Asn Arg Gly Ser Ser Val Gln Met Thr Leu Ser Phe Lys Lys
65                  70                  75                  80

Ala Ser Lys Trp Trp Glu Lys Gly Leu His Pro Asn Met Lys Asp Ile
                85                  90                  95

Lys Ser Ala Glu Asp Leu Val Asp Ser Leu Ser Asn Ala Gly Asp Lys
                100                 105                 110

Leu Val Ile Val Asp Phe Phe Ser Pro Gly Cys Ala Gly Cys Arg Ala
            115                 120                 125

Leu His Pro Lys Ile Cys Gln Phe Ala Glu Leu Asn Pro Asp Val Gln
    130                 135                 140

Phe Leu Gln Leu Asn His Glu Glu His Lys Ser Met Cys Tyr Ser Leu
145                 150                 155                 160

Asn Val His Val Leu Pro Phe Phe Arg Phe Tyr Arg Gly Ala His Gly
                165                 170                 175

Arg Leu Cys Ser Phe Ser Cys Thr Asn Ala Thr Ile Lys Lys Phe Lys
            180                 185                 190

Asp Ala Leu Ala Lys His Ile Thr Glu Arg Cys Ser Leu Gly Pro Ala
        195                 200                 205

Lys Gly Leu Glu Glu Thr Glu Leu Leu Ala Leu Ala Ala Asn Lys Asp
    210                 215                 220

Leu Ser Phe Thr Tyr Thr Arg Thr Pro Val Pro Val Pro Asp Glu Leu
225                 230                 235                 240

Ala Glu Lys Ala Pro Phe Asn Pro Asn Leu Pro Val His Ala Ala Ala
                245                 250                 255

Arg Leu Thr Leu Glu Ser Glu Asp Lys Ala Phe Ala Ala Gly Arg
            260                 265                 270

<210> SEQ ID NO 33
<211> LENGTH: 285
<212> TYPE: PRT
<213> ORGANISM: Capsicum annuum

<400> SEQUENCE: 33

Met Ala Lys Leu Met Asn Lys Gly Phe Val Phe Pro Ser Ser Ser Asp
1               5                   10                  15

Cys Gly His His Arg Pro His Gly Ile Ser Ser Phe Pro Asn Lys Ser
            20                  25                  30

Val Asn Leu Ser Cys Leu Pro Ser Thr Cys Leu Leu Arg Ser Tyr Phe
        35                  40                  45

Tyr Gly Arg Arg Leu Val Ile Asn Glu Ala Leu Pro Lys Arg Asn Ala
    50                  55                  60

His Val Ala Ile Thr Val Gln Met Ser Met Gly Ile Arg Lys Val Gln
65                  70                  75                  80
```

```
Lys Trp Trp Glu Lys Gly Val Gln Pro Asn Met Lys Glu Val Asn Ser
                85                  90                  95

Ala Gln Gly Leu Val Asp Ser Leu Leu Ser Ala Gly Asp Lys Leu Val
            100                 105                 110

Val Val Asp Phe Phe Ser Pro Gly Cys Gly Gly Cys Lys Ala Leu His
        115                 120                 125

Pro Lys Leu Cys Gln Leu Ala Glu Met Asn Pro Asp Val Gln Phe Leu
    130                 135                 140

Gln Val Asn Tyr Glu Glu His Lys Ser Met Cys Tyr Ser Leu Asn Val
145                 150                 155                 160

His Leu Leu Pro Phe Phe Arg Phe Tyr Arg Gly Ala Glu Gly Arg Val
                165                 170                 175

Cys Ser Phe Ser Cys Thr Asn Ala Thr Ile Lys Lys Phe Lys Asp Ala
            180                 185                 190

Leu Ala Lys Tyr Gly Thr Asp Arg Cys Thr Phe Gly Pro Pro Lys Gly
        195                 200                 205

Leu Glu Glu Lys Glu Leu Leu Ala Leu Ala Ala Asn Lys Glu Leu Ser
    210                 215                 220

Phe Asn Tyr Ile Pro Lys Thr Glu Glu Pro Val Leu Val Ala Ser
225                 230                 235                 240

Gln Glu Glu Val Glu Asp Arg Thr Pro Asn Lys Glu Ser Pro Leu Pro
                245                 250                 255

Leu Pro Leu Pro Leu Pro Ile Ser Ser Thr Ser Ser Leu Lys Pro Lys
            260                 265                 270

Gln Asp Thr Glu Lys Glu Ala Tyr Ala Thr Ser Gly Arg
        275                 280                 285

<210> SEQ ID NO 34
<211> LENGTH: 297
<212> TYPE: PRT
<213> ORGANISM: Cicer arietinum

<400> SEQUENCE: 34

Met Ala Glu Ile Leu Thr Lys Thr Ser Leu Val Ser Ser Trp His Gly
1               5                   10                  15

Asn Arg Lys Gln Gln His Arg Arg Leu Ser Met Val Pro Asn Lys Thr
            20                  25                  30

Cys Ser Phe Asn Thr Cys Val Gly Ser Phe Pro Ser Leu Lys Leu Lys
        35                  40                  45

Ser Gln Phe Leu Arg Ser Ser Ser Phe Ser Ser Glu Phe Tyr Gly Lys
    50                  55                  60

Asn Thr Ile Phe Arg Val Asn Arg Ser Ile Pro Asn Arg Ile Asn Ser
65                  70                  75                  80

Gln Phe Ser Val Ser Ala Ala Pro Lys Met Thr Leu Arg Ile Gly Lys
                85                  90                  95

Ile Gln Lys Trp Trp Glu Lys Gly Leu Gln Pro Asn Met Arg Glu Val
            100                 105                 110

Thr Ser Ala Gln Asp Leu Val Asp Ser Leu Leu Asn Ala Gly Asp Lys
        115                 120                 125

Leu Val Ile Val Asp Phe Ser Pro Gly Cys Gly Gly Cys Arg Ala
    130                 135                 140

Leu His Pro Lys Ile Cys Gln Met Ala Glu Met Asn Pro Asp Val Glu
145                 150                 155                 160

Phe Leu Gln Val Asn Tyr Glu Glu His Lys Ser Met Cys Tyr Ser Leu
                165                 170                 175
```

```
Asn Val His Val Leu Pro Phe Arg Phe Tyr Arg Gly Ala His Gly
            180                 185                 190

Arg Leu Cys Ser Phe Ser Cys Thr Asn Ala Thr Ile Lys Lys Phe Lys
        195                 200                 205

Asp Ala Leu Ala Lys His Thr Pro Asp Arg Cys Ser Leu Glu Pro Thr
    210                 215                 220

Lys Gly Leu Glu Glu Lys Glu Leu Ile Ala Leu Ser Glu Asn Lys Asp
225                 230                 235                 240

Leu Asn Phe Thr Tyr Thr Pro Lys Pro Leu Gln Pro Val His Thr Pro
                245                 250                 255

Ala Asn Glu Glu Leu Ala Thr Thr Lys Ala Ser Pro Val Cys Ser Glu
            260                 265                 270

Pro Leu Pro Leu Pro Ser Leu Thr Ser Asn Ser Asp Glu Val Leu Lys
        275                 280                 285

Glu Arg Thr Leu Thr Arg Ala Gly Arg
    290                 295

<210> SEQ ID NO 35
<211> LENGTH: 299
<212> TYPE: PRT
<213> ORGANISM: Solanum lycopersicum

<400> SEQUENCE: 35

Met Thr Lys Leu Met Ser Lys Gly Phe Ile Phe Pro Ser Ser Ser Ser
1               5                   10                  15

Asp Cys Gly Glu Ile Tyr Asp Arg Leu Arg Leu Asn Leu His Gly Ile
            20                  25                  30

Cys Ser Phe Pro Asn Lys Ser Val Asn Leu Ser Cys Leu Pro Ser Leu
        35                  40                  45

Lys Leu Ser Ser Cys Leu Pro Arg Thr Asp Phe Tyr Gly Arg Arg
    50                  55                  60

Leu Val Ile Asn Glu Gly Leu Ser Asn Phe Asn Arg Arg Val Ala Asp
65                  70                  75                  80

Ile Thr Ala Gln Met Ser Val Gly Ile Lys Lys Ala Gln Lys Trp Trp
                85                  90                  95

Glu Lys Gly Val Gln Pro Asn Met Lys Glu Val Asn Ser Ala Gln Glu
            100                 105                 110

Leu Val Asp Ser Leu Leu Ser Ala Gly Asp Lys Leu Val Val Val Asp
        115                 120                 125

Phe Phe Ser Pro Gly Cys Gly Gly Cys Lys Ala Leu His Pro Lys Leu
    130                 135                 140

Cys Gln Leu Ala Glu Met Asn Pro Asp Val Gln Phe Leu Gln Val Asn
145                 150                 155                 160

Tyr Glu Glu His Lys Ser Met Cys Tyr Ser Leu Asn Val His Val Leu
                165                 170                 175

Pro Phe Phe Arg Phe Tyr Arg Gly Ala Glu Gly Arg Val Cys Ser Phe
            180                 185                 190

Ser Cys Thr Asn Ala Thr Ile Lys Lys Phe Arg Asp Ala Leu Ala Lys
        195                 200                 205

Tyr Gly Thr Asp Arg Cys Thr Ile Gly Ser Pro Lys Gly Leu Glu Glu
    210                 215                 220

Lys Glu Leu Leu Ala Leu Ala Ala Asn Lys Asp Leu Ser Phe Asn Tyr
225                 230                 235                 240

Thr Pro Lys Thr Glu Glu Glu Pro Ile Leu Val Thr Ser Gln Lys Glu
```

```
                        245                 250                 255
Val Arg Asp Arg Thr Thr Pro Asn Ile Glu Ser Pro Leu Pro Leu Pro
                260                 265                 270

Leu Pro Leu Pro Ile Thr Ser Thr Ser Ser Gln Thr Ala Lys Arg Asp
            275                 280                 285

Thr Glu Lys Glu Ala Tyr Ala Thr Ser Gly Arg
        290                 295

<210> SEQ ID NO 36
<211> LENGTH: 257
<212> TYPE: PRT
<213> ORGANISM: Solanum lycopersicum

<400> SEQUENCE: 36

Met Glu Lys Leu Leu Asn Lys Ala Val Phe Leu Pro Ser Ile Leu Asn
1               5                   10                  15

Ser Ser Gly Ile Tyr His Ser Asn Gln His Ala Ile Cys Val Phe Pro
            20                  25                  30

Val Lys Phe Asn Arg Arg Tyr His Lys Ser Ala Val Ala Thr Ala Gln
        35                  40                  45

Met Ser Ile Gly Ile Lys Arg Ala Pro Lys Trp Trp Glu Lys Gly Leu
    50                  55                  60

Gln Pro Asn Met Lys Glu Val Thr Gly Ala Gln Asp Leu Val Asp Thr
65                  70                  75                  80

Leu Leu Asn Gly Gly Asp Lys Leu Val Val Asp Phe Leu Ser Pro
                85                  90                  95

Gly Cys Gly Gly Cys Lys Ala Leu His Pro Lys Ile Cys Gln Leu Ala
            100                 105                 110

Glu Met Asn Pro Asp Val Gln Phe Leu His Val Asn Tyr Glu Glu His
        115                 120                 125

Lys Ser Met Cys Tyr Ser Leu Asn Val His Val Leu Pro Phe Phe Arg
    130                 135                 140

Phe Tyr Arg Gly Ala Glu Gly Arg Leu Cys Ser Phe Ser Cys Thr Asn
145                 150                 155                 160

Ala Thr Ile Lys Lys Phe Lys Asp Ala Leu Thr Lys Tyr Gly Ala Asp
                165                 170                 175

Cys Cys Ser Leu Gly Pro Val Lys Gly Leu Glu Glu Lys Glu Leu Leu
            180                 185                 190

Ala Leu Ala Ala Asn Lys Asp Leu Ser Phe Ala Tyr Thr Pro Lys Thr
        195                 200                 205

Glu Glu Pro Val Pro Leu Ala Leu Glu Val Lys Val Ile Lys Thr
    210                 215                 220

Ser Arg Gln Ser Ser His Pro Asn Thr Phe Ser Pro Leu Pro Leu
225                 230                 235                 240

Pro Leu Pro Leu Ala Ser Thr Leu His Thr Ala Lys Gln Asp Ser Lys
                245                 250                 255

Ser

<210> SEQ ID NO 37
<211> LENGTH: 279
<212> TYPE: PRT
<213> ORGANISM: Elaeis guineensis

<400> SEQUENCE: 37

Met Met Glu Val Leu Ser Gln Ser Gly Val Met Ser Pro Cys Gly His
1               5                   10                  15
```

```
Arg Trp Val Val Arg Ser Cys Lys Glu Arg Ser Pro Ser Phe Val Gly
             20                  25                  30

Phe Pro Arg Ser Ser Arg Thr Ile Glu Ser Leu Met Ser Ser Ser
         35                  40                  45

Arg Asn Ser Gly Phe His Gly Arg Arg Leu Ser Ile Gly Ala Trp Arg
 50                  55                  60

Val Asn Ala Val Lys Gly Asn Phe Ser Ser Thr Pro Val Gln Met Ser
65                  70                  75                  80

Leu Cys Val Gly Lys Ala Leu Lys Trp Trp Glu Lys Glu Leu Gln Pro
                 85                  90                  95

Asn Met Lys Glu Ile Glu Ser Ala Gln Asp Leu Val Asp Ser Leu Leu
             100                 105                 110

Asn Ala Gly Asp Lys Leu Val Ile Val Asp Phe Phe Ser Pro Gly Cys
         115                 120                 125

Gly Gly Cys Lys Ala Leu His Pro Lys Ile Cys Gln Phe Ala Lys Leu
130                 135                 140

Asn Pro Asp Val Leu Phe Leu Gln Val Asn Tyr Glu Lys His Lys Ser
145                 150                 155                 160

Met Cys Tyr Ser Leu Asn Val His Val Leu Pro Phe Phe Arg Phe Tyr
                165                 170                 175

Arg Gly Ala His Gly Arg Leu Cys Ser Phe Ser Cys Thr Asn Ala Thr
            180                 185                 190

Ile Lys Lys Phe Lys Asp Ala Leu Ala Lys His Thr Thr Asp Arg Cys
        195                 200                 205

Ser Leu Gly Pro Thr Lys Gly Leu Glu Glu Ser Glu Leu Met Ala Leu
    210                 215                 220

Ala Ala Asn Lys Asp Leu Ser Phe Ser Tyr Thr Arg Lys Pro Val Pro
225                 230                 235                 240

Val Pro Ser Pro Asp Glu Ala Ala Glu Glu Val Val Leu Ser Pro Lys
                245                 250                 255

Leu Pro Val Ser Ser Thr Pro Arg Val Ile Gln Asp Ser Glu Glu Lys
            260                 265                 270

Ala Leu Val Ala Ala Gly Arg
            275

<210> SEQ ID NO 38
<211> LENGTH: 272
<212> TYPE: PRT
<213> ORGANISM: Elaeis guineensis

<400> SEQUENCE: 38

Met Ala Glu Val Leu Gly Arg Ser Gly Val Phe Ser Leu Arg Gly His
1               5                   10                  15

Arg Ser Val Ala Pro Ser Cys Gln Lys Arg Ser Pro Ser Phe Leu Gly
             20                  25                  30

Phe Pro Leu Ser Ser Arg Pro Ile Gly Pro Arg Ser Ser Ser
         35                  40                  45

Arg Arg Phe Val Ile Gly Thr Arg Arg Gly Arg Ser Ile Lys Gly Asn
 50                  55                  60

Ser Ser Ser Ser Arg Val Gln Met Ser Leu Val Gly Lys Ser Leu
65                  70                  75                  80

Lys Trp Trp Glu Lys Gly Val Gln Pro Asn Met Lys Glu Ile Gly Ser
                 85                  90                  95

Ala Gln Asp Leu Val Asp Ser Leu Leu Asn Glu Gly Asp Lys Leu Val
```

-continued

```
                100                 105                 110
Ile Val Asp Phe Phe Ser Pro Gly Cys Gly Gly Cys Lys Ala Leu His
            115                 120                 125

Pro Lys Ile Cys Arg Ile Ala Glu Met Asn Pro His Val Leu Phe Leu
130                 135                 140

Gln Ile Asn Tyr Glu Lys His Lys Ser Met Cys Tyr Ser Leu His Val
145                 150                 155                 160

His Val Leu Pro Phe Phe Arg Phe Tyr Arg Gly Ala His Gly Arg Leu
                165                 170                 175

Cys Ser Phe Ser Cys Thr Asn Ala Thr Ile Lys Lys Phe Lys Asp Ala
            180                 185                 190

Leu Ala Lys His Thr Thr Asp Arg Cys Ser Leu Gly Pro Thr Lys Gly
            195                 200                 205

Leu Glu Glu Ser Glu Leu Val Ala Leu Ala Ala Asn Lys Asp Leu Ser
            210                 215                 220

Phe Asn Tyr Thr Arg Lys Pro Val Pro Val Leu Thr Pro Asp Glu Ala
225                 230                 235                 240

Ala Glu Lys Val Pro Leu Ser Pro Lys Leu Pro Val Ser Ser Ala Pro
                245                 250                 255

Arg Val Ile Lys Asp Ser Glu Asp Lys Ala Leu Val Ala Ala Gly Thr
            260                 265                 270
```

<210> SEQ ID NO 39
<211> LENGTH: 287
<212> TYPE: PRT
<213> ORGANISM: Setaria italic
<220> FEATURE:
<221> NAME/KEY: misc_feature
<222> LOCATION: (276)..(276)
<223> OTHER INFORMATION: Xaa can be any naturally occurring amino acid

<400> SEQUENCE: 39

```
Met Ala Ala Gln Ala Val Ala Lys Gly Ser Val Val Ser Pro Cys
1               5                   10                  15

Gly Ser Arg Ala Ala Pro Gly Leu Leu Ser Arg Arg Gly Ala Val
                20                  25                  30

Ala Thr Arg Met Ala Pro Ser Ala Val Arg Ile Gly Gly Ser Trp Arg
            35                  40                  45

Lys Thr Ala Phe Leu Gly Gly Arg Leu Ala Val Gly Pro Arg Arg Ser
50                  55                  60

Arg Ser Ala Ser Arg Thr Leu Val Ala Ser Pro Val Gln Met Asn Met
65                  70                  75                  80

Asn Leu Ala Ile Gly Lys Ser Met Arg Trp Trp Glu Lys Gly Leu Gln
                85                  90                  95

Pro Asn Met Arg Glu Ile Glu Ser Ala Gln Asp Leu Val Asp Ser Leu
            100                 105                 110

Thr Asn Ala Gly Asp Arg Leu Val Ile Val Asp Phe Phe Ser Pro Gly
            115                 120                 125

Cys Gly Gly Cys Arg Ala Leu His Pro Lys Ile Cys Gln Phe Ala Glu
            130                 135                 140

Gln Asn Pro Asp Val Leu Phe Leu Gln Val Asn His Glu Glu His Lys
145                 150                 155                 160

Ser Met Cys Tyr Ser Leu His Val His Val Leu Pro Phe Phe Arg Phe
                165                 170                 175

Tyr Arg Gly Ala Gln Gly Arg Leu Cys Ser Phe Ser Cys Thr Asn Ala
            180                 185                 190
```

```
Thr Ile Lys Lys Phe Lys Asp Ala Leu Ala Lys His Lys Pro Asp Arg
        195                 200                 205

Cys Ser Ile Gly Pro Thr Arg Gly Leu Glu Glu Ser Glu Leu Leu Ala
    210                 215                 220

Leu Ala Ala Asn Lys Asp Leu Gln Phe Thr Tyr Thr Lys Lys Pro Glu
225                 230                 235                 240

Leu Ile Pro Ser Gly Asp Ala Ala Glu Val Ile Ala Pro Glu Pro
        245                 250                 255

Thr Lys Leu Pro Ala Ala Thr Lys Pro Ser Val Lys Ile Gly Ser Glu
        260                 265                 270

Glu Arg Ser Xaa Trp Ser His Gln Glu Asp Glu Met Asn Asp Leu
        275                 280                 285

<210> SEQ ID NO 40
<211> LENGTH: 273
<212> TYPE: PRT
<213> ORGANISM: Setaria italic

<400> SEQUENCE: 40

Met Ala Ala Ala Gln Ala Met Ala Lys Met Ser Val Gly Ser Pro Ala
1               5                   10                  15

Cys Asn Arg Ala Ala Gly Ser Leu Cys Arg Trp Arg Gly Ala Val Ala
            20                  25                  30

Val Arg Leu Gly Gly Ser Trp Ser Trp Arg Lys Ser Pro Phe Leu Gly
        35                  40                  45

Gly Arg Met Ala Val Gly Pro Arg Arg Ser Arg Pro Val Ser Arg Asn
    50                  55                  60

Pro Val Ala Ser Pro Val Gln Met Asn Leu Ser Phe Gly Lys Thr Met
65                  70                  75                  80

Lys Trp Trp Glu Lys Gly Leu Gln Pro Asn Met Arg Ala Ile His Thr
                85                  90                  95

Ala Gln Glu Leu Val Asp Ser Leu Ile Asn Ala Gly Asp Gly Leu Val
            100                 105                 110

Ile Val Asp Phe Phe Ser Pro Gly Cys Ala Gly Cys His Ala Leu His
        115                 120                 125

Pro Lys Ile Cys Gln Phe Ala Glu Arg Asn Pro Asp Val Gln Phe Leu
    130                 135                 140

Gln Val Asn Phe Glu Glu His Lys Ser Met Cys His Ser Leu His Val
145                 150                 155                 160

His Val Phe Pro Phe Phe Arg Phe Tyr Arg Gly Ala Gln Gly Arg Leu
                165                 170                 175

Cys Ser Phe Ser Cys Thr Asn Ala Thr Ile Lys Lys Phe Lys Asp Ala
            180                 185                 190

Leu Ala Lys His Lys Pro Asp Arg Cys Ser Leu Gly Pro Ile Lys Gly
        195                 200                 205

Leu Glu Glu Ser Glu Leu Leu Ala Leu Ala Ala Asn Arg Asp Leu Gln
    210                 215                 220

Phe Thr Tyr Thr Lys Glu Gln Asp Leu Ala Pro Ser Met Glu Asp Gly
225                 230                 235                 240

Ala Glu Val Ile Thr His Asp His Pro Arg Leu Pro Ala Ala Ala Lys
                245                 250                 255

Pro Leu Val Arg Gln Gly Ser Glu Asp Arg Ala Val Val Ser Ser Gly
            260                 265                 270

Arg
```

<210> SEQ ID NO 41
<211> LENGTH: 274
<212> TYPE: PRT
<213> ORGANISM: Setaria italic

<400> SEQUENCE: 41

Met Ala Glu Ala Leu Cys Asn Gly Val Val Pro Ser Pro Cys Gly Gly
1               5                   10                  15

Asp Val Gly Val Ala Gly Arg Val Ser Gly Ala Ala Ala Leu Ala
            20                  25                  30

Glu Ser Val Pro Ile Gly Gly Tyr Arg Thr Lys Ser Ser Phe Ser Ala
            35                  40                  45

Gly Arg Met Ala Met Thr Asp Arg Lys Met Arg Pro Leu Pro Arg Ser
        50                  55                  60

Ile Glu Ala Ala Pro Gly Gln Met Asn Leu Ser Phe Pro Lys Ala Met
65                  70                  75                  80

Arg Trp Trp Glu Lys Gly Leu Gln Pro Asn Met Arg Glu Ile Glu Ser
                85                  90                  95

Ala Gln Asp Leu Ala Asp Ser Leu Leu Asn Ala Gly Asp Lys Leu Val
            100                 105                 110

Val Val Asp Phe Phe Ser Pro Gly Cys Gly Gly Cys Arg Ala Leu His
        115                 120                 125

Ala Lys Ile Ala Gln Phe Ala Glu Lys Asn Pro Asp Val Met Phe Leu
    130                 135                 140

Gln Val Asn Tyr Glu Thr His Lys Ser Met Cys Tyr Ser Leu His Val
145                 150                 155                 160

His Val Leu Pro Phe Phe Arg Phe Tyr Arg Gly Ala Glu Gly Arg Val
                165                 170                 175

Ser Ser Phe Ser Cys Thr Asn Ala Thr Ile Lys Lys Phe Lys Asp Ala
            180                 185                 190

Leu Ala Lys His Gly Pro Asp Arg Cys Ser Leu Gly Pro Ala Arg Gly
        195                 200                 205

Leu Glu Glu Ser Glu Leu Met Ala Leu Ala Ala Asn Lys Asp Leu Gln
    210                 215                 220

Phe Thr Tyr Glu Lys Pro Gly Leu Val Pro Leu Ala Glu Ala Ile Ala
225                 230                 235                 240

Lys Glu Ala Ala Ala Pro Gly Gly Pro Trp Phe Pro Leu Pro Ala Ser
                245                 250                 255

Ala Thr Gln Phe Leu Thr Gln Gly Ser Glu Asn Ser Leu Leu Ser Ser
            260                 265                 270

Gly Arg

<210> SEQ ID NO 42
<211> LENGTH: 249
<212> TYPE: PRT
<213> ORGANISM: Chlamydomonas reinhardtii

<400> SEQUENCE: 42

Met Ala Ser Ile Leu Asn Arg Ala Gly Ser Arg Ser Leu Val Phe Glu
1               5                   10                  15

Thr Lys Gln Ser Leu Arg Ser Ile Pro Gly Ser Leu Leu Ser Leu Arg
            20                  25                  30

Ser Val Ala Leu Lys Pro Phe Arg Thr Thr Ile Cys Ala Ala Gly Ala
        35                  40                  45

```
Leu Leu Thr Ala Arg Arg Ser Thr Ser Gly Leu Gly Arg Ala Asn Gly
    50                  55                  60

Val Val Cys Gln Ala Gly Arg Ser Thr Gly Glu Trp Trp Lys Lys Asp
65                  70                  75                  80

Asn Pro Pro Asn Met Arg Asp Ile Asn Ser Ile Gln Glu Leu Val Asp
                85                  90                  95

Ala Leu Ser Asp Ala Gly Asp Arg Leu Val Ile Val Glu Phe Tyr Ala
                100                 105                 110

Gln Trp Cys Asn Ala Cys Arg Ala Leu Phe Pro Lys Ile Cys Lys Ile
            115                 120                 125

Met Ala Glu Asn Pro Asp Val Leu Phe Leu Lys Val Asn Phe Asp Asp
130                 135                 140

Asn Arg Asp Ala Cys Arg Thr Leu Ser Val Lys Val Leu Pro Tyr Phe
145                 150                 155                 160

His Phe Tyr Arg Gly Ala Glu Gly Arg Val Ala Ala Phe Ser Ala Thr
                165                 170                 175

Ile Ser Lys Leu Gln Leu Phe Lys Asp Ala Val Glu Thr Tyr Ser Ala
            180                 185                 190

Ala Phe Cys Ser Leu Glu Pro Ala Pro Gly Leu Ala Glu Phe Pro Asp
        195                 200                 205

Leu Ile Ala His Pro Glu Leu His Pro Glu Glu Ala Glu Ala Ala Ala
210                 215                 220

Arg Arg Ala Arg Leu Ala Ser Thr Glu Ser Glu Glu Leu His Pro
225                 230                 235                 240

Leu Ala Asp Thr Pro Thr Val Val Gly
                245

<210> SEQ ID NO 43
<211> LENGTH: 172
<212> TYPE: PRT
<213> ORGANISM: Chlorella

<400> SEQUENCE: 43

Trp Trp Thr Lys Ser Ala Pro Pro Asn Val Val His Ile Lys Ser Val
1               5                   10                  15

Gln His Leu Val Asp Glu Met Val Arg Ala Glu Arg Leu Ala Gly Ala
                20                  25                  30

Gly Glu Arg Leu Val Ile Met Asp Val Phe Ala Pro Trp Cys Ala Ala
            35                  40                  45

Cys Lys Ala Leu Tyr Pro Lys Leu Met Lys Leu Met Glu Glu Arg Pro
        50                  55                  60

Asp Val Leu Leu Leu Thr Val Asn Phe Asp Glu Asn Lys Thr Val Val
65                  70                  75                  80

Lys Ala Met Gly Val Lys Val Leu Pro Tyr Phe Met Phe Tyr Arg Gly
                85                  90                  95

Lys Glu Gly Lys Leu Gln Glu Phe Ser Ala Ser Asn Lys Arg Phe His
                100                 105                 110

Leu Ile Gln Glu Ala Ile Glu Arg His Ser Thr Asp Arg Cys Phe Leu
            115                 120                 125

Asp Ser Thr Asp Glu Glu Pro Val Leu Ala Glu Phe Pro Thr Val Val
        130                 135                 140

Pro Ala Lys Gly Ile Ser Gly Ser Leu Asp Glu Pro Ala Gly Arg Ala
145                 150                 155                 160

Ala Gly Lys Ala Val Gly Gln Pro Gln Pro Val Ala
                165                 170
```

<210> SEQ ID NO 44
<211> LENGTH: 828
<212> TYPE: DNA
<213> ORGANISM: Arabidopsis thaliana

<400> SEQUENCE: 44

| | |
|---|---|
| atgacggaag tgattagcaa aacgagtttg ttcttaggag cttgtggtaa tcatcaccgt | 60 |
| gttgatgatt tctctttctc tccggtgagt tttggtgggt ttggtttgaa aaagagtttc | 120 |
| tcttgtctga agcttaagag tcagaagcct cttagaagtg tattttacgg aaaacagatc | 180 |
| gttttcggag attctcaaga cgagagcttc agaagatcat cagctatcac agctcagaca | 240 |
| actttgagga ttgggacagc tcagaagtgg tgggagaaag gtctgaaaga taacatgaga | 300 |
| gagatctctt cagctcaaga gctcgttgat tctcttacta cgctggtga taagcttgtt | 360 |
| gttgttgatt tcttctcacc tggctgtggt ggctgcaagg ctctccatcc taagatatgt | 420 |
| cagtttgcag atgaacccc ggatgtgcag tttcttcagg tgaattacga ggagcataag | 480 |
| tccatgtgtt atagtcttgg tgtccatgtt ctccctttt tccgattcta ccgtggctct | 540 |
| cagggtcgtg tttgcagctt tagctgtacc aatgccacga tcaagaaatt cagagatgcc | 600 |
| ttggcaaagc atggtccaga taggtgcagc ctcggaccga ccaaaggcct tgaagagaaa | 660 |
| gagcttgtgg cacttgcagc caacaaagaa ctcaacttta cttacacacc aaagcctgta | 720 |
| ccagttgaga agaagcagc cactcctgat tcaaacccaa gtctccctgt tcctcttcct | 780 |
| tcgatgagct ccaatgacga aaaaacattg gtctccgcag ggagatga | 828 |

<210> SEQ ID NO 45
<211> LENGTH: 906
<212> TYPE: DNA
<213> ORGANISM: Solanum tuberosum

<400> SEQUENCE: 45

| | |
|---|---|
| atgatgaaat tgatgagcaa aggttttatg tttccttcgt cttctgattg tggtgaaatt | 60 |
| tatcatcatc gtcctcttaa tctacctggg atctgttctt ttcccaataa atcggtcaat | 120 |
| cttttcttgtc ttccttcgtt gaacctttca tcttcttgtt tgccaagaac cgattttat | 180 |
| ggtcgtagat tggttataaa tgaaggcgta tccaagttca accgaagaaa ttcccaagtt | 240 |
| gttgatatca ctgctcagat gagtattgga atcaggaaag cacagaaatg gtgggagaaa | 300 |
| ggggttcaac ctaacatgaa agaggtgaac agtgcacaag aacttgttga ctctcttttg | 360 |
| agtgcagggg acaaattagt tgttgttgat ttctttcccc ctggctgtgg aggttgtaaa | 420 |
| gctcttcacc ccaagttgtg tcagctggca gagatgaatc cagatgtgca tttttacag | 480 |
| gtgaactatg aggaacacaa gtcgatgtgt tactctctta atgtacatgt tctcccattt | 540 |
| ttccgttct atagaggagc tgaaggccgt gtttgcagct ttagctgtac caatgccacg | 600 |
| atcaaaaaat tcaaagatgc actggcgaag tatggtacag atcgttgcac ccttgggccg | 660 |
| ccaaaagggc tggaggagaa agagctactt gcactggcag ctaacaagga tctctccttt | 720 |
| aattacactc caaaaacaga agaagcaccc gtccttgtta cctcacaaaa ggaagttcag | 780 |
| gatacaactc ctccaaatat agagtcccct ctaccacttc ctcttcctct ccccattgcg | 840 |
| tcaactagct cacagacggc caaacgggat acagagaaag aagcatatgc tacttctggt | 900 |
| agatga | 906 |

<210> SEQ ID NO 46

```
<211> LENGTH: 693
<212> TYPE: DNA
<213> ORGANISM: Solanum tuberosum

<400> SEQUENCE: 46
atgaaattca atagaagaaa tcacaaatca gcagctgcaa ctgctcagat gagcataggt      60
atcaggaaag ctcctaaatg gtgggagaaa ggacttcaac cgaatatgaa agaggtgatg    120
ggtgctcaag acctcgctga caccctctta aacgctgggg ataaactagt cgttgtcgat    180
ttcctttccc ctggctgtgg aggctgcaaa gcccttcatc aaagatatg tcagttagca     240
gagatgaatc cggatgtgca gttttacat gtgaactatg aggaacacaa gtcaatgtgt     300
tactcgctga acgtacatgt tctcccattt tttcgtttct atagaggtgc tgaaggtcgt    360
ctttgtagct ttagttgcac caatgccacg ataaaaaat tcaaagatgc attgacaaag     420
tatggtgcag attgttgcag cctcgaacca gttaaagggc tcgaggagaa agagctactt    480
gccctagcag ctaataagga cctctctttt gcttacacac caaaaacaga gaaccaatg     540
cctgttgcct tacaagatgc taaggtgata aaaacaagca gaacatcttc atcttgtcca    600
aatacattct ccctgttacc acttcccctt cctcttcctc tagcatcaac ttcacataag    660
gccaaacagg actcgaagag tgaagttttt taa                                 693

<210> SEQ ID NO 47
<211> LENGTH: 831
<212> TYPE: DNA
<213> ORGANISM: Zea mays

<400> SEQUENCE: 47
atggcggcag cgcaggcgat ctcgaagggg agcgtggtgt ctccgtgcgg caatcgagcg     60
gcgccgggcc tccttgccag gcggaggggt gccgtggcgg cgcgggtggc gccgtcagcg   120
gcgcggatcg ggggcttctg gaggaagaac gcgtttcctg gcgggaggct aaccctgagg   180
acgaggagat ccagggccgc gtcaccggcg cagatgaaca tgaaccttgc gcttgggaaa   240
tcgatgaggt ggtgggagaa ggggttgcag cccaacatgc gtgagatcga gtccgcccaa   300
gaccttgtcg atgctttgac caacgccggc gacaggctcg tcgtcgtcga cttcttctct   360
cctggctgcg gcggctgccg tgcttttcac cccaagattt gtcaatttgc ggagcagaat   420
ccagatgtgc tgttcttgca agtgaactac gaggagcaca gtctatgtg ccacagcctt    480
catgtccatg tcctacccct tgttcagattc tacaggggag cacagggacg actctgtagc   540
ttcagttgta caaacacaac tattaagaag ttcaggatg cactcgcgaa gcacaagcca    600
gatagatgta gccttggccc aaccagggg ctagaggaat ctgagttatt agccttggcg    660
gcaaacaagg acctgcagtt cacctacgcg aaggaggaac cagaactgat ccccagggga   720
gatgctcctg gggaggtcgt tgctcctgag cctgcaaagc ttcctgcggc tccaaagcct   780
ttggtcaggc tggggtccga ggagaggtca ctggtctcgt caggaagatg a            831

<210> SEQ ID NO 48
<211> LENGTH: 819
<212> TYPE: DNA
<213> ORGANISM: Zea mays

<400> SEQUENCE: 48
atggctgacg cgttgtgcaa cggcgtcgtg gcgtccccgt gcggccggga cgtcgccggc     60
cgggccaggg gcgccgccag ggccgcgctc gcggagtccc tgcaggtcgc cgggcacgcc   120
agcaagacct ccttctccgc cgggaggatg tcggtcaagg acagcaagcc gaggcccctg   180
```

| | |
|---|---|
| tcgcgtagcc tcgaggccgc cgcgccagga cagatgaacc tgtcgttccc caaagccatg | 240 |
| cggtggtgga agaaggggct gcaccccaac atgcgcgagg tcgagtccgc gcaggacctg | 300 |
| gccgactcgc tgctcagcgc cggcgacaag ctcgtggtcg tcgacttctt ctccccaggc | 360 |
| tgcggcggct gccgcgccct ccaccccaag atcgcccagt tcgccgagaa gaacccgggc | 420 |
| gtgcagttct gcaggtgaa ctacgagacg cacaagtcca tgtgctacag cctccgcgtc | 480 |
| cacgtcctcc ctttcttcag gttctaccgg ggagccgagg gccgggtcag cagcttcagc | 540 |
| tgcaccaacg caacgatcaa caagttcaag gacgcgctcg ccaagcacgg ggctgagagg | 600 |
| tgtagcctcg ggcctgcgcg ggggctggac gagtcggagc tcatggcctt ggctgagaac | 660 |
| agggacctgc acttcaccta cgacaagccg ggcggcctcg tcccctcgc cgaagctatt | 720 |
| gccaaggagg ctgccgcacc gggaggcccg tggcttcctc tgcctgcgtc cctgctcggc | 780 |
| cagggatccg acaactcatt gctgccctct ggaagatag | 819 |

<210> SEQ ID NO 49
<211> LENGTH: 666
<212> TYPE: DNA
<213> ORGANISM: Zea mays

<400> SEQUENCE: 49

| | |
|---|---|
| atggcggcgg cgcaggtggt cgcgaagggg agcgtggtgt cgccgtgcgg caatcgagcg | 60 |
| gtgccgggcc tcttgggcag gcggagggat gccgtggcgg cgcagatgac gccgtcggcg | 120 |
| gtgcggatcg ggggctcctg gaggaagaac gcgtttcctg gcgtgaggct agccttgggg | 180 |
| acgaggagat ccaggcccgc gtcccggagt ttctccgcct cgccggtgca gatgaacatg | 240 |
| aaccttgcga ttgggaaatc aatgaggtgg tgggagaagg ggttgcagcc caacatgcgt | 300 |
| gagatcgagt ccgcccaaga ccttgtagat tccttaacca acgccggcga gaggctcgtc | 360 |
| gtcgtcgact tcttctcccc tggctgcggc ggctgccgtg ctcttcaccc gaagatttgc | 420 |
| caatttgcgg agcggaaccc tgatgtgctg ttcttgcaag tgaactacga ggagcacaag | 480 |
| tctatgtgct acagccttcg tgtccatgtg ctaccctcct tcagattcta cagaggagca | 540 |
| cagggacgac tctgcagctt cagctgtaca aacgcaactg taagatcatg tccatgtttc | 600 |
| ttctgttcgt atgattattg gtatgtcctc aataacatgc aacatatcca aaatgacctt | 660 |
| tattga | 666 |

<210> SEQ ID NO 50
<211> LENGTH: 840
<212> TYPE: DNA
<213> ORGANISM: Oryza sativa

<400> SEQUENCE: 50

| | |
|---|---|
| atggcggcga cggcggcgca ggcggtggcg gtgaagggga gcgtggcggt gccgccgtgc | 60 |
| gggagccgcg gccggcggag gggcgccgtg cgtcggtgc gcatggcggc ggcggcggcg | 120 |
| acgtcggcgt tgcggatcgg caggaggagc cccttcctcg gccggaggct ggcggttggg | 180 |
| ccgaggagat ccaggcccgt gccccggaat ctcgtcgcgc cggtgcagat gaatctcgcg | 240 |
| tttgcgaaag ccacgaagtg gtgggagaag ggattgcagc ccaacatgcg ggaggtcgag | 300 |
| tccgcgcaag acctcgtcga ctccttgacc aacgccggcg acaatctcgt catcgtcgac | 360 |
| ttcttctccc ctggctgcgg cggctgccgt gccctccacc ccaagatttg ccagattgca | 420 |
| gagcagaatc cggacgtgct gttcttgcag gtgaactatg aggagcacaa gtctatgtgc | 480 |

| | |
|---|---|
| tacagcctcc atgttcatgt tcttcctttc ttcaggttct acaggggagc tcagggccgg | 540 |
| ctctgcagct tcagctgtac taacgcaact attaagaagt tcaggatgc gcttgctaag | 600 |
| cataaaccag atagatgcag ccttggccca actaggggc tcgaggagtc ggagctattg | 660 |
| gcgctggctg cgaacaagga tctgcagttc aactacacca agaaaccaga actggttcct | 720 |
| agcggagatg ccgcagctgc ccaggaattg gatcgtggaa gcacaaagct ttctccaccc | 780 |
| gcaaaaccat tggtcaagca gggctctgaa gagaggtcct tggtctcatc aggcagatga | 840 |

<210> SEQ ID NO 51
<211> LENGTH: 840
<212> TYPE: DNA
<213> ORGANISM: Oryza sativa

<400> SEQUENCE: 51

| | |
|---|---|
| atggctgagg cactgtgcag cggcagcgtc gcgtccccgt gcggggaggt gggtgtgggg | 60 |
| ttcgccgccg gccttgtgag gggcgccgcg gcggcggcgg cgctcgcgga gtctgtgccg | 120 |
| attggtgggt acagcagcaa gagcacgttc ccgagtggga gggtggcgct cacgagagg | 180 |
| aaggcgaggc ccctgccacg gaatctcgaa gcggcgcatg gcagatgaa cctgacgatt | 240 |
| gggaaggcca tgaggtggtg ggagaagtgc ctgcagccca catgaggga gatcgagtcg | 300 |
| gcgcaagacc tcgccgactc cctcctcaac gccggcgaca agctcgtcgt cgtcgacttc | 360 |
| ttctccccgg gctgcggtgg ctgccgcgcc ctacacccca agattgctca actagccgag | 420 |
| aagaacccgg aggtgctgtt cttgcaagtg aactacgaga agcacaagtc aatgtgctac | 480 |
| agcctccatg ttcatgttct gccattcttc aggttctaca ggggagctca gggccgtgtc | 540 |
| agcagcttca gctgcacaaa cgcaactatc aagaagttca aggatgcact tgccaagcat | 600 |
| ggtccggaca ggtgtggcct cggccgggcg aaggggctcg aggagtcgga gctcatggcg | 660 |
| ttggccataa acagggacct gaacttcacc tacacaccaa accaagacct tgtcccaatt | 720 |
| gcagacgccc tcctgaagga agctgctgca cctggaggtc catggctgcc attgcccgca | 780 |
| acggcgacgc agctgttcat tcagggatct gagaattcgc tgttgtcatc tggaagatag | 840 |

<210> SEQ ID NO 52
<211> LENGTH: 831
<212> TYPE: DNA
<213> ORGANISM: Hordeum vulgare

<400> SEQUENCE: 52

| | |
|---|---|
| atggcgacgg cgcaggcggt ggccaagggg accgtggtct ctccgtgcgg cacccgggcc | 60 |
| gcaggatttg gagcccggcg gcggggcgcc gtggcggccc gcatgtcgcc ctgcgcgccg | 120 |
| gcggcggtgc ggatcggcag gaaaagcccg tttcttggcg ctaggctcac ggtcggtccc | 180 |
| aggagatcca agctcgttcc ccggaatctt gtctcctcac cggtgcagat gaaccttgcg | 240 |
| tttgcgaaat ccaccaagtg gtgggaaaag ggtctgaagc caacatgag ggagatcgag | 300 |
| tccgcccagg acctcgtcga ctcgttggct aacgccggcg acaggctcgt cgttgttgac | 360 |
| ttcttctccc ctggctgcgg cggctgccgt gccctccacc caaagatttg ccagtttggg | 420 |
| gagcagaacc cagatgtgct gttcttgcaa gtgaactacg aggaacacaa gtccatgtgc | 480 |
| tacagcctcc atgtccatgt gctgcccttc ttcaggttct acaggggagc ccagggccgc | 540 |
| ctctgcagct tcagctgtac taacgcaacc ataagaagt cagggatgc gcttgccaag | 600 |
| cataatcctg ataggtgtag cattggtcca accaggggcc tcgaggagtc tgagctgctg | 660 |
| gctttggctg cgaacaagga cctgcagttc acatacacga agcagccaga accagttccg | 720 |

```
agtggtgatt ccgagttcat tgctcctggg agcccaaggc ttcctccacc tgcaaaacca    780
ttggttcggc agggttccgg agagaggacc ttggtctcat caggaagatg a            831

<210> SEQ ID NO 53
<211> LENGTH: 813
<212> TYPE: DNA
<213> ORGANISM: Hordeum vulgare

<400> SEQUENCE: 53
atggccaacg cgctttacgg cggcggcgtg gcggcgccgt gcggtgactt gggcgccgcg    60
gccgcgctcg cggagtcttt gccgatgggc ggcgggtacc gcgcgaggag ctccttcccc   120
gccgggaggg tggcgctggc ggagaggccc ctgccccgga gcctccaggt ggcggccgct   180
gctggacaga tgaacgggaa cctgacgatt ggcaaggcca tgaggtggtg ggagaagggg   240
acgcagccca acatgaggga ggtcgagtcc gcgcaagacc tcgccgactc cctgctcaac   300
gccggcgaca gctcgtcgt cgtcgacttc ttctcccccg ctgcggtgg ctgccgcgcg    360 ctccacccca agattgcgca gttcgccgag cgtaatccgg acgtgctgtt cctgcaagtc   420
aactacgaga agcacaagtc catgtgctac agcctccatg tccatgtcct ccctttcttc   480
aggttctaca ggggagctca gggcagggtc agcagcttca gctgcaccaa cgcaaccata   540
aagaagttca aggacgccct cgcaaagcac tcgccggaca ggtgcagcct cggcccggcg   600
cgggggcttg agaaggcgga gctcttggct ctggctgaga cagggacct ggaattcacc    660 tacagcgaga agccgacact tgtgccgatc gcagaggcca tcaggatgga agctgcctca   720
atcggaggcc catggctgcc attgcctccg gccgcgacgc agccgtttcc tctgggatcc   780
gagaatggct cgctcatccc ctctggaaga tag                                813

<210> SEQ ID NO 54
<211> LENGTH: 822
<212> TYPE: DNA
<213> ORGANISM: Triticum aestivum

<400> SEQUENCE: 54
atggccagcg cgctatgcgg cggcggcagc ggcagcgtgg cggcgccgtg cggggacttg    60
ggcgccgcgg cggcgctcgc ggagtctttg ccgatgggcg ccgggtaccg cgccaagagc   120
tccttccccg ccgggagggt ggcgctggcg gacaggcccc tgcgccgggg cctccaagtg   180
gcggcggctg ctggacagat gaacgggaac ctgacgattg caaggccat gaggtggtgg    240 gagaaggtga cgcaccccaa tatgagggag gtcgagtccg cgcaagacct cgccgactcc   300
ctgctcaacg ccggcgacaa gctcgtcgtc gtcgacttct tctcccccgg ctgcggtggc   360
tgccgcgctc tccaccccaa gattgcgcag ttcgctgagc ggaatccgga cgtgctgttc   420
ctgcaagtca actacgagaa gcacaagtcc atgtgctaca gcctccatgt ccatgtcctc   480
cctttcttca ggttctacag gggagcccag ggcagggtca gcagcttcag ctgcacaaat   540
gcaaccatca agaagttcaa ggacgccctc gcaaagcact cgccggacag gtgcagcctc   600
ggcccggcgc ggggctcga ggaggcggag ctcttggctc tggcggcaaa cagggacctg    660
gaattcacct acaacgagaa gccgacgctg gtgccgatcg ccgaggctat ccagatggaa   720
gctgcctcca ttgcggccc atggatgcca ttgcccgcgg ccgcgacgca gccgctcact    780
ctgggatctg agaatggctc gctgatcccc tccggaagat ag                      822

<210> SEQ ID NO 55
```

<211> LENGTH: 891
<212> TYPE: DNA
<213> ORGANISM: Manihot esculenta

<400> SEQUENCE: 55

```
atggctgatg ttttgagcaa taccaatctg gtttcttctt ccttctcttc atcttttact      60
ggtcaccgaa acgagcagaa aaatagctct tgcaggctaa aagggttccc ccgaaaagtg     120
aatcgtcaga ctttgagatt gaaagcgaca tcgcttggca gtgattttca tggaaagagg     180
gttgttcttc aagacaatca aggcaaaccc aagagaggga tttatcttca aatgtcaatt     240
aaggctcagc atactggcct tagactcaag agtgctccaa atggtgggaa aaaggattg      300
caacccaaca tgagggaggt gacctctgct caagactttg tggactccct cttgaacgct     360
ggagataaac ttgtcattgt tgatttcttc tcccctggtt gtggtggctg caaggctctc     420
catcccaaga tatgtcagtt tgcagagatg aacccagatg tgctgttcct tcatgtgaat     480
tatgaggaac ataaatccat gtgttatagc ctcaatatcc atgtgcttcc cttcttcagg     540
ttttatcgag gggcgcaagg ccggttatgc agctttagct gcactaatgc tacgataaaa     600
aaattcagag atgcactggc caagcactct ccagaccggt gcagtctcgg gccaacaaaa     660
gggctggagg agaaagagct tattgcattg gcttccaaca agatctcaa cttcaaatat      720
gcacagaaac cagatctgcc aacgccaatt cctgccaagg aagagagagt gccagtagta     780
tccccatctc atccaaatcc agctctacct ctacctcttc ctcttcccac agcaagtcca     840
aaatctggac aaggctcaga ggagaaaacg ttggtcggat cagggagatg a              891
```

<210> SEQ ID NO 56
<211> LENGTH: 864
<212> TYPE: DNA
<213> ORGANISM: Manihot esculenta

<400> SEQUENCE: 56

```
atggccgctg tttctagcaa caccaatctt gtttcttctt cttgttcttc atcctttagt      60
tcttcgcaaa accgccccga ataccgctct ccaggctcca gagtgttccc tcaggaattg     120
aatcatcagg ctttgagatt acaaactacg tcgcttggca gtgattttca tggaaagagg     180
gttgttcttc aagaaaaacc aaaatgcaaa caagggattt ccgttcaaag ctcaattaag     240
gctcagcaga ctggccttag actcaagaat gctaaaaatt ggtgggagga ggagttgcaa     300
cccaacatga gggaggtgat ctctgctcaa gatcttgtgg actccctcct taatgctggc     360
gataagcttg tcattgttta tttcttctcc cctggctgtg gtggctgtag gctctccat      420
cccaagatat gtcaattggc aaagaacaat gcagatgtgc agtttcttaa agtgaactat     480
gaggagcaca atccatgtgt tatagcctc aatgttcatg tccttccatt cttcaggttt      540
tacagagggg ctcaaggccg agtctgcagc tttagctgca ccaacgccac gatcaagaaa     600
tttaaaaatg cattgccaa gcacacccca gacagatcca gcctcgagcc aacaaagggg     660
ctggaggaga aagagctcat tgcattggct gccaataaag atctcaactt aacatatgca     720
ccaaaatcag ataagccaat cccagctcca actaaggaag atatagtacc cgaaattccc     780
caatctcttt ctcttgctct tcgtaggagt atggagcttg ctcaaggctc agccgaaaag     840
accttggtcg cttcagggag atga                                           864
```

<210> SEQ ID NO 57
<211> LENGTH: 852
<212> TYPE: DNA
<213> ORGANISM: Sorghum bicolor

<400> SEQUENCE: 57

```
atggcggcag cgcaggcggt cgcgaagggg agcgtggttg cgccgtgcgg caatcgagcg        60
gcgccgggcc tccttggcag gcggaggggt gccgtggcgg cgcggatggc gccgtcggcg       120
gtgcggatcg gggcctcatg gaggaagacc gcgtttacag gcgggaggct agccttgggg       180
ttggggacga ggagatccag gcccgcgtcc cggagttctt tcgcgtcgcc ggcgcagatg       240
aacatgaacc ttgcgattgg gaaatcgatg aggtggtggg agaaggggtt gcagcccaac       300
atgcgtgaga tcgagtccgc ccaagacctt gtcgattcct tgaccaacgc cggcgacaag       360
ctcgtcatcg tcgacttctt ctcccctggc tgcggcggct gccgtgctct tcacccgaag       420
atttgtcaat ttgcggagca gaacccagat gtgctgttct tgcaagtgaa ctacgaggag       480
cacaagtcta tgtgctacag tcttcatgtc catgtcctac ccttcttcag attctacagg       540
ggagcacagg gacggctctg cagcttcagt tgtacaaacg caaccattaa gaagttcaag       600
gatgcacttg cgaagcacaa gccagataga tgtagccttg gcccaaccag ggggctagag       660
gaatcggagt ttttagcctt ggcagcaaac aaggacctgc agttcaccta caccaaggag       720
ccagaactga ttcccagggg agatgctcct ggggaggtca ttgctcccga gcctgcaaag       780
cttcctgcgg ccacaaagcc tttggtcagg ctggggtccg aagaaaggtc cttggtctca       840
tcaggaagat ga                                                           852
```

<210> SEQ ID NO 58
<211> LENGTH: 801
<212> TYPE: DNA
<213> ORGANISM: Sorghum bicolor

<400> SEQUENCE: 58

```
atggcggcgg cgcaggcgat ggcgaaaggg agcgtggggc aggggtctct tggtcggcgg        60
aggggcgccg aggcggcgcg ggtcggagga tcatggagga gagcgcgtt cctcggcggg       120
aggctggcgg ttgggcccag gagaccgaga cccgtgtccc ggattctagt tacgtcgccg       180
gcggtgcagc agacgaacct ttcatttgcg aaagccatga agtggtggca gaagggattg       240
cagcccaaca tgcgggcgat ccagaccgcc caagacctcg ccgattcctt gaccaacgcc       300
ggcgacgggc tcgtcgtcgt cgacttcttc tcacccggct gcgctggctg ccatgctctc       360
cacccccaaga tttgtcagtt gcggagagg aacccggatg tgcagttcct gcaggtgaac       420
tatgaggagc acaagtctat gtgccacagc cttcacgttc atgtgttccc tttcttcagg       480
ttctacaggg gagctcaggg tcggctctgc agcttcagct gtaccaatgc aactattaag       540
aagttcaggg atgcacttgc aaagcacaga gctgatagat gcagccttgg ccctactcgg       600
ggactagaag aatcagaatt gttggccctg ctgcaaaaca aggacctgca gttcacctac       660
accaaggagg cagaactggc tccaagcatg aagatgtcg cagaggttat gactgctgac       720
cgtccagggc ttccgacatc aacaatgcca ttggcaaggc agggatctga ggacagggcc       780
ttggtctcgt caggaagatg a                                                 801
```

<210> SEQ ID NO 59
<211> LENGTH: 618
<212> TYPE: DNA
<213> ORGANISM: Sorghum bicolor

<400> SEQUENCE: 59

```
atggctgagg cgttgtgcaa cggcgtcgtg gcgtcgccgt acggcggcgg ggacgtgggc        60
```

| | |
|---|---|
| gtcgccggcc gggccagggg cgccgccaag gccgcgctcg cggagtccct gccggtcggc | 120 |
| gggtacgcca ccaagagctc cttctcccgc gggaggatgt cggtgtcgga caggaagccg | 180 |
| aggcccctgt ctcggaacct cgaggccgcc gccgcgcctg acagatgaa cctgtcgttt | 240 |
| cccaaggcca tgcggtggtg ggagaagggg ctgcacccca acatgcggga gatcgagtcc | 300 |
| gcgcaggacc tcgccgactc cctcctcaac gccggcgaca agctcgtcgt cgtcgatttt | 360 |
| ttctccccag gctgcggcgg ctgccgcgct ctccacccca agattgccca gttcgccgag | 420 |
| aagaacccgg acgtgctgtt cctgcaagtg aactacgaga cgcacaagtc catgtgctac | 480 |
| agcctccacg tccatgtcct cccgttcttc aggttctaca ggggagccga gggacgggtc | 540 |
| agcagcttca gctgcaccaa tgcaacggta agaatcgacc acctctccaa cttcaagaac | 600 |
| cagcagatga atgaatga | 618 |

<210> SEQ ID NO 60
<211> LENGTH: 786
<212> TYPE: DNA
<213> ORGANISM: Brassica napus

<400> SEQUENCE: 60

| | |
|---|---|
| atggcggaag cagcaatcag cagaacgaat ctgatcttcc gaggagcttg cgtgaatcaa | 60 |
| cacaagcatg tagatgatta ctctgtctca tcacctgtga gtttcggttt gagaaagagc | 120 |
| ttcccttctc tgaaggtgaa gccttttaat caattccaga gctcccgatc atcatcatcc | 180 |
| atcacagctc agacaacgtt gaggattggg acgcctcaga aatggtggga aagggtctg | 240 |
| aaagagaaca tgagagagat ctcttcagct caggagcttg ttgactcttt aaccaacgct | 300 |
| ggtgataagc tcgttgtggt tgacttcttc tctcctggct gtggtggatg caaggctctt | 360 |
| catcctaaga tatgtcagtt ggcagagcag aaccctgatg tgcagtttct tcaggtgaac | 420 |
| tacgaggagc acaagtccat gtgttacagt ctcggtgtcc acgtcctccc gttttcaga | 480 |
| ttctaccgtg gcgctcatgg tcgtgtctgc agcttcagct gcaccaatgc tacgatcaag | 540 |
| aagttcagag atgcattggc gaagcatagt ccggataggt gcagccttgg accgaccaaa | 600 |
| gggcttgaag agaaggagct tgtggcactt gcagccaaca aagaactcaa ctttagttac | 660 |
| acaccgaggg ctgtaccagt tgaggaagaa gaagctcccg tccccgcttc aaaccctggt | 720 |
| ctccctgttg ctcatccatc gatgaaggcc aatgatggaa agacattggt ctcctcaggg | 780 |
| agatga | 786 |

<210> SEQ ID NO 61
<211> LENGTH: 807
<212> TYPE: DNA
<213> ORGANISM: Brassica napus

<400> SEQUENCE: 61

| | |
|---|---|
| atggcggagg taatcagcaa aacgagtttg ttcttccgag agcttgcgt gaatcaccac | 60 |
| caccacgcag atgacttctc cgtctcgccg gtgagtttcg gtctcaaaaa gagtttctct | 120 |
| tctctcaagc agaagcctct tagaagcgac ttctctggaa acagatcct acagaccttc | 180 |
| aacaggagct tccgatcatc atccgttacc gctcagtcaa cgctgaggat tgggacagct | 240 |
| cagaagtggt gggagaaagg tctgcaagag aacatgagag agatctcttc ggcgcaagag | 300 |
| ctcgtcgact ctctcgccga cgctggcgat aagctcgtcg tggttgactt cttctctcct | 360 |
| ggctgcggcg gatgcaaggc tctgcatcct aagatgtgcc agctggcgga gcagagcgct | 420 |
| gatgtgcagt tccttcaggt gaactacgag gagcacaagt ccatgtgtta tagcctcggt | 480 |

```
gtccacgtcc tcccgttttt tcggttctac cgtggcgctc agggtcgcgt ctgtagcttt    540
agctgtacta atgctacgat aaagaaattt agagacgcgt tggcgaagca tagtccggat    600
aggtgcagcc ttggaccaac caaggggctt gaagagaaag agcttgtggc acttgcagcc    660
aataaagaac tcaactttag ttacacgccg aaggttgtac ctgttgagaa agaagcagct    720
attcccactt ccaacccggc actccctgtt cctcatccat cgatgagtgg cagtgaggag    780
aagacattgg tctctgcagg gaggtga                                         807
```

<210> SEQ ID NO 62
<211> LENGTH: 810
<212> TYPE: DNA
<213> ORGANISM: Brassica napus

<400> SEQUENCE: 62

```
atggcggaag cagcaattag cagaacgaat ctgatcttca gaggagcttg cgtgactcac     60
caccaccatg cagatgatta ctctgtctca tcatcacctg tgagtttcgg tctgagaaag    120
agcttctctt ctctcaagct gaagcctccg agacagatcg atactcaatt ccagaccttc    180
acaaggagct cccgagcatc atccatcaca gctcagacga cgctgaggat cgggacgcct    240
cagaaatggt gggagaaggg tctgaaagag aacatgagag agatctcttc agctcaggag    300
cttgttgact ctctaaccaa cgctggtgat aagctcgttg tggttgactt cttctctcct    360
ggctgcggtg gatgcaaggc tcttcatcct aagatatgtc agttggcaga gcagaaccct    420
gatgtgcagt tccttcaggt gaactacgag gagcacaagt ccatgtgtta cagtctcggt    480
gtccacgtcc tccctttctt tcgattctac cgtggcgctc acggtcgtgt ctgcagcttc    540
agctgcacaa atgctacgat caagaagttc agagatgcat tggcgaagca tagtccagat    600
aggtgcagcc tcggaccgac caaagggctt gaagagaagg agcttgtggc gcttgcggcc    660
aacaaagaac tcaactttag ttacacaccg agggctgtac cagttgagga agaagaagct    720
cccgtccccg cttcaaaacc aggtcttgct gttcctcatc catcgatgag cgccaatgat    780
gagaagacat tggtctccgc agggagatga                                      810
```

<210> SEQ ID NO 63
<211> LENGTH: 786
<212> TYPE: DNA
<213> ORGANISM: Brassica napus

<400> SEQUENCE: 63

```
atggcggaag cagcaatcag cagaacgaat ctgatcttcc gaggagcttg cgtgaatcaa     60
cacaagcatg tagatgatta ctctgtctca tcacctgtga gtttcggtct gagaaagagc    120
ttcccttctc tgaaggtgaa gccttttaat caattccaga gctcccgatc atcatcatcc    180
atcacagctc agacagcgtt gaggattggg acgcctcaga gatggtggga agggtttg     240 aaagagaaca tgagagagat ctcttcagct caggagctcg ttgactctct aaccaacgct    300
ggtgataagc tcgttgtggt tgacttcttt tctcctggct gtggtggatg caaggctctt    360
catcctaaga tatgtcagtt ggcagagcag aaccctgatg tgcagtttct tcaggtgaac    420
tacgaggagc acaagtccat gtgttacagt ctcggtgtcc acgtcctccc gttttttcaga    480 ttctaccgtg gcgctcatgg tcgtgtctgc agcttcagct gcaccaatgc tacgataaag    540
aagttcagag atgcattggc gaagcatact ccggataggt gcagccttgg accgaccaaa    600
gggcttgaag agaaggagct tgtggcactt gcagccaaca aagaactcaa ctttagttac    660
```

| | |
|---|---|
| acaccgaagg atgtaccagt tgaggaagag gcagctcccg tccccgtttc aaaccctggt | 720 |
| ctccctgttg ctcatccatc gatgaaggcc aatgatggaa agacattggt ctcctcaggg | 780 |
| agatga | 786 |

<210> SEQ ID NO 64
<211> LENGTH: 819
<212> TYPE: DNA
<213> ORGANISM: Brassica napus

<400> SEQUENCE: 64

| | |
|---|---|
| atggcggagg taatcagcaa aacgagtttg ttcttcggag gaggagcttg cgtgaatcac | 60 |
| caccaccacc acgtagatga cttgtctgtc tcaccggtga gtttcggttt caaaaagagt | 120 |
| ttctcttctt ctctcaagca gaagcctctt agaagcgact tctctggaaa acagatccta | 180 |
| gagaccttca acaggagctt ccgatcatca tccgtcaccg ctcagtcgac gctgaggatt | 240 |
| gggacagctc acaagtggtg ggagaaaggc tctcaagaga acatgagaga gatctcttcg | 300 |
| gcgcaagacc tcgtcgactc tctcgccgac gctggcgata agctcgtcgt ggttgacttc | 360 |
| ttctcccctg gctgcggggg atgcaaggct ctgcatccta agatgtgcca gctggcggag | 420 |
| cagagccctg atgtgcagtt tcttcaggtg aattacgagg agcacaagtc catgtgttac | 480 |
| agtctcggtg tccatgtcct tcccttttt cgattttatc gaggcgctca gggtcgtgtc | 540 |
| tgtagcttta gctgtaccaa tgctacgata aagaaattta gagacgcgtt ggcgaagcat | 600 |
| agtccggata ggtgcagcct tggaccaacc aaggggcttg aagagaaaga gcttgtggcg | 660 |
| cttgcagcta ataaagaact aaagtttagt tacacgccga aggttgtacc tgttgagaaa | 720 |
| gaggttgcca tccccacttc aaaccctggt ctccctgttc ctcatccatc gacgatgagc | 780 |
| ggcagtgagg agaagacgtt ggtctctgca gggaggtga | 819 |

<210> SEQ ID NO 65
<211> LENGTH: 891
<212> TYPE: DNA
<213> ORGANISM: Ricinus communis

<400> SEQUENCE: 65

| | |
|---|---|
| atggctgatg ttttgagcaa gaccaatctt gttccttcgt cttgttgtaa tggttacaag | 60 |
| aaccagaaga aagatggtgc cttcgttcta aaaagaagtt gcagtcttaa ggtgtcatct | 120 |
| aggaaattca atcctcaggc tttcggatca cagaagatat cacttatttc tgatttttat | 180 |
| ggcaagaggg ttattgttca agaaaaacaa ctcaagagag gaattttca tcaattttca | 240 |
| attaaggctc agactggact gagactcaag aatgctccaa aatggtggga aaaggggttg | 300 |
| caaccaaaca tgaaggagat cacctctgca caagaccttg tggactccct tatgaatgct | 360 |
| ggggacaaac ttgtaattgt tgatttcttc tcccctggct gtggtggctg caaagctctc | 420 |
| catccaaaga tatgtcaatt tgcggagatg aaccctgatg tccagtttct tcaggtgaat | 480 |
| tatgaggaac ataaatccat gtgttatagc ctcaatgtac acgtactgcc attctttaga | 540 |
| ttttaccgag gggctcaagg ccgagtatgc agctttagct gtactaatgc cacgattaag | 600 |
| aaatttaaag atgcattagc caagcacacc ccagaccgat gcagcctcgg gccaaccaaa | 660 |
| gggctggagg agaaagagct tattgcgttg gcttctaaca aagatctcaa cttttacatgc | 720 |
| acaccaaaac cagttcaacc aactgctcct gctcaggaag agataatacc agcagcactc | 780 |
| accccagctc atgtgaatca aaccctacct cttcctattc tctctctac aacaagcctg | 840 |
| atgtctgccc aagacttggg ggagaaaacc ttggttactt ctgggagata g | 891 |

<210> SEQ ID NO 66
<211> LENGTH: 879
<212> TYPE: DNA
<213> ORGANISM: Phaseolus vulgaris

<400> SEQUENCE: 66

| | | | | | | |
|---|---|---|---|---|---|---|
| atggctgaag | tttttaccaa | ggcgagtttc | gtttcttctt | tgcttggtag | tagtcaacgc | 60 |
| caccatcgaa | gggtgtcgac | ggttcctgat | acttgtacct | tgtttctgg | cgtcggaggg | 120 |
| tctccttctc | tcaagttaaa | gtctccgatt | ctcagatctt | ggtcccttc | ttctgagttt | 180 |
| cagggtaaac | agcttctctt | tcgtgtaaat | agaggaaagc | ccaacagggt | cagttcgcgg | 240 |
| ttgagagcgt | caactgctgc | tcagatgacc | cttagaatag | ggaaagttca | aaaatggtgg | 300 |
| gaaaaggggc | ttcaacccaa | catgaaagag | gtgacttcgg | cccaagacct | tgtggaatca | 360 |
| ctgttaaacg | caggggacaa | gttggtggtg | gttgatttct | tctctcctgg | ttgtggtggc | 420 |
| tgcaaagccc | ttcaccctaa | gatatgtcaa | ctggcagaga | tgaatcctga | tgttcaattc | 480 |
| cttcaggtga | actatgagga | gcataagtcc | atgtgttata | gcctcaatgt | ccatgttcta | 540 |
| cccttcttcc | gcttctatag | aggtgctcat | ggtcgattat | gtagctttag | ctgcaccaat | 600 |
| gccacgatca | agaagtttag | agacgcattg | gccaaacact | cccagatag | atgcagcttg | 660 |
| ggcccaacca | aagggttaga | ggagaaagag | ctcctagctc | ttgctgccaa | caaagatctt | 720 |
| tcctttacct | tgccaaaacc | tttacaacct | gaacacgcaa | atgaagggtt | ggcaactgct | 780 |
| cctgctcctg | ttcctagttc | agaatctctt | cctttacctt | cactgaccct | caattctgag | 840 |
| gtctcccaag | agagaaacctt | gaccactgct | gggagatga | | | 879 |

<210> SEQ ID NO 67
<211> LENGTH: 876
<212> TYPE: DNA
<213> ORGANISM: Phaseolus vulgaris

<400> SEQUENCE: 67

| | | | | | | |
|---|---|---|---|---|---|---|
| atggctgagg | ttttgaccga | ggcaagtttg | gtttcttcgt | ggcatggtac | tactcaacgc | 60 |
| caccatcgaa | gagtatcgac | agttcccaat | tcttctagct | tcgtttctgg | cgttggaagg | 120 |
| ttcccttctc | tcaagttaaa | gtctcagatt | ctcagatccc | tctcctcttc | ttctgagttt | 180 |
| cagggtaaaa | agcttctctt | tcatgtaaat | agaggactag | ccaacagaat | cagttcgcgg | 240 |
| ttgggagctt | caactgcagc | gcagatgacc | cttagaatag | ggaaaggtca | gaaatggtgg | 300 |
| gaaaaggggc | ttcaacccaa | catgaatgag | gtgacttccg | cccaagatct | tgtagaatca | 360 |
| ctgttaaacg | caggggacaa | gttagtggtg | gttgatttct | tctctcctgg | ttgtggtggc | 420 |
| tgcaaagccc | ttcaccctaa | gatatgtcaa | ctggcagaga | tgaatcctga | tgttcaattc | 480 |
| cttcaggtga | actatgagga | acataagtcc | atgtgttata | gcctcaatgt | ccatgttctt | 540 |
| cccttcttcc | gcttctatag | aggtgctcat | ggtcgattat | gtagctttag | ctgcaccaat | 600 |
| gccacgatca | agaagtttaa | agatgcattg | gccaaacact | cccagatag | atgcagcttg | 660 |
| ggcccaacca | aagggttaga | ggaaaaagag | ctcctagctc | ttgctgccaa | caaagatctt | 720 |
| tcgttcatct | acgcaccaaa | tcccttacaa | cctgaacatg | aaaatgaaga | gttggctact | 780 |
| gctcccgctc | ctgttcctag | ttcagagtct | cttcctttgt | gtcacctcat | ttctgaggtc | 840 |
| tccaaagaga | aaaccttgat | cactgctggg | agatga | | | 876 |

<210> SEQ ID NO 68

```
<211> LENGTH: 864
<212> TYPE: DNA
<213> ORGANISM: Gossypium histrum

<400> SEQUENCE: 68
atggctgaag ttttggggaa gggaaatctg tttacgactt gtaactatag tcagacgaag      60
aatctagaag gtggaacttg tttggttcct aagaaaattt ctgggttttc tttagaaagg     120
aacggttttt cttctttaaa ggttaaatct caggctttaa gaagtgattt taatgggcaa     180
agaatggttt ttttggagaa gaaaagtatg aacaggcgaa ggttttgtca agttcccatc     240
aaagcacaga tgcaaagtgg tcttattggt cgaattcaga atggtgggga gaaagggctt     300
caaccaaata tgaaagaagt tgcatctgca caagacctag tagactctct tctgaatgct     360
ggtgataagc ttgttgtggt agatttcttc tcccctggtt gtggtggttg caaggctctt     420
catcccaaga tttgccaatt tgcagagatg aatccagatg tgcagtttct tcaggttaat     480
tacgaggagc acaagtcaat gtgctatagc cttaatgtcc atgtgctgcc tttcttccgg     540
ttctatcgag gtgcgcaggg gcgtgtatgc agctttagtt gtaccaatgc cacgatcaaa     600
aaattcagag atgcattagc caaacacaca cctgatcggt gtagcctcag cacgacaaaa     660
gggctcgagg agaaggagct tttggcatta tctgcgaaca aagacctttc cttcaactac     720
acaccaattc ccacacatgg agagattctt atatggaaac aagttccatc tgattcaacg     780
agaaagctcc cgctttcagt cccgacaaca tccgcaaaac aaagggacag tgaggagaaa     840
accttggttg gtgtcggaag atga                                            864

<210> SEQ ID NO 69
<211> LENGTH: 840
<212> TYPE: DNA
<213> ORGANISM: Gossypium histrum

<400> SEQUENCE: 69
atggctgaag ttttggggaa gtcaaatctg tttacagctt gtaactatag tcagaagaag      60
catcaagaag gtggcgttcc tttgttttcc aggagaatct ctgtgttttg tttgagaaag     120
aatagttttc cttctttgag gttggaacct caagctttga ggagtggttt taatggtcaa     180
agagtggttt tttagagaa aagaagtcta atgagagaa ggttctgtcg agttcccatt     240
aaagcacaga tgcaaactgg gcttattggt aaaactcaaa agtggtggga gaaggggaat     300
caaccaaata tgaaagaagt gacatctgca caagacctgg tggactcact tttgaatgct     360
ggggataaac ttgttatagt ggatttcttc tctcctggtt gtggtggctg caaggctctt     420
catcccaaga tttgccaatt ggcagagatg aatccggatg tgcagttcct taaggtgaac     480
tatgaggagc ataaatccat gtgttatagc cttaatgtac atgtgttgcc tttctttagg     540
ttctatagag gagctcaggg tcgtctatgc agctttagct gcaccaatgc cacgatcaaa     600
aaattcaaag atgcattggc caagcactca ccagaccgat gcagccttgg ccgacaaaa     660
ggtctcgagg agaaggagct tttggcatta gctgccaaca aagacctttc cttcaactac     720
acaccgaaac cagttcatcc tgcaccggaa gaaattccgg tgctgaaaga agttccatcc     780
ggttcatcct tcaagctaaa agaaagcgag gagaagacct tgattggtgt ggggagatga     840

<210> SEQ ID NO 70
<211> LENGTH: 840
<212> TYPE: DNA
<213> ORGANISM: Gossypium histrum

<400> SEQUENCE: 70
```

```
atggctgaag ttttggggaa gtcaaatctg tttacagctt gtaactgtag tcagaagaag    60
aatcaagaag gtggcgttcc tttgttttct aggagaatct ctgcgttttg tttgagaaag   120
aatagttttc cttctttgaa gttggaacct caagctttga ggagtggttt taatggtcaa   180
agagtggttg ttttagagaa aagaagtcta aatgagagaa ggttctgtcg agttcccatt   240
aaagcacaga tgcaaacagg gcttattggt aaacccaaa agtggtggga aaggggaat    300 caaccaaata tgaaagaagt gacatctgca caagacctgg tggactcact tttgaatgct   360
ggggataaac ttgttatagt ggatttttc tctcctggtt gtggtggctg caaggctctt   420
catcccaaga tttgccaatt ggcagagatg aatccggatg tgcagttcct taagctgaac   480
tatgaggagc ataaatccat gtgttatagc cttaatgtac atgtgttgcc tttctttagg   540
ttctatagag gagctcaggg tcgtttatgc agctttagct gcaccaatgc cacgatcaaa   600
aaattcaaag atgcattggc caagcactca ccagaccgat gcagccttgg gccgacaaaa   660
ggtctcgagg agaaggagct tttggcatta gctgccaaca aagacctttc cttcaactac   720
acaccgaaac cagttcatcc tgcaccagaa gaaatgccgg tgctggaaga agttccatcc   780
ggttcatcct tcaggccaaa agaaagcgag gagaagacct tggttggtgt ggggagatga   840

<210> SEQ ID NO 71
<211> LENGTH: 900
<212> TYPE: DNA
<213> ORGANISM: Glycine max

<400> SEQUENCE: 71
atggcggagg ttttaaccaa ggcgagtttg gtttcatctt cttggcatgg ggttagtcaa    60
cggcatcatc atcgaagggt ttcaacggtt cttttcaaata atacatgtag cttccgttcc   120
ggcgtgggaa agttctcttc tttgaagatg aattctcagg ttctcagatc ttggtcctct   180
tcttctgagt ttcagggtaa aaagcttgtc tttcatgtaa atagaggatt acccaatagg   240
gtcaattcgc ggttgagagc ttctactggg actcagatga accttagact agggaaagtt   300
cagaaatggt gggaaaaggg gcttcaaccc aacatgaaag aggtgacttc agcacaagac   360
tttgtggatt cactgttaaa cgcaggggac aagttggtgg tggttgattt cttctctcct   420
ggttgtggtg gctgcaaagc cctttcatcct aagatatgcc aatttgcaga gatgaatcct   480
gatgttcagt tccttcaggt gaactatgag gagcataagt ccatgtgtta tagccttaat   540
gtccatgttc ttcccttctt ccgattctat agaggcgctc acggtcgatt atgtagcttt   600
agctgcacca atgccacgat caagaagttc aaagatgcat tagccaaaca caccccagac   660
agatgcagct taggcccaac catagggtta gaggagaaag aactcgaagc tcttgctgcc   720
aacaaagatc tttccttcac ctactcacca aaaccattac aaccttcaca tgaaaacgaa   780
gagttggcaa ccgaaactgc ttctgctccg gctcttggtt caggatctct tccttcacct   840
tcaatgaccc tcaatgctgt ggcctctaat gagagaacct tgaccacttc tgggagatga   900

<210> SEQ ID NO 72
<211> LENGTH: 747
<212> TYPE: DNA
<213> ORGANISM: Glycine max

<400> SEQUENCE: 72
atgaagtctc aggttctcag atcttggtcc tcttcttctg agtttcaggg tataaagctt    60
gtctttcatg taaatagagg attacccaat agggtcaatt cgcgcttgag agcttcaact   120
```

| | |
|---|---|
| ggggctcaga tgagctttag actagggaaa gttcagaaat ggtgggaaaa ggggcttcaa | 180 |
| cccaacatga aggaggtgac ttcggcacaa gactttgtgg attcactgtt aagcgcaggg | 240 |
| gacaagttgg tggtggttga tttcttctct cccggttgtg gtggctgcaa agcccttcat | 300 |
| cctaagatat gtcaatttgc agagatgaat cctgatgttc agttccttca ggtgaactat | 360 |
| gaggagcata agtccatgtg ttatagcctt aatgtccatg ttcttccctt cttccgattc | 420 |
| tatagaggtg ctcatggtcg attatgtagc tttagctgca ccaatgccac gatcaagaag | 480 |
| tttaaagatg cattggccaa acacacccca gatagatgca gcttgggccc aaccaaaggg | 540 |
| ttagaagaga aagagcttct agctcttgct gccaacaaag atctttcctt caccaactca | 600 |
| ccagaacctt tacaacctgc acatgcagat gaagagttgg gaaccgaacc tgctcctgct | 660 |
| cctggttcaa aatctcttcc ttcaccttca atgattctca attctgaggt ctctaaaaag | 720 |
| agaaccttaa ccacttcagg gagatga | 747 |

<210> SEQ ID NO 73
<211> LENGTH: 870
<212> TYPE: DNA
<213> ORGANISM: Beta vulgaris

<400> SEQUENCE: 73

| | |
|---|---|
| atggcggatg ttcttaccaa atccagtgtt ttttctccaa caatttctca tcatcatagt | 60 |
| ggaagtaaaa attttccaat taaatgttca gttgcagtga gtaatcgagg gagattagtt | 120 |
| ggaatttctt cgttgaggag tagttttggt ggtgtaagaa ttgcgatcga taaaaatacc | 180 |
| agttttgggt caaaaaggag gaattaccaa tcaattgatg ctaagatggg tctgagcatc | 240 |
| ggcaaagcac agaaatggtg ggagaaagga ctccagccaa atatgagaga gataacttct | 300 |
| gcggaagacc tagtcgattc tttactaaca gcaggagata cattagttgt cgttgatttt | 360 |
| ttctctcctg gatgtggagg ctgcagagct cttcatccta gttgtgtca attggcagag | 420 |
| atgaaccctg atgtccagtt tcttcagatt aactacgaag aacataaatc aatgtgttac | 480 |
| agtcttaatg ttcatgttct tcccttcttt cggttttaca gaggggctga aggccgggtt | 540 |
| tccagcttca gctgtacaaa tgcaacgatt aagaaattca aggatgcttt ggcgaagcat | 600 |
| aacccagcaa ggtgtagcct tgggccaaca aagggcctag aagagaagga gcttcttgct | 660 |
| cttgctgcca acaaagacct ttcatttacc tatacaccaa agcctgtgga agcggaaccc | 720 |
| gtaccgcac ctgcacttga agaagtctct gttaaggctg acgaacaagt cttagcacaa | 780 |
| gaatctctcc cttcttttcaa caggaagcct cttagctcac aaccatcaac cgtgagtgaa | 840 |
| gagaaaactc tagctactgc tgcgagatga | 870 |

<210> SEQ ID NO 74
<211> LENGTH: 837
<212> TYPE: DNA
<213> ORGANISM: Musa acuminate

<400> SEQUENCE: 74

| | |
|---|---|
| atggcggaaa ctttggctca gaggaccctc cttttgcctg gcgggcatct ttctttgccg | 60 |
| ccgttttgcg ggatgcggag ccgcccttct cttgcggcgt tcactctctt ttcacgtacc | 120 |
| aaggttgagc ccttgaggtc ttcttcttgt gatagcaagt tccatgggag gagactggtc | 180 |
| gttggggcgc ggagagggag gccctcgagg gcacgcctcg ttctggctc tgaacagatg | 240 |
| gttctgtcgt tcaagaaggc tataaaatgg tggcagaagg ggcttcaacc caatatggtg | 300 |
| gagatcgagt cggctgagca tctcgtcgac tccttattga acgccggcga caagcttgtt | 360 |

| | |
|---|---|
| attgtggatt tcttctcccc agggtgtgga ggctgcagag cgcttcatcc aaagatttgc | 420 |
| cagttcgccg aatcgaatca aaatgttttg tttctccaaa taaattatga gcaacataag | 480 |
| tcgatgtgct acagcttggg tgtccatgtt ctcccttct ttaggttcta tcgcggagca | 540 |
| cacgggcgcc tgtgcagctt cagctgcacc aatgcaacta ttaagaaatt taagatgct | 600 |
| ttggccaagc acatcactga cagatgcagc cttgggccag ctaggggct ggaggagtca | 660 |
| gagctcttgg ctttggccgc aaacaaagat ctctcattta actacacaag caagccagtt | 720 |
| cctgtgcctg aagagattcc agagagaatt ccaacaagcc cgaaactccc tcttcatgct | 780 |
| gtccgtagac ctgcccagga atccgaggac aaggccctcg ccgcagctgg agatga | 837 |

<210> SEQ ID NO 75
<211> LENGTH: 819
<212> TYPE: DNA
<213> ORGANISM: Musa acuminate

<400> SEQUENCE: 75

| | |
|---|---|
| atggcggatg ctttggctca aatgacgctc ctttcgcccc atggccaccg ttctttgtcg | 60 |
| cgctcttccg accggagaaa ccgccttgtt tgtgcgtcaa aggatgatct cttgaggtct | 120 |
| tcgtcttctt gtaatagcca gttccatggg agaaggctgg ttattggcgc acagagagag | 180 |
| aggccgttga gaggcaaccg aggttctagc tctgtgcaga tgactctgtc ctttaagaag | 240 |
| gcttcgaaat ggtgggagaa ggggcttcat cccaatatga aggacatcaa gtcggctgag | 300 |
| gatctcgtcg actccttgtc gaacgcgggc gacaagctcg tcatcgtgga tttcttctcc | 360 |
| ccaggatgtg caggctgcag agccctccac ccaaagatct gccaattcgc agagttgaat | 420 |
| ccagacgttc aatttctcca actaaaccac gaggaacaca gtccatgtg ctacagcttg | 480 |
| aatgtccatg ttctcccctt ctttaggttc tatcgcggag cgcacggtcg cctgtgcagc | 540 |
| ttcagctgca ccaatgcaac catcaagaaa tttaaggatg ctttggcgaa gcacatcacc | 600 |
| gaaagatgca gtcttgggcc agccaagggg ctggaggaga cggagctcct tgccttggct | 660 |
| gcaaacaagg atctctcctt cacctacaca agaacgcctg ttcccgtacc tgatgagctt | 720 |
| gcagagaaag ctccatttaa cccaaaccta cctgtgcatg ctgctgctag actcaccctg | 780 |
| gaatctgagg acaaggcttt tgccgcagcc ggtagatga | 819 |

<210> SEQ ID NO 76
<211> LENGTH: 858
<212> TYPE: DNA
<213> ORGANISM: Capsicum annuum

<400> SEQUENCE: 76

| | |
|---|---|
| atggcaaaat tgatgaacaa aggttttgtg tttccttcat cttctgattg tggtcatcat | 60 |
| cgccctcatg ggatttcttc tttccccaat aaatcggtca atctttcttg tcttccatct | 120 |
| acttgtctgc taagaagcta ttttatggt cgtagattgg tcataaatga agccctaccc | 180 |
| aaaagaaatg cccacgttgc aatcactgtc cagatgagta tgggaatcag gaaagtacag | 240 |
| aaatggtggg agaaaggggt tcaacctaac atgaaagaag tgaacagtgc tcaaggcctt | 300 |
| gttgactctc ttttgagtgc aggagataaa ttagtagttg ttgatttctt ttcccctggc | 360 |
| tgcggtggct gcaaagccct tcaccctaag ttgtgtcagc tggcagagat gaatccagat | 420 |
| gtgcagtttt tacaggtgaa ctatgaggaa cacaagtcca tgttactc tcttaacgtg | 480 |
| caccttctcc cattttccg tttctataga ggagctgaag gtcgtgtttg cagctttagc | 540 |

| | |
|---|---|
| tgtaccaatg ccacgataaa aaaatttaaa gatgcattgg caaagtatgg tacagatcgt | 600 |
| tgcacctttg gaccaccgaa agggcttgag gagaaagagc tacttgcatt ggcagctaac | 660 |
| aaggaactct cgtttaatta cattccaaaa acagaagaag aacctgtcct tgttgcctca | 720 |
| caagaggaag ttgaggacag aactccaaat aaagagtccc ctctaccact tcctcttcct | 780 |
| ctacccatta gctcaactag ctcactgaag cccaaacagg atacagagaa agaagcgtat | 840 |
| gctacttctg gtagatag | 858 |

<210> SEQ ID NO 77
<211> LENGTH: 894
<212> TYPE: DNA
<213> ORGANISM: Cicer arietinum

<400> SEQUENCE: 77

| | |
|---|---|
| atggctgaaa ttttgaccaa gacaagtttg gtttcatctt ggcatgggaa cagaaaacag | 60 |
| caacatcgaa ggttgtccat ggttcccaat aagacttgta gcttcaacac ttgcgtggga | 120 |
| agtttcccat ctttgaagct aaaatctcag tttcttagat cttcctcttt ttcatctgag | 180 |
| ttttatggga aaaatactat cttttcgtgta aatagatcaa tacccaacag gattaattca | 240 |
| caattttcag tttcagctgc gcctaagatg acacttagaa taggaaaaat tcagaaatgg | 300 |
| tgggaaaagg ggcttcaacc taacatgaga gaagtgactt cagctcaaga tcttgtagat | 360 |
| tcacttttaa acgcagggga caaacttgtc attgttgact ttttctctcc tggttgtggt | 420 |
| ggctgcagag cccttcaccc taagatatgt caaatggcag agatgaatcc tgatgttgag | 480 |
| ttccttcaag tgaactatga agagcataaa tccatgtgtt atagccttaa tgttcatgtc | 540 |
| cttcctttct tccgcttcta tagaggcgct catggtcgct tatgcagctt tagctgcacc | 600 |
| aatgccacga tcaagaagtt taaagatgca ttggccaaac acactccaga tagatgcagc | 660 |
| ttggaaccaa ccaaagggtt agaggagaaa gagctcatag ctttatctga aaacaaagat | 720 |
| cttaacttca catacacacc aaaacctctt caacctgtgc atacacctgc aaatgaagag | 780 |
| ttggcgacaa ccaaagcctc tcctgttttgt tcggagcctc ttcctttacc ttcattgacc | 840 |
| tcgaattctg atgaagtctt gaaggagaga accctgacaa gggctggaag atga | 894 |

<210> SEQ ID NO 78
<211> LENGTH: 900
<212> TYPE: DNA
<213> ORGANISM: Solanum lycopersicum

<400> SEQUENCE: 78

| | |
|---|---|
| atgacgaaat tgatgagcaa aggttttatc tttccttctt cttcttctga ttgtggtgaa | 60 |
| atttatgatc gtcttcgtct taatctacat gggatctgtt cttttcccaa taaatcggtc | 120 |
| aatctttctt gtcttccttc gttgaagctt tcttcttctt gtttgccaag aaccgatttt | 180 |
| tatggtcgta gattggttat aaatgaaggc ttatccaatt tcaaccgaag agttgctgat | 240 |
| atcactgctc agatgagtgt tggaatcaag aaagcacaga atggtggga gaaagggggtt | 300 |
| caacctaaca tgaaagaagt gaacagtgca caagaacttg ttgactctct attgagtgca | 360 |
| ggggataaat tagttgttgt tgatttcttt tctcctggct gtggaggttg taagctctct | 420 |
| caccccaagt tgtgtcagct ggcagagatg aatccagatg tgcagttttt acaggtgaac | 480 |
| tatgaggaac acaagtcgat tgtgttactct cttaatgtac atgttctccc gtttttccgt | 540 |
| ttctatagag gagctgaagg ccgtgttttgc agctttagct gtaccaatgc cacgatcaaa | 600 |
| aaattcagag atgcattggc gaagtatggt acagatcgtt gcaccattgg gtcacccaaa | 660 |

```
gggcttgagg agaaagagct acttgcattg gcagctaaca aggatctttc ctttaattac    720
actccaaaaa cagaagaaga acccatcctc gttacctcac aaaaggaagt tcgggataga    780
actactccaa atatagagtc ccctctacca cttcctcttc ctctccccat tacgtcaact    840
agctcacaga cggccaaacg ggatacagag aaagaagcat atgctacttc tggtagatga    900

<210> SEQ ID NO 79
<211> LENGTH: 774
<212> TYPE: DNA
<213> ORGANISM: Solanum lycopersicum

<400> SEQUENCE: 79
atggagaaat tgttgaataa ggcagtattt cttccatcaa ttttgaattc tagtggtatt     60
tatcattcta atcaacatgc gatttgtgtt tttccagtga aattcaatag aagatatcac    120
aaatcagcag ttgctactgc tcagatgagc ataggtatca agagagctcc taaatggtgg    180
gagaaaggac ttcaaccgaa tatgaaagag gtgacgggtg ctcaagacct cgttgacacc    240
cttctaaacg gtggggataa actagtcgtt gttgatttcc tttccctgg ctgtggaggc     300 tgcaaagccc ttcatccaaa gatatgtcag ttagcagaga tgaatccgga tgtgcagttt    360
ttgcatgtga actatgagga acacaagtca atgtgttact cgctgaacgt acatgttctc    420
ccatttttcc gtttctatag aggtgctgaa ggtcgtcttt gtagctttag ttgcaccaat    480
gccacgataa aaaaattcaa agatgcattg acaaagtatg gtgcagattg ttgcagcctc    540
ggaccagtta aagggctcga ggagaaagag ctacttgccc tagcggctaa taaggaccta    600
tcttttgctt acacaccaaa aacagaagaa ccagtgcctc ttgccttaga agaagttaag    660
gtgataaaaa caagtagaca atcttcatct catcccaata cattctcccc attaccactt    720
cctcttcctc tagcatcaac tttgcatacg gccaaacagg actcaaagag ttaa          774

<210> SEQ ID NO 80
<211> LENGTH: 840
<212> TYPE: DNA
<213> ORGANISM: Elaeis guineensis

<400> SEQUENCE: 80
atgatggagg ttttgagtca gagcggtgtt atgtcgccgt gcgggcatcg ttgggtggtc     60
cgttcttgca aggagaggag cccttctttt gttgggtttc ctcgctcttc ctctcggacg    120
atcgagtctc tgatgtcttc ttctcggaat agcggtttcc atgggaggag attgagcatt    180
ggggcttgga gagtgaatgc cgtgaagggg aattttagtt ctaccccgt acagatgagc    240 ctctgcgttg gaaaggcttt gaaatggtgg gagaaggagc tccagcccaa catgaaggag    300
atcgagtcgg cccaggatct cgtcgactct ttattgaacg caggagacaa gcttgtcata    360
gtagatttct tctcccctgg ttgtggaggc tgcaaagccc tccatccaaa gatttgccag    420
tttgcaaagc tgaacccaga tgttctcttc ctccaagtaa actatgaaaa gcacaaatcc    480
atgtgttata gcttaaatgt ccatgttctt ccctttttta ggttttacag gggagcacac    540
ggtcgtcttt gtagcttcag ctgcaccaat gcaactatta gaaaatttaa agatgctttg    600
gccaagcaca ccacagacag atgcagcctg ggcccaacaa aggggctgga ggaatcagag    660
ctcatggctc tggctgcaaa caaggatctc tctttcagtt acacaagaaa gccagtccct    720
gttccctcgc cagatgaggc tgcagaggaa gttgtgctca gcccaaaact tccggtttct    780
tcaactccaa gagtcatcca agattcggag gagaaggctc tggtggcagc tgggagatga    840
```

<210> SEQ ID NO 81
<211> LENGTH: 819
<212> TYPE: DNA
<213> ORGANISM: Elaeis guineensis

<400> SEQUENCE: 81

| | | | | | |
|---|---|---|---|---|---|
| atggcggagg | ttttgggcag | gagcggcgtg | ttctcgctgc | gcgggcaccg | ttccgtggcc | 60 |
| ccttcttgcc | agaagaggag | cccttctttt | cttgggtttc | ctctctcatc | ctctcggccg | 120 |
| atcgggcctc | ctaggtcgtc | ttctcggaga | tttgttatcg | ggactcggag | agggaggtcc | 180 |
| atcaagggaa | attctagctc | ttcccgtgta | cagatgagcc | tcggcgttgg | aaagtcattg | 240 |
| aagtggtggg | agaagggtgt | gcagcccaac | atgaaggaga | ttggatcggc | ccaggatctt | 300 |
| gttgactcct | tattgaatga | aggagacaag | cttgttatcg | tagatttctt | ctcccctggt | 360 |
| tgtggaggct | gcaaagccct | ccatccaaag | atttgccgga | ttgcggagat | gaacccacat | 420 |
| gttctcttcc | tccaaataaa | ctatgagaag | cacaagtcca | tgtgttatag | cttgcatgtt | 480 |
| cacgttctcc | ccttttttag | gttttaccgg | ggagctcacg | gtcgcctttg | tagcttcagc | 540 |
| tgcaccaatg | caactattaa | gaaatttaaa | gatgcattgg | ccaaacacac | cacagacaga | 600 |
| tgcagccttg | ggccaacaaa | ggggctggaa | gaatcagagc | ttgtggctct | ggctgcaaac | 660 |
| aaggatctct | ccttcaatta | cacaagaaaa | ccggttcctg | ttctcacacc | agacgaggct | 720 |
| gcagagaaag | ttcctcttag | cccaaaactt | ccagtgtctt | cagccccaag | agtcatcaaa | 780 |
| gattctgagg | acaaggccct | cgttgcagct | gggacatga | | | 819 |

<210> SEQ ID NO 82
<211> LENGTH: 864
<212> TYPE: DNA
<213> ORGANISM: Setaria italic
<220> FEATURE:
<221> NAME/KEY: misc_feature
<222> LOCATION: (826)..(827)
<223> OTHER INFORMATION: n is a, c, g, or t

<400> SEQUENCE: 82

| | | | | | |
|---|---|---|---|---|---|
| atggcggcgg | cgcaggcggt | cgcgaagggc | agcgtggtgt | cgccgtgcgg | cagcagggcc | 60 |
| gcgccgggcc | tcctgagtcg | gcggagggc | gccgtggcga | cgcggatggc | gccgtcggcg | 120 |
| gtgcggatcg | ggggctcctg | gaggaagacc | gcgttcctcg | gcggtaggct | ggcggtcggg | 180 |
| ccgaggagat | ccaggtccgc | gtcccggacc | ctcgtcgcgt | cgccggtgca | gatgaacatg | 240 |
| aaccttgcga | ttgggaaatc | catgaggtgg | tgggagaagg | ggctgcagcc | caacatgcgg | 300 |
| gagatcgagt | ccgcccagga | tctcgtcgat | tccttgacca | acgccggcga | cagactcgtc | 360 |
| atcgtggact | tcttctcccc | cggctgcggc | ggttgccgtg | ctcttcaccc | caagatttgc | 420 |
| cagtttgcgg | agcagaaccc | ggatgtgctg | ttcttgcaag | tgaaccatga | ggagcacaag | 480 |
| tctatgtgct | acagcctcca | tgtccacgtc | ctcccattct | tcaggttcta | caggggagct | 540 |
| cagggacggc | tctgcagctt | cagttgtacc | aacgcaacta | tcaagaagtt | caaggatgca | 600 |
| cttgcaaagc | acaaaccgga | tagatgtagc | attgcccaa | ctagagggct | ggaggaatca | 660 |
| gagttattag | cattggctgc | aaacaaggac | ttgcagttca | cctacaccaa | gaagccagaa | 720 |
| ctgatcccca | gcggagatgc | tgctgctgag | gtcattgctc | ccgagcctac | aaagcttcct | 780 |
| gcggcaacaa | agccgtcggt | caagataggg | tccgaggaga | ggtccnnttg | gtctcatcag | 840 |
| gaagatgaga | tgaatgacct | ctag | | | | 864 |

<210> SEQ ID NO 83
<211> LENGTH: 822
<212> TYPE: DNA
<213> ORGANISM: Setaria italic

<400> SEQUENCE: 83

| | | | | | |
|---|---|---|---|---|---|
| atggcggcag | cgcaggcgat | ggcgaagatg | agcgtggggt | cgccggcctg | caatcgggct | 60 |
| gcgggatccc | tctgccggtg | gaggggagcc | gtggcggtgc | ggctcggagg | atcctggtcc | 120 |
| tggaggaaga | gcccgttcct | cggcgggagg | atggcggttg | gcccaggag | atcgaggccc | 180 |
| gtgtcccgga | atcctgttgc | gtcgccggtg | cagatgaacc | tttcatttgg | gaaaaccatg | 240 |
| aagtggtggg | agaagggatt | gcagcccaac | atgcgggcga | tccacaccgc | ccaagaactc | 300 |
| gtcgattcct | tgatcaacgc | cggcgacggg | ctcgtcatag | tcgacttctt | ctcacctggc | 360 |
| tgcgccggct | gccatgccct | ccatcccaag | atttgccagt | ttgcggagcg | aacccagat | 420 |
| gtgcagttcc | tgcaagtgaa | ctttgaggag | cacaagtcta | tgtgccacag | ccttcatgtt | 480 |
| catgtgttcc | ctttcttcag | attctacagg | ggagctcagg | gccggctctg | cagcttcagc | 540 |
| tgtaccaatg | caactatcaa | gaagttcaag | gatgcgcttg | caaagcacaa | accagataga | 600 |
| tgtagccttg | gcccaattaa | ggggctagag | gaatcagagc | tactggcttt | ggctgcaaac | 660 |
| agggacctgc | agttcaccta | caccaaggag | caagatctgg | ctccgagcat | ggaagatggc | 720 |
| gcagaggtca | tcactcatga | ccatccaagg | cttcctgcag | cagcaaagcc | gctggtcagg | 780 |
| caggggtctg | aggacagggc | tgtggtctca | tcgggaagat | aa | | 822 |

<210> SEQ ID NO 84
<211> LENGTH: 825
<212> TYPE: DNA
<213> ORGANISM: Setaria italic

<400> SEQUENCE: 84

| | | | | | |
|---|---|---|---|---|---|
| atggctgagg | ctttgtgcaa | cggcgtcgtg | ccgtcgccgt | gcggcgggga | cgtgggcgtg | 60 |
| gccggccggg | tcagtggcgc | cgcggcgcg | ctagcggagt | ccgtgccgat | cggcggctac | 120 |
| cgcaccaaga | gctccttctc | cgcagggagg | atggccatga | ccgacaggaa | gatgaggccc | 180 |
| ctgcctcgga | gcatcgaggc | cgcgcctgga | cagatgaacc | tgtcgtttcc | taaggccatg | 240 |
| cggtggtggg | agaaggggct | gcagcccaac | atgcgggaga | tcgagtccgc | gcaagacctc | 300 |
| gccgactccc | tgctcaacgc | cggcgacaag | ctcgtcgtcg | tcgacttctt | ctcccctggc | 360 |
| tgcggcggct | gccgcgccct | gcatgccaag | attgcccagt | ttgccgagaa | gaacccagat | 420 |
| gtgatgttcc | tgcaagtgaa | ctatgagacg | cacaagtcca | tgtgctacag | cctccatgtc | 480 |
| catgtcctcc | ctttcttcag | gttctacagg | ggagccgagg | gacgggtcag | cagcttcagc | 540 |
| tgcacaaatg | caactatcaa | gaagttcaag | gacgcgctcg | caaagcacgg | acctgacagg | 600 |
| tgcagcctcg | gcctgcacg | ggggctggag | gagtcggagc | tcatggcctt | ggctgcaaac | 660 |
| aaggacctgc | aattcaccta | cgagaagccg | gccttgtcc | cacttgcaga | agccattgcc | 720 |
| aaggaggctg | ctgcaccagg | aggcccgtgg | ttcccttgc | ctgcgtccgc | gacgcagttc | 780 |
| ctcactcagg | gatcagagaa | ttcattgctg | tcatccggaa | gatag | | 825 |

<210> SEQ ID NO 85
<211> LENGTH: 750
<212> TYPE: DNA
<213> ORGANISM: Chlamydomonas reinhardtii

<400> SEQUENCE: 85

```
atggccagca tactaaatcg tgccggttca aggtcgttag ttttgagac taagcagtca    60 ttgcgttcta ttcctggcag ccttttatcg ctgcggtcag tggcgctgaa gccattccgg   120
acaaccatct gcgcggcggg agcgctgctg actgcacggc gctcgacatc aggcctcggg   180
cgcgccaacg gggtcgtttg ccaagcaggg cgtagcactg gggaatggtg aagaaggac   240 aacccccaa acatgcggga catcaactca attcaggagc tggttgacgc tctgtcggat    300
gccggagacc gcctcgtcat tgtggagttc tacgcccagt ggtgcaacgc ctgccgcgcg   360
ctattcccca agatctgcaa atcatggct gagaacccgg acgtgctctt cctcaaagtg    420
aactttgacg acaaccgtga cgcgtgccgc accctgagcg tcaaggtgct gccgtacttc   480
cacttctacc gcggtgcgga gggccgtgtg gcggccttca gcgccaccat cagcaagttg   540
cagctgttca aggatgccgt ggagacctac agcgccgcct tctgcagcct ggagcccgcg   600
ccggggctgg cggagttccc cgacctcatc gcgcacccgg agctgcaccc ggaggaggcc   660
gcagaggcgg cgcggcgcgc gcggctggcg tccaccgagt cggaggagga gttgcatccg   720
ctggccgaca cgccgactgt ggtgggatag                                    750

<210> SEQ ID NO 86
<211> LENGTH: 519
<212> TYPE: DNA
<213> ORGANISM: Chlorella

<400> SEQUENCE: 86
tggtggacca gtctgcgcc gcccaatgta gtgcacatca gtctgtgca gcacttggtg     60 gacgaaatgg tgagggctga gaggctggcg ggcgctggcg agcggctggt gatcatggat    120
gtgtttgcgc cctggtgcgc cgcctgcaag gcgctgtacc ccaagctgat gaagctgatg   180
gaggagcgcc ccgatgtgct gctgctgacg gtaaactttg atgagaacaa gacggtggtg    240
aaggccatgg gggtcaaggt cctgccgtac ttcatgttct atcgcggcaa ggagggcaag   300
ctgcaggagt tctcggccag caacaagcga ttccacctca tccaggaagc cattgagcgg   360
cacagcaccg atcgctgctt cctggatagc accgacgagg agcctgtgct tgcagagttc   420
cccactgtcg tccccgccaa gggcatcagc ggcagcttgg atgagccggc cggccgtgcg   480
gccggcaagg cggtgggcca gccgcagccc gtggcctga                          519

<210> SEQ ID NO 87
<211> LENGTH: 47
<212> TYPE: PRT
<213> ORGANISM: Arabidopsis thaliana

<400> SEQUENCE: 87

Lys Glu Leu Asn Phe Thr Tyr Thr Pro Lys Pro Val Pro Val Glu Lys
1               5                   10                  15

Glu Ala Ala Thr Pro Asp Ser Asn Pro Ser Leu Pro Val Pro Leu Pro
                20                  25                  30

Ser Met Ser Ser Asn Asp Glu Lys Thr Leu Val Ser Ala Gly Arg
            35                  40                  45

<210> SEQ ID NO 88
<211> LENGTH: 69
<212> TYPE: PRT
<213> ORGANISM: Solanum tuberosum

<400> SEQUENCE: 88

Ala Ala Asn Lys Asp Leu Ser Phe Asn Tyr Thr Pro Lys Thr Glu Glu
1               5                   10                  15
```

```
Ala Pro Val Leu Val Thr Ser Gln Lys Glu Val Gln Asp Thr Thr Pro
             20                  25                  30

Pro Asn Ile Glu Ser Pro Leu Pro Leu Pro Leu Pro Ile Ala
         35                  40                  45

Ser Thr Ser Ser Gln Thr Ala Lys Arg Asp Thr Glu Lys Glu Ala Tyr
 50                  55                  60

Ala Thr Ser Gly Arg
 65

<210> SEQ ID NO 89
<211> LENGTH: 68
<212> TYPE: PRT
<213> ORGANISM: Solanum tuberosum

<400> SEQUENCE: 89

Ala Ala Asn Lys Asp Leu Ser Phe Ala Tyr Thr Pro Lys Thr Glu Glu
 1               5                  10                  15

Pro Met Pro Val Ala Leu Gln Asp Ala Lys Val Ile Lys Thr Ser Arg
             20                  25                  30

Thr Ser Ser Cys Pro Asn Thr Phe Ser Leu Leu Pro Leu Pro Leu
         35                  40                  45

Pro Leu Pro Leu Ala Ser Thr Ser His Lys Ala Lys Gln Asp Ser Lys
 50                  55                  60

Ser Glu Val Phe
 65

<210> SEQ ID NO 90
<211> LENGTH: 228
<212> TYPE: PRT
<213> ORGANISM: Arabidopsis thaliana

<400> SEQUENCE: 90

Met Thr Glu Val Ile Ser Lys Thr Ser Leu Phe Leu Gly Ala Cys Gly
 1               5                  10                  15

Asn His His Arg Val Asp Asp Phe Ser Phe Ser Pro Val Ser Phe Gly
             20                  25                  30

Gly Phe Gly Leu Lys Lys Ser Phe Ser Cys Leu Lys Leu Lys Ser Gln
         35                  40                  45

Lys Pro Leu Arg Ser Val Phe Tyr Gly Lys Gln Ile Val Phe Gly Asp
 50                  55                  60

Ser Gln Asp Glu Ser Phe Arg Arg Ser Ser Ala Ile Thr Ala Gln Thr
 65                  70                  75                  80

Thr Leu Arg Ile Gly Thr Ala Gln Lys Trp Trp Glu Lys Gly Leu Lys
                 85                  90                  95

Asp Asn Met Arg Glu Ile Ser Ser Ala Gln Glu Leu Val Asp Ser Leu
                100                 105                 110

Thr Asn Ala Gly Asp Lys Leu Val Val Asp Phe Phe Ser Pro Gly
            115                 120                 125

Cys Gly Gly Cys Lys Ala Leu His Pro Lys Ile Cys Gln Phe Ala Glu
130                 135                 140

Met Asn Pro Asp Val Gln Phe Leu Gln Val Asn Tyr Glu Glu His Lys
145                 150                 155                 160

Ser Met Cys Tyr Ser Leu Gly Val His Val Leu Pro Phe Phe Arg Phe
                165                 170                 175

Tyr Arg Gly Ser Gln Gly Arg Val Cys Ser Phe Ser Cys Thr Asn Ala
                180                 185                 190
```

Thr Ile Lys Lys Phe Arg Asp Ala Leu Ala Lys His Gly Pro Asp Arg
            195                 200                 205

Cys Ser Leu Gly Pro Thr Lys Gly Leu Glu Glu Lys Glu Leu Val Ala
    210                 215                 220

Leu Ala Ala Asn
225

<210> SEQ ID NO 91
<211> LENGTH: 232
<212> TYPE: PRT
<213> ORGANISM: Solanum tuberosum

<400> SEQUENCE: 91

Met Met Lys Leu Met Ser Lys Gly Phe Met Phe Pro Ser Ser Ser Asp
1               5                   10                  15

Cys Gly Glu Ile Tyr His His Arg Pro Leu Asn Leu Pro Gly Ile Cys
            20                  25                  30

Ser Phe Pro Asn Lys Ser Val Asn Leu Ser Cys Leu Pro Ser Leu Asn
        35                  40                  45

Leu Ser Ser Ser Cys Leu Pro Arg Thr Asp Phe Tyr Gly Arg Arg Leu
50                  55                  60

Val Ile Asn Glu Gly Val Ser Lys Phe Asn Arg Arg Asn Ser Gln Val
65                  70                  75                  80

Val Asp Ile Thr Ala Gln Met Ser Ile Gly Ile Arg Lys Ala Gln Lys
                85                  90                  95

Trp Trp Glu Lys Gly Val Gln Pro Asn Met Lys Glu Val Asn Ser Ala
            100                 105                 110

Gln Glu Leu Val Asp Ser Leu Leu Ser Ala Gly Asp Lys Leu Val Val
        115                 120                 125

Val Asp Phe Phe Ser Pro Gly Cys Gly Gly Cys Lys Ala Leu His Pro
130                 135                 140

Lys Leu Cys Gln Leu Ala Glu Met Asn Pro Asp Val His Phe Leu Gln
145                 150                 155                 160

Val Asn Tyr Glu Glu His Lys Ser Met Cys Tyr Ser Leu Asn Val His
                165                 170                 175

Val Leu Pro Phe Phe Arg Phe Tyr Arg Gly Ala Glu Gly Arg Val Cys
            180                 185                 190

Ser Phe Ser Cys Thr Asn Ala Thr Ile Lys Lys Phe Lys Asp Ala Leu
        195                 200                 205

Ala Lys Tyr Gly Thr Asp Arg Cys Thr Leu Gly Pro Pro Lys Gly Leu
    210                 215                 220

Glu Glu Lys Glu Leu Leu Ala Leu
225                 230

<210> SEQ ID NO 92
<211> LENGTH: 162
<212> TYPE: PRT
<213> ORGANISM: Solanum tuberosum

<400> SEQUENCE: 92

Met Lys Phe Asn Arg Arg Asn His Lys Ser Ala Ala Thr Ala Gln
1               5                   10                  15

Met Ser Ile Gly Ile Arg Lys Ala Pro Lys Trp Trp Glu Lys Gly Leu
            20                  25                  30

Gln Pro Asn Met Lys Glu Val Met Gly Ala Gln Asp Leu Ala Asp Thr
        35                  40                  45

```
Leu Leu Asn Ala Gly Asp Lys Leu Val Val Asp Phe Leu Ser Pro
         50                  55                  60

Gly Cys Gly Cys Lys Ala Leu His Pro Lys Ile Cys Gln Leu Ala
 65                  70                  75                  80

Glu Met Asn Pro Asp Val Gln Phe Leu His Val Asn Tyr Glu Glu His
                 85                  90                  95

Lys Ser Met Cys Tyr Ser Leu Asn Val His Val Leu Pro Phe Phe Arg
             100                 105                 110

Phe Tyr Arg Gly Ala Glu Gly Arg Leu Cys Ser Phe Ser Cys Thr Asn
             115                 120                 125

Ala Thr Ile Lys Lys Phe Lys Asp Ala Leu Thr Lys Tyr Gly Ala Asp
             130                 135                 140

Cys Cys Ser Leu Glu Pro Val Lys Gly Leu Glu Glu Lys Glu Leu Leu
145                 150                 155                 160

Ala Leu

<210> SEQ ID NO 93
<211> LENGTH: 16
<212> TYPE: PRT
<213> ORGANISM: Arabidopsis thaliana

<400> SEQUENCE: 93

Ala Pro Asp Phe Glu Ala Glu Val Phe Asp Gln Glu Phe Ile Lys
 1               5                  10                  15

<210> SEQ ID NO 94
<211> LENGTH: 24
<212> TYPE: PRT
<213> ORGANISM: Arabidopsis thaliana

<400> SEQUENCE: 94

Leu Asn Thr Glu Val Leu Gly Val Ser Val Asp Ser Val Phe Ser His
 1               5                  10                  15

Leu Ala Trp Val Gln Thr Asp Arg
                 20

<210> SEQ ID NO 95
<211> LENGTH: 17
<212> TYPE: PRT
<213> ORGANISM: Arabidopsis thaliana

<400> SEQUENCE: 95

Ser Gly Gly Leu Gly Asp Leu Asn Tyr Pro Leu Ile Ser Asp Val Thr
 1               5                  10                  15

Lys

<210> SEQ ID NO 96
<211> LENGTH: 14
<212> TYPE: PRT
<213> ORGANISM: Arabidopsis thaliana

<400> SEQUENCE: 96

Ser Phe Gly Val Leu Ile His Asp Gln Gly Ile Ala Leu Arg
 1               5                  10

<210> SEQ ID NO 97
<211> LENGTH: 7
<212> TYPE: PRT
<213> ORGANISM: Arabidopsis thaliana
```

```
<400> SEQUENCE: 97

Gly Leu Phe Ile Ile Asp Lys
1               5

<210> SEQ ID NO 98
<211> LENGTH: 16
<212> TYPE: PRT
<213> ORGANISM: Arabidopsis thaliana

<400> SEQUENCE: 98

Glu Gly Val Ile Gln His Ser Thr Ile Asn Asn Leu Gly Ile Gly Arg
1               5                   10                  15

<210> SEQ ID NO 99
<211> LENGTH: 25
<212> TYPE: PRT
<213> ORGANISM: Arabidopsis thaliana

<400> SEQUENCE: 99

Thr Leu Gln Ala Leu Gln Tyr Ile Gln Glu Asn Pro Asp Glu Val Cys
1               5                   10                  15

Pro Ala Gly Trp Lys Pro Gly Glu Lys
            20                  25

<210> SEQ ID NO 100
<211> LENGTH: 16
<212> TYPE: PRT
<213> ORGANISM: Arabidopsis thaliana

<400> SEQUENCE: 100

Leu Ile Asp Ile Pro Val Ser Asn Cys Leu Asn Ser Asn Ile Ser Lys
1               5                   10                  15

<210> SEQ ID NO 101
<211> LENGTH: 14
<212> TYPE: PRT
<213> ORGANISM: Arabidopsis thaliana

<400> SEQUENCE: 101

Ile Tyr Val Leu Thr Gln Phe Asn Ser Ala Ser Leu Asn Arg
1               5                   10

<210> SEQ ID NO 102
<211> LENGTH: 28
<212> TYPE: PRT
<213> ORGANISM: Arabidopsis thaliana

<400> SEQUENCE: 102

Asn Glu Gly Phe Val Glu Val Leu Ala Ala Gln Gln Ser Pro Glu Asn
1               5                   10                  15

Pro Asn Trp Phe Gln Gly Thr Ala Asp Ala Val Arg
            20                  25

<210> SEQ ID NO 103
<211> LENGTH: 16
<212> TYPE: PRT
<213> ORGANISM: Arabidopsis thaliana

<400> SEQUENCE: 103

Glu Gly Val Ile Gln His Ser Thr Ile Asn Asn Leu Gly Ile Gly Arg
1               5                   10                  15

<210> SEQ ID NO 104
```

-continued

```
<211> LENGTH: 12
<212> TYPE: PRT
<213> ORGANISM: Arabidopsis thaliana

<400> SEQUENCE: 104

Val Asp Thr Thr Ile Leu Gly Leu Asp Asp Gln Arg
1               5                   10

<210> SEQ ID NO 105
<211> LENGTH: 15
<212> TYPE: PRT
<213> ORGANISM: Arabidopsis thaliana

<400> SEQUENCE: 105

Glu Met Pro Phe Ile Ala Ser Met Gly Ile Tyr Val Val Ser Arg
1               5                   10                  15

<210> SEQ ID NO 106
<211> LENGTH: 23
<212> TYPE: PRT
<213> ORGANISM: Arabidopsis thaliana

<400> SEQUENCE: 106

Asn Gln Phe Pro Gly Ala Asn Asp Phe Gly Ser Glu Val Ile Pro Gly
1               5                   10                  15

Ala Thr Ser Leu Gly Leu Arg
            20

<210> SEQ ID NO 107
<211> LENGTH: 28
<212> TYPE: PRT
<213> ORGANISM: Arabidopsis thaliana

<400> SEQUENCE: 107

Val Gln Ala Tyr Leu Tyr Asp Gly Tyr Trp Glu Asp Ile Gly Thr Ile
1               5                   10                  15

Glu Ala Phe Tyr Asn Ala Asn Leu Gly Ile Thr Lys
            20                  25

<210> SEQ ID NO 108
<211> LENGTH: 11
<212> TYPE: PRT
<213> ORGANISM: Arabidopsis thaliana

<400> SEQUENCE: 108

Lys Pro Val Pro Asp Phe Ser Phe Tyr Asp Arg
1               5                   10

<210> SEQ ID NO 109
<211> LENGTH: 18
<212> TYPE: PRT
<213> ORGANISM: Arabidopsis thaliana

<400> SEQUENCE: 109

Met Leu Asp Ala Asp Val Thr Asp Ser Val Ile Gly Glu Gly Cys Val
1               5                   10                  15

Ile Lys

<210> SEQ ID NO 110
<211> LENGTH: 12
<212> TYPE: PRT
<213> ORGANISM: Arabidopsis thaliana

<400> SEQUENCE: 110
```

```
Ile Ile Asn Ser Asp Asn Val Gln Glu Ala Ala Arg
1               5                  10
```

<210> SEQ ID NO 111
<211> LENGTH: 15
<212> TYPE: PRT
<213> ORGANISM: Arabidopsis thaliana

<400> SEQUENCE: 111

```
Cys Ile Leu Gly Leu Asp Asp Gln Arg Ala Lys Glu Met Pro Phe
1               5                  10                  15
```